US005744426A

United States Patent [19]

von dem Bussche-Hünnefeld et al.

[11] Patent Number: 5,744,426

[45] Date of Patent: Apr. 28, 1998

[54] SUBSTITUTED 3-PHENYLPYRAZOLES

[75] Inventors: Christoph-Sweder von dem Bussche-Hünnefeld, Mannheim; Ralf Klintz, Gruenstadt; Gerhard Hamprecht, Weinheim; Elisabeth Heistracher, Ludwigshafen; Peter Schäfer, Ottersheim; Klaus Ditrich, Gönnheim; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 750,231

[22] PCT Filed: May 31, 1995

[86] PCT No.: PCT/EP95/02062

§ 371 Date: Nov. 26, 1996

§ 102(e) Date: Nov. 26, 1996

[87] PCT Pub. No.: WO95/33728

PCT Pub. Date: Dec. 14, 1995

[30] Foreign Application Priority Data

Jun. 3, 1994 [DE] Germany .......................... 44 19 517.6

[51] Int. Cl.$^6$ .......................... A01N 43/56; C07D 231/20

[52] U.S. Cl. .......................... 504/282; 548/366.1

[58] Field of Search .......................... 548/366.1; 504/282

[56] References Cited

U.S. PATENT DOCUMENTS 4,008,249 2/1977 Fischer et al. .

FOREIGN PATENT DOCUMENTS

| | | |
|---|---|---|
| 443 059 | 2/1990 | European Pat. Off. . |
| 447 055 | 9/1991 | European Pat. Off. . |
| 300 173 | 9/1988 | Japan . |
| 093 774 | 9/1989 | Japan . |
| 047 180 | 4/1990 | Japan . |
| 081 275 | 5/1990 | Japan . |
| 02509 | 2/1992 | WIPO . |
| 06962 | 4/1992 | WIPO . |

OTHER PUBLICATIONS

Miura et al., Chemical Abstracts 115 (1991), 20789t (English Abstract of JP–A 03/151 367.

Miura et al., Chemical Abstracts 115 (1991), 49684h (English Abstract of JP–A–03/072 460.

*Primary Examiner*—Robert W. Ramsuer

*Attorney, Agent, or Firm*—Keil & Weinkauf

[57] ABSTRACT

Substituted 3-phenylpyrazoles I

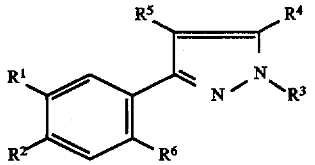

I are used as herbicides.

5 Claims, No Drawings

SUBSTITUTED 3-PHENYLPYRAZOLES

This application is a 371 of PCT/EP95/02062 filed May 31, 1995.

The present invention relates to novel substituted 3-phenylpyrazoles of the formula I

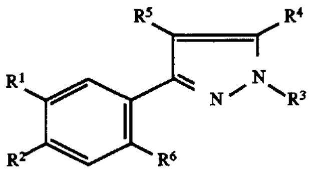

I where $R^1$ is —$C(R^8)$=$C(R^7,R^{12})$,

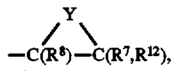

—$C(R^9, R^{10})$—$C(R^8,R^{11},R^{12})$,

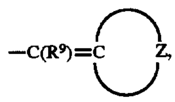

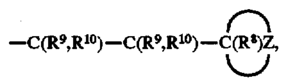

—$C(R^9)$=$C(R^8)$-phenyl or —$C(R^9,R^{10})$—$C(R^8,R^{13})$-phenyl, in which each phenyl ring may if desired carry from one to three substituents selected form the group consisting of nitro, cyano, fluorine, chlorine, bromine, trifluoromethyl, hydroxyl, hydroxycarbonyl, $C_1$–$C_4$-alkoxy and ($C_1$–$C_4$-alkoxy ) carbonyl;

$R^2$ is cyano, trifluoromethyl or halogen;

$R^3$ is hydrogen, $C_1$–$C_4$-alkyl, $C_1$–$C_4$-haloalkyl or $C_1$–$C_4$-alkoxy-$C_1$–$C_4$-alkyl;

$R^4$ is $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-halo-alkylsulfinyl, $C_1$–$C_4$-alkylsulfonyl or $C_1$–$C_4$-haloalkylsulfonyl;

$R^5$ is hydrogen, nitro, halogen, —$COOR^{15}$ or —CO—N ($R^{16}$,$R^{17}$);

$R^6$is hydrogen or halogen;

Y is oxygen, sulfur or methylene;

is a 2- to 5-membered chain of methylene units and, if desired, one or two of the following members: —O—, —S—, —CS—, —CO— or —CH($C_1$–$C_4$-alkyl)— or —$N(R^{14})$—, in which $R^{14}$ is hydrogen, $C_1$–$C_4$-alkyl, phenyl or benzyl;

$R^7$ is cyano, halogen, $C_1$–$C_4$-alkyl, $C_1$–$C_4$-haloalkyl, $C_2$–$C_4$-alkenyl, —$COOR^{18}$ or —CO—$N(R^{19},R^{20})$;

$R^8$, $R^9$, $R^{10}$ and $R^{13}$ independently of one another are hydrogen, cyano, halogen, $C_1$–$C_4$-alkyl, $C_1$–$C_4$-haloalkyl, $C_2$–$C_4$-alkenyl, —$COOR^{21}$, —CO—N ($R^{22}$, $R^{23}$), —$N(R^{22},R^{23})$ or —$N(R^{24})$—CO—$R^{25}$;

$R^{11}$ is cyano, halogen, —$COOR^{26}$, —CO—$N(R^{27},R^{28})$, —$N(R^{27},R^{28})$, azido, hydroxyl, $C_1$–$C_8$-alkoxy, $C_1$–$C_8$-haloalkoxy, $C_3$–$C_6$-alkenyloxy or ($C_1$–$C_4$-alkyl) carbonyloxy;

$R^{12}$ is isoxazolidinylcarbonyl, —$COOR^{29}$, —CO—$SR^{29}$, —CO—N ($R^{34}$) —$OR^{29}$, —CO—O—N=$C(R^{31})$—($C_1$–$C_6$-alkyl), —CO—O—N=$C(R^{31})$—($C_1$–$C_6$-alkyl), —CO—O—N=$C(R^{31})$—($C_1$–$C_4$-alkyl) —CO—O—($C_1$–$C_4$-alkyl), —CO—O—$CH_2$—$R^{14}$, —CO—O—$C(R^{14})$—($C_1$–$C_4$-alkyl), —CO—N($R^{34}$, $R^{35}$), —CS—N($R^{34}$,$R^{35}$), —CO—NH—$SO_2$—($C_1$–$C_4$-alkyl), —CO—$R^{36}$, —CO—O—($C_1$–$C_4$-alkyl)—$C(R^{14})$=N—O—($C_1$–$C_4$-alkyl), —CO—N ($R^{34}$)—C($R^{35}$,$R^{30}$)—$COOR^{29}$, cyclopentyliminooxycarbonyl or cyclohexyliminooxycarbonyl, in which the carbocycles may if desired carry from one to three $C_1$–$C_4$-alkyl radicals;

$R^{15}$, $R^{18}$, $R^{21}$, $R^{26}$ and $R^{29}$ are independently of one another hydrogen, $C_1$–$C_8$-alkyl, $C_1$–$C_8$-haloalkyl, $C_3$–$C_6$-alkenyl, $C_3$–$C_6$-haloalkenyl, cyano-$C_1$–$C_8$-alkyl, $C_3$–$C_6$-alkynyl, $C_1$–$C_4$-alkoxy-$C_1$–$C_4$-alkyl, 2-tetrahydrofuranyl-$C_1$–$C_8$-alkyl, 3-oxetanyl, 3-thietanyl, carboxy-$C_1$–$C_6$-alkyl, ($C_1$–$C_8$-alkoxy) carbonyl-$C_1$–$C_6$-alkyl, $C_1$–$C_4$-alkoxy-($C_1$–$C_4$-alkoxy) carbonyl-$C_1$–$C_6$-alkyl, cyclopropylmethyl, (1-methylthiocycloprop-1-yl)methyl, $C_3$–$C_9$-(α-alkylalkylidene)iminooxy-$C_1$–$C_6$-alkyl, ($C_1$–$C_4$-alkyl) carbonyl, $C_1$–$C_4$-alkyl which is substituted by —$C(R^{32})$=N—O—($C_1$–$C_4$-alkyl), —$C(R^{32})$=N—O—($C_1$–$C_4$-haloalkyl), —$C(R^{32})$=N—O—($C_2$–$C_6$-alkenyl), —$C(R^{32})$=N—O—($C_2$–$C_6$-haloalkenyl) or —$C(R^{32})$=N—O—($C_1$–$C_4$-alkyl)—$R^{37}$, or are $C_3$–$C_7$-cycloalkyl or $C_5$–$C_7$-cycloalkenyl each of which may if desired carry from one to three $C_1$–$C_3$-alkyl radicals, or are 5- or 6-membered saturated heterocyclyl or heterocyclyl-$C_1$–$C_6$-alkyl having in each case one oxygen, sulfur or aza ring member and, if desired, a further oxygen or sulfur ring member and/or a carbonyl or thiocarbonyl ring member, where each hydrogen atom attached to a ring member may if desired be replaced by one of the following substituents: hydroxyl, halogen, $C_1$–$C_4$-alkyl, $C_1$–$C_4$-alkoxy, ($C_1$–$C_4$-alkoxy)carbonyl, ($C_1$–$C_4$-alkyl) carbonyloxy or ($C_1$–$C_4$-haloalkyl)- carbonyloxy, or are phenyl, phenyl-$C_1$–$C_6$-alkyl, phenyl-$C_2$–$C_6$-alkenyl, phenyl-$C_2$–$C_6$-alkynyl or phenoxy-$C_1$–$C_6$-alkyl, where each phenyl ring may be unsubstituted or may carry from one to three radicals in each case selected from the group consisting of nitro, cyano, halogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy and $C_2$–$C_6$-alkenyl, or are 5- or 6-membered hetaryl, hetaryl-$C_1$–$C_6$-alkyl, hetaryl-$C_2$–$C_6$-alkenyl, hetaryl-$C_2$–$C_6$-alkynyl or (hetaryl)oxy-$C_1$–$C_6$-alkyl, in which each hetaryl radical contains from one to three heteroatoms selected from a group consisting of one or two nitrogen atoms and one oxygen or sulfur atom and may also if desired carry on each substitutable ring atom a radical selected from the group consisting of hydroxyl, halogen, $C_1$–$C_4$-alkyl, $C_1$–$C_4$-haloalkyl, $C_1$–$C_4$-alkoxy, $C_1$–$C_4$-alkylthio and $C_1$–$C_4$-haloalkoxy;

$R^{16}$, $R^{17}$, $R^{19}$, $R^{20}$, $R^{22}$, $R^{23}$, $R^{27}$, $R^{28}$, $R^{34}$ and $R^{35}$ are independently of one another hydrogen, cyano, $C_1$–$C_8$-alkyl, $C_2$–$C_8$-alkenyl, $C_2$–$C_8$-alkynyl, $C_1$–$C_8$-haloalkyl, $C_1$–$C_4$-alkoxy-$C_1$–$C_4$-alkyl, $C_1$–$C_4$-alkylthio-$C_1$–$C_4$-alkyl, cyano-$C_1$–$C_4$-alkyl, carboxy-$C_1$–$C_4$-alkyl, ($C_1$–$C_4$-alkoxy)carbonyl-$C_1$–$C_4$-alkyl, $C_1$–$C_4$-alkylsulfonyl-$C_1$–$C_4$-alkyl, $C_3$–$C_8$-cycloalkyl, $C_1$–$C_6$-alkoxy, ($C_3$–$C_6$-cyclo-alkyl)oxycarbonyl-$C_1$–$C_4$-alkyl, $C_1$–$C_4$-alkoxy-($C_1$–$C_4$-alkoxy)-carbonyl-$C_1$–$C_4$-alkyl, ($C_1$–$C_4$-alkyl)carbonyl, ($C_1$–$C_4$-haloalkyl)carbonyl, aminocarbonyl, or are phenyl or phenyl-$C_1$–$C_4$-alkyl in which the phenyl ring may in each case be unsubstituted or may carry from one to three radicals selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, or are 5- or 6-membered hetaryl or hetaryl-C–$C_4$-alkyl in which the hetaryl radical contains from one to three heteroatoms selected from a group consisting of one or two nitrogen atoms and one oxygen or sulfur atom and may also if desired carry on each substitutable ring atom a radical selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl; or $R^{16}$ and $R^{17}$ and/or $R^{19}$ and $R^{20}$ and/or $R^{22}$ and $R^{23}$ and/or $R^{27}$ and $R^{28}$ and/or $R^{34}$ and $R^{35}$ together are a propylene, tetramethylene, pentamethylene or ethyleneoxyethylene chain;

$R^{24}$ is hydrogen, $C_1$–$C_4$-alkyl, $C_3$–$C_6$-alkenyl, $C_3$–$C_6$-alkynyl, $C_1$–$C_4$-alkoxy-$C_1$–$C_4$-alkyl or the equivalent of an agriculturally usable cation;

$R^{25}$ and $R^{30}$ are hydrogen, $C_1$–$C_6$-alkyl, $C_1$–$C_6$-haloalkyl, $C_1$–$C_4$-alkoxy-$C_1$–$C_4$-alkyl, or are $C_3$–$C_7$-cycloalkyl which may if desired carry from one to three radicals selected from the group consisting of halogen, $C_1$–$C_4$-alkyl, $C_1$–$C_4$-alkoxy and $C_1$–$C_4$-alkylthio, or are phenyl or phenyl-$C_1$–$C_6$-alkyl in which the phenyl ring may in each case be unsubstituted or may carry from one to three radicals selected from the group consisting of halogen, nitro, $C_1$–$C_4$-alkyl, $C_1$–$C_4$-alkoxy, $C_1$–$C_4$-alkylthio and $C_1$–$C_4$-haloalkyl;

$R^{31}$ is $C_1$–$C_6$-alkyl, $C_1$–$C_4$-haloalkyl, $C_1$–$C_6$-alkoxy-$C_1C_4$-alkyl, ($C_1$–$C_6$-alkoxy)carbonyl-($C_1$–$C_4$-alkyl), di-[($C_1$–$C_6$-alkoxy)carbonyl]-$C_1$–$C_4$-alkyl, $C_3$–$C_6$-cycloalkyl, $C_1$–$C_6$-alkoxy, ($C_1$–$C_6$-alkoxy)carbonyl, 2-furyl or phenyl which may be unsubstituted or may in turn carry from one to three radicals selected from the group consisting of halogen, $C_1$–$C_4$-alkyl and $C_1$–$C_4$-alkoxy;

$R^{32}$ is hydrogen, $C_1$-$C_4$-alkyl, phenyl or benzyl;

$R^{36}$ is hydrogen, halogen, $C_1$–$C_4$-alkyl, $C_2$–$C_4$-alkenyl, $C_1$–$C_4$-halo-alkyl, $C_1$–$C_4$-alkoxy-$C_1$–$C_4$-alkyl or $C_1$–$C_4$-alkylthio-$C_1$–$C_4$-alkyl;

$R^{37}$ is phenyl or 5- or 6-membered hetaryl having from one to three heteroatoms selected from a group consisting of one or two nitrogen atoms and one oxygen or sulfur atom, where the phenyl ring and the hetaryl rings may if desired carry at each substitutable carbon atom one of the following substituents: nitro, cyano, hydroxy, halogen, $C_1$–$C_4$-alkyl, $C_1$–$C_4$-alkoxy, $C_1$–$C_4$-alkylthio or $C_1$–$C_4$-haloalkyl.

The invention also relates to the use of these compounds as herbicides, to herbicidal compositions comprising the compounds I as active substances, to processes for producing these herbicidal compositions and to methods of combating unwanted plant growth with the compounds I.

JP 03 151 367 describes herbicidally active 1-(1-alkyl-4-halo-5-haloalkoxy-1H-pyrazol-3-yl)-4,6-dihalophenyl derivates having various substituents in position 3 of the phenyl ring, especially compounds having the following substitution pattern IIa:

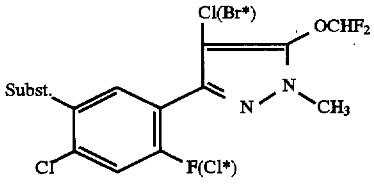
IIa

*)one compound in each case

Furthermore, EP-A 443 059 teaches that 1-alkyl- and 1-haloalkyl-3(4-chloro-6-halophenyl)pyrazoles and -4-halopyrazoles which carry specific substituents in position 3 of the phenyl ring and are substituted in position 5 of the pyrazole ring by hydroxyl, mercapto, lower alkoxy, alkylthio, haloalkoxy or haloalkylthio are suitable for controlling unwanted plants.

Furthermore, JP-A 03/072 460 discloses the fact that 3-substituted phenylpyrazoles of the formula IIb

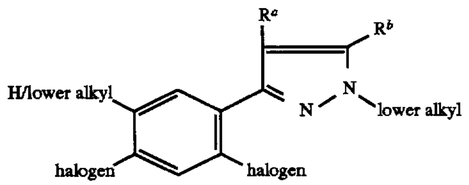
IIb in which $R^a$ is hydrogen, halogen or cyano and $R^b$ is lower alkoxy, haloalkoxy, alkylthio, haloalkylthio, alkylsulfinyl, haloalkylsulfinyl, alkylsulfonyl or haloalkylsulfonyl are herbicidally active. EP-A 447 055 discloses that 1-(lower alkyl)-3-(4-chloro-6-halophenyl)-4-halo-5-difluoromethoxypyrazoles which carry in position of the phenyl ring an alkylthiocarbonyl-, alkenylthiocarbonyl- or benzylthiocarbonyl-methoxycarbonyl group display herbicidal activity.

In JP-A 03/047 180 and JP-A 03/081 275 it is disclosed that, inter alia, pyrazole derivatives of the formulae IIc and IId

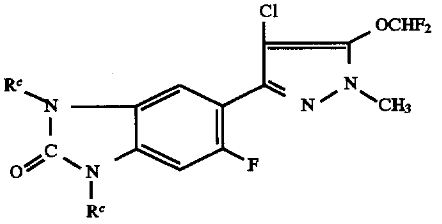
IIc

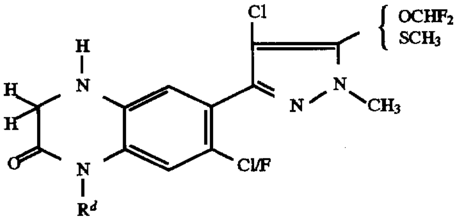
IId in which $R^c$ is hydrogen, methyl or allyl and $R^d$ is hydrogen, ethyl, allyl or propargyl are suitable as herbicides.

According to JP-A 02/300 173 and JP-A 03/093 774, certain 1-alkyl-3-phenylpyrazoles which may carry on the phenyl ring from one to four halogen atoms likewise display herbicidal activity. Those mentioned in particular are 1-methyl-3-(2,4-dichlorophenyl)pyrazoles and three 1-methyl-5-chloro-3-(2-fluoro-4-chlorophenyl)-pyrazoles.

Finally, WO 92/06962 describes herbicidal 4-halo-5-haloalkyl-3-phenylpyrazoles having various substituents on the phenyl ring.

However, the herbicidal properties of the known herbicides with respect to harmful plants give only limited satisfaction.

It is an object of the present invention to provide novel herbicidally active compounds which can be used to give targeted control of unwanted plants which represents an improvement on the prior art.

We have found that this object is achieved by the substituted 3-phenylpyrazoles of the formula I. We have also found herbicidal compositions which comprise the compounds I and possess a very good herbicidal action. We have additionally found processes for producing these compositions and methods of combating unwanted plant growth with the compounds I.

With regard to the use of the substituted 3-phenylpyrazoles I as herbicides, preference is given to compounds I in which the variables are as defined below, in each case individually or in combination:

$R^1$ is $—C(R^8)=C(R^7,R^{12})$,

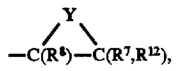

$—C(R^9,R^{10})—C(R^8,R^{11}\ R^{12})$,

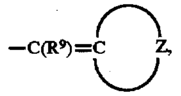

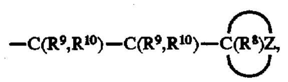

or is $—C(R^9)=C(R^8)$-phenyl in which the phenyl ring may if desired carry from one to three substituents selected from the group consisting of nitro, cyano, fluorine, chlorine, bromine, trifluoromethyl, hydroxyl, hydroxycarbonyl, $C_1$–$C_4$-alkoxy and $C_1$–$C_4$-alkoxycarbonyl;

particularly preferably $—C(R^8)=C(R^7,R^{12})$ or $—C(R^9,R^{10})—C(R^8,R^{11},R^{12})$;

$R^2$ is trifluoromethyl, halogen or cyano; particularly preferably halogen or cyano;

$R^3$ is $C_1$–$C_4$-alkyl or $C_1$–$C_4$-haloalkyl; particularly preferably $C_1$–$C_4$-alkyl;

$R^4$ is $C_1$–$C_4$-alkoxy, $C_1$–$C_4$-haloalkoxy, $C_1$–$C_4$-alkylthio or $C_1$–$C_4$-haloalkylthio; particularly preferably $C_1$–$C_4$-haloalkoxy or $C_1$–$C_4$-haloalkylthio;

$R^5$ is nitro, halogen, $—COOR^{15}$ or $—CO—N(R^{16},R^{17})$; particularly preferably halogen or cyano;

$R^6$ is hydrogen or halogen;

is a 2- to 5-membered chain of methylene units and, if desired, one or two of the following members: —O—, —S—, $—N(R^{33})—$, —CS—, —CO— or $—CH(C_1–C_4\text{-alkyl})—N(R^{14})—$, in which $R^{14}$ is hydrogen, $C_1$–$C_4$-alkyl, phenyl or benzyl; particularly preferably a 4- to 5-membered chain of methylene units and, if desired, one or two of the following members: —O—, —CO— or $—CH(C_1–C_4\text{-alkyl})—$ or $—N(R^{14})—$, in which $R^{14}$ is hydrogen or $C_1$–$C_4$-alkyl;

$R^7$ is cyano, halogen, $C_1$–$C_4$-alkyl, $C_1$–$C_4$-haloalkyl, $C_2$–$C_4$-alkenyl, $—COOR^{18}$ or $—CO—N(R^{19},R^{20})$; particularly preferably cyano, halogen, $C_1$–$C_4$-alkyl, $C_1$–$C_4$-haloalkyl, $—COOR^{18}$ or $—CO—N(R^{19},R^{20})$;

$R^8$, $R^9$, $R^{10}$, $R^{13}$ are independently of one another hydrogen, cyano, halogen, $C_1$–$C_4$-alkyl, $C_1$–$C_4$-haloalkyl, $—COOR^{21}$, stop $—CO—N(R^{22},R^{23})$, $—N(R^{22},R^{23})$ or $—N(R^{24})—CO—R^{25}$; particularly preferably hydrogen;

$R^{11}$ is cyano, halogen, $—COOR^{26}$, $—CO—N(R^{27},R^{28})$, $—N(R^{27},R^{28})$, hydroxyl, $C_1$–$C_8$-alkoxy, $C_1$–$C_8$-haloalkoxy, $C_3$–$C_6$-alkenyloxy or $(C_1$–$C_4$-alkyl)carbonyloxy;

$R^{12}$ is isoxazolidinylcarbonyl, $—COOR^{29}$, $—CO—SR^{29}$, $—CO—N(R^{34})—OR^{29}$, $—CO—O—N=C(R^{31})—(C_1–C_6\text{-alkyl})$, $—CO—O—N=C(R^{31})—CO—O—(C_1–C_6\text{-alkyl})$, $—CO—O—N=C(R^{31})—(C_1–C_4\text{-alkyl})—CO—O—(C_1–C_4\text{-alkyl})$, $—O—CH_2—R^{14}$, $—CO—O—C(R^{14})—(C_1–C_4\text{-alkyl})$, $—CO—N(R^{34},R^{35})$, $—CS—N(R^{34},R^{35})$, $—CO—NH—SO_2—(C_1–C_4\text{-alkyl})$, $—CO—R^{36}$, $—CO—O—(C_1–C_4\text{-alkyl})—C(R^{33})=N—O—(C_1–C_4\text{-alkyl})$, $—CO—N(R^{34})—C(R^{35},R^{30})—COOR^{29}$, cyclopentyliminooxycarbonyl or cyclohexyliminooxycarbonyl, in which the carbocycles may if desired carry one to three $C_1$–$C_4$-alkyl radicals; particularly preferably $—COOR^{29}$, $—CO—O—C(R^{14})—(C_1–C_4\text{-alkyl})$, $—CO—N(R^{34},R^{35})$ or $—CO—N(R^{34})—C(R^{35},R^{30})—COOR^{29}$;

$R^{15}$, $R^{18}$, $R^{21}$, $R^{26}$ are independently of one another $C_1$–$C_4$-alkyl, $C_1$–$C_4$-haloalkyl or $C_2$–$C_4$-alkenyl; particularly preferably $C_1$–$C_4$-alkyl;

$R^{16}$, $R^{17}$, $R^{19}$, $R^{20}$, $R^{22}$, $R^{23}$, $R^{27}$, $R^{28}$ are independently of one another hydrogen, cyano, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy-$C_1$–$C_4$-alkyl, $(C_1$–$C_4$-alkoxy)carbonyl-$C_1$–$C_4$-alkyl, $C_1$–$C_4$-alkylsulfonyl-$C_1$–$C_4$-alkyl, $C_3$–$C_8$-cycloalkyl, $(C_1$–$C_4$-alkyl)carbonyl, aminocarbonyl, phenyl or phenyl-$C_1$–$C_4$-alkyl, in which the phenyl ring may in each case be unsubstituted or may carry from one to three radicals selected from the group consisting of halogen, nitro, cyano, $C_1$–$C_4$-alkyl, $C_1$–$C_4$-alkoxy and $C_1$–$C_4$-haloalkyl; and are particularly preferably hydrogen, $C_1$–$C_4$-alkyl or $(C_1$–$C_4$-alkyl)carbonyl;

$R^{29}$ is hydrogen, $C_1$–$C_8$-alkyl, $C_1$–$C_8$-haloalkyl, $C_3$–$C_6$-alkenyl, $C_3$–$C_6$-haloalkenyl, $C_2$–$C_8$-cyanoalkyl, $C_3$–$C_6$-alkynyl, $C_2$–$C_8$-alkoxyalkyl, 2-tetrahydrofuranyl-$C_1$–$C_8$-alkyl, 3-oxetanyl, 3-thietanyl, carboxy-$C_1$–$C_6$-alkyl, $(C_1$–$C_8$-alkoxy)carbonyl-$C_1$–$C_6$-alkyl, $C_1$–$C_4$-alkoxy-$(C_1$–$C_4$-alkoxy)carbonyl-$C_1$–$C_6$-alkyl, cyclopropylmethyl, (1-methylthiocycloprop-1-yl)methyl, $C_3$–$C_9$-(α-alkylalkylidene)iminooxy-$C_1$–$C_6$-alkyl, $C_1$–$C_4$-alkyl which is substituted by $—C(R^{32})=N—O—(C_1–C_4\text{-alkyl})$, $—C(R^{32})=N—O—(C_1–C_4\text{-haloalkyl})$, $—C(R^{32})=N—O—(C_2–C_6\text{-alkenyl})$, $—C(R^{32})=N—O—(C_3–C_6\text{-haloalkenyl})$ or $—C(R^{32})=N—O—(C_1–C_4\text{-alkyl})\text{-}R^{37}$, or is $C_3$–$C_7$-cycloalkyl or $C_5$–$C_7$-cycloalkenyl, each of which may if desired carry from one to three $C_1$–$C_3$-alkyl radicals, or is phenyl, phenyl-$C_1$–$C_6$-alkyl, phenyl-$C_2$–$C_6$-alkenyl, phenyl-$C_2$–$C_6$-alkynyl or phenoxy-$C_1$–$C_6$-alkyl, in which the phenyl ring may in each case be unsubstituted or may carry from one to three radicals selected from the group consisting of nitro, cyano, halogen, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy and $C_2$–$C_6$-alkenyl, or is 5- or 6-membered hetaryl, hetaryl-$C_1$–$C_6$-alkyl, hetaryl-$C_2$–$C_6$-alkenyl, hetaryl-$C_2$–$C_6$-alkynyl or hetaryl-oxy-$C_1$–$C_6$-alkyl, in which the hetaryl radical contains in each case from one to three heteroatoms selected from a group consisting of one or two nitrogen atoms and one oxygen or sulfur atom and may also if desired carry on each substitutable ring atom a radical selected from the group consisting of hydroxyl, halogen, $C_1$–$C_4$-alkyl, $C_1$–$C_4$-haloalkyl, $C_1$–$C_4$-alkoxy, $C_1$–$C_4$-alkylthio and $C_1$–$C_4$-haloalkoxy;

particularly preferred radicals $R^{29}$ are $C_1$–$C_4$-alkyl, $C_1$–$C_4$-haloalkyl, $C_3$–$C_6$-alkenyl, cyano-$C_1$–$C_4$-alkyl, $C_3$–$C_6$-alkynyl, $C_1$–$C_4$-alkoxy-$C_1$–$C_4$-alkyl and ($C_1$–$C_4$-alkoxy)carbonyl-$C_1$–$C_6$-alkyl;

$R^{34}$ and-$R^{35}$ are independently of one another hydrogen, cyano, $C_1$–$C_4$-alkyl, $C_2$–$C_6$-alkenyl, $C_3$–$C_6$-alkynyl, $C_1$–$C_4$-haloalkyl, $C_1$–$C_4$-alkoxy-$C_1$–$C_4$-alkyl, $C_1$–$C_4$-alkylthio-$C_1$–$C_4$-alkyl, cyano-$C_1$–$C_4$-alkyl, carboxy-$C_1$–$C_4$-alkyl, ($C_1$–$C_4$-alkoxy) carbonyl-$C_1$–$C_4$-alkyl, $C_1$–$C_4$-alkylsulfonyl-$C_1$–$C_4$-alkyl, $C_3$–$C_6$-cycloalkyl, $C_1$–$C_4$-alkoxy, ($C_3$–$C_6$-cycloalkoxy)carbonyl-$C_1$–$C_4$-alkyl, $C_1$–$C_4$-alkoxy ($C_1$–$C_4$-alkoxy)carbonyl-$C_1$–$C_4$-alkyl, ($C_1$–$C_4$-alkyl)carbonyl, ($C_1$–$C_4$-haloalkyl)carbonyl, aminocarbonyl, phenyl or phenyl-$C_1$–$C_4$-alkyl, in which the phenyl ring may in each case be unsubstituted or may carry from one to three radicals selected from the group consisting of halogen, nitro, cyano, $C_1$–$C_4$-alkyl, $C_1$–$C_4$-alkoxy and $C_1$–$C_4$-haloalkyl;

or $R^{34}$ and $R^{35}$ together are a propylene, tetramethylene, pentamethylene or ethyleneoxyethylene chain;

particularly preferred radicals $R^{34}$ and $R^{35}$ are hydrogen, cyano, $C_1$–$C_4$-alkyl, $C_2$–$C_4$-alkenyl, $C_3$–$C_6$-alkynyl, $C_1$–$C_4$-alkoxy-$C_1$–$C_4$-alkyl, ($C_1$–$C_4$-alkoxy)carbonyl-$C_1$–$C_4$-alkyl, $C_1$–$C_4$-alkylsulfonyl-$C_1$–$C_4$-alkyl, cyclopropyl, ($C_1$–$C_4$-alkyl)carbonyl or phenyl-$C_1$–$C_4$-alkyl, in which the phenyl ring may be unsubstituted or may carry from one to three radicals selected from the group consisting of halogen, nitro, cyano, $C_1$–$C_4$-alkyl, $C_1$–$C_4$-alkoxy, $C_1$–$C_4$-haloalkyl and $C_2$–$C_6$-alkenyl, or $R^{34}$ and $R^{35}$ together are a propylene or tetramethylene chain;

$R^{24}$ is hydrogen, $C_1$–$C_4$-alkyl, $C_3$–$C_6$-alkenyl, $C_1$–$C_4$-alkoxy-$C_1$–$C_4$-alkyl or the equivalent of an agriculturally usable cation; particularly preferably hydrogen, $C_1$–$C_4$-alkyl or the equivalent of an agriculturally usable cation;

$R^{25}$ and $R^{30}$ are independently of one another hydrogen, $C_1$–$C_4$-alkyl, $C_1$–$C_4$-haloalkyl, $C_1$–$C_4$-alkoxy-$C_1$–$C_4$-alkyl or $C_3$–$C_7$-cycloalkyl which may if desired carry one or two radicals selected from the group consisting of halogen, $C_1$–$C_4$-alkyl, $C_1$–$C_4$-alkoxy and $C_1$–$C_4$-alkylthio; and are particularly preferably hydrogen or $C_1$–$C_4$-alkyl;

$R^{31}$ is $C_1$–$C_6$-alkyl, $C_1$–$C_4$-haloalkyl, $C_1$–$C_4$-alkoxy-$C_1$–$C_4$-alkyl, ($C_1$–$C_4$-alkoxy)carbonyl-($C_1$–$C_4$-alkyl), di-[($C_1$–$C_4$-alkoxy)carbonyl]-$C_1$–$C_4$-alkyl, $C_3$–$C_6$-cycloalkyl, $C_1$–$C_4$-alkoxy, ($C_1$–$C_4$-alkoxy)carbonyl, 2-furyl or phenyl which may be unsubstituted or may in turn carry from one to three radicals selected from the group consisting of halogen, $C_1$–$C_4$-alkyl and $C_1$–$C_4$-alkoxy; and is preferably $C_1$–$C_4$-alkyl;

$R^{32}$ hydrogen or $C_1$–$C_4$-alkyl;

$R^{36}$ is hydrogen, halogen, $C_1$–$C_4$-alkyl, $C_2$–$C_4$-alkenyl, $C_1$–$C_4$-haloalkyl, $C_1$–$C_4$-alkoxy-$C_1$–$C_4$-alkyl or $C_1$–$C_4$-alkylthio-$C_1$–$C_4$-alkyl; particularly preferably $C_1$–$C_4$-alkyl or $C_1$–$C_4$-haloalkyl, and $R^{37}$ is phenyl or 5- or 6-membered hetaryl having from one to three heteroatoms selected from a group consisting of one or two nitrogen atoms and one oxygen or sulfur atom, where the phenyl ring and the hetaryl rings may if desired carry on each substitutable carbon atom one of the following substituents: nitro, cyano, hydroxyl, halogen, $C_1$–$C_4$-alkyl, $C_1$–$C_4$-alkoxy, $C_1$–$C_4$-alkylthio or $C_1$–$C_4$-haloalkyl.

The organic moieties indicated for substituents $R^1$ to $R^{37}$ or as radicals on (hetero)aromatic structures, and also the definition halogen (halo), represent collective designations for individual members of the groups. All carbon chains, ie. all alkyl, alkylcarbonyl, alkenyl, alkynyl, haloalkyl, haloalkylcarbonyl, haloalkenyl, haloalkynyl, cyanoalkyl, phenylalkyl, carboxyalkyl, alkoxy, alkylthio, alkylcarbonyl, alkoxycarbonyl and alkylsulfonyl moieties and the α-alkylalkylidene moiety may be straight-chain or branched. Halogenated substituents preferably carry from 1 to 5 identical or different halogen atoms.

Specific examples are:

for halogen: fluorine, chlorine, bromine and iodine, preferably fluorine and chlorine;

for $C_1$–$C_4$-alkyl and the alkyl moieties of —CO—O—N=C($R^{31}$)—($C_1$–$C_4$-alkyl)—CO—O—($C_1$–$C_4$-alkyl), —CO—O—C($R^{14}$)—($C_1$–$C_4$-alkyl), —CO—NH—$SO_2$—($C_1$–$C_4$-alkyl), —CO—O—($C_1$–$C_4$-alkyl) —C($R^{14}$)=N—O—($C_1$–$C_4$-alkyl), $C_1$–$C_6$-alkoxy-$C_1$–$C_4$-alkyl, di-[($C_1$–$C_6$-alkoxy)carbonyl]-$C_1$–$C_4$-alkyl, $C_1$–$C_4$-alkoxy-$C_1$–$C_4$-alkyl, $C_1$–$C_4$-alkylthio-$C_1$–$C_4$-alkyl, ($C_1$–$C_6$-alkoxy)carbonyl-$C_1$–$C_4$-alkyl, ($C_1$–$C_4$-alkoxy)carbonyl-$C_1$–$C_4$-alkyl, di-[($C_1$–$C_6$-alkoxy)carbonyl]-$C_1$–$C_4$-alkyl, $C_1$–$C_4$-alkylsulfonyl-$C_1$–$C_4$-alkyl, ($C_3$–$C_6$-cycloalkyl)oxycarbonyl-$C_1$–$C_4$-alkyl ($C_1$–$C_4$-alkyl)carbonyloxy and $C_1$–$C_4$-alkoxy-($C_1$–$C_4$-alkoxy)carbonyl-$C_1$–$C_4$-alkyl: methyl, ethyl, n-propyl, 1-methylethyl, n-butyl, 1-methylpropyl, 2-methylpropyl and 1,1-dimethylethyl, preferably methyl and ethyl; for $C_1$–$C_6$-alkyl and the $C_1$–$C_6$-alkyl moieties of —CO—O—N=C($R^{31}$)—($C_1$–$C_6$-alkyl), —CO—O—N=C($R^{31}$)—CO—O—($C_1$–$C_6$-alkyl), carboxy-$C_1$–$C_6$-alkyl, ($C_1$–$C_8$-alkoxy)carbonyl-$C_1$–$C_6$-alkyl, $C_1$–$C_4$-alkoxy-($C_1$–$C_4$-alkoxy)carbonyl-$C_1$–$C_6$-alkyl, $C_3$–$C_9$-(α-alkyl-alkylidene)iminooxy-$C_1$–$C_6$-alkyl, phenoxy-$C_1$–$C_6$-alkyl and (hetaryl)oxy-$C_1$–$C_6$-alkyl: methyl, ethyl, n-propyl, 1-methylethyl, n-butyl, 1-methylpropyl, 2-methylpropyl, 1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_1$–$C_4$-alkyl as above, especially methyl and ethyl;

for $C_1$–$C_8$-alkyl and the alkyl moieties of 2-tetrahydrofuranyl-$C_1$–$C_8$-alkyl and cyano-$C_1$–$C_8$-alkyl: $C_1$–$C_6$-alkyl as above and, for example, n-heptyl, n-octyl, preferably $C_1$–$C_6$-alkyl, especially $C_1$–$C_4$-alkyl as above;

for $C_2$–$C_4$-alkenyl: ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl and 2-methylprop-2-en-1-yl, preferably ethenyl and allyl;

for $C_2$–$C_6$-alkenyl and the alkenyl moieties of phenyl-$C_2$–$C_6$-alkenyl and hetaryl-$C_2$–$C_6$-alkenyl: ethenyl, prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl, 2-methyl-prop-2-en-1-yl, n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop- 1-en-1-yl, 1,2-dimethyl-prop-2-en-1-yl, 1-ethyl-prop-1-en-2-yl, 1-ethyl-prop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methyl-pent-1-en-1-yl, 3-methyl-pent-1-en-1-yl, 4-methyl-pent-1-en-1-yl, 1-methyl-pent-2-en-1-yl, 2-methyl-pent-2-en-1-yl, 3-methyl-pent-2-en-1-yl, 4-methyl-pent-2-en-1-yl, 1-methyl-pent-3-en-1-yl, 2-methyl-pent-3-en-1-yl, 3-methyl-pent-3-en-1-yl, 4-methyl-pent-3-en-1-yl, 1-methyl-pent-4-en-t-yl, 2-methyl-pent-4-en-1-yl, 3-methyl-pent-4-en-1-yl, 4-methyl-pent-4-en-1-yl, 1,1-dimethyl-but-2-en-1-yl, 1,1-dimethyl-but-3-en-1-yl, 1,2-dimethyl-but-1-en-1-yl, 1,2-dimethyl-but-2-en-1-yl, 1,2-dimethyl-but-3-en-1-yl, 1,3-dimethyl-but-1-en-1-yl, 1,3-dimethyl-but-2-en-1-yl, 1,3-dimethyl-but-3-en-1-yl, 2,2-dimethyl-but-3-en-1-yl, 2,3-dimethyl-but-1-en-1-yl, 2,3-dimethyl-but-2-en-1-yl, 2,3-dimethyl-but-3-en-1-yl, 3,3-dimethyl-but-1-en-1-yl, 3,3-dimethyl-but-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethyl-prop-2-en-1-yl, 1-ethyl-1-methyl-prop-2-en-1-yl, 1-ethyl-2-methyl-prop-1-en-1-yl and 1-ethyl-2-methyl-prop-2-en-1-yl, preferably $C_2$–$C_4$-alkenyl as above;

for $C_2$–$C_8$-alkenyl: $C_2$–$C_6$-alkenyl as above and, for example, n-hept-2-en-1-yl, n-oct-2-en-1-yl, preferably $C_2$–$C_6$-alkenyl; for $C_3$–$C_6$-alkenyl: prop-1-en-1-yl, prop-2-en-1-yl, 1-methyl-ethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl, 2-methyl-prop-2-en-1-yl, n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl-prop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methyl-pent-1-en-1-yl, 3-methyl-pent-1-en-1-yl, 4-methyl-pent-1-en-1-yl, 1-methyl-pent-2-en-1-yl, 2-methyl-pent-2-en-1-yl, 3-methyl-pent-2-en-1-yl, 4-methyl-pent-2-en-1-yl, 1-methyl-pent-3-en-1-yl, 2-methyl-pent-3-en-1-yl, 3-methyl-pent-3-en-1-yl, 4-methyl-pent- 3-en-1-yl, 1-methyl-pent-4-en-1-yl, 2-methyl-pent-4-en-1-yl, 3-methyl-pent-4-en-1-yl, 4-methyl-pent-4-en-1-yl, 1,1-dimethyl-but-2-en-1-yl, 1,1-dimethyl-but-3-en-1-yl, 1,2-dimethyl-but-1-en-1-yl, 1-2-dimethyl-but-2-en-1-yl, 1,2-dimethyl-but-3-en-1-yl, 1,3-dimethyl-but-1-en-1-yl, 1,3-dimethyl-but-2-en-1-yl, 1,3-dimethyl-but-3-en-1-yl, 2,2-dimethyl-but-3-en-1-yl, 2,3-dimethyl-but-1-en-1-yl, 2,3-dimethyl-but-2-en-1-yl, 2,3-dimethyl-but-3-en-1-yl, 3,3-dimethyl-but-1-en-1-yl, 3,3-dimethyl--but-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethyl-prop-2-en-1-yl, 1-ethyl-1-methyl-prop-2-en-1-yl, 1-ethyl-2-methyl-prop-1-en-1-yl and 1-ethyl-2-methyl-prop-2-en-1-yl, preferably $C_3$- or $C_4$-alkenyl;

for $C_2$–$C_6$-alkynyl and the alkynyl moieties of phenyl-$C_2$–$C_6$-alkynyl and hetaryl-$C_2$–$C_6$-alkynyl: ethynyl, prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-1-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl, 4-methyl-pent-2-yn-5-yl, preferably $C_2$–$C_4$-alkynyl such as ethynyl, prop-1-yn-1-yl, prop-2-yn-3-yl, n-but-1-yn-1-yl, n-but-1-yn-4-yl and n-but-2-yn-1-yl;

for $C_2$–$C_8$-alkynyl: $C_2$–$C_6$-alkynyl as above and, for example, n-hept-2-yn-1-yl, n-oct-3-yn-1-yl, preferably $C_2$–$C_6$-alkynyl as specified above individually and as preferred;

for $C_3$–$C_6$-alkynyl: prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-1-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl and 4-methyl-pent-2-yn-5-yl, preferably $C_3$-or $C_4$-alkynyl, especially ethynyl and prop-2-yn-3-yl;

for $C_1$–$C_4$-haloalkyl: $C_1$–$C_4$-alkyl as above which is partially or completely substituted by fluorine, chlorine and/or bromine, ie. eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloropropyl, heptafluoropropyl, preferably trifluoromethyl and 1,2-dichloroethyl;

for $C_1$–$C_6$-haloalkyl: $C_1$–$C_6$-alkyl as above which is partially or completely substituted by fluorine, chlorine and/or bromine, ie. eg. $C_1$–$C_4$-haloalkyl as above, preferably $C_1$–$C_4$-haloalkyl as specified above individually and as preferred;

for $C_1$–$C_8$-haloalkyl: $C_1$–$C_8$-alkyl as above which is partially or completely substituted by fluorine, chlorine and/or bromine, ie. eg. for $C_1$–$C_4$-haloalkyl as above and for 7-chloro-hept-1-yl, preferably for $C_1$–$C_6$-haloalkyl as above, especially for $C_1$–$C_4$-haloalkyl as above;

for $C_3$–$C_6$-haloalkenyl: $C_3$–$C_6$-alkenyl as above which is partially or completely substituted by fluorine, chlorine and/or bromine, ie. eg. 2-chloroallyl, 3-chloroallyl, 3,3-dichloroallyl, preferably $C_3$- or $C_4$-haloalkenyl; for cyano-$C_1$–$C_8$-alkyl: cyano-$C_1$–$C_4$-alkyl such as cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methyl-prop-3-yl, 2-cyano-2-methyl-prop-3-yl, 3-cyano-2-methyl-prop-3-yl and 2-cyanomethyl-prop-2-yl, preferably cyano-$C_1$–$C_4$-alkyl, especially 2-cyanoeth-1-yl;

for phenyl-$C_1$–$C_4$-alkyl: benzyl, 1-phenyleth-1-yl, 2-phenyleth-1-yl, 1-phenylprop-1-yl, 2-phenylprop-1-yl, 3-phenylprop-1-yl, 1-phenylprop-2-yl, 2-phenylprop-2-yl, 1-phenylbut-1-yl, 2-phenylbut-1-yl, 3-phenylbut-1-yl, 4-phenylbut-1-yl, 1-phenylbut-2-yl, 2-phenylbut-2-yl, 1-phenylbut-3-yl, 2-phenylbut-3-yl, 1-phenyl-2-methyl-prop-3-yl, 2-phenyl-2-methyl-prop-3-yl, 3-phenyl-2-methyl-prop-3-yl and 2-benzyl-prop-2-yl;

for phenyl-$C_1$–$C_6$-alkyl: phenyl-$C_1$–$C_4$-alkyl as above and, for example, 2-phenyl-hex-6-yl, preferably phenyl-$C_1$–$C_4$-alkyl as above;

for hetaryl-$C_1$–$C_6$-alkyl: hetaryl-$C_1$–$C_4$-alkyl such as hetarylmethyl, 1-(hetaryl)eth-1-yl, 2-(hetaryl)eth-1-yl, 1-(hetaryl)prop-1-yl, 2-(hetaryl)prop-1-yl, 3-(hetaryl)-prop-1-yl, 1-(hetaryl)prop-2-yl, 2-(hetaryl)prop-2-yl, 1-(hetaryl)but-1-yl, 2-(hetaryl)but-1-yl, 3-(hetaryl)-but-1-yl, 4-(hetaryl)but-1-yl, 1-(hetaryl)but-2-yl, 2-(hetaryl)but-2-yl, 1-(hetaryl)but-3-yl, 2-(hetaryl)-but-3-yl, 1-(hetaryl)-2-methyl-prop-3-yl, 2-(hetaryl)-2-methyl-prop-3-yl, 3-(hetaryl)-2-methyl-prop-3-yl and 2-(hetarylmethyl)-prop-2-yl, preferably hetaryl-$C_1$–$C_4$-alkyl;

for carboxy-$C_1$–$C_4$-alkyl: carboxymethyl, 1-carboxyethyl, 2-carboxyethyl, 1-carboxyprop-1-yl, 2-carboxyprop-1-yl, 3-carboxyprop-1-yl, 1-carboxybut-1-yl, 2-carboxybut-1-yl, 3-carboxybut-1-yl, 4-carboxybut-1-yl, 1-carboxybut-2-yl, 2-carboxybut-2-yl, 3-carboxybut-2-yl, 3-carboxybut-2-yl, 4-carboxybut-2-yl, 1-(carboxymethyl)-eth-1-yl, 1-(carboxymethyl)-1-(methyl)-eth-1-yl and 1-(carboxymethyl)-prop-1-yl, preferably carboxymethyl and carboxyethyl;

for carboxy-$C_1$–$C_6$-alkyl: carboxy-$C_1$–$C_4$-alkyl as above and, for example, 5-carboxypent-1-yl, preferably carboxy-$C_1$–$C_4$-alkyl;

for $C_1$–$C_4$-alkoxy and the alkoxy moieties of $C_1$–$C_4$-alkoxy-$C_1$–$C_4$-alkyl, ($C_1$–$C_4$-alkoxy)carbonyl-$C_1$–$C_4$-alkyl, $C_1$–$C_4$-alkoxy-($C_1$–$C_4$-alkoxy)carbonyl-$C_1$–$C_6$-alkyl, $C_1$–$C_4$-alkoxy-($C_1$–$C_4$-alkoxy)carbonyl-$C_1$–$C_4$-alkyl and $C_1$–$C_4$-alkoxy-$C_1$–$C_4$-alkoxy: methoxy, ethoxy, n-propoxy, 1-methylethoxy, n-butoxy, 1-methylpropoxy, 2-methylpropoxy and 1,1-dimethylethoxy, preferably methoxy, ethoxy and 1-methylethoxy;

for the alkoxy moiety $C_1$–$C_6$-alkoxy-$C_1$–$C_4$-alkyl: $C_1$–$C_4$-alkoxy as above and n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably $C_1$–$C_4$-alkoxy, especially methoxy, ethoxy and 1-methylethoxy;

for $C_1$–$C_4$-alkylthio and the alkylthio moiety of $C_1$–$C_4$-alkyl-thio-$C_1$–$C_4$-alkyl: methylthio, ethylthio, n-propylthio, 1-methylethylthio, n-butylthio, 1-methylpropylthio, 2-methyl-propylthio and 1,1-dimethylethylthio, preferably methylthio, ethylthio and 1-methylethylthio;

for $C_1$–$C_6$-alkylthio: $C_1$–$C_4$-alkylthio as above and n-pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, n-hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, preferably methylthio, ethylthio and 1-methylethylthio;

for ($C_1$–$C_4$-alkyl)carbonyl: methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl;

for ($C_1$–$C_4$-haloalkyl)carbonyl: ($C_1$–$C_4$-alkyl)carbonyl as above which is partially or completely substituted by fluorine, chlorine and/or bromine, ie. eg. chloromethylcarbonyl, dichloromethylcarbonyl, trichloromethylcarbonyl, fluoromethylcarbonyl, difluoromethylcarbonyl, trifluoromethylcarbonyl, chlorofluoromethylcarbonyl, dichlorofluoromethylcarbonyl, chlorodifluoromethylcarbonyl, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 3-chloropropylcarbonyl and heptafluoropropylcarbonyl; for ($C_1$–$C_4$-alkoxy) carbonyl and the alkoxycarbonyl moieties of ($C_1$–$C_4$-alkoxy)carbonyl-$C_1$–$C_4$-alkyl, $C_1$–$C_4$-alkoxy-($C_1$–$C_4$-alkoxy)carbonyl-$C_1$–$C_6$-alkyl and $C_1$–$C_4$-alkoxy-($C_1$–$C_4$-alkoxy)carbonyl-$C_1$–$C_4$-alkyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, preferably methoxycarbonyl, ethoxycarbonyl and 1-methylethoxycarbonyl;

for ($C_1$–$C_6$-alkoxy)carbonyl and the alkoxycarbonyl moieties of ($C_1$–$C_6$-alkoxy)carbonyl-$C_1$–$C_4$-alkyl and di-[($C_1$–$C_6$-alkoxy)-carbonyl]-$C_1$–$C_4$-alkyl: ($C_1$–$C_4$-alkoxy)carbonyl as above and n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl and 1-ethyl-2-methylpropoxycarbonyl, preferably ($C_1$–$C_4$-alkoxy) carbonyl, especially methoxycarbonyl, ethoxycarbonyl and 1-methylethoxycarbonyl;

for the alkoxycarbonyl moiety of ($C_1$–$C_8$-alkoxy) carbonyl-$C_1$–$C_6$-alkyl: ($C_1$–$C_6$-alkoxy)carbonyl as above and, for example, n-heptoxycarbonyl, n-octoxycarbonyl, preferably ($C_1$–$C_6$-alkoxy)carbonyl, especially ($C_1$–$C_4$-alkoxy)carbonyl;

for $C_1$–$C_4$-alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, preferably methylsulfinyl and ethylsulfinyl;

for $C_1$–$C_4$-haloalkylsulfinyl: $C_1$–$C_4$-alkylsulfinyl as above which is partially or completely substituted by fluorine, chlorine and/or bromine, ie. eg. chloromethylsulfinyl, dichloromethylsulfinyl, trichloromethylsulfinyl, fluoromethylsulfinyl, difluoromethylsulfinyl, trifluoromethylsulfinyl, chlorofluoromethylsulfinyl, dichlorofluoromethylsulfinyl, chlorodifluoromethylsulfinyl, 1-fluoroethylsulfinyl, 2-fluoroethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, pentafluoroethylsulfinyl, 3-chloropropylsulfinyl and heptafluoropropylsulfinyl, preferably trifluoromethylsulfinyl;

for $C_1$–$C_4$-alkylsulfonyl and the alkylsulfonyl moiety of $C_1$–$C_4$-alkylsulfonyl-$C_1$–$C_4$-alkyl: methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, preferably methylsulfonyl and ethylsulfonyl;

for $C_1$–$C_4$-haloalkylsulfonyl: $C_1$–$C_4$-alkylsulfonyl as above which is partially or completely substituted by fluorine, chlorine and/or bromine, ie. eg. chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 1-fluoroethylsulfonyl, 2-fluoroethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 3-chloropropylsulfonyl and heptafluoropropylsulfonyl;

for the $C_3$–$C_9$-(α-alkylalkylidene) moiety of $C_3$–$C_9$-(α-alkyl-alkylidene)iminooxy-$C_1$–$C_6$-alkyl: α-methylethylidene, α-methylpropylidene, α-ethylpropylidene, especially α-methylethylidene;

for $C_3$–$C_6$-cycloalkyl and the cycloalkyl moiety of ($C_3$–$C_6$-cycloalkyl)oxycarbonyl-$C_1$–$C_4$-alkyl: cyclopropyl, cyclobutyl, cyclopentyl and cyclohexyl, preferably cyclopropyl and cyclopentyl;

for $C_3$–$C_7$-cycloalkyl: $C_3$–$C_6$-cycloalkyl as above and cycloheptyl, preferably cyclopropyl and cyclopentyl;

for $C_3$–$C_8$-cycloalkyl: $C_3$–$C_6$-cycloalkyl as above and cycloheptyl and cyclooctyl, preferably cyclopropyl, cyclopentyl and cyclohexyl;

for $C_5$–$C_7$-cycloalkenyl: cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept- 3-enyl and cyclohept-4-enyl, preferably cyclo-pent-1-enyl;

for 5- or 6-membered hetaryl and the hetaryl moieties of hetaryl-$C_1$–$C_4$-alkyl, hetaryl-$C_1$–$C_6$-alkyl, hetaryl-$C_2$–$C_6$-alkenyl, hetaryl-$C_2$–$C_6$-alkynyl and (hetaryl) oxy-$C_1$–$C_6$-alkyl: eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, preferably 3-pyrazolyl, 2-pyridinyl and 2-thienyl;

for 5- or 6-membered heterocyclyl and the heterocyclyl moiety of heterocyclyl-$C_1$–$C_6$-alkyl:

eg. 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 1,3-dioxolan-2-yl, 1,3-dioxolan-4-yl, 1,3-oxathiolan-2-yl, 1,3-dithiolan-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1-piperidinyl, 2-piperidinyl, 3-piperidinyl, 4-piperidinyl, 1,3-dioxan-2-yl, 1,3-dioxan-5-yl, 1,4-dioxan-2-yl, morpholin-2-yl, morpholin-3-yl, morpholin-4-yl, 1,4-thioxan-2-yl, 1,4-thioxan-3-yl, 1,4-dithian-2-yl, 1,3-dithian-2-yl, 1,3-dithian-5-yl, thiomorpholin-4-yl.

Cations which are suitable as the agriculturally usable cations are in particular those which do not have an adverse effect on the herbicidal action of the compounds I, especially the ions of the alkali metals, preferably sodium and potassium, of the alkaline earth metals, preferably calcium, magnesium and barium, and of the transition metals, preferably manganese, copper, zinc and iron, and the ammonium ion which may, if desired, carry from one to three $C_1$–$C_4$-alkyl and/or hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl-(2-hydroxyethyl)ammonium, and also phosphonium ions, sulfonium ions, preferably tri-($C_1$–$C_4$-alkyl) sulfonium, and sulfoxonium ions, preferably tri-($C_1$–$C_4$-alkyl)-sulfoxonium.

The 3-phenylpyrazole derivatives of the formula I can be obtained in a variety of ways, in particular by one of the following methods:

A) reaction of a β-ketocarboxylic acid derivative III with hydrazine or a hydrazine derivative in an inert solvent (cf. eg. JP-A 04/225 937 and JP-A 03/072 460) and alkylation of the product IV:

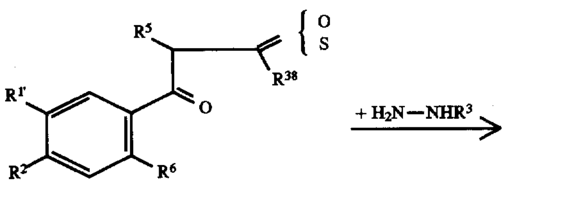

III

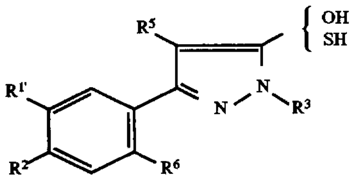

IV

IV + $L^1$—($C_1$–$C_4$-alkyl) or + $L^1$—($C_1$–$C_4$-haloalkyl) → I ($R^4$ = $C_1$–$C_4$-alkoxy, $C_1$–$C_4$-haloalkoxy, $C_1$–$C_4$-alkylthio or $C_1$–$C_4$-haloalkylthio)

$L^1$ is a conventional leaving group such as halogen, —O—$SO_2CH_3$, —O—$SO_2CF_3$, —O—$SO_2C_4F_9$ or —O—$SO_2$(p-$CH_3$—$C_6H_4$);

$R^{38}$ is preferably $C_1$–$C_4$-alkoxy, $C_1$–$C_4$-alkylcarbonyloxy or halogen and; $R^{1'}$ is as defined for $R^1$ and additionally hydrogen, nitro, amino, alkyl, haloalkyl, hydroxyl or $L^2$, where $L^2$ is a conventional leaving group, for example as mentioned for $L^1$.

The solvent may be aprotic or protic. Suitable examples are organic acids such as acetic acid, hydrocarbons, halogenated hydrocarbons, ethers such as ethylene glycol dimethyl ether, alcohols such as methanol or ethanol, and sulfoxides. However, working in the absence of solvents is also possible.

The reaction temperature depends primarily on the melting point of the solvent or the compound III and on the boiling point of the reaction mixture. It is preferred to work at from about 60° to 120° C.

In general from about 0.95 to 5 times the molar amount, advantageously from 1 to 1.4 times the amount, of hydrazine or hydrazine derivative are employed, based on the β-ketocarboxylic acid derivate III.

The quantity of alkylating agent $L^1$-($C_1$–$C_4$-alkyl) or $L^1$-($C_1$–$C_4$-haloalkyl) is usually likewise from 0.95 to 5 times the molar amount, based on the intermediate IV.

With regard to the preferred radicals $R^3$ on the 3-phenylpyrazoles I, particularly preferred hydrazine derivatives are those which carry an alkyl group.

Alkylation is normally carried out with the halide, preferably with the chloride or bromide, or with the sulfate of an alkane or haloalkane, if desired in the presence of an organic base, eg. a trialkylamine or pyridine, or of an inorganic base, eg. an alkali metal carbonate.

The alkylation is expediently carried out in an inert organic solvent, eg. in an aliphatic or cyclic ether such as 1,2-dimethoxyethane, tetrahydrofuran or dioxane, in an aliphatic ketone such as acetone, in an amide such as dimethylformamide, in a sulfoxide such as dimethyl sulfoxide or in a mixture of one of these solvents and water.

The reaction can generally be performed at from 0° C. to the boiling temperature of the reaction mixture. It is preferred to work at from about 20° to 80° C.

When Z is S the product can be oxidized in a manner known per se to the sulfoxide or sulfone (cf. eg. Houben-Weyl, Methoden der Organischen Chemie [Methods of Organic Chemistry], Vol. 9, 4th Edition 1955, pp. 211 and 227; Org. Synth. Coll. Vol. V, 791):

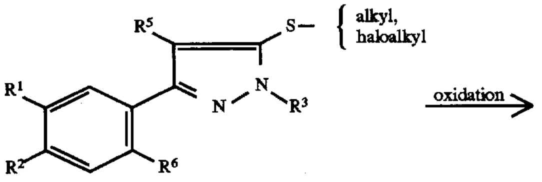

I ($R^4$ = $C_1$–$C_4$-alkylthio or $C_1$–$C_4$-haloalkylthio)

I ($R^4$ = $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl)

B) Halogenation of compounds I' where $R^5$ is hydrogen:

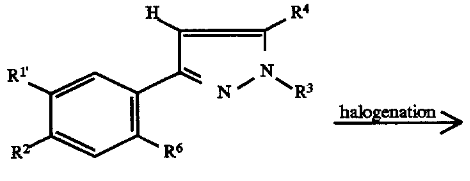

I' ($R^5$ = H)

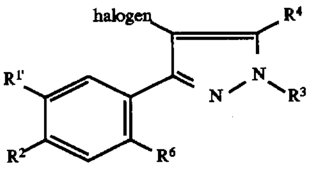

I' ($R^5$ = halogen)

The reaction can be carried out in an inert solvent or diluent or without solvent.

Examples of suitable solvents are organic acids, inorganic acids, hydrocarbons, halogenated hydrocarbons, aromatic hydrocarbons, ethers, sulfides, sulfoxides and sulfones. Examples of suitable halogenating agents are chlorine, bromine, N-bromosuccinimides, N-chlorosuccinimides or sulfuryl chloride. Depending on the starting compound and halogenating agent the addition of a free-radical initiator, for example an organic peroxide such as dibenzoyl peroxide or an azo compound such as azobisisobutyronitrile, or irradiation with light, may have an advantageous effect on the course of the reaction.

The quantity of halogenating agent is not critical. Both substoichiometric quantities and large excesses of halogenating agent, based on the compound I to be halogenated where $R^5$ is hydrogen, are possible.

When a free-radical initiator is used, a catalytic amount is generally sufficient.

The reaction is normally carried out at from −100° to 200° C., preferably at from 10° to 100° C. or at the boiling point of the reaction mixture.

C) Olefinization of 3-(formylphenyl)pyrazoles V to compounds I in which $R^1$ is unsaturated:

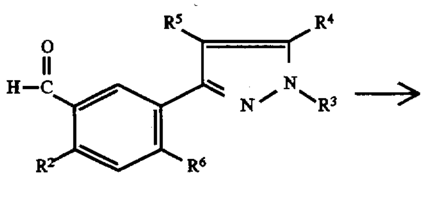

V

I ($R^1$ = —CH=C($R^7$,$R^{12}$),

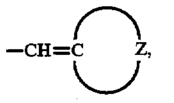

—CH=($R^8$)-phenyl)

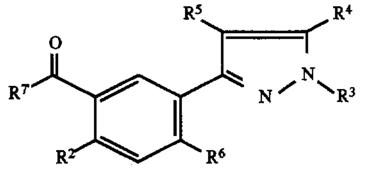

VI in which $R^{7'}$ is as defined for $R^7$ with the exception of halogen (for example reacting V with a suitable salt $MR^{7'}$ in which M is eg. lithium or magnesium and then oxidizing the alcohol formed) and subsequently subjecting the products to the Wittig reaction.

The phosphonium salts, phosphonates or phosphorylides required as reactants are known or can be prepared in a manner known per se {cf. eg. Houben-Weyl, Methoden d. Org. Chemie {Methods of Organic Chemistry], Vol. E 1, p. 636 ff and Vol. E 2, p. 345 ff, Georg Thieme Verlag Stuttgart 1982; Chem. Ber. 95, (1962) 3993}.

The aldol condensation can be carried out in a manner known per se (see e.g. Synthesis 1978, 56; Synthesis 1978, 58; Synth. Commun. 18(7), (1988) 717, Synthesis 1986, 1026; Chem. Rev. 1993, 1449).

The 3-(formylphenyl)pyrazoles V can be obtained, for example, by halogenation of 3-(methylphenyl)pyrazoles VII followed by acid hydrolysis of 3-(dihalomethylphenyl) pyrazoles VIIIa or oxidation of 3-(halomethylphenyl) pyrazoles VIIIb:

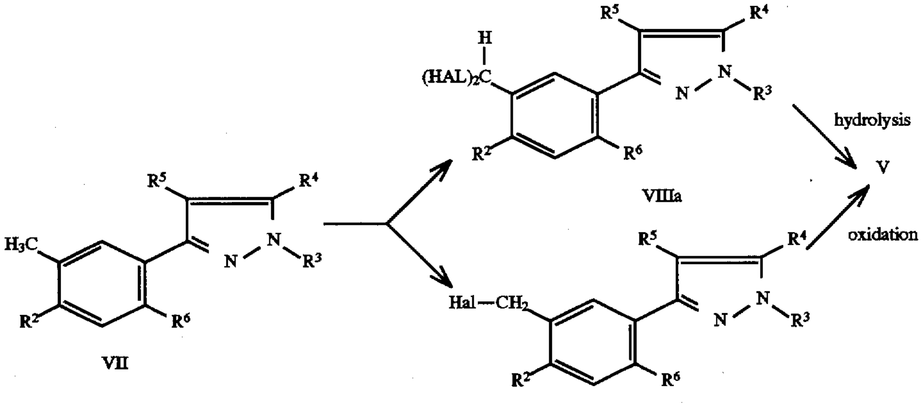

VII VIIIa VIIIb

Olefinization is carried out preferably by the method of Wittig or one of its modifications, with suitable reactants being phosphorylides, phosphonium salts and phosphonates, or by aldol condensation.

When using a phosphonium salt or a phosphonate it is advisable to work in the presence of a base, among which the following are particularly suitable: alkali metal alkyls such as n-butyllithium, alkali metal hydrides and alcoholates such as sodium hydride, sodium ethanolate and potassium tert-butanolate, and alkali metal hydroxides and alkaline earth metal hydroxides such as calcium hydroxide.

For complete reaction, all of the reactants are employed in an approximately stoichiometric ratio; however, it is preferred to use an excess of phosphorus compound and/or base of up to about 10 mol %, based on V.

The reaction temperature is generally from −40° to 150° C. A further possibility for preparing compounds I is first of all to convert the 3-(formylphenyl)pyrazoles V in a manner known per se into the corresponding ketones VI Hal=halogen, preferably chlorine or bromine.

With respect to the solvents, proportions and reaction temperature for the halogenation, reference is made to the comments under method B). Photochemical halogenation can also be used to carry out halogenation at $R^3$ of compounds VIIIa where $R^3$ is methyl (VIIIa, $R^3$=$CH_2R^{39}$, $R^{39}$= halogen):

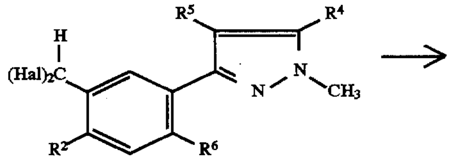

(VIIIa, $R^3$=$CH_3$)

-continued

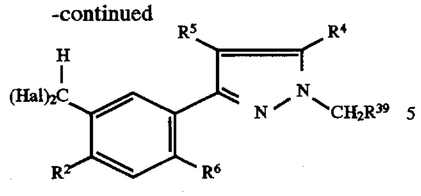

(VIIIa, $R^3{=}CH_2R^{39}$)

$R^{39}$ is halogen or $C_1$–$C_4$-alkoxy.

The reaction products may then if desired be converted in a manner known per se using oxygen nucleophiles or halogen nucleophiles to compounds VIIIa ($R^3{=}CH_2R^{39}$, $R^{39}$=halogen or $C_1$–$C_4$-alkoxy).

The hydrolysis of VIIIa is preferably carried out without solvents in an acid such as hydrochloric acid, sulfuric acid or acetic acid, especially concentrated sulfuric acid, or in a mixture of acetic acid and water (eg. 3:1).

The reaction temperature is normally from 0° to 120° C.

The reaction products can generally be worked up in a manner known per se.

The oxidation of the compounds VIIIb can be carried out, for example, by the method of Kornblum (in this respect see, in particular, pages 179 to 181 of "Methods for the Oxidation of Organic Compounds" by Alan H. Haines, Academic Press 1988, in the series "Best Synthetic Methods").

One example of a suitable solvent is dimethyl sulfoxide.

Further possibilities for preparing different compounds I from 3-(formylphenyl)pyrazoles V include the aldol condensation, which is known per se (suitable conditions for this can be found in, for example, Nielsen, Org. React. 16, (1968) 1 ff), and condensation reactions according to Knoevenagel or Perkin. Examples of suitable conditions are described in Org. React. 15, (1967) 204 ff {Knoevenagel} and Johnson, Org. React. 1, (1942) 210 ff {nach Perkin}.

D) Diazotization of anilines IX in a manner known per se and arylation of the resulting diazonium compounds by the method of Meerwein {see eg. C. S. Rondestvedt, Org. React. 11, (1960) pp. 189–260 and, in particular, H. P. Doyle, B. Siegfried. R. C. Elliot, J. F. Dellaria, J. Org. Chem. 42, (1977) 2431}:

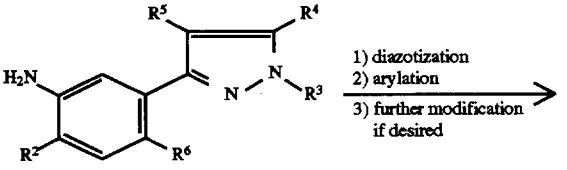

IX

I ($R^1$-

$-C(R^9, R^{10})-C(R^8, R^{11}, R^{12})$

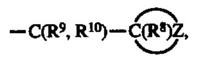

$-C(R^9, R^{10})-C(R^8, R^{13})$-phenyl)

The diazonium salt can be obtained advantageously in a manner known per se by reacting an aniline IX in an aqueous acid solution, for example in hydrochloric acid, hydrobromic acid or sulfuric acid, with a nitrite such as sodium nitrite or potassium nitrite.

The reaction can also be carried out, however, without water, for example in glacial acetic acid which contains hydrogen chloride, in absolute alcohol, in dioxane or tetrahydrofuran, in acetonitrile or in acetone, in this case reacting the aniline IX with a nitrous ester such as tert-butyl nitrite or isopentyl nitrite.

The subsequent reaction of the diazonium salt with an olefin or alkine in the presence of a copper salt, preferably a copper halide such as copper(I) chloride, copper(II) chloride, copper (I) bromide or copper(II) bromide, by the method of Meerwein can be carried out, for example, in water, in a ketone such as acetone, diethyl ketone or methyl ethyl ketone, in a nitrile such as acetonitrile, in an ether such as dioxane or tetrahydrofuran, or in an alcohol such as methanol or ethanol.

Diazotization and arylation can be carried out at from −30 to ±50° C. The components of the diazotization reaction are usually employed in an approximately stoichiometric ratio, although an excess of one or other component may be advantageous.

In general the olefins or alkines to be arylated are employed in a large excess; however, it is also possible to use only a slight excess, an equivalent amount or a substoichiometric amount.

The copper halide is conventionally employed in an approximately stoichiometric quantity based on the diazonium salt or, if it is not isolated, on the aniline IX, although an excess or substoichiometric amount is also possible.

Diazotization and arylation can also be undertaken in one step. In this case diazotization is carried out in the presence of the olefin or alkine component and of the copper halide.

The anilines IX can in turn be obtained by reduction of the corresponding nitro compounds X:

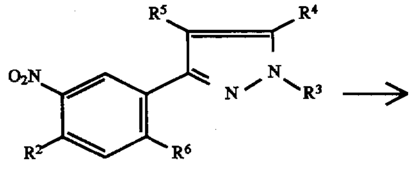

X

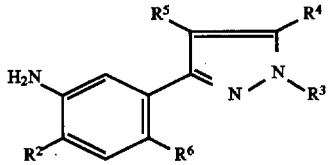

IX

The reduction can be carried out with a metal such as iron, zinc or tin under acidic reaction conditions or with a complex hydride such as lithium aluminum hydride or sodium borohydride, with examples of suitable solvents—depending on the reducing agent chosen—being water, alcohols such as methanol, ethanol or isopropanol, or ethers such as diethyl ether, methyl tert-butyl ether, dioxane, tetrahydrofuran or ethylene glycol dimethyl ether.

When carrying out reduction with a metal, it is preferred to work without solvent in an inorganic acid, especially concentrated or dilute hydrochloric acid, or in an organic acid such as acetic acid. However, it is also possible to add an inert solvent, for example one of those mentioned above, to the acid.

The starting compound X and the reducing agent are advantageously employed in approximately equimolar quantities; however, in order to optimize the course of the reaction it may be advantageous to employ one of the two components in excess, up to about 10 times the molar amount.

The quantity of acid is not critical. In order to maximize reduction of the starting compound it is advantageous to use an at least equivalent quantity of acid.

The reaction temperature is in general from −30 to 200° C., preferably from 0° to 80° C.

The reaction mixture is usually worked up by diluting it with water and isolating the product by filtration, crystallization or extraction with a solvent which is substantially immiscible with water, for example with ethyl acetate, diethyl ether or methylene chloride. Subsequently the product can if desired be purified in a conventional manner.

The nitro group of the nitro compounds X can also be hydrogenated catalytically using hydrogen.

Catalysts suitable for this purpose are, for example, Raney nickel, palladium on charcoal, palladium oxide, platinum and platinum oxide, with a quantity of catalyst of from 0.05 to 10.0 mol %, based on the compound to be reduced, generally being sufficient.

The reaction is carried out either without solvent or in an inert solvent or diluent, for example in acetic acid, in a mixture of acetic acid and water, or in ethyl acetate, ethanol or toluene.

After the catalyst has been separated off the reaction solution can be worked up in a conventional manner to give the product.

Hydrogenation can be carried out at atmospheric pressure or under superatmospheric pressure.

The nitro compounds X are in turn accessible, for example, by nitration of phenylpyrazoles XI:

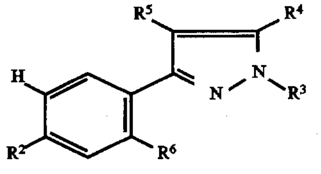

XI

Examples of suitable nitrating reagents are nitric acid at various concentrations, including concentrated and fuming nitric acid, mixtures of sulfuric acid and nitric acid, acetyl nitrates and alkyl nitrates.

The reaction can be carried out either without solvent in an excess of the nitrating reagent or in an inert solvent or diluent, examples of suitable such solvents being water, mineral acids, organic acids, chlorinated hydrocarbons such as methylene chloride, anhydrides such as acetic anhydride, and mixtures of these solvents.

Starting compound XI and nitrating reagent are advantageously employed in approximately equimolar quantities: in order to optimize the conversion of the compound to be nitrated, however, it may be advantageous to use the nitrating reagent in an excess, up to about 10 times the molar quantity. When the reaction is carried out without solvent in the nitrating reagent, the latter is used in an even larger excess.

The reaction is generally carried out from −100° to 200° C., preferably at from −30° to 50° C.

The reaction mixture can be worked up in a known manner, for example by diluting the reaction solution with water and then isolating the product by means of filtration, crystallization or solvent extraction.

E) Reaction of phenyl triflates XIII, which are obtainable in turn from phenols XII, with Grignard compounds or olefins:

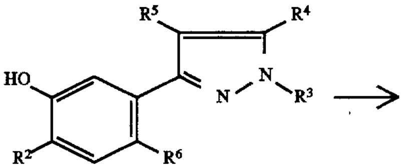

XIII

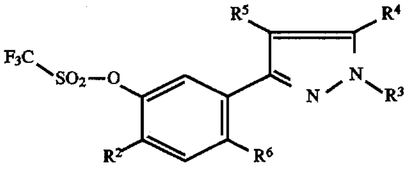

XIII

XIII + Grignard compound or olefin
Catalysis by palladium(0) or nickel(0)
I

From the phenyl triflates XIII it is possible, in a manner known per se - for example by alkylation (see eg. J. Org. Chem.57, (1992) 4066–4068 and the literature cited therein)—to prepare compounds I in which $R^1$ is a substituted or unsubstituted alkyl radical.

Compounds I in which $R^1$ is an unsaturated radical can be obtained from the phenyl triflates XIII with suitable palladium catalysis {see eg. Heterocycles 26, (1987) 355–358 and the literature cited therein under Lit. 1}.

F) Derivatization of the substituents $R^1$

F1) Hydrogenation of double bonds in a manner known per se:

Examples of suitable reducing agents are elemental metals such as iron, tin and zinc, hydrogen in the presence of appropriate catalysts such as palladium on charcoal, platinum on charcoal and Raney nickel, complex metal hydrides such as lithium aluminum hydride and sodium borohydride, if desired in the presence of one of the abovementioned catalysts.

Depending on the reducing agent used, examples of suitable solvents are acids such as acetic acid and propionic acid, alcohols such as methanol and ethanol, ethers such as diethyl ether, methyl tert-butyl ether, tetrahydrofuran and dioxane, or aromatic compounds such as benzene and toluene. Mixtures of the solvents mentioned can also be used.

The reactions can be carried out at from −100° C. to the boiling temperature of the respective reaction mixture.

The starting materials are commonly employed in an approximately stoichiometric ratio, although in order to optimize the conversion of the compound I to be derivatized it may be advantageous to employ this compound in a substoichiometric quantity.

F2) Substitution of a halogen atom on substituent $R^1$, preferably a chlorine or bromine atom, by a nitrogen, oxygen or carbon nucleophile in a manner known per se:

Especially with regard to the reaction of compounds I in which the substituent $R^1$ carries, in addition to the halogen atom, a carboxyl group and also two further substituents on the same carbon atom, the presence of a nickel catalyst has proven to be particularly advantageous.

Depending on the reactants, examples of suitable solvents are aprotic solvents such as acetone, diethyl ketone, methyl ethyl ketone, dimethylformamide, diethylformamide, N-methylpyrrolidone, dimethyl sulfoxide, sulfolane and chlorinated hydrocarbons, for example methylene chloride or chloroform. Mixtures of the solvents mentioned are also suitable.

The reactions are generally carried out at from −30° C. to the boiling temperature of the respective solvent or solvent mixture.

The starting materials are conventionally reacted in an approximately stoichiometric ratio, although in order to optimize the conversion of the compound I to be derivatized it may be advantageous to employ this compound in a substoichiometric quantity.

F3) Conversion of compounds I in which the radical $R^1$ contains a carboxylic ester, to carboxylic acids and derivatives thereof in a manner known per se:

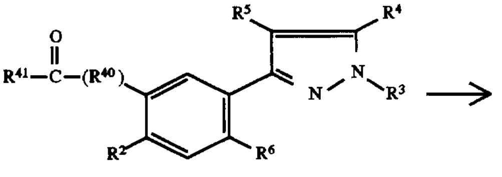

I ($R^1$=—($R^{40}$)—CO—$R^{41}$)

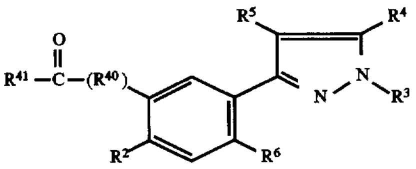

I ($R^1$=—($R^{40}$)—CO—$R^{41}$)

$R^{40}$ here is preferably —C($R^8$)=C($R^7$)—,

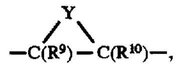

—C($R^9$,$R^{10}$)—C($R^8$,$R^{11}$)—, —C($R^9$,$R^{10}$)—C($R^9$,$R^{10}$)— or —C($R^9$,$R^{10}$)—C($R^8$,phenyl)—.

$R^{41}$ is in particular $OR^{29}$, Halogen, N($R^{34}$,$R^{35}$), $SR^{29}$, N($R^{34}$)—$OR^{29}$.

Thus, for example, esters ($R^{41}$=$OR^{29}$) can be hydrolyzed to carboxylic acids ($R^{41}$=OH) (see eg. Houben-Weyl, Methoden der Organischen Chemie [Methods of Organic Chemistry], Vol. 8, Georg Thieme Verlag, Stuttgart, 1952, p. 418ff.) from which the carbonyl halides ($R^{41}$ =$C_1$) are accessible (Houben-Weyl, Methoden der Organischen Chemie [Methods of Organic Chemistry], Vol. 8, Georg Thieme Verlag Stuttgart, 1952, p. 471ff.).

Carboxylic acids or their halides ($R^{41}$=OH, Cl) can in turn be converted to carboxamides ($R^{41}$=N($R^{34}$,$R^{35}$), N($R^{34}$)—$OR^{29}$), carboxylic esters ($R^{41}$=$OR^{29}$) or thioesters ($R^{41}$=$SR^{29}$) (see eg. Houben-Weyl, Methoden der Organischen Chemie [Methods of Organic Chemistry], Georg Thieme Verlag, Vol. 8, 4th Edition, 1952, p. 516 ff; Vol. 9, 4th Edition 1955, p. 753ff; Vol. E5, supplementary and subsequent volume to the 4th Edition, 1985, p. 941ff.).

F4) Reaction of compounds I in which $R^1$ is —C($R^8$)═C($R^7$,$R^{12}$) to give compounds I where $R^1$=

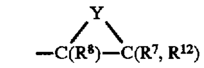

in a manner known per se (see eg. Houben-Weyl, Methoden der Organischen Chemie {Methods of Organic Chemistry], Georg Thieme Verlag, Stuttgart, Vol. 6/3, 4th Edition 1965, p. 385ff; Vol. 9, 4th Edition 1955, p. 153ff; Vol 4/3, 4th Edition 1942, p. 32ff.).

G) Nucleophilic cyanide substitution of compounds I where $R^1$=NO2 and $R^2$ is fluorine:

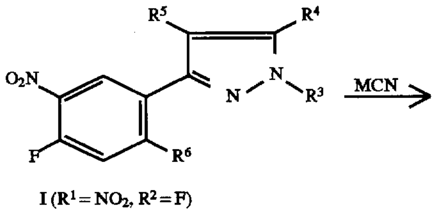

I ($R^1$=$NO_2$, $R^2$=F)

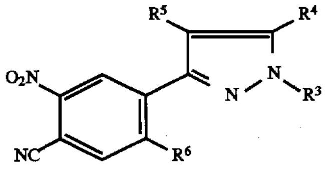

I ($R^1$=$NO_2$, $R^2$=CN)

Suitable cyanide sources MCN are in general any desired cyanide salts of metallic or organic cations, preferably alkali metal cyanides or tetraalkylammonium cyanides.

The reaction is carried out in a polar aprotic solvent at between the melting and boiling points of the latter, preferably in dimethyl sulfoxide, N,N-dimethylformamide or sulfolane at from 0° to 100° C.

It-is preferred to use a slight molar excess of the cyanide MCN based on the starting compound. However, in order to optimize the conversion it may be advantageous to use a large excess of MCN, up to about five times the molar quantity.

The reaction mixture can be worked up in a known manner, for instance by diluting the reaction mixture with water and then isolating the product by filtration, crystallization or solvent extraction.

Unless stated otherwise, the reactions described above are advantageously carried out under atmospheric pressure or under the autogenous pressure of the respective reaction mixture.

The substituted 3-phenylpyrazoles I may in the course of their preparation be obtained as isomer mixtures which, however, may if desired be separated into pure isomers by the methods which are conventional for this purpose, such as crystallization or chromatography, including chromatography on an optically active adsorbate. Pure optically active isomers can advantageously be prepared from corresponding optically active starting products.

Substituted 3-phenylpyrazoles I in which $R^8$, $R^9$, $R^{10}$ or $R^{13}$ is a radical —N($R^{24}$)—CO—$R^{25}$ and $R^{24}$ is an alkali metal can be obtained by treating compounds I where $R^{24}$ is hydrogen, for example with sodium hydroxide or potassium hydroxide in aqueous solution or in an organic solvent such as methanol, ethanol, acetone or toluene, or with sodium hydride in an organic solvent such as dimethylformamide.

Salt formation normally takes place at a sufficient speed even at about 20° C.

The salt can be isolated by, for example, precipitation with a suitable inert solvent or by evaporation of the solvent.

Substituted 3-phenylpyrazoles I in which $R^8$, $R^9$, $R^{10}$ or $R^{13}$ is the radical —N($R^{24}$)—CO—$R^{25}$ and $R^{24}$ is an agriculturally usable cation which does not belong to the group of alkali metals can be prepared conventionally by salt exchange of the corresponding compound I where $R^{24}$ is an alkali metal ion.

Compounds I in which $R^{24}$ is, for example, a manganese, copper, zinc, iron, calcium, magnesium or barium ion can be prepared from the compounds I where $R^{24}$ is sodium in a conventional manner, as can compounds I where $R^{24}$ is an ammonium or phosphonium using ammonia, phosphonium hydroxides, sulfonium hydroxides or sulfoxonium hydroxides.

Both as isomer mixtures and in the form of the pure isomers, the substituted 3-phenylpyrazoles I and salts thereof are suitable as herbicides. In crops such as wheat, rice, maize, soybean and cotton they are able to provide very effective control of broad-leaved weeds and grass weeds without noticeably damaging the crop plants. This effect occurs especially at low application rates.

Depending on the particular application method, the compounds I or herbicidal compositions comprising them can additionally be employed in a further number of crop plants in order to eliminate unwanted plants. Examples of suitable crops are the following:

*Allium cepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa , Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera and Zea mays.*

Moreover, the compounds I can also be employed in crops which have been rendered substantially resistant to the action of I by breeding and/or by employment of methods of genetic manipulation.

The compounds I and/or the herbicidal compositions comprising them can be applied, for example, in the form of directly sprayable aqueous solutions, powders, suspensions, including highly concentrated aqueous, oily or other suspensions or dispersions, emulsions, oil dispersions, pastes, dusting compositions, broadcasting compositions or granules, by spraying, atomizing, dusting, broadcasting or watering. The application forms depend on the intended uses; they should in each case if possible guarantee very fine dispersion of the active compounds according to the invention.

Suitable inert auxiliaries for the production of directly sprayable solutions, emulsions, pastes or oil dispersions are essentially: mineral oil fractions of medium to high boiling point such as kerosene and diesel oil, and also coaltar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous application forms can be prepared from emulsion concentrates, suspensions, pastes, wettable powders or water-dispersible granules by addition of water. For the production of emulsions, pastes or oil dispersions, the substrates as such or dissolved in an oil or solvent can be homogenized in water by means of wetting agents, adhesives, dispersants or emulsifiers. However, concentrates consisting of active substance, wetting agents, adhesives, dispersants or emulsifiers and possibly solvents or oil can also be prepared, which are suitable for dilution with water.

Suitable surface-active substances are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powders; broadcasting and dusting compositions can be produced by mixing or conjoint grinding of the active substances with a solid carrier.

Granules, eg. coated, impregnated and homogeneous granules, can be produced by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground plastics, fertilizers such as ammonium sulfate, ammonium phosphate, ammonium nitrate, ureas and vegetable products such as cereal meal, tree bark meal, sawdust, nutshell meal, cellulose powders or other solid carriers.

The concentrations of the active compounds I in the ready-to-use preparations can be varied within wide ranges, for example from 0.01 to 95% by weight, preferably from 0.5 to 90% by weight. The active compounds are in this case employed in a purity of from 90% to 100%, preferably from 95% to 100% (according to NMR spectrum).

The following formulation examples elucidate the production of such formulations:

I. 20 parts by weight of the compound No. Ia.002 are dissolved in a mixture which consists of 80 parts by weight of alkylated benzene, 10 parts by weight of the addition product of from 8 to 10 mol of ethylene oxide with 1 mol of oleic acid N-monoethanolamide, 5 parts by weight of calcium salt of dodecylbenzenesulfonic acid and 5 parts by weight of the addition product of 40 mol of ethylene oxide with 1 mol of castor oil. Fine dispersion of the mixture in 100,000 parts by weight of water gives an aqueous dispersion which contains 0.02% by weight of the active compound.

II. 20 parts by weight of the compound No. Ia.003 are dissolved in a mixture which consists of 40 parts by weight of cyclohexanone, 30 parts by weight of isobutanol, 20 parts by weight of the addition product of 7 mol of ethylene oxide with 1 mol of isooctylphenol and 10 parts by weight of the addition product of 40 mol of ethylene oxide with 1 mol of castor oil. Fine dispersion of the solution in 100,000 parts by weight of water gives an aqueous dispersion which contains 0.02% by weight of the active compound.

III. 20 parts by weight of the active compound No. Ia.020 are dissolved in a mixture which consists of 25 parts by weight of cyclohexanone, 65 parts by weight of a mineral oil fraction of boiling point 210° to 280° C. and 10 parts by weight of the addition product of 40 mol of ethylene oxide with 1 mol of castor oil. Fine dispersion of the solution in 100,000 parts by weight of water gives an aqueous dispersion which contains 0.02% by weight of the active compound.

IV. 20 parts by weight of the active compound No. Ia.055 are mixed thoroughly with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel and the mixture is ground in a hammer mill. Fine dispersion of the mixture in 20,000 parts by weight of water gives a spray formulation which contains 0.1% by weight of the active compound.

V. 3 parts by weight of the active compound No. Ia.002 are mixed with 97 parts by weight of finely divided kaolin. In this way a dusting composition is obtained which contains 3% by weight of the active compound.

VI. 20 parts by weight of the active compound No. Ia.003 are mixed intimately with 2 parts by weight of the calcium salt of dodecylbenzenesulfonic acid, 8 parts by weight of fatty alcohol polyglycol ether, 2 parts by weight of the sodium salt of a phenol-urea-formaldehyde condensation product and 68 parts by weight of a paraffinic mineral oil. A stable oily dispersion is obtained.

The active compounds I and/or the herbicidal compositions can be applied pre-emergence or post-emergence. If the active compounds are less tolerable to certain crop plants, application techniques can be used in which the herbicidal compositions are sprayed with the aid of the spray equipment in such a way that the leaves of the sensitive crop plants are where possible unaffected, while the active compounds reach the leaves of unwanted plants growing under them or the uncovered soil surface (post-directed, lay-by).

The application rates of active compound are, depending on the objective of control, the time of year, the target plants and the stage of growth, from 0.001 to 3.0 kg, preferably from 0.01 to 1 kg/ha of active substance (a.s.).

In order to broaden the spectrum of action and to achieve synergistic effects, the substituted 3-phenylpyrazoles I can be mixed with numerous representatives of other herbicidal or growth-regulating active compound groups and applied together. For example, suitable cocomponents are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry in position 2, for example, a carboxyl or carbimino group, quinolinecarboxylic derivatives, imidazolinones, sulfonamides, sulfonylureas, aryloxy- and hetaryloxyphenoxypropionic acids, and their salts, esters and amides, et cetera.

In addition it may be of use to mix the compounds I, alone or in combination with other herbicides, additionally with further plant protection compositions and to apply them together, for example with pesticides, fungicides or bactericides intended for combating organisms which harm plants. Also of interest is the possibility of mixing them with mineral salt solutions which are employed to eliminate nutritional and trace element deficiencies. Nonphytotoxic oils and oil concentrates can also be added.

PREPARATION EXAMPLES

Example 1

Methyl 2-bromo-3-(2,4-dichloro-5-[4-chloro-5-difluoromethoxy-1-methyl-1H-pyrazol-3-yl]phenyl) propenoate (Ib.006)

2.9 g (6.9 mol) of methoxycarbonylbromomethylenetriphenylphosphorane were added to a solution of 2.2 g (6.2 mmol) of 4-chloro-3-(2,4-dichloro-5-formylphenyl)-5-difluoromethoxy-1-methyl-1H-pyrazole in 100 ml of ethanol. The mixture was stirred at 25° C. for 4 hours and then the solvent was removed under reduced pressure. The residue was taken up in toluene and this mixture was filtered over silica gel. Concentration by evaporation of the solvent under reduced pressure gave 1.1 g of product.

$^1$H-NMR (270 MHz, in $CDCl_3$): δ [ppm]=3.85 (s,3H), 3.95 (s,3H), 6.74 (t,1H), 7.62 (s,1H), 8.02 (s,1H), 8.32 (s,1H).

Preparation of the precursors:

Example 2

Ethyl 4-chlorobenzoylacetate 200 g (1.29 mol) of 4-chloroacetophenone (dissolved in 500 ml of diethyl carbonate) were added dropwise at 60° C. to a mixture of 296.4 g (2.59 mol) of potassium tert-butylate and 2.25 l of diethyl carbonate. The suspension, which could be stirred with difficulty, was stirred at 60° C. for 3 h and then introduced into 2.7 l of 10% strength sulfuric acid. Extraction with ethyl acetate, drying of the organic phase over magnesium sulfate and concentration in vacuo gave the crude product, which was purified further by distillation (b.p. 130° C., 0.4 mbar). Yield: 268 g.

Example 3

Ethyl 2,4-dichloro-5-methylbenzoylacetate

Example 2 was repeated using 148 g of 2,4-dichloro-5-methylacetophenone instead of 4-chloroacetophenone. Yield: 80.4 g; b.p. (0.5 mbar): 170° C.

Example 4

3-(4-Chlorophenyl)-1-methyl-2-pyrazolin-5-one 71.2 g (1.55 mol) of methylhydrazine were added dropwise over the course of 40 minutes to a suspension of 267 g (1.19 mol) of ethyl 4-chlorobenzoylacetate in 1.5 l of acetic acid, the temperature rising to 50° C. The reaction solution was stirred at 100° C. for 2 hours and cooled, and then about 1.5 l each of ether and water were added. The precipitate formed (66.5 g) was filtered off and washed with petroleum ether/ether (1:1). The organic phase was washed four times with saturated sodium hydrogen carbonate solution and concentrated, and the residue was taken up in water.

Once again the precipitate formed was filtered off and washed with petroleum ether/ether (1:1). Overall yield: 171 g; m.p. 189° C.

Example 5

3-(2,4-Dichloro-5-methylphenyl)-1-methyl-2-pyrazolin-5-one 13.5 g (292 mol) of methylhydrazine were added slowly to 80.4 g (292 mmol) of ethyl 2,4-dichloro-5-methylbenzoylacetate in 300 m of diethylene glycol dimethyl ether. The reaction solution was heated at 100° C. for 4 hours and then stirred into 11 of ice-water. The precipitate formed was filtered off, washed with a little-methylene chloride and dried. Yield: 38.8 g; m.p. 196°–198° C.;

1H-NMR (270 MHz, in d6-dimethyl sulfoxide): 6 [ppm] =2.32 (s,3H), 3.60 (s,3H), 5.89 (s,1H), 7.58 (s,1H), 7.76 (s,1H), 11.12 (s,1H).

Example 6

3-(4-Chlorophenyl)-5-difluoromethoxy-1-methyl-1H-pyrazole

A solution of 162 g (4.0 mol) of sodium hydroxide in 1 1 of water was added to a solution of 169.1 g (0,811 mol) of 3-(4-chlorophenyl)-1-methyl-2-pyrazolin-5-one in 2.5 1 of dioxane. Chlorodifluoromethane (about 175 g) was passed in over the course of 5 hours at 60°–65° C., after which the reaction solution was stirred into 1.5 1 of water. Extraction three times with methyl tertbutyl ether, followed by drying of the organic phase and removal of the solvent in vacuo, gave the crude product, which was purified further by chromatography on silica gel (hexane/ethyl acetate 7:3). Yield: 142.9 g; 1H-NMR (400 MHz, in $CDCl_3$): δ [ppm]= 7.60 (d,2H), 7.28 (d,2H), 6.54 (t,1H), 6.08 (s,1H), 3.69 (s,3H).

Example 7

3-(2,4-Dichloro-5-methylphenyl)-5-difluoromethoxy-1-methyl-1H-pyrazole

Example 6 was repeated with 37 g (144 mmol) of 3-(2, 4-dichloro-5-methylphenyl)-1-methyl-2-pyrazolin-5-one instead of 3-(4-chlorophenyl)-1-methyl-2-pyrazolin-5-one. Yield: 35.1 g;

$^1$H-NMR (270 MHz, in $CDCl_3$): δ [ppm]=7.70 (s,1H), 7.46 (s,1H), 6.59 (t,1H), 6.45 (s,1H), 3.84 (s,3H), 2.39 (s,3H).

Example 8

4-Chloro-3-(4-chlorophenyl)-5-difluoromethoxy-1-methyl-1H-pyrazole

A solution of 74.0 g (0,549 mol) of sulfuryl chloride in 200 ml of carbon tetrachloride was added slowly to a solution of 128.9 g (0.5 mol) of 3-(4-chlorophenyl)-5-difluoromethoxy-1-methyl-1H-pyrazole in 500 ml of carbon tetrachloride. After the exothermic reaction with evolution of gas had subsided, the reaction mixture was stirred at 20°–25° C. for 2 hours more. The reaction solution was then washed with water, saturated sodium hydrogen carbonate solution and saturated sodium chloride solution, and finally dried and concentrated. Yield: 139.3 g; $^1$H-NMR (270 MHz, in $CDCl_3$): δ [ppm]=7,79 (d,2H), 7,43 (d,2H), 6,70 (t, 1H), 3,85 (s,3H).

Example 9

4-Chloro-3-(2,4-dichloro-5-methylphenyl)-5-difluoromethoxy-1-methyl-1H-pyrazole

Analogously to Example 8, 35 g (114 mmol) of 3-(2,4-dichloro-5-methylphenyl)-5-difluoromethoxy-1-methyl-1H-pyrazole were reacted with 16.9 g (125 mmol) of sulfuryl chloride. Yield: 30.8 g; 1H-NMR (270 MHz, in $CDCl_3$): δ [ppm]=7.49 (s,1H), 7.30 (s,1H), 6.74 (t,1H), 3.85 (s,3H), 2.39 (s,3H).

Example 10

3-(3-Dibromomethyl-4-chlorophenyl)-4-chloro-5-difluoromethoxy-1-methyl-1H-pyrazole 10.5 g (58.8 mmol) of N-bromosuccinimide were added to a solution of 3.0 g (9.8 mmol) of 4-chloro-5-difluoromethoxy-3-(4-chloro-3-methylphenyl)-1-methyl-1H-pyrazole (prepared analogously to Example 8) in 100 ml of carbon tetrachloride. The reaction solution was then heated at reflux for 1 hour while being irradiated with a 150 W high-pressure mercury lamp. Filtration and removal of the solvent under reduced pressure gave 3.9 g of the crude product, which was reacted further without additional purification.

$^1$H-NMR (400 MHz, in $CDCl_3$): δ [ppm]=8.56 (s,1H), 7.79 (d,1H), 7.46 (d,1H), 7.15 (d,1H), 6.70 (t,1H), 3.85 (s,3H).

Example 11

3-(5-Dibromomethyl-2,4-dichlorophenyl)-4-chloro-5-difluoromethoxy-1-methyl-1H-pyrazole Analogously to Example 10, 28 g (82 mmol) of 4-chloro-3-(2,4-dichloro-5-methylphenyl)-4-chloro-5-difluoromethoxy-1-methyl-1H-pyrazole were reacted with 99.3 g (560 mmol) of N-bromosuccinimide. Yield: 49.5 g. $^1$H-NMR (270 MHz, in $CDCl_3$): δ [ppm]=8.08 (s,1H), 7.50 (s,1H), 7.05 (s,1H), 6.75 (t,1H), 3.88 (s,3H).

Example 12

4-Chloro-3-(4-chloro-3-formylphenyl)-5-difluoromethoxy-1-methyl-1H-pyrazole

At 85° C., 4.65 g (10 mmol) of 3-(3-dibromomethyl-4-chloro-phenyl)-4-chloro-5-difluoromethoxy-1-methyl-1H-pyrazole were introduced a little at a time into 7 ml of concentrated sulfuric acid. The reaction solution was then stirred at 100° C. for 5 minutes, then stirred into 40 ml of ice-water. The solid product formed was filtered off and dried. Yield: 3.0 g;

1H-NMR-(270 MHz, in $CDCl_3$): δ [ppm]=10.50 (s,1H), 8.45 (s,1H), 8.06 (d,1H), 7.52 (d,1H), 6.71 (t,1H), 3.82 (s,3H).

Example 13

4-Chloro-3-(2,4-dichloro-5-formylphenyl)-5-difluoromethoxy-1-methyl-1H-pyrazole

Analogously to Example 12, 45.5 g (91 mmol) of 3-(5-dibromomethyl-2,4-dichlorophenyl)-4-chloro-5-difluoromethoxy-1-methyl-1H-pyrazole were introduced into 65 ml of concentrated sulfuric acid. After working up, 20 g of the product were obtained. $^1$H-NMR (270 MHz, in $CDCl_3$): δ [ppm]=10.41 (s,1H), 8.02 (s,1H), 7.65 (s,1H), 6.77 (t,1H), 3.87 (s,3H).

Example 14

Ethyl 3-(2,4-dichloro-5-(4-chloro-5-difluoromethoxy-1-methyl-1H-pyrazol-3-yl)phenyl)-2-cyanopropenoate (ib.223)

2.4 g (21 mmol) of ethyl cyanoacetate and 0.3 g (4.2 mmol) of sodium ethanolate were added to a solution of 7.5 g (21 mmol) of 4-chloro-3-(2,4-dichloro-5-formylphenyl)-5-difluoromethoxy-1-methyl-1H-pyrazole in 70 ml of ethanol. The mixture was stirred for 4 hours then poured into ice-water, after which the solid product was filtered off, washed with n-hexane and then dried. Yield: 4.9 g.

Example 15

Ethyl 3-(2,4-dichloro-5-(4-chloro-5-difluoromethoxy-1-methyl-1H-pyrazol-3-yl)phenyl)-2-cyanooxirane-2-carboxylate (Ib.265)

1.4 g (12 mmol) of 30% strength aqueous hydrogen peroxide solution were added to 2.7 g (6 mmol) of ethyl 3-(2,4-dichloro-5-(4-chloro-5-difluoromethoxy-1-methyl-1H-pyrazol-3-yl)Phenyl)-2-cyanopropenoate in 30 ml of ethanol. After 12 hours the mixture was poured into water. The product was extracted from the aqueous phase using ethyl acetate, after which the organic phase was dried over magnesium sulfate and then concentrated. Purification of the crude product was carried out by means of column chromatography on silica gel (eluent: hexane/ethyl acetate=4:1). Yield: 1 g.

Example 16

2-Chloro-3-(2,4-dichloro-5-(4-chloro-5-difluoromethoxy-1-methyl-1H-pyrazol-3-yl)phenyl)propenoic acid (Ib.001)

85 ml of trifluoroacetic acid were added dropwise to a solution of 34.4 g (70 mmol) of tert-butyl 2-chloro-3-(2,4-dichloro-5-(4-chloro-5-difluoromethoxy-1-methyl-1H-pyrazol-3-yl)phenyl)-propenoate in 85 ml of dichloromethane. After 3 hours the mixture was concentrated. The residue was triturated with n-hexane, then filtered off and dried. Yield: 19.9 g.

Example 17

2-Chloro-3-(2,4-dichloro-5-(4-chloro-5-difluoromethoxy-1-methyl-1H-pyrazol-3-yl)phenyl)propenoyl chloride 3 drops of dimethylformamide and then 11.1 g (87 mmol) of oxalyl chloride were added dropwise to a solution of 12.5 g (29 mmol) of 2-chloro-3-(2,4-dichloro-5-(4-chloro-5-difluoromethoxy-1-methyl-1H-pyrazol-3-yl)phenyl) propenoic acid in 300 ml of toluene. The reaction mixture was stirred at reflux temperature for 5 hours and then concentrated. Yield: quantitative.

Example 18

N-Allyl-N-aminocarbonyl-2-chloro-3-(2,4-dichloro-5-(4-chloro-5-difluoromethoxy-1-methyl-1H-pyrazol-3-yl) phenyl)propenamide (Ib.242)

0.36 g (4.4 mmol) of allylcyanamide were added to a suspension of 2 g (4.4 mmol) of 2-chloro-3-(2,4-dichloro-5-(4-chloro-5-difluoromethoxy-1-methyl-1H-pyrazol-3-yl) phenyl)Propenoyl chloride and 0.8 g (5.8 mmol) of potassium carbonate (ground) in 50 ml of tetrahydrofuran. The reaction mixture was stirred at 50 to 60° C. for 5 hours and then concentrated. The residue was taken up in ethyl acetate, after which the organic phase was washed with water, dried over magnesium sulfate and concentrated. The crude product was purified by means of column chromatography on silica gel (eluent: ethyl acetate) followed by crystallization from diisopropyl ether. Yield: 0.2 g.

Example 19

S-(Ethoxycarbonylmethyl) 2-chloro-3-(2,4-dichloro-5-(4-chloro-5-difluoromethoxy-1-methyl-1H-pyrazol-3-yl) phenyl)thiopropenoate (ib.068)

0.95 g (7.3 mmol) of pyridine and 0.88 g (7.3 mmol) of ethyl mercaptoacetate were added to a solution of 3.3 g (6.7 mmol) of 2-chloro-3-(2,4-dichloro-5-{4-chloro-5-difluoromethoxy-1-methyl-1H-pyrazol-3-yl)phenyl) propenoyl chloride in 70 ml of tetrahydrofuran. The reaction mixture was stirred for 8 hours and then concentrated. The crude product was purified by chromatography on silica gel (eluent: hexane/ethyl acetate =1:1). Yield: 2.1 g.

Example 20

4-Acetoxytetrahydrofuran-3-yl 2-chloro-3-(2,4-dichloro-5-(4-chloro-5-difluoromethoxy-1-methyl-1H-pyrazol-3-yl) phenyl)propenoate (Ib.230)

1.0 g (10.2 mmol) of triethylamine and 0.82 g (5.6 mmol) of 4-acetoxytetrahydrofuran-3-ol were added to a solution of 2.3 g (5.1 mmol}of 2-chloro-3-(2,4-dichloro-5-(4-chloro-5-difluoro-methoxy-1-methyl-1H-pyrazol-3-yl)phenyl) propenoyl chloride in 50 ml of ethyl acetate. The reaction was stirred for 5 hours and then washed with water, dried over magnesium sulfate and subsequently concentrated. The crude product was purified by chromatography on silica gel (eluent: hexane/ethyl acetate=2:1). Yield: 0.6 g.

Example 21

N-Ethoxy-2-chloro-3-(2,4-dichloro-5-(4-chloro-5-difluoromethoxy-1-methyl-1H-pyrazol-3-yl)phenyl) propenamide (Ib.064}

0.6 g (3.9 mmol) of carbonyldiimidazole was added to a solution of 1.5 g (3.5 mmol) of 2-chloro-3-(2,4-dichloro-5-(4-chloro-5-difluoromethoxy-1-methyl-1H-pyrazol-3-yl) phenyl)propenoic acid in 50 ml of tetrahydrofuran. The reaction mixture was stirred for 1 hour and then 0.6 g (3.9 mmol) of 0-ethylhydroxylamine hemi-dihydrogen sulfate and 0.4 g (3.9 mmol) of triethylamine were added. The reaction mixture was subsequently stirred overnight and then concentrated. The residue was taken up in ethyl acetate, after which the solution obtained was washed with water, dried over magnesium sulfate and finally concentrated. The crude product was purified by chromatography on silica gel (eluent: hexane/40 ethyl acetate=1:1). Yield: 0.6 g.

Example 22

2-(N-Butoxy) iminoethyl 2-chloro-3-(2,4-dichloro-5-(4-chloro-5-difluoromethoxy-1-methyl-1H-pyrazol-3-yl) phenyl)propenoate (Ib.075)

0.63 g o(4.6 mmol) of ground potassium carbonate followed dropwise by 0.5 g (3.5 mmol) of 0-butyl-2-chloroacetaldehyde oxime were added to a solution of 1.5 g (3.5 mmol) of 2-chloro-3-(2,4-di-chloro-5-(4-chloro-5-difluoromethoxy-1-methyl-1H-pyrazol-3-yl)-phenyl) propenoic acid in 35 ml of dimethylformamide. The mixture was heated at from 50° to 60° C. for 3 hours and then concentrated. The residue was taken up in ethyl acetate, and the resulting organic phase was then washed with water, dried over magnesium sulfate and finally concentrated. The crude product was purified by chromatography on silica gel (eluent: hexane/ethyl acetate=4:1). Yield: 1.1 g.

Example 23 tert-Butyl 2-chloro-3-(2-chloro-5-(4-chloro-5-difluoromethoxy-1-methyl-1H-pyrazol-3-yl)phenyl)propanoate (Ia.118) and tert-butyl 3-(2-chloro-5-(4-chloro-5-difluoromethoxy-1-methyl-1H-pyrazol-3-yl)phenyl)-2-hydroxypropanoate (Ia.173)

14.1 g (0.10 mol) of copper(II) chloride and 14.7 g (0.14 mol) of tert-butyl nitrite were added to 26.1 g (2.03 mol) of tert-butyl acrylate in 500 ml of acetonitrile. 29.3 g (95 mmol) of 3-(3-amino-4-chlorophenyl)-4-chloro-5-difluoromethoxy-1-methyl-1H-pyrazole were subsequently added a little at a time to this mixture, and the resulting mixture was then stirred for 3 hours. tert-Butyl methyl ether was then added to the reaction mixture. The resulting organic phase was subsequently washed with 1N hydrochloric acid and aqueous sodium chloride solution, dried over magnesium sulfate and finally concentrated. The crude product was purified by chromatography on silica gel (eluent:

hexane/ethyl acetate=4:1). Yield: 21.2 g of α-chloro ester Ia.118 and 3.9 g of α-hydroxy ester Ia.173.

Example 24

4-Chloro-3-(4-cyano-3-nitrophenyl)-5-difluoromethoxy-1-methyl-1H-pyrazole 1.1 g (17 mmol) of potassium cyanide were added to a solution of 5.0 g (15.6 mmol) of 4-chloro-3-(4-fluoro-3-nitrophenyl)-5-difluoromethoxy-1-methyl-1H-pyrazole in 70 ml of dimethyl sulfoxide. The solution obtained was then stirred at 50° C. for 5 hours and then at room temperature for 3 days, after which it was poured into ice-water. The product was then extracted from the aqueous phase using methyl tert-butyl ether. The organic phase was finally dried over magnesium sulfate and then concentrated. The crude product was purified by column chromatography on silica gel (eluent: hexane/ethyl acetate=3:1). Yield: 2.7 g;

$^1$H-NMR δ250 MHz, in $CDCl_3$): δ[ppm]=3.88(s,3H); 6.71(t, 1H); 7.95(d,1H); 8.4(m, 1H); 8.93(m,1H).

Example 25

1-Bromomethyl-4-chloro-3-(2,4-dichloro-5-(dibromomethyl)phenyl)-5-difluoromethoxy-1H-pyrazole A solution of 6 g (12 mmol) of 4-chloro-3-(2,4-dichloro-5-(di-bromomethyl)phenyl)-5-difluoromethoxy-1-methyl-1H-pyrazole and 6.4 g (36 mmol) of N-bromosuccinimide in 800 ml of tetrachloromethane was irradiated for 2 hours with a 150 W high-pressure mercury lamp and a UV lamp. The solids were then removed by filtration, and the filtrate was concentrated. Silica gel chromatography of the residue (eluent: hexane/ethyl acetate=4:1) gave 2 g of the target product. $^1$H-NMR (250 MHz, in $CDCl_3$): δ [ppm]=5.87(s, 2H); 6.82(t,1H); 7.03(s,1H); 7.52(s,1H); 8.08(s,1H).

Example 26

4-Chloro-3-(2,4-dichloro-5-(dibromomethyl)phenyl)-5-difluoro-methoxy-1-methoxymethyl-1H-pyrazole 1.3 g (7 mmol) of a 30% strength methanolic sodium methylate solution were added to a solution of 1.2 g (2 mmol) of 1-bromo-methyl-4-chloro-3-(2,4-dichloro-5-(dibromomethyl)phenyl)-5-difluoromethoxy-1H-pyrazole in 30 ml of methanol. The reaction mixture was then heated at reflux temperature for 2.5 hours and then concentrated. The residue was taken up in methyl tert-butyl ether. The ether phase was subsequently washed with water, dried over magnesium sulfate and concentrated. Yield: 0.8 g; $^1$H-NMR (270 MHz, in $CDCl_3$): δ [ppm]=3.45(s,3H); 5.44(s,2H); 6.75(t,1H); 7.05(s,1H); 7.52(s,1H); 8.06(s,1H).

Tables 1–31 below list further compounds I which were prepared in analogy to the Examples or can be prepared either in accordance with the methods described above or by methods which are known per se.

TABLE 1

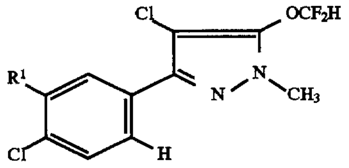

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS($mz^{-1}$) |
|---|---|---|
| Ia.001 | $-CH=C(Cl)-COOH$ | |
| Ia.002 | $-CH=C(Cl)-CO-OCH_3$ | 98–100° C. |
| Ia.003 | $-CH=C(Cl)-CO-OC_2H_5$ | 59–61° C. |
| Ia.004 | $-CH=C(Cl)-CO-OCH(CH_3)_2$ | |
| Ia.005 | $-CH=C(Br)-COOH$ | |
| Ia.006 | $-CH=C(Br)-CO-OCH_3$ | 118–121° C. |
| Ia.007 | $-CH=C(Br)-CO-OC_2H_5$ | |
| Ia.008 | $-CH=C(Br)-CO-OCH(CH_3)_2$ | |
| Ia.009 | $-CH=C(Cl)-CO-NH_2$ | |
| Ia.010 | $-CH=C(Cl)-CO-NH-CH_3$ | |
| Ia.011 | $-CH=C(Cl)-CO-N(CH_3)_2$ | |
| Ia.012 | $-CH=C(Br)-CO-NH_2$ | |
| Ia.013 | $-CH=C(Br)-CO-NH-CH_3$ | |
| Ia.014 | $-CH=C(Br)-CO-N(CH_3)_2$ | |
| Ia.015 | −CH=C(Br)−CO−NH-cyclopropyl | |
| Ia.016 | −CH=C(Cl)−CO−NH-cyclopropyl | |
| Ia.017 | −CH=(cyclopropylene) | |
| Ia.018 | −CH=(cyclopentylene) | |
| Ia.019 | −CH=(cyclohexylene) | |
| Ia.020 | 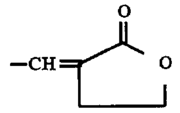 | 140–144° C. |

TABLE 1-continued
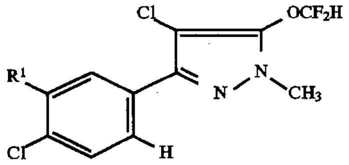
I ($R^2$,$R^5$ = Cl; $R^3$ = $CH_3$;
$R^4$ = $OCF_2H$; $R^6$ = H)
| No. | $R^1$ | m.p./$^1$H-NMR[ppm]/ MS(mz$^{-1}$) |
|---|---|---|
| Ia.021 | 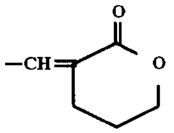 | |
| Ia.022 | 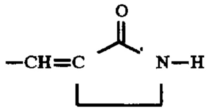 | |
| Ia.023 | 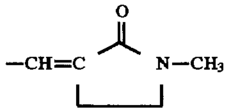 | |
| Ia.024 | 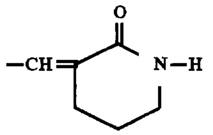 | |
| Ia.025 | 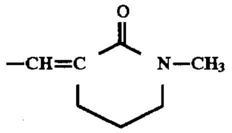 | |
| Ia.026 | 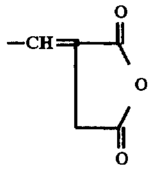 | |
| Ia.027 | 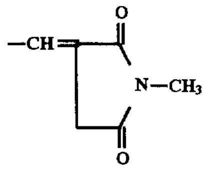 | |
| Ia.028 | $-CH=C(CH_3)-CO-OC_2H_5$ | |
| Ia.029 | $-CH=C(CH_3)-CO-OCH_3$ | |
| Ia.030 | $-CH=C(CH_3)-CO-NH_2$ | |
| Ia.031 | $-CH=C(CH_3)-CO-NH-CH_3$ | |
| Ia.032 | $-CH=C(CH_3)-CO-N(CH_3)_2$ | |
| Ia.033 | $-CH=C(CN)-CO-OCH_3$ | |
| Ia.034 | $-CH_2-CH(CN)-CO-OCH_3$ | |
| Ia.035 | $-CH_2-CH(CN)-CO-OC_2H_5$ | |
| Ia.036 | $-CH_2-CH(CN)-CO-NH_2$ | |
| Ia.037 | $-CH_2-CH(CN)-CO-NH-CH_3$ | |
| Ia.038 | $-CH_2-CH(CN)-CO-N(CH_3)_2$ | |
| Ia.039 | $-CH_2-CH(CN)-CO-NH-SO_2-CH_3$ | |
| Ia.040 | $-CH_2-CH(Cl)-CO-OCH_3$ | 7.84(s, 1H); 7.77(d, 1H); |

TABLE 1-continued

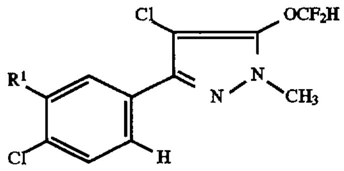

I ($R^2$,$R^5$ = Cl; $R^3$ = $CH_3$;
$R^4$ = $OCF_2H$; $R^6$ = H)

| No. | $R^1$ | m.p./$^1$H-NMR[ppm]/ MS(mz$^{-1}$) |
| --- | --- | --- |
| | | 7.58(d, 1H); 6.72(t, 1H); 4.68(t, 1H); 3.83(s, 3H); 3.75(s, 3H); 3.59–3,36 (m, 2H) |
| Ia.041 | $-CH_2-CH(Cl)-CO-OC_2H_5$ | 7.84(s, 1H); 7.76(d, 1H); 7.44(d, 1H); 6.70(t, 1H); 4.65(t, 1H); 4.22(q, 2H); 3.80(s, 3H); 3.58–3,37 (m, 2H); 1.25(t, 3H) |
| Ia.042 | $-CH_2-CH(Cl)-CO-NH_2$ | |
| Ia.043 | $-CH_2-CH(Cl)-CO-NH-CH_3$ | |
| Ia.044 | $-CH_2-CH(Cl)-CO-N(CH_3)_2$ | |
| Ia.045 | $-CH_2-CH(Cl)-CO-NH-SO_2-CH_3$ | |
| Ia.046 | $-CH_2-CH(Br)-CO-OCH_3$ | 7.82(s, 1H); 7.76(d, 1H); 7.45(d, 1H); 6.69(t, 1H); 4.62(t, 1H); 3.83(s, 3H); 3.74(s, 3H); 3.64(dd, 1H); 3.45(dd, 1H) |
| Ia.047 | $-CH_2-CH(Br)-CO-OC_2H_5$ | 7.82(s, 1H); 7.75(d, 1H), 7.42(d, 1H); 6.67(t, 1H); 4.61(t, 1H); 4.25–4.10 (m, 2H); 3.80(s, 3H); 3.60(dd, 1H); 3.42(dd, 1H); 1.26(t, 3H) |
| Ia.048 | $-CH_2-CH(Br)-CO-OCH(CH_3)_2$ | |
| Ia.049 | $-CH_2-CH(Br)-CO-NH_2$ | |
| Ia.050 | $-CH_2-CH(Br)-CO-NH-CH_3$ | |
| Ia.051 | $-CH_2-CH(Br)-CO-N(CH_3)_2$ | |
| Ia.052 | $-CH_2-CH(Cl)-CO-CH(CH_3)_2$ | |
| Ia.053 | $-CH_2-CH(CN)-CO-CH(CH_3)_2$ | |
| Ia.054 | $-CH=CH$-(4-fluorophenyl) | |
| Ia.055 | $-CH=CH$-(4-chlorophenyl) | 96–98° C. |
| Ia.056 | $-CH=CH$-(3-trifluoromethylphenyl) | 462[M]$^+$ |
| Ia.057 | $-CH=CH$-(2,4-dichlorophenyl) | |
| Ia.058 | $-CH=C(Cl)-CO-$O-cyclohexyl | |
| Ia.059 | $-CH=C(Cl)-CO-OC(CH_3)_3$ | |
| Ia.060 | $-CH=C(Cl)-CO-OCH_2-CH(CH_3)_2$ | |
| Ia.061 | $-CH=C(Cl)-CO-NH-CH_2-CO-OCH_3$ | |
| Ia.062 | $-CH=C(Cl)-CO-N(CH_3)-CH_2-CO-OCH_3$ | |
| Ia.063 | $-CH=C(Cl)-CO-NH-CH(CH_3)-CO-OC_2H_5$ | |
| Ia.064 | $-CH=C(Cl)-CO-NH-OC_2H_5$ | |
| Ia.065 | $-CH-C(Cl)-CO-NH-OCH_3$ | |
| Ia.066 | $-CH=C(Cl)-CO-NH-OCH_2-CH=CHCl$ | |
| Ia.067 | $-CH=C(Cl)-CO-NH-OCH_2$-(4-chlorophenyl) | |
| Ia.068 | $-CH=C(Cl)-CO-SCH_2-CO-OC_2H_5$ | |
| Ia.069 | $-CH=C(Cl)-CO-SCH_2-C_2H_5$ | |
| Ia.070 | $-CH=C(Cl)-CO-SCH_2$-(4-chlorophenyl) | |
| Ia.071 | $-CH=C(CO-OC_2H_5)_2$ | |
| Ia.072 | $-CH=C(CO-OCH_3)_2$ | |
| Ia.073 | $-CH=C(Cl)-CO-OCH_2-CH=N-OCH_3$ | |
| Ia.074 | $-CH=C(Cl)-CO-OCH_2-CH=N-OC_2H_5$ | |
| Ia.075 | $-CH=C(Cl)-CO-OCH_2-CH=N-OCH_2-CH_2-C_2H_5$ | |
| Ia.076 | $-CH=C(Cl)-CO-OCH_2-CH=N-O-CH_2$-phenyl | |
| Ia.077 | $-CH=C(Br)-CO-$O-cyclohexyl | |
| Ia.078 | $-CH=C(Br)-CO-OC(CH_3)_3$ | |
| Ia.079 | $-CH=C(Br)-CO-OCH_2-CH(CH_3)_2$ | |
| Ia.080 | $-CH=C(Br)-CO-NH-CH_2-CO-OCH_3$ | |
| Ia.081 | $-CH=C(Br)-CO-N(CH_3)-CH_2-CO-OCH_3$ | |
| Ia.082 | $-CH=C(Br)-CO-NH-OC_2H_5$ | |
| Ia.083 | $-CH=C(Br)-CO-NH-OCH_3$ | |
| Ia.084 | $-CH=C(Br)-CO-NH-OCH_2-CH=CHCl$ | |
| Ia.085 | $-CH=C(Br)-CO-NH-OCH_2$-(4-chlorophenyl) | |
| Ia.086 | $-CH=C(Br)-CO-SCH_2-CO-OC_2H_5$ | |
| Ia.087 | $-CH=C(Br)-CO-SCH_2-C_2H_5$ | |

TABLE 1-continued

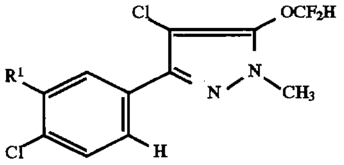

I ($R^2$,$R^5$ = Cl; $R^3$ = $CH_3$;
$R^4$ = $OCF_2H$; $R^6$ = H)

| No. | $R^1$ | m.p./$^1$H-NMR[ppm]/ MS($mz^{-1}$) |
|---|---|---|
| Ia.088 | $-CH=C(Br)-CO-SCH_2$-(4-chlorophenyl) | |
| Ia.089 | $-CH=C(Br)-CO-OCH_2-CH=N-OCH_2-CH=CH_2$ | |
| Ia.090 | $-CH=C(Br)-CO-OCH_2-CH=N-OCH_2-CH=CHCl$ | |
| Ia.091 | $-CH=C(Br)-CO-OCH_2-CH=N-OCH_3$ | |
| Ia.092 | $-CH=C(Br)-CO-OCH_2-CH=N-OC_2H_5$ | |
| Ia.093 | $-CH=C(Br)-CO-OCH_2-CH=N-OCH_2-CH_2-C_2H_5$ | |
| Ia.094 | $-CH=C(Br)-CO-OCH_2-CH=N-OCH_2$-phenyl | |
| Ia.095 | $-CH_2-CH(Cl)-CO-O$-cyclohexyl | 7.80(s, 1H); 7.75(d, 1H); 7.44(d, 1H); 6.71(t, 1H); 4.80(m, 1H); 4.60(t, 1H); 3.81(s, 3H); 4.55–3.36 (m, 2H); 1.84–1.29 (m, 10H) |
| Ia.096 | $-CH_2-CH(Cl)-CO-OC(CH_3)_3$ | 7.84(s, 1H); 7.77(d, 1H); 7.57(d, 1H); 6.71(t, 1H); 4.58(t, 1H); 3.84(s, 3H); 3.52–3,34(m, 2H); 1.44(s, 9H) |
| Ia.097 | $-CH_2-CH(Cl)-CO-OCH_2-CH(CH_3)_2$ | 7.83(s, 1H); 7.77(d, 1H); 7.45(d, 1H); 6.70(t, 1H); 4.67(t, 1H); 3.94(m, 2H); 3.79(s, 3H); 3.55–3.38 (m, 2H); 1.96(m, 1H); 0.97–0.89(m, 6H) |
| Ia.098 | $-CH_2-CH(Cl)-CO-NH-CH_2-CO-OCH_3$ | 97° C. |
| Ia.099 | $-CH_2-CH(Cl)-CO-N(CH_3)-CH_2-CO-OCH_3$ | 484[M+H]$^+$, 448[M–Cl]$^+$ |
| Ia.100 | $-CH_2-CH(Cl)-CO-NH-CH(CH_3)-CO-OC_2H_5$ | 76–78° C. |
| Ia.101 | $-CH_2-CH(Cl)-CO-NH-OC_2H_5$ | 441[M]$^+$, 406[M–Cl]$^+$ |
| Ia.102 | $-CH_2-CH(Cl)-CO-NH-OCH_3$ | |
| Ia.103 | $-CH_2-CH(Cl)-CO-NH-CCH_2-CH=CHCl$ | 487[M]$^+$, 452[M–Cl]$^+$ |
| Ia.104 | $-CH_2-CH(Cl)-CO-NH-OCH_2$-(4-chlorophenyl) | |
| Ia.105 | $-CH_2-CH(Cl)-CO-SCH_2-CO-OC_2H_5$ | 500[M]$^+$, 465[M–Cl]$^+$ |
| Ia.106 | $-CH_2-CH(Cl)-CO-SCH_2-C_2H_5$ | |
| Ia.107 | $-CH_2-CH(Cl)-CO-SCH_2$-(4-chlorophenyl) | |
| Ia.108 | $-CH_2-C(Cl)(CO-OC_2H_5)_2$ | |
| Ia.109 | $-CH_2-C(Cl)(CO-OCH_3)_2$ | |
| Ia.110 | $-CH_2-CH(Cl)-CO-OCH_2-CH=N-OCH_3$ | |
| Ia.111 | $-CH_2-CH(Cl)-CO-OCH_2-CH=N-OC_2H_5$ | 483[M]$^+$, 448[M–Cl]$^+$ |
| Ia.112 | $-CH_2-CH(Cl)-CO-OCH_2-CH=N-OCH_2-CH_2-C_2H_5$ | |
| Ia.113 | $-CH_2-CH(Cl)-CO-OCH_2-CH=N-OCH_2$-phenyl | |
| Ia.114 | $-CH_2-CH(Cl)-CO-OCH_2-CH=N-OCH_2-CH=CH_2$ | |
| Ia.115 | $-CH_2-CH(Cl)-CO-OCH_2-CH=N-OCH_2-CH=CHCl$ | 487[M]$^+$, 452[M–Cl]$^+$ |
| Ia.116 | $-CH_2-CH(Cl)-CO-OCH_2-CH=N-OCH_2$-(4-chlorophenyl) | |
| Ia.117 | $-CH_2-CH(Cl)-CO-OCH_2-CH=N-OCH(CH_3)$-(4-chlorophenyl) | |
| Ia.118 | $-CH_2-CH(Cl)-COOH$ | 7.85(s, 1H); 7.78(d, 1H); 7.60(d, 1H); 7.48(t, 1H); 4.72(t, 1H); 3.80(s, 3H); 3.58–3.30(m, 2H) |
| Ia.119 | $-CH_2-CH(Cl)-CO-NH$-cyclopropyl | 104–105° C. |
| Ia.120 | $-CH_2-CH(Cl)-CO-N(CH_3)-CH_2-CO-OC_2H_5$ | 497[M]$^+$, 462[M–Cl]$^+$ |
| Ia.121 | $-CH_2-CH(Cl)-CO-NH-CH(CH(CH_3)_2)-CO-OC_2H_5$ | 525[M]$^+$, 490[M–Cl]$^+$ |
| Ia.122 | $-CH_2-CH(Cl)-CO-NH-CH(CH_2CH(CH_3)_2)-CO-OCH_3$ | 8.78(m, 1H); 7.75(m, 1H); 7.58(m, 1H); 7.47(t, 1H):; 4.75(m, 1H); 4.37–4.16 (m, 1H); 3.80(s, 3H); 3.61–3.48(m, 2H); 3.35–3.20(m, 2H), 1.60–1.05(m, 3H); 0.90–0.52(m, 6H) |
| Ia.123 | $-CH_2-CH(Cl)-CO$-(2-methoxycarbonyl-pyrrolidin-1-yl) | 509[M]$^+$, 474[M–Cl]$^+$ |
| Ia.124 | $-CH_2-CH(Cl)-CO-NH$-(tetrahydrofuran-2-on-3-yl) | |
| Ia.125 | $-CH_2-CH(Cl)-CO-N(CN)-CH_2CH_2-C_2H_5$ | |
| Ia.126 | $-CH_2-CH(Cl)-CO-N(CN)$-cyclopropyl | |
| Ia.127 | $-CH_2-CH(Cl)-CO-N(CN)-CH_2-CH=CH_2$ | |

TABLE 1-continued

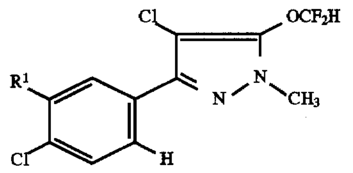

I ($R^2$,$R^5$ = Cl; $R^3$ = $CH_3$;
$R^4$ = $OCF_2H$; $R^6$ = H)

| No. | $R^1$ | m.p./$^1$H-NMR[ppm]/ MS(mz$^{-1}$) |
|---|---|---|
| Ia.128 | $-CH_2-CH(Cl)-CO-N(CONH_2)-CH_2CH_2-C_2H_5$ | |
| Ia.129 | $-CH_2-CH(Cl)-CO-N(CONH_2)$-cyclopropyl | |
| Ia.130 | $-CH_2-CH(Cl)-CO-N(CONH_2)-CH_2-CH=CH_2$ | |
| Ia.131 | $-CH_2-CH(Cl)-CO-$O-(4-acetoxytetra-hydrofuran-3-yl) | |
| Ia.132 | $-CH_2-CH(Br)-CO-$O-cyclohexyl | 7.84(s, 1H); 7.76(d, 1H); 7.45(d, 1H); 6.72(t, 1H); 4.80(m, 1H); 4.61(t, 1H) 3.85(s, 3H); 3.63–3.48 (m, 2H); 1.88–1.28 (m, 10H) |
| Ia.133 | $-CH_2CH(Br)-CO-OC(CH_3)_3$ | 7.83(s, 1H); 7.76(d, 1H); 7.44(d, 1H); 6.70(t, 1H); 4.53(t, 1H); 3.84(s, 3H); 3.58–3.42(m, 2H); 1.43(s, 9H) |
| Ia.134 | $-CH_2-CH(Br)-CO-OCH_2-CH(CH_3)_2$ | 7.82(s, 1H); 7.75(d, 1H); 7.44(d, 1H); 6.70(t, 1H); 4.66(t, 1H); 3.92(m, 2H) 3.80(s, 3H); 3.62–3.45 (m, 2H); 1.96(m, 1H) 0.93(m, 6H) |
| Ia.135 | $-CH_2-CH(Br)-CO-NH-CH_2-CO-OCH_3$ | 102–103° C. |
| Ia.136 | $-CH_2-CH(Br)-CO-N(CH_3)-CH_2-CO-OCH_3$ | |
| Ia.137 | $-CH_2-CH(Br)-CO-NH-CH(CH_3)-CO-OC_2H_5$ | 541[M]$^+$, 506[M–Cl]$^+$ |
| Ia.138 | $-CH_2-CH(Br)-CO-NH-OC_2H_5$ | |
| Ia.139 | $-CH_2-CH(Br)-CO-NH-OCH_3$ | |
| Ia.140 | $-CH_2-CH(Br)-CO-NH-OCH_2-CH=CHCl$ | |
| Ia.141 | $-CH_2-CH(Br)-CO-NH-OCH_2$-(4-chlorophenyl) | |
| Ia.142 | $-CH-CH(Br)-CO-SCH_2-CO-OC_2H_5$ | |
| Ia.143 | $-CH_2-CH(Br)-CO-SCH_2-C_2H_5$ | |
| Ia.144 | $-CH_2-CH(Br)-CO-SCH_2$-(4-chlorophenyl) | |
| Ia.145 | $-CH_2-C(Br)(CO-OC_2H_5)_2$ | |
| Ia.146 | $-CH_2-C(Br)(CO-OCH_3)_2$ | |
| Ia.147 | $-CH_2-CH(Br)-CO-OCH_2-CH=N-OCH_3$ | |
| Ia.148 | $-CH_2-CH(Br)-CO-OCH_2-CH=N-OC_2H_5$ | |
| Ia.149 | $-CH_2-CH(Br)-CO-OCH_2-CH=N-OCH_2CH_2-C_2H_5$ | |
| Ia.150 | $-CH_2-CH(Br)-CO-OCH_2-CH=N-OCH_2$-phenyl | |
| Ia.151 | $-CH_2-CH(Br)-CO-OCH_2-CH=N-OCH_2-CH=CH_2$ | |
| Ia.152 | $-CH_2-CH(Br)-CO-OCH_2-CH=N-OCH_2-CH=CHCl$ | |
| Ia.153 | $-CH_2-CH(Br)-CO-OCH_2-CH=N-OCH_2$-(4-chlorophenyl) | |
| Ia.154 | $-CH_2-CH(Br)-CO-OCH_2-CH=N-OCH(CH_3)$-(4-chlorophenyl) | |
| Ia.155 | $-CH_2-CH(Br)-COOH$ | 7.91(s, 1H), 7.70(d, 1H); 7.47(d, 1H); 6.72(t, 1H); 4.66(t, 1H); 3.86(s, 3H); 3.68–3.43(m, 2H) |
| Ia.156 | $-CH_2-CH(Br)-CO-$NH-cyclopropyl | 121–122° C. |
| Ia.157 | $-CH_2-CH(Br)-CO-N(CH_3)-CH_2-CO-OC_2H_5$ | 541[M]$^+$, 462[M–Br]$^+$ |
| Ia.158 | $-CH_2-CH(Br)-CO-NH-CH(CH(CH_3)_2)-CO-OC_2H_5$ | 569[M]$^+$, 490[M–Br]$^+$ |
| Ia.159 | $-CH_2-CH(Br)-CO-NH-CH(CH_2CH(CH_3)_2)-CO-OCH_3$ | 569[M]$^+$, 534[M–Cl]$^+$ |
| Ia.160 | $-CH_2-CH(Br)-$CO-(2-methoxycarbonyl-pyrrolidin-1-yl) | 553[M]$^+$, 474[M–Br]$^+$ |
| Ia.161 | $-CH_2-CH(Br)-CO-$NH-(tetrahydro-furan-2-on-3-yl) | |
| Ia.162 | $-CH_2-CH(Br)-CO-N(CN)-CH_2CH_2-C_2H_5$ | |
| Ia.163 | $-CH_2-CH(Br)-CO-N(CN)$-cyclopropyl | |
| Ia.164 | $-CH_2-CH(Br)-CO-N(CN)-CH_2-CH=CH_2$ | |
| Ia.165 | $-CH_2-CH(Br)-CO-N(CONH_2)-CH_2CH_2-C_2H_5$ | |
| Ia.166 | $-CH_2-CH(Br)-CO-N(CONH_2)$-cyclopropyl | |
| Ia.167 | $-CH_2-CH(Br)-CO-N(CONH_2)-CH_2-CH=CH_2$ | |
| Ia.168 | $-CH_2-CH(Br)-CO-$O-(4-acetoxytetra-hydrofuran-3-yl) | |
| Ia.169 | $-CH_2-CH(OH)-COOH$ | |
| Ia.170 | $-CH_2-CH(OH)-CO-OCH_3$ | |
| Ia.171 | $-CH_2-CH(OH)-CO-OC_2H_5$ | |
| Ia.172 | $-CH_2-CH(OH)-CO-OCH_2-CH=N-OCH_3$ | |
| Ia.173 | $-CH_2-CH(OH)-CO-OC(CH_3)_3$ | 436[M]$^+$ |
| Ia.174 | $-CH_2-CH(OH)-CO-NH_2$ | |

TABLE 1-continued

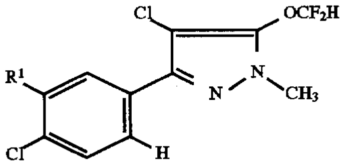

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS($mz^{-1}$) |
|---|---|---|
| Ia.175 | $-CH_2-CH(OH)-CO-NH-CH_3$ | |
| Ia.176 | $-CH_2-CH(OH)-CO-$NH-cyclopropyl | |
| Ia.177 | $-CH_2-CH(OCH_3)-COOH$ | 394[M]$^+$ |
| Ia.178 | $-CH_2-CH(OCH_3)-CO-OCH_3$ | |
| Ia.179 | $-CH_2-CH(OCH_3)-CO-OC_2H_5$ | |
| Ia.180 | $-CH_2-CH(OCH_3)-CO-OCH_2-CH=N-OCH_3$ | |
| Ia.181 | $-CH_2-CH(OCH_3)-CO-OC(CH_3)_3$ | 450[M]$^+$ |
| Ia.182 | $-CH_2-CH(OCH_3)-CO-NH_2$ | |
| Ia.183 | $-CH_2-CH(OCH_3)-CO-NH-CH_3$ | |
| Ia.184 | $-CH_2-CH(OCH_3)-CO-$NH-cyclopropyl | |
| Ia.185 | $-CH_2-CH(O-COCH_3)-COOH$ | |
| Ia.186 | $-CH_2-CH(O-COCH_3)-CO-OCH_3$ | |
| Ia.187 | $-CH_2-CH(O-COCH_3)-CO-OC_2H_5$ | |
| Ia.188 | $-CH_2-CH(O-COCH_3)-CO-OCH_2-CH=N-OCH_3$ | |
| Ia.189 | $-CH_2-CH(O-COCH_3)-CO-OC(CH_3)_3$ | |
| Ia.190 | $-CH_2-CH(O-COCH_3)-CO-NH_2$ | |
| Ia.191 | $-CH_2-CH(O-COCH_3)-CO-NH-CH_3$ | |
| Ia.192 | $-CH_2-CH(O-COCH_3)-CO-$NH-cyclopropyl | |
| Ia.193 | $-CH_2-CH(NH_2)-COOH$ | |
| Ia.194 | $-CH_2-CH(NH_2)-CO-OCH_3$ | |
| Ia.195 | $-CH_2-CH(NH_2)-CO-OC_2H_5$ | |
| Ia.196 | $-CH_2-CH(NH_2)-CO-OC(CH_3)_3$ | |
| Ia.197 | $-CH_2-CH(NH_2)-CO-NH_2$ | |
| Ia.198 | $-CH_2-CH(NH_2)-CO-NH-CH_3$ | |
| Ia.199 | $-CH_2-CH(N_3)-COOH$ | |
| Ia.200 | $-CH_2-CH(N_3)-CO-OCH_3$ | |
| Ia.201 | $-CH_2-CH(N_3)-CO-OC_2H_5$ | |
| Ia.202 | $-CH_2-CH(N_3)-CO-OC(CH_3)_3$ | |
| Ia.203 | $-CH_2-CH(N_3)-CO-NH_2$ | |
| Ia.204 | $-CH_2-CH(N_3)-CO-NH-CH_3$ | |
| Ia.205 | $-CH_2-CH(NH-COCH_3)-COOH$ | |
| Ia.206 | $-CH_2-CH(NH-COCH_3)-CO-OCH_3$ | |
| Ia.207 | $-CH_2-CH(NH-COCH_3)-CO-OC_2H_5$ | |
| Ia.208 | $-CH_2-CH(NH-COCH_3)-CO-OC(CH_3)_3$ | |
| Ia.209 | $-CH_2-CH(NH-COCH_3)-CO-NH_2$ | |
| Ia.210 | $-CH_2-CH(NH-COCH_3)-CO-NH-CH_3$ | |
| Ia.211 | $-CH_2-CH_2$-cyclohexyl | |
| Ia.212 | $-CH_2-CH_2$-cyclopentyl | |
| Ia.213 | $-CH_2-CH_2$-cyclopropyl | |
| Ia.214 | $-CH_2-CH_2$-phenyl | |
| Ia.215 | $-CH=C(CN)-CO-OC_2H_5$ | |
| Ia.216 | $-CH=C(CN)-CO-OCH(CH_3)_2$ | |
| Ia.217 | $-CH=C(CN)-CO-OC(CH_3)_3$ | |
| Ia.218 | $-CH=C(Cl)-CO-OCH_2-CH=N-OCH_2-CH=CH_2$ | |
| Ia.219 | $-CH=C(Cl)-CO-OCH_2-CH=N-OCH_2-CH=CHCl$ | |
| Ia.220 | $-CH=C(Cl)-CO-OCH_2-CH=N-OCH_2$-4-chlorophenyl) | |
| Ia.221 | $-CH=C(Cl)-CO-OCH_2-CH=N-OCH(CH_3)$-(4-chlorophenyl) | |
| Ia.222 | $-CH=C(Cl)-CO-O-$(4-acetoxytetrahydrofuran-3-yl) | |
| Ia.223 | $-CH=C(Cl)-CO-$NH-cyclohexyl | |
| Ia.224 | $-CH=C(Cl)-CO-N(CH_3)-CH_2-CO-OC_2H_5$ | |
| Ia.225 | $-CH=C(Cl)-CO-NH-CH(CH(CH_3)_2)-CO-OC_2H_5$ | |
| Ia.226 | $-CH=C(Cl)-CO-NH-CH(CH_2CH(CH_3)_2)-CO-OCH_3$ | |
| Ia.227 | $-CH=C(Cl)-CO$-(2-methoxycarbonyl-pyrrolidin-1-yl) | |
| Ia.228 | $-CH=C(Cl)-CO-NH-$(tetrahydrofuran-2-on-3-yl) | |
| Ia.229 | $-CH=C(Cl)-CO-N(CN)-CH_2CH_2-C_2H_5$ | |
| Ia.230 | $-CH=C(Cl)-CO-N(CN)$-cyclopropyl | |
| Ia.231 | $-CH=C(Cl)-CO-N(CN)-CH_2-CH=CH_2$ | |
| Ia.232 | $-CH=C(Cl)-CO-N(CONH_2)-CH_2CH_2-C_2H_5$ | |
| Ia.233 | $-CH=C(Cl)-CO-N(CONH_2)$-cyclopropyl | |
| Ia.234 | $-CH=C(Cl)-CO-N(CONH_2)-CH_2-CH=CH_2$ | |
| Ia.235 | $-CH=C(Br)-CO-OCH_2-CH=N-OCH_2$-(4-chlorophenyl) | |
| Ia.236 | $-CH=C(Br)-CO-OCH_2-CH=N-OCH(CH_3)$-(4-chlorophenyl) | |
| Ia.237 | $-CH=C(Br)-CO-O-$(4-acetoxytetrahydrofuran-3-yl) | |
| Ia.238 | $-CH=C(Br)-CO-$NH-cyclohexyl | |

TABLE 1-continued

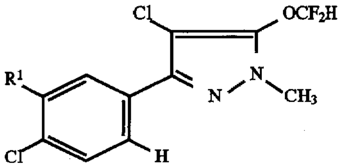

I ($R^2$,$R^5$ = Cl; $R^3$ = $CH_3$;
$R^4$ = $OCF_2H$; $R^6$ = H)

| No. | $R^1$ | m.p./$^1$H-NMR[ppm]/ MS($mz^{-1}$) |
|---|---|---|
| Ia.239 | $-CH=C(Br)-CO-N(CH_3)-CH_2-CO-OC_2H_5$ | |
| Ia.240 | $-CH=C(Br)-CO-NH-CH(CH(CH_3)_2)-CO-OC_2H_5$ | |
| Ia.241 | $-CH=C(Br)-CO-NH-CH(CH_2CH(CH_3)_2)-CO-OCH_3$ | |
| Ia.242 | $-CH=C(Br)$ $-CO-$(2-methoxycarbonyl-pyrrolidin-1-yl) | |
| Ia.243 | $-CH=C(Br)-CO-$NH-(tetrahydrofuran-2-on-3-yl) | |
| Ia.244 | $-CH=C(Br)-CO-N(CN)-CH_2CH_2-C_2H_5$ | |
| Ia.245 | $-CH=C(Br)-CO-N(CN)$-cyclopropyl | |
| Ia.246 | $-CH=C(Br)-CO-N(CN)-CH_2-CH=CH_2$ | |
| Ia.247 | $-CH=C(Br)-CO-N(CONH_2)-CH_2CH_2-C_2H_5$ | |
| Ia.248 | $-CH=C(Br)-CO-N(CONH_2)$-cyclopropyl | |
| Ia.249 | $-CH=C(Br)-CO-N(CONH_2)-CH_2-CH=CH_2$ | |
| Ia.250 | $-CH_2-CH(Cl)-CO-N(C_2H_5)_2$ | |
| Ia.251 | $-CH_2-CH(Br)-CO-N(C_2H_5)_2$ | |
| Ia.252 | $-CH=C(Br)-CO-N(C_2H_5)_2$ | |
| Ia.253 | $-CH=C(Cl)-CO-N(C_2H_5)_2$ | |
| Ia.254 | 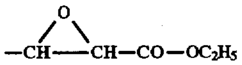 | |
| Ia.255 | 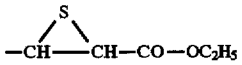 | |
| Ia.256 | 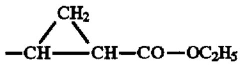 | |
| Ia.257 | 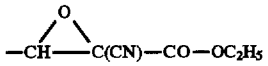 | |
| Ia.258 | 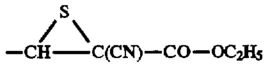 | |
| Ia.259 | 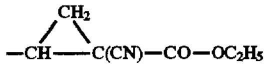 | |
| Ia.260 | 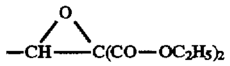 | |
| Ia.261 | 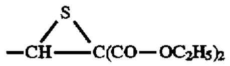 | |
| Ia.262 | 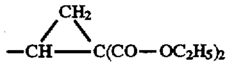 | |

TABLE 2

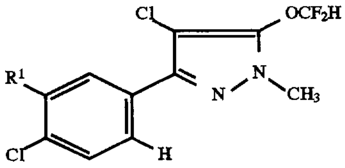

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS[$mz^{-1}$] |
|---|---|---|
| Ib.001 | $-CH=C(Cl)-COOH$ | 182–185° C. |
| Ib.002 | $-CH=C(Cl)-CO-OCH_3$ | 8.10(s, 1H); 8.07(s, 1H); 7.62(s, 1H); 6.74(t, 1H); 3.95/s, 3H); 3.85(s, 3H) |
| Ib.003 | $-CH=C(Cl)-CO-OC_2H_5$ | 110–112° C. |
| Ib.004 | $-CH=C(Cl)-CO-OCH(CH_3)_2$ | |
| Ib.005 | $-CH=C(Br)-COOH$ | |
| Ib.006 | $-CH=C(Br)-CO-OCH_3$ | 8.30(s, 1H); 8.00(s, 1H); 7.60(s, 1H); 6.72(t, 1H); 3.94(s, 3H); 3.86(s, 3H) |
| Ib.007 | $-CH=C(Br)-CO-OC_2H_5$ | |
| Ib.008 | $-CH=C(Br)-CO-OCH(CH_3)_2$ | |
| Ib.009 | $-CH=C(Cl)-CO-NH_2$ | |
| Ib.010 | $-CH=C(Cl)-CO-NH-CH_3$ | |
| Ib.011 | $-CH=C(Cl)-CO-N(CH_3)_2$ | |
| Ib.012 | $-CH=C(Br)-CO-NH_2$ | |
| Ib.013 | $-CH=C(Br)-CO-NH-CH_3$ | |
| Ib.014 | $-CH=C(Br)-CO-N(CH_3)$ | |
| Ib.015 | $-CH=C(Br)-CO-$NH-cyclopropyl | |
| Ib.016 | $-CH=C(Cl)-CO-$NH-cyclopropyl | 78–81° C. |
| Ib.017 | $-CH=$(cyclopropylene) | |
| Ib.018 | $-CH=$(cyclopentylene) | |
| Ib.019 | $-CH=$(cyclohexylene) | |
| Ib.020 | 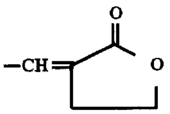 | 169–171° C. |
| Ib.021 | 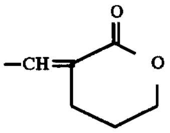 | |
| Ib.022 | 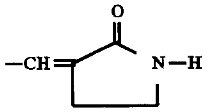 | |
| Ib.023 | 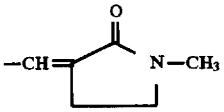 | |
| Ib.024 | 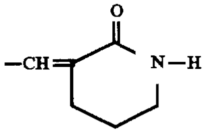 | |
| Ib.025 | 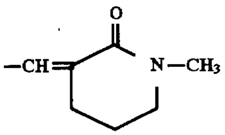 | |

TABLE 2-continued

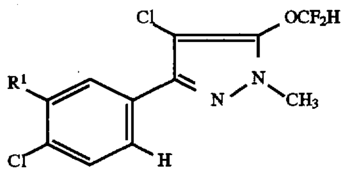

I ($R^2$,$R^5$=Cl; $R^3$=$CH_3$; $R^4$=$OCF_2H$; $R^6$=H)

| No. | $R^1$ | m.p./$^1$H-NMR[ppm]/ MS[$mz^{-1}$] |
|---|---|---|
| Ib.026 | 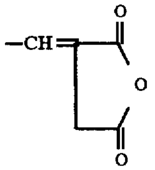 | |
| Ib.027 | 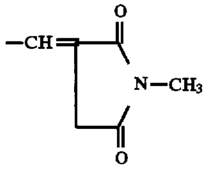 | |
| Ib.028 | $-CH{=}C(CH_3)-CO-OC_2H_5$ | |
| Ib.029 | $-CH{=}C(CH_3)-CO-OCH_3$ | |
| Ib.030 | $-CH{=}C(CH_3)-CO-NH_2$ | |
| Ib.031 | $-CH{=}C(CH_3)-CO-NH-CH_3$ | |
| Ib.032 | $-CH{=}C(CH_3)-CO-N(CH_3)_2$ | |
| Ib.033 | $-CH{=}C(CN)-CO-OCH_3$ | |
| Ib.034 | $-CH_2-CH(CN)-CO-OCH_3$ | |
| Ib.035 | $-CH_2-CH(CN)-CO-OC_2H_5$ | |
| Ib.036 | $-CH_2-CH(CN)-CO-NH_2$ | |
| Ib.037 | $-CH_2-CH(CN)-CO-NH-CH_3$ | |
| Ib.038 | $-CH_2-CH(CN)-CO-N(CH_3)_2$ | |
| Ib.039 | $-CH_2-CH(CN)-CO-NH-SO_2-CH_3$ | |
| Ib.040 | $-CH_2-CH(Cl)-CO-OCH_3$ | 7.52(s, 1H); 7.36(s, 1H); 6.71(t, 1H); 4.60(t, 1H); 3.84(s, 3H); 3.75(s, 3H); 3.50(dd, 1H); 3.28(dd, 1H) |
| Ib.041 | $-CH_2-CH(Cl)-CO-OC_2H_5$ | 7.54(s, 1H); 7.36(s, 1H); 6.73(t, 1H); 4.59(t, 1H); 4.25–4,15(m, 2H); 3.85(s, 3H); 3.50(dd, 1H); 3.30(dd, 1H); 1.25(s, 3H) |
| Ib.042 | $-CH_2-CH(Cl)-CO-NH_2$ | |
| Ib.043 | $-CH_2-CH(Cl)-CO-NH-CH_3$ | |
| Ib.044 | $-CH_2-CH(Cl)-CO-N(CH_3)_2$ | |
| Ib.045 | $-CH_2-CH(Cl)-CO-NH-SO_2-CH_3$ | |
| Ib.046 | $-CH_2-CH(Br)-CO-OCH_3$ | 7.52(s, 1H); 7.34(s, 1H); 6.71(t, 1H); 4.55(t, 1H); 3.82(s, 3H); 3.74(s, 3H); 3.55(dd, 1H); 3.36(dd, 1H) |
| Ib.047 | $-CH_2-CH(Br)-CO-OC_2H_5$ | 7.52(s, 1H); 7.36(s, 1H); 6.70(t, 1H); 4.53(t, 1H); 4.28–4,10(m, 2H); 3.84(s, 3H); 3.56(dd, 1H); 3.39(dd, 1H); 1.25(t, 3H) |
| Ib.048 | $-CH_2-CH(Br)-CO-OCH(CH_3)_2$ | |
| Ib.049 | $-CH_2-CH(Br)-CO-NH_2$ | |
| Ib.050 | $-CH_2-CH(Br)-CO-NH-CH_3$ | |
| Ib.051 | $-CH_2-CH(Br)-CO-N(CH_3)_2$ | |
| Ib.052 | $-CH_2-CH(Cl)-CO-CH(CH_3)_2$ | |
| Ib.053 | $-CH_2-CH(CN)-CO-CH(CH_3)_2$ | |
| Ib.054 | $-CH{=}CH$-(4-fluorophenyl) | 446[M]$^+$ |
| Ib.055 | $-CH{=}CH$-(4-chlorophenyl) | 462[M]$^+$ |
| Ib.056 | $-CH{=}CH$-(4-trifluoromethylphenyl) | |
| Ib.057 | $-CH{=}CH$-(2,4-dichlorophenyl) | |

TABLE 2-continued

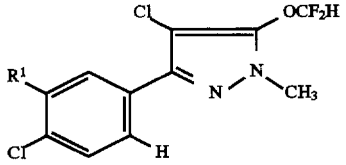

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS[$mz^{-1}$] |
|---|---|---|
| Ib.058 | $-CH=C(Cl)-CO-O$-cyclohexyl | |
| Ib.059 | $-CH=C(Cl)-CO-OC(CH_3)_3$ | 8.08(s, 1H); 8.01(s, 1H); 7.60(s, 1H); 6.73(t, 1H); 3.86(s, 3H); 1.60(s, 9H) |
| Ib.060 | $-CH=C(Cl)-CO-OCH_2-CH(CH_3)_2$ | |
| Ib.061 | $-CH=C(Cl)-CO-NH-CH_2-CO-OCH_3$ | |
| Ib.062 | $-CH=C(Cl)-CO-N(CH_3)-CH_2-CO-OCH_3$ | 7.90(m, 1H); 7.59(s, 1H); 7.15–7,04(m, 1H); 6.72(t, 1H); 4.22(s, 2H); 3.85(s, 3H); 3.80(s, 3H); 3.25–3,05(m, 3H) |
| Ib.063 | $-CH=C(Cl)-CO-NH-CH(CH_3)-CO-OC_2H_5$ | |
| Ib.064 | $-CH=C(Cl)-CO-NH-OC_2H_5$ | 9.19(s, 1H); 8.15(s, 1H); 7.88(s, 1H); 7.61(s, 1H); 6.72(t, 1H); 4.08(q, 2H); 3.85(s, 3H); 1.33(t, 3H) |
| Ib.065 | $-CH=C(Cl)-CO-NH-OCH_3$ | |
| Ib.066 | $-CH=C(Cl)-CO-NH-OCH_2-CH=CHCl$ | 519[M]$^+$, 484[M–Cl]$^+$ |
| Ib.067 | $-CH=C(Cl)-CO-NH-OCH_2$-(4-chlorophenyl) | 569[M]$^+$ |
| Ib.068 | $-CH=C(Cl)-CO-SCH_2-CO-OC_2H_5$ | 532[M]$^+$, 497[M–Cl]$^+$ |
| Ib.069 | $-CH=C(Cl)-CO-SCH_2-C_2H_5$ | 8.06(s, 1H); 8.03(s, 1H); 7.61(s, 1H); 6.72(t, 1H); 3.86(s, 3H); 3,00(t, 2H); 1,70(m, 2H); 1,03(t, 3H); |
| Ib.070 | $-CH-C(Cl)-CO-SCH_2$-(4-chlorophenyl) | |
| Ib.071 | $-CH=C(CO-OC_2H_5)_2$ | |
| Ib.072 | $-CH=C(CO-OCH_3)_2$ | |
| Ib.073 | $-CH=C(Cl)-CO-OCH_2-CH=N-OCH_3$ | |
| Ib.074 | $-CH=C(Cl)-CO-OCH_2-CH=N-OC_2H_5$ | |
| Ib.075 | $-CH=C(Cl)-CO-OCH_2-CH=N-OCH_2-CH_2-C_2H_5$ | 8.12(m, 1H); 8.08(m, 1H); 7.62(s, 1H); 7.53 and 6.88 (2t, together 1H); 6.72(t, 1H); 5.10 and 4.89 (2d, together 2H); 4.10(m, 2H); 3.85(s, 3H); 1.63(q, 2H); 1.40(q, 2H), 0.95( t, 3H) |
| Ib.076 | $-CH=C(Cl)-CO-OCH_2-CH=N-OCH_2$-phenyl | |
| Ib.077 | $-CH-C(Br)-CO-O$-cyclohexyl | |
| Ib.078 | $-CH=C(Br)-CO-OC(CH_3)_3$ | |
| Ib.079 | $-CH=C(Br)-CO-OCH_2-CH(CH_3)_2$ | |
| Ib.080 | $-CH=C(Br)-CO-NH-CH_2-CO-OCH_3$ | |
| Ib.081 | $-CH-C(Br)-CO-N(CH_3)-CH_2-CO-OCH_3$ | |
| Ib.082 | $-CH=C(Br)-CO-NH-OC_2H_5$ | |
| Ib.083 | $-CH=C(Br)-CO-NH-OCH_3$ | |
| Ib.084 | $-CH=C(Br)-CO-NH-OCH_2-CH=CHCl$ | |
| Ib.085 | $-CH=C(Br)-CO-NH-OCH_2$-(4-chlorophenyl) | |
| Ib.086 | $-CH=C(Br)-CO-SCH_2-CO-OC_2H_5$ | |
| Ib.087 | $-CH=C(Br)-CO-SCH_2-C_2H_5$ | |
| Ib.088 | $-CH=C(Br)-CO-SCH_2$-(4-chlorophenyl) | |
| Ib.089 | $-CH=C(Br)-CO-OCH_2-CH=N-OCH_2-CH=CH_2$ | |
| Ib.090 | $-CH-C(Br)-CO-OCH_2-CH=N-OCH_2-CH=CHCl$ | |
| Ib.091 | $-CH=C(Br)-CO-OCH_2-CH=N-OCH_3$ | |
| Ib.092 | $-CH=C(Br)-CO-OCH_2-CH=N-OC_2H_5$ | |
| Ib.093 | $-CH=C(Br)-CO-OCH_2-CH=N-OCH_2-CH_2-C_2H_5$ | |
| Ib.094 | $-CH=C(Br)-CO-OCH_2-CH=N-OCH_2$-phenyl | |
| Ib.095 | $-CH_2-CH(Cl)-CO-O$-cyclohexyl | 7.52(s, 1H); 7.35(s, 1H); 6.70(t, 1H); 4.79(m, 1H) 4.56(t, 1H); 3.83(s, 3H); 3.50(dd, 1H); 3.29(dd, 1H); 1.90–1.15(m, 10H) |
| Ib.096 | $-CH_2-CH(Cl)-CO-OC(CH_3)_3$ | 7.53(s, 1H); 7.36(s, 1H); 6.71(t, 1H); 4.49(t, 1H); |

TABLE 2-continued

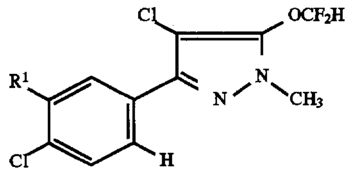

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS[$mz^{-1}$] |
|---|---|---|
| | | 3.83(s, 3H); 3.45(dd, 1H); 3.24(dd, 1H); 1.44(s, 9H) |
| Ib.097 | $-CH_2-CH(Cl)-CO-OCH_2-CH(CH_3)_2$ | 7.54(s, 1H); 7.35(s, 1H); 6.70(t, 1H); 4.60(t, 1H) 3.90(m, 2H); 3.83(s, 3H); 3.50(dd, 1H); 3.28(dd, 1H); 1.91(m, 1H); 0.89(d, 6H). |
| Ib.098 | $-CH_2-CH(Cl)-CO-NH-CH_2-CO-OCH_3$ | 503[M]$^+$, 468[M−Cl]$^+$ |
| Ib.099 | $-CH_2-CH(Cl)-CO-N(CH_3)-CH_2-CO-OCH_3$ | 518[M+H]$^+$, 482[M−Cl]$^+$ |
| Ib.100 | $-CH_2-CH(Cl)-CO-NH-CH(CH_3)-CO-OC_2H_5$ | |
| Ib.101 | $-CH_2-CH(Cl)-CO-NH-OC_2H_5$ | |
| Ib.102 | $-CH_2-CH(Cl)-CO-NH-OCH_3$ | |
| Ib.103 | $-CH_2-CH(Cl)-CO-NH-OCH_2-CH=CHCl$ | |
| Ib.104 | $-CH_2-CH(Cl)-CO-NH-OCH_2$-(4-chlorophenyl) | |
| Ib.105 | $-CH_2-CH(Cl)-CO-SCH_2-CO-OC_2H_5$ | |
| Ib.106 | $-CH_2-CH(Cl)-CO-SCH_2-C_2H_5$ | |
| Ib.107 | $-CH_2-CH(Cl)-CO-SCH_2$-(4-chlorophenyl) | |
| Ib.108 | $-CH_2-C(Cl)(CO-OC_2H_5)_2$ | |
| Ib.109 | $-CH_2-C(Cl)(CO-OCH_3)_2$ | |
| Ib.110 | $-CH_2-CH(Cl)-CO-OCH_2-CH=N-OCH_3$ | |
| Ib.111 | $-CH_2-CH(Cl)-CO-OCH_2-CH=N-OC_2H_5$ | |
| Ib.112 | $-CH_2-CH(Cl)-CO-OCH_2-CH=N-OCH_2-CH_2-C_2H_5$ | |
| Ib.113 | $-CH_2-CH(Cl)-CO-OCH_2-CH=N-OCH_2$-phenyl | |
| Ib.114 | $-CH_2-CH(Cl)-CO-OCH_2-CH=N-OCH_2-CH=CH_2$ | |
| Ib.115 | $-CH_2-CH(Cl)-CO-OCH_2-CH=N-OCH_2-CH=CHCl$ | |
| Ib.116 | $-CH_2-CH(Cl)-CO-OCH_2-CH=N-OCH_2$-(4-chlorophenyl) | |
| Ib.117 | $-CH_2-CH(Cl)-CO-OCH_2-CH=N-OCH(CH_3)$-(4-chlorophenyl) | |
| Ib.118 | $-CH_2-CH(Cl)-COOH$ | 125–127° C. |
| Ib.119 | $-CH_2-CH(Cl)-CO-NH$-cyclopropyl | 7.64(s, 1H); 7.38(s, 1H); 6.71(t, 1H); 6.55(s, 1H); 4.56(dd, 1H); 3.84 (s, 3H); 3.73(dd, 1H); 3.20(dd, 1H); 2.72(m, 1H); 0.80(m, 2H); 0.64(m, 2H) |
| Ib.120 | $-CH_2-CH(Cl)-CO-N(CH_3)-CH_2-CO-OC_2H_5$ | 7.80(m, 1H); 7,59 and 7.53(2s, together 1H); 7.40(t, 1H); 5.27–5.07(m, 1H); 4.48–4.00(m, 4H); 3.82(s, 3H); 3.35(m, 2H); 3.14 and 2.88 (2s, together 3H); 1.20(t, 3H) |
| Ib.121 | $-CH_2-CH(Cl)-CO-NH-CH(CH(CH_3)_2)-CO-OC_2H_5$ | 7.52(s, 1H); 7.39(s, 1H); 6.92(d, 1H); 6.71(t, 1H); 4.65(dd, 1H); 4.52(dd, 1H); 4.25–4.10(m, 2H); 3.83(s, 3H); 3.75(m, 1H); 3.17(m, 1H); 2.20(m, 1H); 1.28(t, 3H); 0.90(m, 6H) |
| Ib.122 | $-CH_2-CH(Cl)-CO-NH-CH(CH_2CH(CH_3)_2)-CO-OCH_3$ | 560[M+H]$^+$, 524[M−Cl]$^+$ |
| Ib.123 | $-CH_2-CH(Cl)-CO$-(2-methoxycarbonyl-pyrrolidin-1-yl) | 544[M+H]$^+$, 508[M−Cl]$^+$ |
| Ib.124 | $-CH_2-CH(Cl)-CO-NH$-(tetrahydrofuran-2-on-3-yl) | |
| Ib.125 | $-CH_2-CH(Cl)-CO-N(CN)-CH_2CH_2-C_2H_5$ | |
| Ib.126 | $-CH_2-CH(Cl)-CO-N(CN)$-cyclopropyl | 7.55(s, 1H); 7.38(s, 1H); 6.71(t, 1H); 5.05(m, 1H); 3.84(s, 3H); 3.52(dd, 1H); 3.38(dd, 1H); 3.07(m, 1H); 1.12–0.80 (m, 4H) |
| Ib.127 | $-CH_2-CH(Cl)-CO-N(CN)-CH_2-CH=CH_2$ | |

TABLE 2-continued

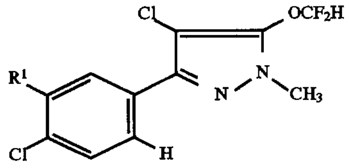

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS[$mz^{-1}$] |
|---|---|---|
| Ib.128 | $-CH_2-CH(Cl)-CO-N(CONH_2)-CH_2CH_2-C_2H_5$ | |
| Ib.129 | $-CH_2-CH(Cl)-CO-N(CONH_2)$-cyclopropyl | |
| Ib.130 | $-CH_2-CH(Cl)-CO-N(CONH_2)-CH_2-CH=CH_2$ | |
| Ib.131 | $-CH_2-CH(Cl)-CO-O$-(4-acetoxytetrahydrofuran-3-yl) | |
| Ib.132 | $-CH_2-CH(Br)-CO-O$-cyclohexyl | 7.52(s, 1H); 7.34(s, 1H); 6.70(t, 1H); 4.78(m, 1H); 4.53(t, 1H); 3.84(s, 3H); 3.55(dd, 1H); 3.38(dd, 1H); 1.90–1.20(m, 10H) |
| Ib.133 | $-CH_2-CH(Br)-CO-OC(CH_3)_3$ | 7.52(s, 1H); 7.35(s, 1H); 6.70(t, 1H); 4.45(t, 1H); 3.83(s, 3H); 3.50(dd, 1H); 3.32(dd, 1H); 1.41(s, 9H). |
| Ib.134 | $-CH_2-CH(Br)-CO-OCH_2-CH(CH_3)_2$ | 7.53(s, 1H); 7.35(s, 1H); 6.70(t, 1H); 4.57(t, 1H); 3.92(m, 2H); 3.82(s, 3H); 3.56(dd, 1H); 3.37(dd, 1H); 1.93(m, 1H); 0.90(d, 6H); |
| Ib.135 | $-CH_2-CH(Br)-CO-NH-CH_2-CO-OCH_3$ | |
| Ib.136 | $-CH_2-CH(Br)-CO-N(CH_3)-CH_2-CO-OCH_3$ | |
| Ib.137 | $-CH_2-CH(Br)-CO-NH-CH(CH_3)-CO-OC_2H_5$ | |
| Ib.138 | $-CH_2-CH(Br)-CO-NH-OC_2H_5$ | |
| Ib.139 | $-CH_2-CH(Br)-CO-NH-OCH_3$ | |
| Ib.140 | $-CH_2-CH(Br)-CO-NH-OCH_2-CH=CHCl$ | |
| Ib.141 | $-CH_2-CH(Br)-CO-NH-OCH_2$-(4-chlorophenyl) | |
| Ib.142 | $-CH_2-CH(Br)-CO-SCH_2-CO-OC_2H_5$ | |
| Ib.143 | $-CH_2-CH(Br)-CO-SCH_2-C_2H_5$ | |
| Ib.144 | $-CH_2-CH(Br)-CO-SCH_2$-(4-chlorophenyl) | |
| Ib.145 | $-CH_2-C(Br)(CO-OC_2H_5)_2$ | |
| Ib.146 | $-CH_2-C(Br)(CO-OCH_3)_2$ | |
| Ib.147 | $-CH_2-CH(Br)-CO-OCH_2-CH=N-OCH_3$ | |
| Ib.148 | $-CH_2-CH(Br)-CO-OCH_2-CH=N-OC_2H_5$ | |
| Ib.149 | $-CH_2-CH(Br)-CO-OCH_2-CH=N-OCH_2-CH_2-C_2H_5$ | |
| Ib.150 | $-CH_2-CH(Br)-CO-OCH_2-CH=N-OCH_2$-phenyl | |
| Ib.151 | $-CH_2-CH(Br)-CO-OCH_2-CH=N-OCH_2-CH=CH_2$ | |
| Ib.152 | $-CH_2-CH(Br)-CO-OCH_2-CH=N-OCH_2-CH=CHCl$ | |
| Ib.153 | $-CH_2-CH(Br)-CO-OCH_2-CH=N-OCH_2$-(4-chlorophenyl) | |
| Ib.154 | $-CH_2-CH(Br)-CO-OCH_2-CH=N-OCH(CH_3)$-(4-chlorophenyl) | |
| Ib.155 | $-CH_2-CH(Br)-COOH$ | 7.81(s, 1H); 7.51(s, 1H); 7.39(t, 1H); 4.69(t, 1H); 3.80(s, 3H); 3.53(dd, 1H); 3.34(dd, 1H) |
| Ib.156 | $-CH_2-CH(Br)-CO-NH$-cyclopropyl | |
| Ib.157 | $-CH_2-CH(Br)-CO-N(CH_3)-CH_2-CO-OC_2H_5$ | |
| Ib.158 | $-CH_2-CH(Br)-CO-NH-CH(CH(CH_3)_2)-CO-OC_2H_5$ | 7.51(s, 1H); 7.39(s, 1H); 6.70(t, 1H); 6.68(d, 1H); 4.63(m, 1H); 4.50(m, 1H); 4.25–4.13(m, 2H); 3.83(s, 3H); 3.71(dd, 1H) 3.33(dd, 1H); 2.25–2.08(m, 1H); 1.28(m, 3H); 0.98–0.80(m, 6H) |
| Ib.159 | $-CH_2-CH(Br)-CO-NH-CH(CH_2CH(CH_3)_2)-CO-OCH_3$ | |
| Ib.160 | $-CH_2-CH(Br)-CO$-(2-methoxycarbonyl-pyrrolidin-1-yl) | |
| Ib.161 | $-CH_2-CH(Br)-CO-NH$-(tetrahydrofuran-2-on-3-yl) | |
| Ib.162 | $-CH_2-CH(Br)-CO-N(CN)-CH_2CH_2-C_2H_5$ | |
| Ib.163 | $-CH_2-CH(Br)-CO-N(CN)$-cyclopropyl | |
| Ib.164 | $-CH_2-CH(Br)-CO-N(CN)-CH_2-CH=CH_2$ | |
| Ib.165 | $-CH_2-CH(Br)-CO-N(CONH_2)-CH_2CH_2-C_2H_5$ | |
| Ib.166 | $-CH_2-CH(Br)-CO-N(CONH_2)$-cyclopropyl | |
| Ib.167 | $-CH_2-CH(Br)-CO-N(CONH_2)-CH_2-CH=CH_2$ | |
| Ib.168 | $-CH_2-CH(Br)-CO-O$(4-acetoxytetrahydrofuran-3-yl) | |

TABLE 2-continued

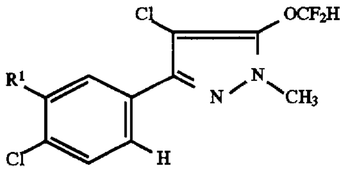

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS[$mz^{-1}$] |
| --- | --- | --- |
| Ib.169 | $-CH_2-CH(OH)-COOH$ | |
| Ib.170 | $-CH_2-CH(OH)-CO-OCH_3$ | |
| Ib.171 | $-CH_2-CH(OH)-CO-OC_2H_5$ | |
| Ib.172 | $-CH_2-CH(OH)-CO-OCH_2-CH{=}N-OCH_3$ | |
| Ib.173 | $-CH_2-CH(OH)-CO-OC(CH_3)_3$ | |
| Ib.174 | $-CH_2-CH(OH)-CO-NH_2$ | |
| Ib.175 | $-CH_2-CH(OH)-CO-NH-CH_3$ | |
| Ib.176 | $-CH_2-CH(OH)-CO-$NH-cyclopropyl | |
| Ib.177 | $-CH_2-CH(OCH_3)-COOH$ | |
| Ib.178 | $-CH_2-CH(OCH_3)-CO-OCH_3$ | |
| Ib.179 | $-CH_2-CH(OCH_3)-CO-OC_2H_5$ | |
| Ib.180 | $-CH_2-CH(OCH_3)-CO-OCH_2-CH{=}N-OCH_3$ | |
| Ib.181 | $-CH_2-CH(OCH_3)-CO-OC(CH_3)_3$ | |
| Ib.182 | $-CH_2-CH(OCH_3)-CO-NH_2$ | |
| Ib.183 | $-CH_2-CH(OCH_3)-CO-NH-CH_3$ | |
| Ib.184 | $-CH_2-CH(OCH_3)-CO-$NH-cyclopropyl | |
| Ib.185 | $-CH_2-CH(O-COCH_3)-COOH$ | |
| Ib.186 | $-CH_2-CH(O-COCH_3)-CO-OCH_3$ | |
| Ib.187 | $-CH_2-CH(O-COCH_3)-CO-OC_2H_5$ | |
| Ib.188 | $-CH_2-CH(O-COCH_3)-CO-OCH_2-CH{=}N-OCH_3$ | |
| Ib.189 | $-CH_2-CH(O-COCH_3)-CO-OC(CH_3)_3$ | |
| Ib.190 | $-CH_2-CH(O-COCH_3)-CO-NH_2$ | |
| Ib.191 | $-CH_2-CH(O-COCH_3)-CO-NH-CH_3$ | |
| Ib.192 | $-CH_2-CH(O-COCH_3)-CO-$NH-cyclopropyl | |
| Ib.193 | $-CH_2-CH(NH_2)-COOH$ | |
| Ib.194 | $-CH_2-CH(NH_2)-CO-OCH_3$ | |
| Ib.195 | $-CH_2-CH(NH_2)-CO-OC_2H_5$ | |
| Ib.196 | $-CH_2-CH(NH_2)-CO-OC(CH_3)_3$ | |
| Ib.197 | $-CH_2-CH(NH_2)-CO-NH_2$ | |
| Ib.198 | $-CH_2-CH(NH_2)-CO-NH-CH_3$ | |
| Ib.199 | $-CH_2-CH(N_3)-COOH$ | |
| Ib.200 | $-CH_2-CH(N_3)-CO-OCH_3$ | |
| Ib.201 | $-CH_2-CH(N_3)-CO-OC_2H_5$ | |
| Ib.202 | $-CH_2-CH(N_3)-CO-OC(CH_3)_3$ | |
| Ib.203 | $-CH_2-CH(N_3)-CO-NH_2$ | |
| Ib.204 | $-CH_2-CH(N_3)-CO-NH-CH_3$ | |
| Ib.205 | $-CH_2-CH(NHCOCH_3)-COOH$ | |
| Ib.206 | $-CH_2-CH(NHCOCH_3)-CO-OCH_3$ | |
| Ib.207 | $-CH_2-CH(NHCOCH_3)-CO-OC_2H_5$ | |
| Ib.208 | $-CH_2-CH(NHCOCH_3)-CO-OC(CH_3)_3$ | |
| Ib.209 | $-CH_2-CH(NHCOCH_3)-CO-NH_2$ | |
| Ib.210 | $-CH_2-CH(NHCOCH_3)-CO-NH-CH_3$ | |
| Ib.211 | $-CH_2-CH_2$-cyclohexyl | |
| Ib.212 | $-CH_2-CH_2$-cyclopentyl | |
| Ib.213 | $-CH_2-CH_2$-cyclopropyl | |
| Ib.214 | $-CH_2-CH_2$-phenyl | |
| Ib.215 | $-CH{=}C(CN)-CO-OC_2H_5$ | 135–137° C. |
| Ib.216 | $-CH{=}C(CN)-CO-OCH(CH_3)_2$ | |
| Ib.217 | $-CH{=}C(CN)-CO-OC(CH_3)_3$ | |
| Ib.218 | $-CH{=}C(Cl)-CO-OCH_2-CH{=}N-OCH_2-CH{=}CH_2$ | 8.17–8.08(m, 2H); 7.61(s, 1H); 7.60 and 6.90 (2t, together 1H); 6.72(t, 1H); 6.00(m, 1H); 5.39–5.23(m, 2H); 5.11 and 4.89(2d, together 2H); 4.63 (m, 2H); 3.85(s, 3H) |
| Ib.219 | $-CH{=}C(Cl)-CO-OCH_2-CH{=}N-OCH_2-CH{=}CHCl$ | |
| Ib.220 | $-CH{=}C(Cl)-CO-OCH_2-CH{=}N-OCH_2$-(4-chlorophenyl) | 611[M]$^+$ |
| Ib.221 | $-CH{=}C(Cl)-CO-OCH_2-CH{=}N-OCH(CH_3)$-(4-chlorophenyl) | |
| Ib.222 | $-CH{=}C(Cl)-CO-O$-(4-acetoxytetrahydrofuran-3-yl) | 8.07(s, 1H); 8.03(s, 1H); 7.94(s, 1H); 7.41(t, 1H); 5.51(q, 1H); 5.40(q, 1H); |

TABLE 2-continued

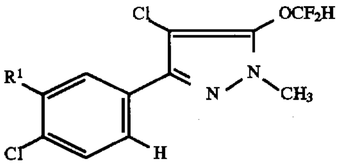

I ($R^2$,$R^5$ = Cl; $R^3$ = $CH_3$; $R^4$ = $OCF_2H$; $R^6$ = H)

| No. | $R^1$ | m.p./$^1$H-NMR[ppm]/ MS[$mz^{-1}$] |
| --- | --- | --- |
| | | 4.10–3.75(m, 4H); 3.83(s, 3H); 2.03(s, 3H) |
| Ib.223 | $-CH=C(Cl)-CO-NH$-cyclohexyl | |
| Ib.224 | $-CH=C(Cl)-CO-N(CH_3)-CH_2-CO-OC_2H_5$ | 7.96–7.86(m, 1H); 7.60(s, 1H); 7.15–7.04(m, 1H); 6.72(t, 1H); 4.30–4.15(m, 4H); 3.85(s, 3H); 3.27–3.05(m, 3H); 1.35–1.25(m, 3H) |
| Ib.225 | $-CH=C(Cl)-CO-NH-CH(CH(CH_3)_2)-CO-OC_2H_5$ | 8.15(s, 1H); 7.92(s, 1H); 7.62(s, 1H); 7.26(d, 1H); 6.73(t, 1H); 4.62(dd, 1H); 4.26(q, 2H); 3.85(s, 3H); 2.28(m, 1H); 1.32(t, 3H); 0.98(m, 6H) |
| Ib.226 | $-CH=C(Cl)-CO-NH-CH(CH_2CH(CH_3)_2)-CO-OCH_3$ | |
| Ib.227 | $-CH=C(Cl)-CO-$(2-methoxycarbonyl-pyrrolidin-1-yl) | |
| Ib.228 | $-CH=C(Cl)-CO-NH$-(tetrahydrofuran-2-on-3-yl) | |
| Ib.229 | $-CH=C(Cl)-CO-N(CN)-CH_2CH_2-C_2H_5$ | 8.02(s, 1H); 7.63(m, 2H); 6.74(t, 1H); 3.86(s, 3H); 3.74(t, 2H); 1.80(m, 2H); 1.45(q, 2H); 1.00(t, 3H) |
| Ib.230 | $-CH=C(Cl)-CO-N(CN)$-cyclopropyl | |
| Ib.231 | $-CH=C(Cl)-CO-N(CN)-CH_2-CH=CH_2$ | |
| Ib.232 | $-CH=C(Cl)-CO-N(CONH_2)-CH_2CH_2-C_2H_5$ | |
| Ib.233 | $-CH=C(Cl)-CO-N(CONH_2)$-cyclopropyl | 127–129° C. |
| Ib.234 | $-CH=C(Cl)-CO-N(CONH_2)-CH_2-CH=CH_2$ | 110–112° C. |
| Ib.235 | $-CH=C(Br)-CO-OCH_2-CH=N-OCH_2$-(4-chlorophenyl) | |
| Ib.236 | $-CH=C(Br)-CO-OCH_2-CH=N-OCH(CH_3)$-(4-chlorophenyl) | |
| Ib.237 | $-CH=C(Br)-CO-O$-(4-acetoxytetrahydrofuran-3-yl) | |
| Ib.238 | $-CH=C(Br)-CO-NH$-cyclohexyl | |
| Ib.239 | $-CH=C(Br)-CO-N(CH_3)-CH_2-CO-OC_2H_5$ | |
| Ib.240 | $-CH=C(Br)-CO-NH-CH(CH(CH_3)_2)-CO-OC_2H_5$ | |
| Ib.241 | $-CH=C(Br)-CO-NH-CH(CH_2CH(CH_3)_2)-CO-OCH_3$ | |
| Ib.242 | $-CH=C(Br)-CO$-(2-methoxycarbonyl-pyrrolidin-1-yl) | |
| Ib.243 | $-CH=C(Br)-CO-NH$-(tetrahydrofuran-2-on-3-yl) | |
| Ib.244 | $-CH=C(Br)-CO-N(CN)-CH_2CH_2-C_2H_5$ | |
| Ib.245 | $-CH=C(Br)-CO-N(CN)$-cyclopropyl | |
| Ib.246 | $-CH=C(Br)-CO-N(CN)-CH_2-CH=CH_2$ | |
| Ib.247 | $-CH=C(Br)-CO-N(CONH_2)-CH_2CH_2-C_2H_5$ | |
| Ib.248 | $-CH=C(Br)-CO-N(CONH_2)$-cyclopropyl | |
| Ib.249 | $-CH=C(Br)-CO-N(CONH_2)-CH_2-CH=CH_2$ | |
| Ib.250 | $-CH_2-CH(Cl)-CO-N(C_2H_5)_2$ | |
| Ib.251 | $-CH_2-CH(Br)-CO-N(C_2H_5)_2$ | |
| Ib.252 | $-CH=C(Br)-CO-N(C_2H_5)_2$ | |
| Ib.253 | $-CH=C(Cl)-CO-N(C_2H_5)_2$ | 485[M]$^+$, 450[M–Cl]$^+$ |
| Ib.254 | 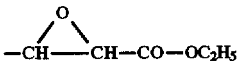 | |
| Ib.255 | 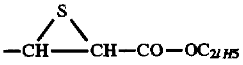 | |
| Ib.256 | 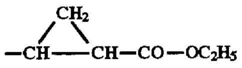 | |

TABLE 2-continued

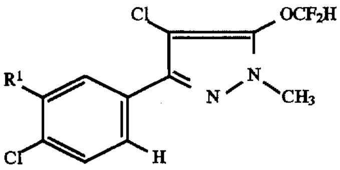

I ($R^2$,$R^5$ = Cl; $R^3$ = $CH_3$;
$R^4$ = $OCF_2H$; $R^6$ = H)

| No. | $R^1$ | m.p./$^1$H-NMR[ppm]/ MS[$mz^{-1}$] |
|---|---|---|
| Ib.257 | 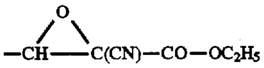 | 7.63(s, 1H); 7.48(s, 1H); 6.71(t, 1H); 4.73(s, 1H); 4.45(q, 2H); 3.85(s, 3H); 1.42(t, 3H) |
| Ib.258 | 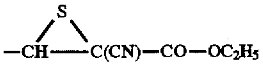 | |
| Ib.259 | 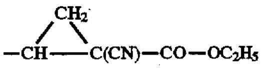 | |
| Ib.260 | 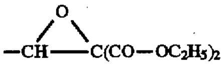 | |
| Ib.261 | 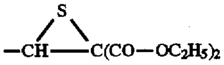 | |
| Ib.262 | 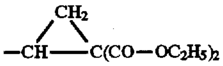 | |

TABLE 3

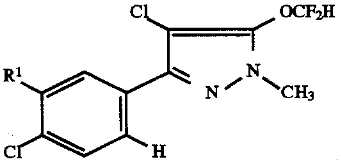

I ($R^2$,$R^5$ = Cl; $R^3$ = $CH_3$;
$R^4$ = O $F_2$HH; $R^6$ = F)

| No. | $R^1$ | m.p./$^1$H-NMR[ppm] MS[$mz^{-1}$] |
|---|---|---|
| Ic.001 | $-CH=C(Cl)-COOH$ | |
| Ic.002 | $-CH=C(Cl)-CO-OCH_3$ | 91° C. |
| Ic.003 | $-CH=C(Cl)-CO-OC_2H_5$ | 88–89° C. |
| Ic.004 | $-CH=C(Cl)-CO-OCH(CH_3)_2$ | 8.25(d, 1H); 8.10(s, 1H); 7.34(d, 1H); 6.73(t, 1H); 5.20(m, 1H); 3.85(s, 3H); 1.38(d, 6H); |
| Ic.005 | $-CH=C(Br)-COOH$ | |
| Ic.006 | $-CH=C(Br)-CO-OCH_3$ | 99° C. |
| Ic.007 | $-CH=C(Br)-CO-OC_2H_5$ | |
| Ic.008 | $-CH=C(Br)-CO-OCH(CH_3)_2$ | |
| Ic.009 | $-CH=C(Cl)-CO-NH_2$ | |
| Ic.010 | $-CH=C(Cl)-CO-NH-CH_3$ | |
| Ic.011 | $-CH=C(Cl)-CO-N(CH_3)_2$ | |
| Ic.012 | $-CH=C(Br)-CO-NH_2$ | |
| Ic.013 | $-CH=C(Br)-CO-NH-CH_3$ | |
| Ic.014 | $-CH=C(Br)-CO-N(CH_3)$ | |
| Ic.015 | $-CH=C(Br)-CO-$NH-cyclopropyl | |
| Ic.016 | $-CH=C(Cl)-CO-$NH-cyclopropyl | |
| Ic.017 | $-CH=$(cyclopropylene) | |
| Ic.018 | $-CH=$(cyclopentylene) | |
| Ic.019 | $-CH=$(cyclohexylene) | |

TABLE 3-continued
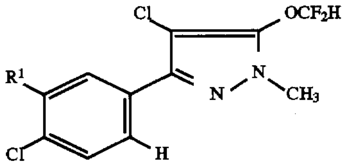
I ($R^2$,$R^5$ = Cl; $R^3$ = $CH_3$; $R^4$ = O $F_2HH$; $R^6$ = F)
| No. | $R^1$ | m.p./$^1$H-NMR[ppm] MS[$mz^{-1}$] |
|---|---|---|
| Ic.020 | 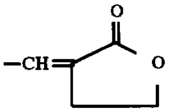 | 123–125° C. |
| Ic.021 | 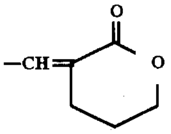 | |
| Ic.022 | 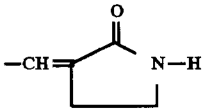 | |
| Ic.023 | 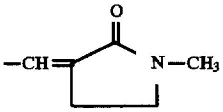 | |
| Ic.024 | 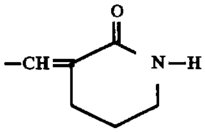 | |
| Ic.025 | 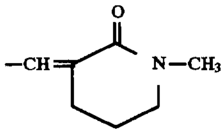 | |
| Ic.026 | 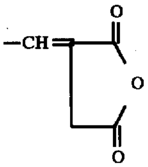 | |
| Ic.027 | 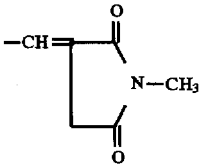 | |
| Ic.028 | $-CH=C(CH_3)-CO-OC_2H_5$ | |
| Ic.029 | $-CH=C(CH_3)-CO-OCH_3$ | |
| Ic.030 | $-CH=C(CH_3)-CO-NH_2$ | |
| Ic.031 | $-CH=C(CH_3)-CO-NH-CH_3$ | |
| Ic.032 | $-CH=C(CH_3)-CO-N(CH_3)_2$ | |
| Ic.033 | $-CH=C(CN)-CO-OCH_3$ | |

TABLE 3-continued

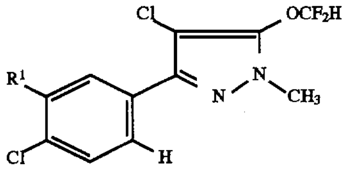

I ($R^2$,$R^5$ = Cl; $R^3$ = $CH_3$; $R^4$ = O $F_2$HH; $R^6$ = F)

| No. | $R^1$ | m.p./$^1$H-NMR[ppm] MS[$mz^{-1}$] |
|---|---|---|
| Ic.034 | $-CH_2-CH(CN)-CO-OCH_3$ | |
| Ic.035 | $-CH_2-CH(CN)-CO-OC_2H_5$ | |
| Ic.036 | $-CH_2-CH(CN)-CO-NH_2$ | |
| Ic.037 | $-CH_2-CH(CN)-CO-NH-CH_3$ | |
| Ic.038 | $-CH_2-CH(CN)-CO-N(CH_3)_2$ | |
| Ic.039 | $-CH_2-CH(CN)-CO-NH-SO_2-CH_3$ | |
| Ic.040 | $-CH_2-CH(Cl)-CO-OCH_3$ | 7.50(d, 1H); 7.25(d, 1H); 6.70(t, 1H); 4.61(dd, 1H); 3.85(s, 3H); 3.78(s, 3H); 3.54(dd, 1H); 3.30(dd, 1H) |
| Ic.041 | $-CH_2-CH(Cl)-CO-OC_2H_5$ | 7.50(d, 1H); 7.26(d, 1H); 6.70(t, 1H); 4.57(t, 1H); 4.22(q, 2H); 3.84(s, 3H); 3.51(dd, 1H); 3.28(dd, 1H); 1.25(t, 3H) |
| Ic.042 | $-CH_2-CH(Cl)-CO-NH_2$ | |
| Ic.043 | $-CH_2-CH(Cl)-CO-NH-CH_3$ | |
| Ic.044 | $-CH_2-CH(Cl)-CO-N(CH_3)_2$ | |
| Ic.045 | $-CH_2-CH(Cl)-CO-NH-SO_2-CH_3$ | |
| Ic.046 | $-CH_2-CH(Br)-CO-OCH_3$ | |
| Ic.047 | $-CH_2-CH(Br)-CO-OC_2H_5$ | 7.50(d, 1H); 7.25(d, 1H); 6.70(t, 1H); 4.54(t, 1H); 4.28–4.10(m, 2H); 3.83(s, 3H); 3.57(dd, 1H); 3.38(dd, 1H); 1.25(t, 3H) |
| Ic.048 | $-CH_2-CH(Br)-CO-OCH(CH_3)_2$ | |
| Ic.049 | $-CH_2-CH(Br)-CO-NH_2$ | |
| Ic.050 | $-CH_2-CH(Br)-CO-NH-CH_3$ | |
| Ic.051 | $-CH_2-CH(Br)-CO-N(CH_3)_2$ | |
| Ic.052 | $-CH_2-CH(Cl)-CO-CH(CH_3)_2$ | |
| Ic.053 | $-CH_2-CH(CN)-CO-CH(CH_3)_2$ | |
| Ic.054 | $-CH=CH$-(4-fluorophenyl) | 7.85–6.44(m, 9H); 3.85 and 3.75(2s, together 3H) |
| Ic.055 | $-CH=CH$-(4-chlorophenyl) | 7.50–6.45(m, 9H); 3.85 and 3.77(2s, together 3H) |
| Ic.056 | $-CH=CH$-(3-trifluoromethylphenyl) | 480[M]$^+$ |
| Ic.057 | $-CH=CH$-(2,4-dichlorophenyl) | |
| Ic.058 | $-CH=C(Cl)-CO-$O-cyclohexyl | |
| Ic.059 | $-CH=C(Cl)-CO-OC(CH_3)_3$ | 8.25(d, 1H); 8.05(s, 1H); 7.33(d, 1H); 6.73(t, 1H); 3.86(s, 3H); 1.60(s, 9H) |
| Ic.060 | $-CH=C(Cl)-CO-OCH_2-CH(CH_3)_2$ | |
| Ic.061 | $-CH=C(Cl)-CO-NH-CH_2-CO-OCH_3$ | |
| Ic.062 | $-CH=C(Cl)-CO-N(CH_3)-CH_2-CO-OCH_3$ | 8.05(m, 1H); 7.34–7.02(m, 2H); 6.70(t, 1H); 4.21(s, 2H); 3.85(s, 3H); 3.79(s, 3H); 3.24 and 3.09 (2s, together 3H); |
| Ic.063 | $-CH=C(Cl)-CO-NH-CH(CH_3)-CO-OC_2H_5$ | |
| Ic.064 | $-CH=C(Cl)-CO-NH-OC_2H_5$ | |
| Ic.065 | $-CH=C(Cl)-CO-NH-OCH_3$ | |
| Ic.066 | $-CH=C(Cl)-CO-NH-OCH_2-CH=CHCl$ | |
| Ic.067 | $-CH=C(Cl)-CO-NH-OCH_2$-(4-chlorophenyl) | |
| Ic.068 | $-CH=C(Cl)-CO-SCH_2-CO-OC_2H_5$ | |
| Ic.069 | $-CH=C(Cl)-CO-SCH_2-C_2H_5$ | |
| Ic.070 | $-CH=C(Cl)-CO-SCH_2$-(4-chlorophenyl) | |
| Ic.071 | $-CH=C(CO-OC_2H_5)_2$ | |
| Ic.072 | $-CH=C(CO-OCH_3)_2$ | |
| Ic.073 | $-CH=C(Cl)-CO-OCH_2-CH=N-OCH_3$ | |
| Ic.074 | $-CH=C(Cl)-CO-OCH_2-CH=N-OC_2H_5$ | |
| Ic.075 | $-CH=C(Cl)-CO-OCH_2-CH=N-OCH_2-CH_2-C_2H_5$ | |

TABLE 3-continued

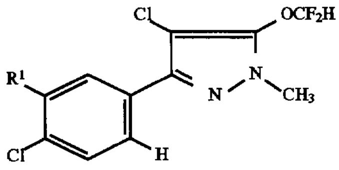

I ($R^2$,$R^5$ = Cl; $R^3$ = $CH_3$;
$R^4$ = O $F_2$HH; $R^6$ = F)

| No. | $R^1$ | m.p./$^1$H-NMR[ppm] MS[$mz^{-1}$] |
|---|---|---|
| Ic.076 | $-CH=C(Cl)-CO-OCH_2-CH=N-OCH_2$-phenyl | |
| Ic.077 | $-CH=C(Br)-CO-O$-cyclohexyl | |
| Ic.078 | $-CH=C(Br)-CO-OC(CH_3)_3$ | |
| Ic.079 | $-CH=C(Br)-CO-OCH_2-CH(CH_3)_2$ | |
| Ic.080 | $-CH=C(Br)-CO-NH-CH_2-CO-OCH_3$ | |
| Ic.081 | $-CH=C(Br)-CO-N(CH_3)-CH_2-CO-OCH_3$ | 8.00(m, 1H); 7.33–7.16(m, 2H); 6.71(t, 1H); 4.24(s, 2H); 3.85(s, 3H); 3.79(s, 3H); 3.23 and 3.08 (2s, together 3H) |
| Ic.082 | $-CH=C(Br)-CO-NH-OC_2H_5$ | |
| Ic.083 | $-CH=C(Br)-CO-NH-OCH_3$ | |
| Ic.084 | $-CH=C(Br)-CO-NH-OCH_2-CH=CHCl$ | |
| Ic.085 | $-CH=C(Br)-CO-NH-OCH_2$-(4-chlorophenyl) | |
| Ic.086 | $-CH=C(Br)-CO-SCH_2-CO-OC_2H_5$ | |
| Ic.087 | $-CH=C(Br)-CO-SCH_2-C_2H_5$ | |
| Ic.088 | $-CH=C(Br)-CO-SCH_2$-(4-chlorophenyl) | |
| Ic.089 | $-CH=C(Br)-OCH_2-CH=N-OCH_2-CH=CH_2$ | |
| Ic.090 | $-CH=C(Br)-CO-OCH_2-CH=N-OCH_2-CH=CHCl$ | |
| Ic.091 | $-CH=C(Br)-CO-OCH_2-CH=N-OCH_3$ | |
| Ic.092 | $-CH=C(Br)-CO-OCH_2-CH=N-OC_2H_5$ | |
| Ic.093 | $-CH=C(Br)-CO-OCH_2-CH=N-OCH_2-CH_2-C_2H_5$ | |
| Ic.094 | $-CH=C(Br)-CO-OCH_2-CH=N-OCH_2$-phenyl | |
| Ic.095 | $-CH_2-CH(Cl)-CO-O$-cyclohexyl | 7.48(d, 1H); 7.24(d, 1H); 6.72(t, 1H); 4.78(m, 1H); 4.56(t, 1H); 3.83(s, 3H); 3.50(dd, 1H); 3.31(dd, 1H); 1.90–1.20(m, 10H) |
| Ic.096 | $-CH_2-CH(Cl)-CO-OC(CH_3)_3$ | 7.50(d, 1H); 7.25(d, 1H); 6.71(t, 1H); 4.48(t, 1H); 3.83(s, 3H); 3.48(dd, 1H); 3.27(dd, 1H); 1.42(s, 9H) |
| Ic.097 | $-CH_2-CH(Cl)-CO-OCH_2-CH(CH_3)_2$ | |
| Ic.098 | $-CH_2-CH(Cl)-CO-NH-CH_2-CO-OCH_3$ | |
| Ic.099 | $-CH_2-CH(Cl)-CO-N(CH_3)-CH_2-CO-OCH_3$ | 7.77(m, 1H); 7.50(m, 1H); 6.71(t, 1H); 4.81(s, 2H); 4.50(t, 1H); 3.85(s, 9H); 3.47(dd, 1H); 3.25(dd, 1H) |
| Ic.100 | $-CH_2-CH(Cl)-CO-NH-CH(CH_3)-CO-OC_2H_5$ | |
| Ic.101 | $-CH_2-CH(Cl)-CO-NH-OC_2H_5$ | |
| Ic.102 | $-CH_2-CH(Cl)-CO-NH-OCH_3$ | |
| Ic.103 | $-CH_2-CH(Cl)-CO-NH-OCH_2-CH=CHCl$ | |
| Ic.104 | $-CH_2-CH(Cl)-CO-NH-OCH_2$-(4-chlorophenyl) | |
| Ic.105 | $-CH_2-CH(Cl)-CO-SCH_2-CO-OC_2H_5$ | |
| Ic.106 | $-CH_2-CH(Cl)-CO-SCH_2-C_2H_5$ | |
| Ic.107 | $-CH_2-CH(Cl)-CO-SCH_2$-(4-chlorophenyl) | |
| Ic.108 | $-CH_2-C(Cl)(CO-OC_2H_5)_2$ | |
| Ic.109 | $-CH-C(Cl)(CO-OCH_3)_2$ | |
| Ic.110 | $-CH_2-CH(Cl)-CO-OCH_2-CH=N-OCH_3$ | |
| Ic.111 | $-CH_2-CH(Cl)-CO-OCH_2-CH=N-OC_2H_5$ | |
| Ic.112 | $-CH_2-CH(Cl)-CO-OCH_2-CH=N-OCH_2-CH_2-C_2H_5$ | |
| Ic.113 | $-CH_2-CH(Cl)-CO-OCH_2-CH=N-OCH_2$-phenyl | |
| Ic.114 | $-CH_2-CH(Cl)-CO-OCH_2-CH=N-OCH_2-CH=CH_2$ | |
| Ic.115 | $-CH_2-CH(Cl)-CO-OCH_2-CH=N-OCH_2-CH=CHCl$ | |
| Ic.116 | $-CH_2-CH(Cl)-CO-OCH_2-CH=N-OCH_2$-(4-chlorophenyl) | |
| Ic.117 | $-CH_2-CH(Cl)-CO-OCH_2-CH=N-OCH(CH_3)$-(4-chlorophenyl) | |
| Ic.118 | $-CH_2-CH(Cl)-COOH$ | 8.50(s, 1H); 7,48(d, 1H); 7,29(d, 1H); 6,73(t, 1H); 4,67(dd, 1H); 3,89(s, 3H); 3,55(dd, 1H); 3,30(dd, 1H) |
| Ic.119 | $-CH_2-CH(Cl)-CO-NH$-cyclopropyl | |
| Ic.120 | $-CH_2-CH(Cl)-CO-N(CH_3)-CH_2-CO-OC_2H_5$ | |
| Ic.121 | $-CH_2-CH(Cl)-CO-NH-CH(CH(CH_3)_2)-CO-OC_2H_5$ | 7.50(m, 1H); 7.26(d, 1H); |

TABLE 3-continued

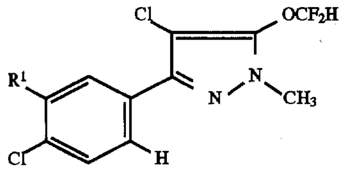

I ($R^2$,$R^5$ = Cl; $R^3$ = $CH_3$;
$R^4$ = O $F_2HH$; $R^6$ = F)

| No. | $R^1$ | m.p./$^1$H-NMR[ppm] MS[$mz^{-1}$] |
|---|---|---|
| | | 6.93 (m, 1H); 6.70(t, 1H); 4.65(dd, 1H); 4.52(dd, 1H); 4.28–4,13(m, 2H); 3.84(s, 3H); 3.76(m, 1H); 3.19(m, 1H); 2.19(m, 1H); 1.30(m, 3H); 0.90(m, 6H) |
| Ic.122 | $-CH_2-CH(Cl)-CO-NH-CH(CH_2CH(CH_3)_2)-CO-OCH_3$ | |
| Ic.123 | $-CH_2-CH(Cl)-CO$-(2-methoxycarbonyl-pyrrolidin-1-yl) | |
| Ic.124 | $-CH_2-CH(Cl)-CO-NH$-(tetrahydrofuran-2-on-3-yl) | |
| Ic.125 | $-CH_2-CH(Cl)-CO-N(CN)-CH_2CH_2-C_2H_5$ | |
| Ic.126 | $-CH_2-CH(Cl)-CO-N(CN)$-cyclopropyl | |
| Ic.127 | $-CH_2-CH(Cl)-CO-N(CN)-CH_2-CH=CH_2$ | |
| Ic.128 | $-CH_2-CH(Cl)-CO-N(CONH_2)-CH_2CH_2-C_2H_5$ | |
| Ic.129 | $-CH_2-CH(Cl)-CO-N(CONH_2)$-cyclopropyl | |
| Ic.130 | $-CH_2-CH(Cl)-CO-N(CONH_2)-CH_2-CH-CH_2$ | |
| Ic.131 | $-CH_2-CH(Cl)-CO-O$-(4-acetoxytetrahydrofuran-3-yl) | |
| Ic.132 | $-CH_2-CH(Br)-CO-O$-cyclohexyl | |
| Ic.133 | $-CH_2-CH(Br)-CO-OC(CH_3)_3$ | 7.50(d, 1H); 7.25(d, 1H); 6.72(t, 1H); 4.47(t, 1H); 3.83(s, 3H); 3.52(dd, 1H); 3.35(dd, 1H); 1.42(s, 9H) |
| Ic.134 | $-CH_2-CH(Br)-CO-OCH_2-CH(CH_3)_2$ | |
| Ic.135 | $-CH_2-CH(Br)-CO-NH-CH_2-CO-OCH_3$ | |
| Ic.136 | $-CH_2-CH(Br)-CO-N(CH_3)-CH_2-CO-OCH_3$ | 546[M+H]$^+$, 510[M–Cl]$^+$ |
| Ic.137 | $-CH_2-CH(Br)-CO-NH-CH(CH_3)-CO-OC_2H_5$ | |
| Ic.138 | $-CH_2-CH(Br)-CO-NH-OC_2H_5$ | |
| Ic.139 | $-CH_2-CH(Br)-CO-NH-OCH_3$ | |
| Ic.140 | $-CH_2-CH(Br)-CO-NH-OCH_2-CH=CHCl$ | |
| Ic.141 | $-CH_2-CH(Br)-CO-NH-OCH_2$-(4-chlorophenyl) | |
| Ic.142 | $-CH_2-CH(Br)-CO-SCH_2-CO-OC_2H_5$ | |
| Ic.143 | $-CH_2-CH(Br)-CO-SCH_2-C_2H_5$ | |
| Ic.144 | $-CH_2-CH(Br)-CO-SCH_2$-(4-chlorophenyl) | |
| Ic.145 | $-CH_2-C(Br)(CO-OC_2H_5)_2$ | |
| Ic.146 | $-CH_2-C(Br)(CO-OCH_3)_2$ | |
| Ic.147 | $-CH_2-CH(Br)-CO-OCH_2-CH=N-OCH_3$ | |
| Ic.148 | $-CH_2-CH(Br)-CO-OCH_2-CH=N-OC_2H_5$ | |
| Ic.149 | $-CH_2-CH(Br)-CO-OCH_2-CH=N-OCH_2-CH_2-C_2H_5$ | |
| Ic.150 | $-CH_2-CH(Br)-CO-OCH_2-CH=N-OCH_2$-phenyl | |
| Ic.151 | $-CH_2-CH(Br)-CO-OCH_2-CH=N-OCH_2-CH=CH_2$ | |
| Ic.152 | $-CH_2-CH(Br)-CO-OCH_2-CH=N-OCH_2-CH=CHCl$ | |
| Ic.153 | $-CH_2-CH(Br)-CO-OCH_2-CH=N-OCH_2$-(4-chlorophenyl) | |
| Ic.154 | $-CH_2-CH(Br)-CO-OCH_2-CH=N-OCH(CH_3)$-(4-chlorophenyl) | |
| Ic.155 | $-CH_2-CH(Br)-COOH$ | 9.50(s, 1H); 7.48(d, 1H); 7.28(d, 1H); 6.74(t, 1H); 4.61(t, 1H); 3.88(s, 3H); 3.58(dd, 1H); 3.40(dd, 1H) |
| Ic.156 | $-CH_2-CH(Br)-CO-NH$-cyclopropyl | |
| Ic.157 | $-CH_2-CH(Br)-CO-N(CH_3)-CH_2-CO-OC_2H_5$ | |
| Ic.158 | $-CH_2-CH(Br)-CO-NH-CH(CH(CH_3)_2)-CO-OC_2H_5$ | 7.50(d, 1H); 7.23(d, 1H); 6.70(t, 1H); 6.61(d, 1H); 4.65–4.45(m, 2H); 4.28–4.10(m, 2H); 3.85(s, 3.H); 3.72(m, 1H); 3.32(m, 1H); 2.15(m, 1H); 1.10(m, 3H); 1.00–0.80(m, 6H) |
| Ic.159 | $-CH_2-CH(Br)-CO-NH-CH(CH_2CH(CH_3)_2)-CO-OCH_3$ | |
| Ic.160 | $-CH_2-CH(Br)-CO$-(2-methoxycarbonyl-pyrrolidin-1-yl) | |
| Ic.161 | $-CH_2-CH(Br)-CO-NH$-(tetrahydrofuran-2-on-3-yl) | |
| Ic.162 | $-CH_2-CH(Br)-CO-N(CN)-CH_2CH_2-C_2H_5$ | |
| Ic.163 | $-CH_2-CH(Br)-CO-N(CN)$-cyclopropyl | |
| Ic.164 | $-CH_2-CH(Br)-CO-N(CN)-CH_2-CH=CH_2$ | |
| Ic.165 | $-CH_2-CH(Br)-CO-N(CONH_2)-CH_2CH_2-C_2H_5$ | |

TABLE 3-continued

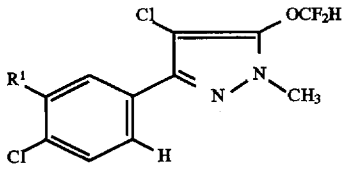

I ($R^2$,$R^5$ = Cl; $R^3$ = $CH_3$;
$R^4$ = O $F_2HH$; $R^6$ = F)

| No. | $R^1$ | m.p./$^1$H-NMR[ppm] MS[$mz^{-1}$] |
|---|---|---|
| Ic.166 | $-CH_2-CH(Br)-CO-N(CONH_2)$-cyclopropyl | |
| Ic.167 | $-CH_2-CH(Br)-CO-N(CONH_2)-CH_2-CH{=}CH_2$ | |
| Ic.168 | $-CH_2-CH(Br)-CO-$O-(4-acetoxytetrahydrofuran-3-yl) | |
| Ic.169 | $-CH_2-CH(OH)-COOH$ | |
| Ic.170 | $-CH_2-CH(OH)-CO-OCH_3$ | |
| Ic.171 | $-CH_2-CH(OH)-CO-OC_2H_5$ | |
| Ic.172 | $-CH_2-CH(OH)-CO-OCH_2-CH{=}N-OCH_3$ | |
| Ic.173 | $-CH_2-CH(OH)-CO-OC(CH_3)_3$ | |
| Ic.174 | $-CH_2-CH(OH)-CO-NH_2$ | |
| Ic.175 | $-CH_2-CH(OH)-CO-NH-CH_3$ | |
| Ic.176 | $-CH_2-CH(OH)-CO-$NH-cyclopropyl | |
| Ic.177 | $-CH_2-CH(OCH_3)-COOH$ | |
| Ic.178 | $-CH_2-CH(OCH_3)-CO-OCH_3$ | |
| Ic.179 | $-CH_2-CH(OCH_3)-CO-OC_2H_5$ | |
| Ic.180 | $-CH_2-CH(OCH_3)-CO-OCH_2-CH{=}N-OCH_3$ | |
| Ic.181 | $-CH_2-CH(OCH_3)-CO-OC(CH_3)_3$ | |
| Ic.182 | $-CH_2-CH(OCH_3)-CO-NH_2$ | |
| Ic.183 | $-CH_2-CH(OCH_3)-CO-NH-CH_3$ | |
| Ic.184 | $-CH_2-CH(OCH_3)-CO-$NH-cyclopropyl | |
| Ic.185 | $-CH_2-CH(O-COCH_3)-COOH$ | |
| Ic.186 | $-CH_2-CH(O-COCH_3)-CO-OCH_3$ | |
| Ic.187 | $-CH_2-CH(O-COCH_3)-CO-OC_2H_5$ | |
| Ic.188 | $-CH_2-CH(O-COCH_3)-CO-OCH_2-CH{=}N-OCH_3$ | |
| Ic.189 | $-CH_2-CH(O-COCH_3)-CO-OC(CH_3)_3$ | |
| Ic.190 | $-CH_2-CH(O-COCH_3)-CO-NH_2$ | |
| Ic.191 | $-CH_2-CH(O-COCH_3)-CO-NH-CH_3$ | |
| Ic.192 | $-CH_2-CH(O-COCH_3)-CO-$NH-cyclopropyl | |
| Ic.193 | $-CH_2-CH(NH_2)-COOH$ | |
| Ic.194 | $-CH_2-CH(NH_2)-CO-OCH_3$ | |
| Ic.195 | $-CH_2-CH(NH_2)-CO-OC_2H_5$ | |
| Ic.196 | $-CH_2-CH(NH_2)-CO-OC(CH_3)_3$ | |
| Ic.197 | $-CH_2-CH(NH_2)-CO-NH_2$ | |
| Ic.198 | $-CH_2-CH(NH_2)-CO-NH-CH_3$ | |
| Ic.199 | $-CH_2-CH(N_3)-COOH$ | |
| Ic.200 | $-CH_2-CH(N_3)-CO-OCH_3$ | |
| Ic.201 | $-CH_2-CH(N_3)-CO-OC_2H_5$ | |
| Ic.202 | $-CH_2-CH(N_3)-CO-OC(CH_3)3$ | |
| Ic.203 | $-CH_2-CH(N_3)-CO-NH_2$ | |
| Ic.204 | $-CH_2-CH(N_3)-CO-NH-CH_3$ | |
| Ic.205 | $-CH_2-CH(NH-COCH_3)-COOH$ | |
| Ic.206 | $-CH_2-CH(NH-COCH_3)-CO-OCH_3$ | |
| Ic.207 | $-CH_2-CH(NH-COCH_3)-CO-OC_2H_5$ | |
| Ic.208 | $-CH_2-CH(NH-COCH_3)-CO-OC(CH_3)_3$ | |
| Ic.209 | $-CH_2-CH(NH-COCH_3)-CO-NH_2$ | |
| Ic.210 | $-CH_2-CH(NH-COCH_3)-CO-NH-CH_3$ | |
| Ic.211 | $-CH_2-CH_2$-cyclohexyl | |
| Ic.212 | $-CH_2-CH_2$-cyclopentyl | |
| Ic.213 | $-CH_2-CH_2$-cyclopropyl | |
| Ic.214 | $-CH_2-CH_2$-phenyl | |
| Ic.215 | $-CH{=}C(CN)-CO-OC_2H_5$ | |
| Ic.216 | $-CH{=}C(CN)-CO-OCH(CH_3)_2$ | |
| Ic.217 | $-CH{=}C(CN)-CO-OC(CH_3)3$ | |
| Ic.218 | $-CH{=}C(Cl)-CO-OCH_2-CH{=}N-OCH_2-CH{=}CH_2$ | |
| Ic.219 | $-CH{=}C(Cl)-CO-OCH_2-CH{=}N-OCH_2-CH{=}CHCl$ | |
| Ic.220 | $-CH{=}C(Cl)-CO-OCH_2-CH{=}N-OCH_2$-(4-chlorophenyl) | |
| Ic.221 | $-CH{=}C(Cl)-CO-OCH_2-CH{=}N-OCH(CH_3)$-(4-chlorophenyl) | |
| Ic.222 | $-CH{=}C(Cl)-CO-$O-(4-acetoxytetrahydrofuran-3-yl) | |
| Ic.223 | $-CH{=}C(Cl)-CO-$NH-cyclohexyl | |
| Ic.224 | $-CH{=}C(Cl)-CO-N(CH_3)-CH_2-CO-OC_2H_5$ | 8.06(m, 1H);<br>7.35–7.05(m, 2H);<br>6.72(t, 1H);<br>4.30–4.15(m, 4H);<br>3.85(s, 3H);<br>3.25 and 3.10 |

TABLE 3-continued

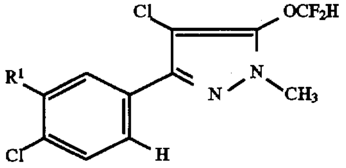

I ($R^2$,$R^5$ = Cl; $R^3$ = $CH_3$;
$R^4$ = O $F_2$HH; $R^6$ = F)

| No. | $R^1$ | m.p./$^1$H-NMR[ppm] MS[$mz^{-1}$] |
|---|---|---|
| | | (2s, together 3H); 1.30(m, 3H) |
| Ic.225 | $-CH=C(Cl)-CO-NH-CH(CH(CH_3)_2)-CO-OC_2H_5$ | |
| Ic.226 | $-CH=C(Cl)-CO-NH-CH(CH_2CH(CH_3)_2)-CO-OCH_3$ | |
| Ic.227 | $-CH=C(Cl)-$CO-(2-methoxycarbonyl-pyrrolidin-1-yl) | |
| Ic.228 | $-CH=C(Cl)-CO-$NH-(tetrahydrofuran-2-on-3-yl) | |
| Ic.229 | $-CH=C(Cl)-CO-N(CN)-CH_2CH_2-C_2H_5$ | |
| Ic.230 | $-CH=C(Cl)-CO-$N(CN)-cyclopropyl | |
| Ic.231 | $-CH=C(Cl)-CO-N(CN)-CH_2-CH=CH_2$ | |
| Ic.232 | $-CH=C(Cl)-CO-N(CONH_2)-CH_2CH_2-C_2H_5$ | |
| Ic.233 | $-CH=C(Cl)-CO-N(CONH_2)$-cyclopropyl | |
| Ic.234 | $-CH=C(Cl)-CO-N(CONH_2)-CH_2-CH=CH_2$ | |
| Ic.235 | $-CH=C(Br)-CO-OCH_2-CH=N-OCH_2$-(4-chlorophenyl) | |
| Ic.236 | $-CH=C(Br)-CO-OCH_2-CH=N-OCH(CH_3)$-(4-chlorophenyl) | |
| Ic.237 | $-CH=C(Br)-CO-$O-(4-acetoxytetrahydrofuran-3-yl) | |
| Ic.238 | $-CH=C(Br)-CO-$NH-cyclohexyl | |
| Ic.239 | $-CH=C(Br)-CO-N(CH_3)-CH_2-CO-OC_2H_5$ | 7.98(m, 1H); 7.35–7.18(m, 2H); 6.73(t, 1H); 4.30–4.15(m, 4H); 3.86(s, 3H); 3.24 and 3.10 (2s, together 3H); 1.30(m, 3H) |
| Ic.240 | $-CH=C(Br)-CO-NH-CH(CH(CH_3)_2)-CH-OC_2H_5$ | |
| Ic.241 | $-CH=C(Br)-CO-NH-CH(CH_2CH(CH_3)_2)-CO-OCH_3$ | |
| Ic.242 | $-CH=C(Br)-$CO-(2-methoxycarbonyl-pyrrolidin-1-yl) | |
| Ic.243 | $-CH=C(Br)-CO-$NH-(tetrahydrofuran-2-on-3-yl) | |
| Ic.244 | $-CH=C(Br)-CO-N(CN)-CH_2CH_2-C_2H_5$ | |
| Ic.245 | $-CH=C(Br)-CO-$N(CN)-cyclopropyl | |
| Ic.246 | $-CH=C(Br)-CO-N(CN)-CH_2-CH=CH_2$ | |
| Ic.247 | $-CH=C(Br)-CO-N(CONH_2)-CH_2CH_2-C_2H_5$ | |
| Ic.248 | $-CH=C(Br)-CO-N(CONH_2)$-cyclopropyl | |
| Ic.249 | $-CH=C(Br)-CO-N(CONH_2)-CH_2-CH=CH_2$ | |
| Ic.250 | $-CH_2-CH(Cl)-CO-N(C_2H_5)_2$ | |
| Ic.251 | $-CH_2-CH(Br)-CO-N(C_2H_5)_2$ | |
| Ic.252 | $-CH=C(Br)-CO-N(C_2H_5)_2$ | |
| Ic.253 | $-CH=C(Cl)-CO-N(C_2H_5)_2$ | |
| Ic.254 | 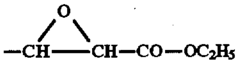 | |
| Ic.255 | 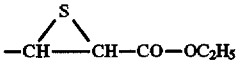 | |
| Ic.256 | 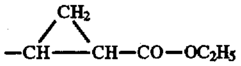 | |
| Ic.257 | 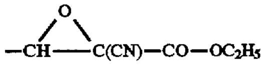 | |
| Ic.258 | 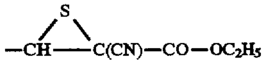 | |
| Ic.259 | 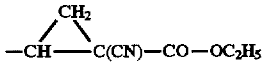 | |
| Ic.260 | 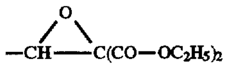 | |

TABLE 3-continued

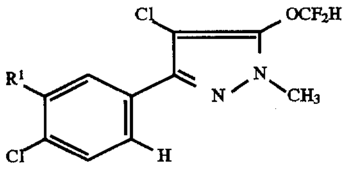

I ($R^2$,$R^5$ = Cl; $R^3$ = $CH_3$;
$R^4$ = O $F_2$HH; $R^6$ = F)

| No. | $R^1$ | m.p./$^1$H-NMR[ppm] MS[$mz^{-1}$] |
|---|---|---|
| Ic.261 | 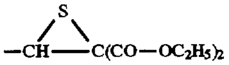 | |
| Ic.262 | 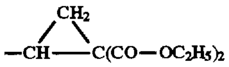 | |

TABLE 4

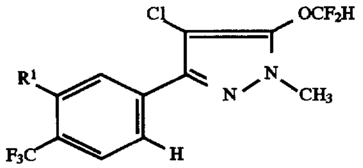

I ($R^2$ = $CF_3$; $R^3$ = $CH_3$;
$R^4$ = $OCF_2H$; $R^5$ = Cl; $R^6$ = H)

| No. | $R^1$ | m.p./$^1$H-NMR[ppm] MS[$mz^{-1}$] |
|---|---|---|
| Id.001 | $-CH_2-CH(CN)-CO-OC_2H_5$ | |
| Id.002 | $-CH_2-CH(CN)-CO-NH_2$ | |
| Id.003 | $-CH_2-CH(CN)-CO-N(CH_3)_2$ | |
| Id.004 | $-CH_2-CH(Cl)-CO-OC_2H_5$ | |
| Id.005 | $-CH_2-CH(Cl)-CO-NH_2$ | |
| Id.006 | $-CH_2-CH(Cl)-CO-N(CH_3)_2$ | |
| Id.007 | $-CH_2-CH(Br)-CO-OC_2H_5$ | |
| Id.008 | $-CH_2-CH(Br)-CO-OCH_3$ | |
| Id.009 | $-CH_2-CH(Br)-CO-NH_2$ | |
| Id.010 | $-CH_2-CH(Br)-CO-N(CH_3)_2$ | |
| Id.011 | $-CH=C(Cl)-COOH$ | |
| Id.012 | $-CH=C(Cl)-CO-OCH_3$ | |
| Id.013 | $-CH=C(Cl)-CO-OC_2H_5$ | |
| Id.014 | $-CH=C(Cl)-CO-OCH(CH_3)_2$ | |
| Id.015 | $-CH=C(Br)-COOH$ | |
| Id.016 | $-CH=C(Br)-CO-OCH_3$ | |
| Id.017 | $-CH=C(Br)-CO-OC_2H_5$ | |
| Id.018 | $-CH=C(Br)-CO-OCH(CH_3)_2$ | |
| Id.019 | $-CH=C(Cl)-CO-NH_2$ | |
| Id.020 | $-CH=C(Cl)-CO-NH-CH_3$ | |
| Id.021 | $-CH=C(Br)-CO-NH_3$ | |
| Id.022 | $-CH=C(Br)-CO-NH-CH_3$ | |
| Id.023 | $-CH=$(cyclohexylene) | |
| Id.024 | 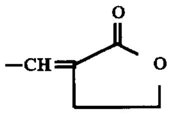 | |
| Id.025 | $-CH=C(CH_3)-CO-OC_2H_5$ | |
| Id.026 | $-CH=C(CH_3)-CO-OCH_3$ | |
| Id.027 | $-CH=C(CH_3)-CO-NH_2$ | |
| Id.028 | $-CH=C(CH_3)-CO-NH-CH_3$ | |
| Id.029 | $-CH=C(CN)-CO-OCH_3$ | |
| Id.030 | $-CH_2-CH(CN)-CO-OCH_3$ | |
| Id.031 | $-CH_2-CH(Cl)-CO-OCH_3$ | |
| Id.032 | $-CH_2-CH(Cl)-CO-NH-CH_3$ | |

TABLE 4-continued

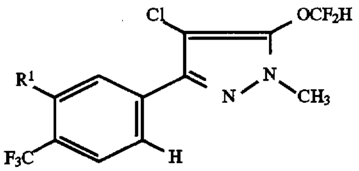

I ($R^2 = CF_3$; $R^3 = CH_3$;
$R^4 = OCF_2H$; $R^5 = Cl$; $R^6 = H$)

| No. | $R^1$ | m.p./$^1$H-NMR[ppm] MS[$mz^{-1}$] |
|---|---|---|
| Id.033 | $-CH_2-CH(Br)-CO-OCH(CH_3)_2$ | |
| Id.034 | $-CH_2-CH(Br)-CO-NH-CH_3$ | |
| Id.035 | $-CH=CH$-(4-chlorophenyl) | |
| Id.036 | $-CH=C(Cl)-CO-OC(CH_3)_3$ | |
| Id.037 | $-CH=C(Cl)-CO-NH-CH_2-CO-OCH_3$ | |
| Id.038 | $-CH=C(Cl)-CO-N(CH_3)-CH_2-CO-OCH_3$ | |
| Id.039 | $-CH=C(Cl)-CO-NH-OC_2H_5$ | |
| Id.040 | $-CH=C(Cl)-CO-SCH_2-C_2H_5$ | |
| Id.041 | $-CH=C(CO-OC_2H_5)_2$ | |
| Id.042 | $-CH=C(CO-OCH_3)_2$ | |
| Id.043 | $-CH=C(Cl)-CO-OCH_2-CH=N-OC_2H_5$ | |
| Id.044 | $-CH=C(Br)-CO-OC(CH_3)_3$ | |
| Id.045 | $-CH=C(Br)-CO-NH-CH_2-CO-OCH_3$ | |
| Id.046 | $-CH=C(Br)-CO-N(CH_3)-CH_2-CO-OCH_3$ | |
| Id.047 | $-CH=C(Br)-CO-NH-OC_2H_5$ | |
| Id.048 | $-CH=C(Br)-CO-SCH_2-C_2H_5$ | |
| Id.049 | $-CH=C(Br)-CO-OCH_2-CH=N-OC_2H_5$ | |
| Id.050 | $-CH_2-CH(Cl)-CO-OC(CH_3)_3$ | |
| Id.051 | $-CH_2-CH(Cl)-CO-NH-CH_2-CO-OCH_3$ | |
| Id.052 | $-CH_2-CH(Cl)-CO-N(CH_3)-CH_2-CO-OCH_3$ | |
| Id.053 | $-CH_2-CH(Cl)-CO-NH-OC_2H_5$ | |
| Id.054 | $-CH_2-CH(Cl)-CO-SCH_2-C_2H_5$ | |
| Id.055 | $-CH_2-CH(Cl)-CO-OCH_2-CH=N-OC_2H_5$ | |
| Id.056 | $-CH_2-CH(Cl)-COOH$ | |
| Id.057 | $-CH_2-CH(Br)-CO-OC(CH_3)_3$ | |
| Id.058 | $-CH_2-CH(Br)-CO-NH-CH_2-CO-OCH_3$ | |
| Id.059 | $-CH_2-CH(Br)-CO-N(CH_3)-CH_2-CO-OCH_3$ | |
| Id.060 | $-CH_2-CH(Br)-CO-NH-OC_2H_5$ | |
| Id.061 | $-CH_2-CH(Br)-CO-SCH_2-C_2H_5$ | |
| Id.062 | $-CH_2-CH(Br)-CO-OCH_2-CH=N-OC_2H_5$ | |
| Id.063 | $-CH_2-CH(Br)-COOH$ | |
| Id.064 | $-CH_2-CH(OH)-COOH$ | |
| Id.065 | $-CH_2-CH(OH)-CO-OCH_3$ | |
| Id.066 | $-CH_2-CH(NH_2)-COOH$ | |
| Id.067 | $-CH_2-CH(NH_2)-CO-OCH_3$ | |
| Id.068 | $-CH_2-CH_2$-cyclohexyl | |
| Id.069 | $-CH_2-CH_2$-phenyl | |

TABLE 5

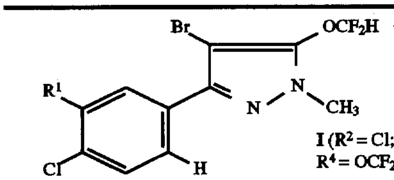

I ($R^2 = Cl$; $R^3 = CH_3$;
$R^4 = OCF_2H$; $R^5 = Br$; $R^6 = H$)

| No. | $R^1$ | m.p./$^1$H-NMR [ppm] MS [$mz^{-1}$] |
|---|---|---|
| Ie.001 | $-CH_2-CH(CN)-CO-OC_2H_5$ | |
| Ie.002 | $-CH_2-CH(CN)-CO-NH_2$ | |
| Ie.003 | $-CH_2-CH(CN)-CO-N(CH_3)_2$ | |
| Ie.004 | $-CH_2-CH(Cl)-CO-OC_2H_5$ | |
| Ie.005 | $-CH_2-CH(Cl)-CO-NH_2$ | |
| Ie.006 | $-CH_2-CH(Cl)-CO-N(CH_3)_2$ | |
| Ie.007 | $-CH_2-CH(Br)-CO-OC_2H_5$ | |
| Ie.008 | $-CH_2-CH(Br)-CO-OCH_3$ | |
| Ie.009 | $-CH_2-CH(Br)-CO-NH_2$ | |

TABLE 5-continued

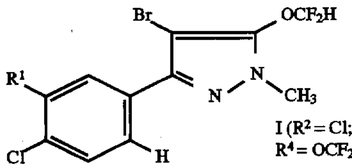

I ($R^2 = Cl$; $R^3 = CH_3$;
$R^4 = OCF_2H$; $R^5 = Br$; $R^6 = H$)

| No. | $R^1$ | m.p./$^1$H-NMR [ppm] MS [$mz^{-1}$] |
|---|---|---|
| Ie.010 | $-CH_2-CH(Br)-CO-N(CH_3)_2$ | |
| Ie.011 | $-CH=C(Cl)-CO-OC_2H_5$ | |
| Ie.012 | $-CH=C(Cl)-CO-NH_2$ | |
| Ie.013 | $-CH=C(Cl)-CO-N(CH_3)_2$ | |
| Ie.014 | $-CH=C(Br)-CO-OC_2H_5$ | |
| Ie.015 | $-CH=C(Br)-CO-NH_2$ | |
| Ie.016 | $-CH=C(Br)-CO-N(CH_3)_2$ | |
| Ie.017 | $-CH=C(CN)-CO-OC_2H_5$ | |
| Ie.018 | $-CH=C(CN)-CO-NH_2$ | |

TABLE 5-continued

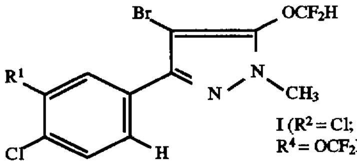

I ($R^2$ = Cl; $R^3$ = $CH_3$; $R^4$ = $OCF_2H$; $R^5$ = Br; $R^6$ = H)

| No. | $R^1$ | m.p./$^1$H-NMR [ppm] MS [$mz^{-1}$] |
|---|---|---|
| Ie.019 | $-CH=C(CN)-CO-N(CH_3)_2$ | |
| Ie.020 | $-CH=C(CH_3)-CO-OC_2H_5$ | |
| Ie.021 | $-CH=C(CH_3)-CO-NH_2$ | |
| Ie.022 | $-CH=C(CH_3)-CO-N(CH_3)_2$ | |

TABLE 6

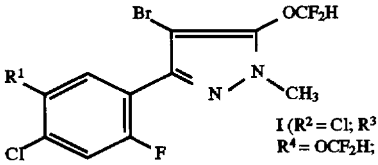

I ($R^2$ = Cl; $R^3$ = $CH_3$; $R^4$ = $OCF_2H$; $R^5$ = Br; $R^6$ = F)

| No. | $R^1$ | m.p./$^1$H-NMR [ppm] MS [$mz^{-1}$] |
|---|---|---|
| If.001 | $-CH_2-CH(CN)-CO-OC_2H_5$ | |
| If.002 | $-CH_2-CH(CN)-CO-NH_2$ | |
| If.003 | $-CH_2-CH(CN)-CO-N(CH_3)_2$ | |
| If.004 | $-CH_2-CH(Cl)-CO-OC_2H_5$ | |
| If.005 | $-CH_2-CH(Cl)-CO-NH_2$ | |
| If.006 | $-CH_2-CH(Cl)-CO-N(CH_3)_2$ | |
| If.007 | $-CH_2-CH(Br)-CO-OC_2H_5$ | |
| If.008 | $-CH_2-CH(Br)-CO-OCH_3$ | |
| If.009 | $-CH_2-CH(Br)-CO-NH_2$ | |
| If.010 | $-CH_2-CH(Br)-CO-N(CH_3)_2$ | |
| If.011 | $-CH=C(Cl)-CO-OC_2H_5$ | |
| If.012 | $-CH=C(Cl)-CO-NH_2$ | |
| If.013 | $-CH=C(Cl)-CO-N(CH_3)_2$ | |
| If.014 | $-CH=C(Br)-CO-OC_2H_5$ | |
| If.015 | $-CH=C(Br)-CO-NH_2$ | |
| If.016 | $-CH=C(Br)-CO-N(CH_3)_2$ | |
| If.017 | $-CH=C(CN)-CO-OC_2H_5$ | |
| If.018 | $-CH=C(CN)-CO-NH_2$ | |
| If.019 | $-CH=C(CN)-CO-N(CH_3)_2$ | |
| If.020 | $-CH=C(CH_3)-CO-OC_2H_5$ | |
| If.021 | $-CH=C(CH_3)-CO-NH_2$ | |
| If.022 | $-CH=C(CH_3)-CO-N(CH_3)_2$ | |

TABLE 7

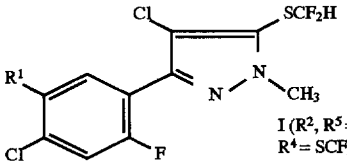

I ($R^2$, $R^5$ = Cl; $R^3$ = $CH_3$; $R^4$ = $SCF_2H$; $R^6$ = F)

| No. | $R^1$ | m.p./$^1$H-NMR [ppm] MS [$mz^{-1}$] |
|---|---|---|
| Ig.001 | $-CH_2-CH(CN)-CO-OC_2H_5$ | |
| Ig.002 | $-CH_2-CH(CN)-CO-NH_2$ | |
| Ig.003 | $-CH_2-CH(CN)-CO-N(CH_3)_2$ | |
| Ig.004 | $-CH_2-CH(Cl)-CO-OC_2H_5$ | |
| Ig.005 | $-CH_2-CH(Cl)-CO-NH_2$ | |
| Ig.006 | $-CH_2-CH(Cl)-CO-N(CH_3)_2$ | |
| Ig.007 | $-CH_2-CH(Br)-CO-OC_2H_5$ | |
| Ig.008 | $-CH_2-CH(Br)-CO-OCH_3$ | |
| Ig.009 | $-CH_2-CH(Br)-CO-NH_2$ | |
| Ig.010 | $-CH_2-CH(Br)-CO-N(CH_3)_2$ | |
| Ig.011 | $-CH=C(Cl)-CO-OC_2H_5$ | |
| Ig.012 | $-CH=C(Cl)-CO-NH_2$ | |
| Ig.013 | $-CH=C(Cl)-CO-N(CH_3)_2$ | |
| Ig.014 | $-CH=C(Br)-CO-OC_2H_5$ | |
| Ig.015 | $-CH=C(Br)-CO-NH_2$ | |
| Ig.016 | $-CH=C(Br)-CO-N(CH_3)_2$ | |
| Ig.017 | $-CH=C(CN)-CO-OC_2H_5$ | |
| Ig.018 | $-CH=C(CN)-CO-NH_2$ | |
| Ig.019 | $-CH=C(CN)-CO-N(CH_3)_2$ | |
| Ig.020 | $-CH=C(CH_3)-CO-OC_2H_5$ | |
| Ig.021 | $-CH=C(CH_3)-CO-NH_2$ | |
| Ig.022 | $-CH=C(CH_3)-CO-N(CH_3)_2$ | |

TABLE 8

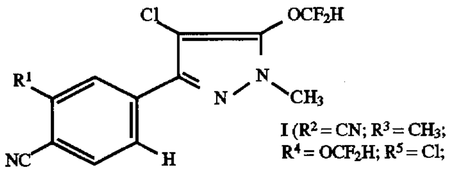

I ($R^2$ = CN; $R^3$ = $CH_3$; $R^4$ = $OCF_2H$; $R^5$ = Cl; $R^6$ = H)

| No. | $R^1$ | m.p./$^1$H-NMR [ppm] MS [$mz^{-1}$] |
|---|---|---|
| Ih.001 | $-CH=C(Cl)-COOH$ | |
| Ih.002 | $-CH=C(Cl)-CO-OCH_3$ | |
| Ih.003 | $-CH=C(Cl)-CO-OC_2H_5$ | |
| Ih.004 | $-CH=C(Cl)-CO-OCH(CH_3)_2$ | |
| Ih.005 | $-CH=C(Br)-COOH$ | |
| Ih.006 | $-CH=C(Br)-CO-OCH_3$ | |
| Ih.007 | $-CH=C(Br)-CO-OC_2H_5$ | |
| Ih.008 | $-CH=C(Br)-CO-OCH(CH_3)_2$ | |
| Ih.009 | $-CH=C(Cl)-CO-NH_2$ | |
| Ih.010 | $-CH=C(Cl)-CO-NH-CH_3$ | |
| Ih.011 | $-CH=C(Cl)-CO-N(CH_3)_2$ | |
| Ih.012 | $-CH=C(Br)-CO-NH_2$ | |
| Ih.013 | $-CH=C(Br)-CO-NH-CH_3$ | |
| Ih.014 | $-CH=C(Br)-CO-N(CH_3)_2$ | |
| Ih.015 | $-CH=C(Br)-CO-$NH-cyclopropyl | |
| Ih.016 | $-CH=C(Cl)-CO-$NH-cyclopropyl | |
| Ih.017 | $-CH=$(cyclopropylene) | |
| Ih.018 | $-CH=$(cyclopentylene) | |
| Ih.019 | $-CH=$(cyclohexylene) | |
| Ih.020 | 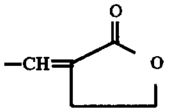 | |
| Ih.021 | 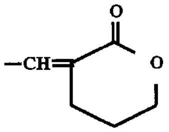 | |
| Ih.022 | 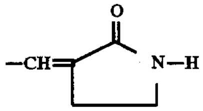 | |
| Ih.023 | 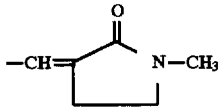 | |
| Ih.024 | 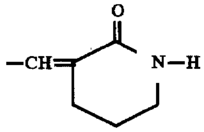 | |
| Ih.025 | 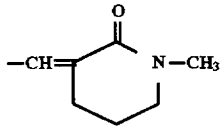 | |
| Ih.026 | 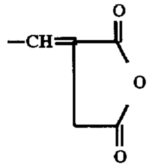 | |

TABLE 8-continued

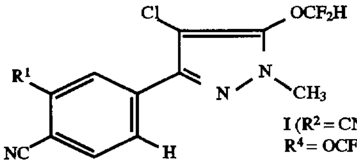

I ($R^2$ = CN; $R^3$ = $CH_3$; $R^4$ = $OCF_2H$; $R^5$ = Cl; $R^6$ = H)

| No. | $R^1$ | m.p./$^1$H-NMR [ppm] MS [$mz^{-1}$] |
|---|---|---|
| Ih.027 | 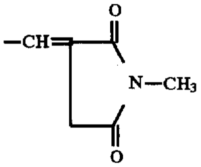 | |
| Ih.028 | $-CH=C(CH_3)-CO-OC_2H_5$ | |
| Ih.029 | $-CH=C(CH_3)-CO-OCH_3$ | |
| Ih.030 | $-CH=C(CH_3)-CO-NH_2$ | |
| Ih.031 | $-CH=C(CH_3)-CO-NH-CH_3$ | |
| Ih.032 | $-CH=C(CH_3)-CO-N(CH_3)_2$ | |
| Ih.033 | $-CH=C(CN)-CO-OCH_3$ | |
| Ih.034 | $-CH_2-CH(CN)-CO-OCH_3$ | |
| Ih.035 | $-CH_2-CH(CN)-CO-OC_2H_5$ | |
| Ih.036 | $-CH_2-CH(CN)-CO-NH_2$ | |
| Ih.037 | $-CH_2-CH(CN)-CO-NH-CH_3$ | |
| Ih.038 | $-CH_2-CH(CN)-CO-N(CH_3)_2$ | |
| Ih.039 | $-CH_2-CH(CN)-CO-NH-SO_2-CH_3$ | |
| Ih.040 | $-CH_2-CH(Cl)-CO-OCH_3$ | 7.94(m, 2H);<br>7.72(d, 1H);<br>6.70(t, 1H);<br>4.46(dd, 1H);<br>3.85(s, 3H);<br>3.80(s, 3H);<br>3.66(dd, 1H);<br>3.45(dd, 1H) |
| Ih.041 | $-CH_2-CH(Cl)-CO-OC_2H_5$ | 7.93(m, 2H);<br>7.71(d, 1H);<br>6.71(t, 1H);<br>4.64(dd, 1H);<br>4.26(q, 2H);<br>3.84(s, 3H);<br>3.66(dd, 1H);<br>3.46(dd, 1H);<br>1.30(t, 3H) |
| Ih.042 | $-CH_2-CH(Cl)-CO-NH_2$ | |
| Ih.043 | $-CH_2-CH(Cl)-CO-NH-CH_3$ | |
| Ih.044 | $-CH_2-CH(Cl)-CO-N(CH_3)_2$ | |
| Ih.045 | $-CH_2-CH(Cl)-CO-NH-SO_2-CH_3$ | |
| Ih.046 | $-CH_2-CH(Br)-CO-OCH_3$ | |
| Ih.047 | $-CH_2-CH(Br)-CO-OC_2H_5$ | |
| Ih.048 | $-CH_2-CH(Br)-CO-OCH(CH_3)_2$ | |
| Ih.049 | $-CH_2-CH(Br)-CO-NH_2$ | |
| Ih.050 | $-CH_2-CH(Br)-CO-NH-CH_3$ | |
| Ih.051 | $-CH_2-CH(Br)-CO-N(CH_3)_2$ | |
| Ih.052 | $-CH_2-CH(Cl)-CO-CH(CH_3)_2$ | |
| IH.053 | $-CH_2-CH(CN)-CO-CH(CH_3)_2$ | |
| Ih.054 | −CH=CH-(4-fluorophenyl) | |
| Ih.055 | −CH=CH-(4-chlorophenyl) | |
| Ih.056 | −CH=CH-(3-trifluoromethylphenyl) | |
| Ih.057 | −CH=CH-(2,4-dichlorophenyl) | |
| Ih.058 | −CH=C(Cl)−CO−O-cyclohexyl | |
| Ih.059 | $-CH=C(Cl)-CO-OC(CH_3)_3$ | |
| Ih.060 | $-CH=C(Cl)-CO-OCH_2-CH(CH_3)_2$ | |
| Ih.061 | $-CH=C(Cl)-CO-NH-CH_2-CO-OCH_3$ | |
| Ih.062 | $-CH=C(Cl)-CO-N(CH_3)-CH_2-CO-OCH_3$ | |
| Ih.063 | $-CH=C(Cl)-CO-NH-CH(CH_3)-CO-OC_2H_5$ | |
| Ih.064 | $-CH=C(Cl)-CO-NH-OC_2H_5$ | |
| Ih.065 | $-CH=C(Cl)-CO-NH-OCH_3$ | |
| Ih.066 | $-CH=C(Cl)-CO-NH-OCH_2-CH-CHCl$ | |
| Ih.067 | $-CH=C(Cl)-CO-NH-OCH_2$-(4-chlorophenyl) | |
| Ih.068 | $-CH=C(Cl)-CO-SCH_2-CO-OC_2H_5$ | |
| Ih.069 | $-CH=C(Cl)-CO-SCH_2-C_2H_5$ | |

TABLE 8-continued

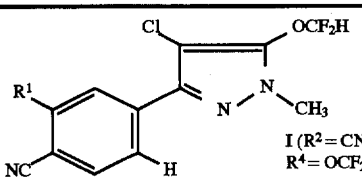

I ($R^2$ = CN; $R^3$ = $CH_3$; $R^4$ = $OCF_2H$; $R^5$ = Cl; $R^6$ = H)

| No. | $R^1$ | m.p./$^1$H-NMR [ppm] MS [$mz^{-1}$] |
|---|---|---|
| Ih.070 | $-CH{=}C(Cl)-CO-SCH_2$-(4-chlorophenyl) | |
| Ih.071 | $-CH{=}C(CO-OC_2H_5)_2$ | |
| Ih.072 | $-CH{=}C(CO-OCH_3)_2$ | |
| Ih.073 | $-CH{=}C(Cl)-CO-OCH_2-CH{=}N-OCH_3$ | |
| Ih.074 | $-CH{=}C(Cl)-CO-OCH_2-CH{=}N-OC_2H_5$ | |
| Ih.075 | $-CH{=}C(Cl)-CO-OCH_2-CH{=}N-OCH_2-CH_2-C_2H_5$ | |
| Ih.076 | $-CH{=}C(Cl)-CO-OCH_2-CH{=}N-OCH_2$-phenyl | |
| Ih.077 | $-CH{=}C(Br)-CO-O$-cyclohexyl | |
| Ih.078 | $-CH{=}C(Br)-CO-OC(CH_3)_3$ | |
| Ih.079 | $-CH{=}C(Br)-CO-OCH_2-CH(CH_3)_2$ | |
| Ih.080 | $-CH{=}C(Br)-CO-NH-CH_2-CO-OCH_3$ | |
| Ih.081 | $-CH{=}C(Br)-CO-N(CH_3)-CH_2-CO-OCH_3$ | |
| Ih.082 | $-CH{=}C(Br)-CO-NH-OC_2H_5$ | |
| Ih.083 | $-CH{=}C(Br)-CO-NH-OCH_3$ | |
| Ih.084 | $-CH{=}C(Br)-CO-NH-OCH_2-CH{=}CHCl$ | |
| Ih.085 | $-CH{=}C(Br)-CO-NH-OCH_2$-(4-chlorophenyl) | |
| Ih.086 | $-CH{=}C(Br)-CO-SCH_2-CO-OC_2H_5$ | |
| Ih.087 | $-CH{=}C(Br)-CO-SCH_2-C_2H_5$ | |
| Ih.088 | $-CH{=}C(Br)-CO-SCH_2$-(4-chlorophenyl) | |
| Ih.089 | $-CH{=}C(Br)-CO-OCH_2-CH{=}N-OCH_2-CH{=}CH_2$ | |
| Ih.090 | $-CH{=}C(Br)-CO-OCH_2-CH{=}N-OCH_2-CH{=}CHCl$ | |
| Ih.091 | $-CH{=}C(Br)-CO-OCH_2-CH{=}N-OCH_3$ | |
| Ih.092 | $-CH{=}C(Br)-CO-OCH_2-CH{=}N-OC_2H_5$ | |
| Ih.093 | $-CH{=}C(Br)-CO-OCH_2-CH{=}N-OCH_2-CH_2-C_2H_5$ | |
| Ih.094 | $-CH{=}C(Br)-CO-OCH_2-CH{=}N-OCH_2$-phenyl | |
| Ih.095 | $-CH_2-CH(Cl)-CO-O$-cyclohexyl | |
| Ih.096 | $-CH_2-CH(Cl)-CO-OC(CH_3)_3$ | |
| Ih.997 | $-CH_2-CH(Cl)-CO-OCH_2-CH(CH_3)_2$ | |
| Ih.098 | $-CH_2-CH(Cl)-CO-NH-CH_2-CO-OCH_3$ | |
| Ih.099 | $-CH_2-CH(Cl)-CO-N(CH_3)-CH_2-CO-OCH_3$ | |
| Ih.100 | $-CH_2-CH(Cl)-CO-NH-CH(CH_3)-CO-OC_2H_5$ | |
| Ih.101 | $-CH_2-CH(Cl)-CO-NH-OC_2H_5$ | |
| Ih.102 | $-CH_2-CH(Cl)-CO-NH-OCH_3$ | |
| Ih.103 | $-CH_2-CH\ (Cl)-CO-NH-OCH_2-CH{=}CHCl$ | |
| Ih.104 | $-CH_2-CH(Cl)-CO-NH-OCH_2$-(4-chloro-phenyl) | |
| Ih.105 | $-CH_2-CH(Cl)-CO-SCH_2-CO-OC_2H_5$ | |
| Ih.106 | $-CH_2-CH(Cl)-CO-SCH_2-C_2H_5$ | |
| Ih.107 | $-CH_2-CH(Cl)-CO-SCH_2$-(4-chlorophenyl) | |
| Ih.108 | $-CH_2-C(Cl)(CO-OC_2H_5)_2$ | |
| Ih.109 | $-CH_2-C(Cl)(CO-OCH_3)_2$ | |
| Ih.110 | $-CH_2-CH(Cl)-CO-OCH_2-CH{=}N-OCH_3$ | |
| Ih.111 | $-CH_2-CH(Cl)-CO-OCH_2-CH{=}N-OC_2H_5$ | |
| Ih.112 | $-CH_2-CH(Cl)-CO-OCH_2-CH{=}N-OCH_2-CH_2-C_2H_5$ | |
| Ih.113 | $-CH_2-CH(Cl)-CO-OCH_2-CH{=}N-OCH_2$-phenyl | |
| Ih.114 | $-CH_2-CH(Cl)-CO-OCH_2-CH{=}N-OCH_2-CH{=}CH_2$ | |
| Ih.115 | $-CH_2-CH(Cl)-CO-OCH_2-CH{=}N-OCH_2-CH{=}CHCl$ | |
| Ih.116 | $-CH_2-CH(Cl)-CO-OCH_2-CH{=}N-OCH_2$-(4-chlorophenyl) | |
| Ih.117 | $-CH_2-CH(Cl)-CO-OCH_2-CH{=}N-OCH(CH_3)$-(4-chlorophenyl) | |
| Ih.118 | $-CH_2-CH(Cl)-COOH$ | |
| Ih.119 | $-CH_2-CH(Cl)-CO-NH$-cyclopropyl | |
| Ih.120 | $-CH_2-CH(Cl)\ CO-N(CH_3)-CH_2-CO-OC_2H_5$ | |
| Ih.121 | $-CH_2-CH(Cl)-CO-NH-CH(CH(CH_3)_2)-CO-OC_2H_5$ | |
| Ih.122 | $-CH_2-CH(Cl)-CO-NH-CH(CH_2CH(CH_3)_2)-CO-OCH_3$ | |
| Ih.123 | $-CH_2-CH(Cl)-CO-$(2-methoxycarbonyl-pyrrolidin-1-yl) | |
| Ih.124 | $-CH_2-CH(Cl)-CO-NH$-(tetrahydro-furan-2-on-3-yl) | |
| Ih.125 | $-CH_2-CH(Cl)-CO-N(CN)-CH_2CH_2-C_2H_5$ | |
| Ih.126 | $-CH_2-CH(Cl)-CO-N(CN)$-cyclopropyl | |
| Ih.127 | $-CH_2-CH(Cl)-CO-N(CN)-CH_2-CH{=}CH_2$ | |
| Ih.128 | $-CH_2-CH(Cl)-CO-N(CONH_2)-CH_2CH_2-C_2H_5$ | |
| Ih.129 | $-CH_2-CH(Cl)-CO-N(CONH_2)$-cyclopropyl | |

TABLE 8-continued

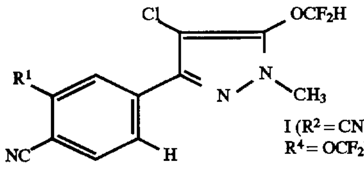

I ($R^2$ = CN; $R^3$ = $CH_3$; $R^4$ = $OCF_2H$; $R^5$ = Cl; $R^6$ = H)

| No. | $R^1$ | m.p./$^1$H-NMR [ppm] MS [$mz^{-1}$] |
|---|---|---|
| Ih.130 | $-CH_2-CH(Cl)-CO-N(CONH_2)-CH_2-CH=CH_2$ | |
| Ih.131 | $-CH_2-CH(Cl)-CO-$O-(4-acetoxytetra-hydrofuran-3-yl) | |
| Ih.132 | $-CH_2-CH(Br)-CO-$O-cyclohexyl | |
| Ih.133 | $-CH_2-CH(Br)-CO-OC(CH_3)_3$ | |
| Ih.134 | $-CH_2-CH(Br)-CO-OCH_2-CH(CH_3)_2$ | |
| Ih.135 | $-CH_2-CH(Br)-CO-NH-CH_2-CO-OCH_3$ | |
| Ih.136 | $-CH_2-CH(Br)-CO-N(CH_3)-CH_2-CO-OCH_3$ | |
| Ih.137 | $-CH_2-CH(Br)-CO-NH-CH(CH_3)-CO-OC_2H_5$ | |
| Ih.138 | $-CH_2-CH(Br)-CO-NH-OC_2H_5$ | |
| Ih.139 | $-CH_2-CH(Br)-CO-NH-OCH_3$ | |
| Ih.140 | $-CH_2-CH(Br)-CO-NH-OCH_2-CH=CHCl$ | |
| Ih.141 | $-CH_2-CH(Br)-CO-NH-CH_2-$(4-chloro-phenyl) | |
| Ih.142 | $-CH_2-CH(Br)-CO-SCH_2-CO-OC_2H_5$ | |
| Ih.143 | $-CH_2-CH(Br)-CO-SCH_2-C_2H_5$ | |
| Ih.144 | $-CH_2-CH(Br)-CO-SCH_2$-(4-chlorophenyl) | |
| Ih.145 | $-CH_2-C(Br)(CO-OC_2H_5)_2$ | |
| Ih.146 | $-CH_2-C(Br)(CO-OCH_3)2$ | |
| Ih.147 | $-CH_2-CH(Br)-CO-OCH_2-CH=N-OCH_3$ | |
| Ih.148 | $-CH_2-CH(Br)-CO-OCH_2-CH=N-OC_2H_5$ | |
| Ih.149 | $-CH_2-CH(Br)-CO-OCH_2-CH=N-OCH_2-CH_2-C_2H_5$ | |
| Ih.150 | $-CH_2-CH(Br)-CO-OCH_2-CH=N-OCH_2$-phenyl | |
| Ih.151 | $-CH_2-CH(Br)-CO-OCH_2-CH=N-OCH_2-CH=CH_2$ | |
| Ih.152 | $-CH_2-CH(Br)-CO-OCH_2-CH=N-OCH_2-CH=CHCl$ | |
| Ih.153 | $-CH_2-CH(Br)-CO-OCH_2-CH=N-OCH_2$-(4-chlorophenyl) | |
| Ih.154 | $-CH_2-CH(Br)-CO-OCH_2-CH=N-OCH(CH_3)$-(4-chlorophenyl) | |
| Ih.155 | $-CH_2-CH(Br)-COOH$ | |
| Ih.156 | $-CH_2-CH(Br)-CO-$NH-cyclopropyl | |
| Ih.157 | $-CH_2-CH(Br)-CO-N(CH_3)-CH_2-CO-OC_2H_5$ | |
| Ih.158 | $-CH_2-CH(Br)-CO-NH-CH(CH(CH_3)_2)-CO-OC_2H_5$ | |
| Ih.159 | $-CH_2-CH(Br)-CO-NH-CH(CH_2CH(CH_3)_2)-CO-OCH_3$ | |
| Ih.160 | $-CH_2-CH(Br)-CO-$(2-methoxycarbonyl-pyrrolidin-1-yl) | |
| Ih.161 | $-CH_2-CH(Br)-CO-$NH-(tetrahydro-furan-2-on-3-yl) | |
| Ih.162 | $-CH_2-CH(Br)-CO-N(CN)-CH_2CH_2-C_2H_5$ | |
| Ih.163 | $-CH_2-CH(Br)-CO-N(CN)$-cyclopropyl | |
| Ih.164 | $-CH_2-CH(Br)-CO-N(CN)-CH_2-CH=CH_2$ | |
| Ih.165 | $-CH_2-CH(Br)-CO-N(CONH_2)-CH_2CH_2-C_2H_5$ | |
| Ih.166 | $-CH_2-CH(Br)-CO-N(CONH_2)$-cyclopropyl | |
| Ih.167 | $-CH_2-CH(Br)-CO-N(CONH_2)-CH_2-CH=CH_2$ | |
| Ih.168 | $-CH_2-CH(Br)-CO-$O-(4-acetoxytetra-hydrofuran-3-yl) | |
| Ih.169 | $-CH_2-CH(OH)-COOH$ | |
| Ih.170 | $-CH_2-CH(OH)-CO-OCH_3$ | |
| Ih.171 | $-CH_2-CH(OH)-CO-OC_2H_5$ | |
| Ih.172 | $-CH_2-CH(OH)-CO-OCH_2-CH=N-OCH_3$ | |
| Ih.173 | $-CH_2-CH(OH)-CO-OC(CH_3)_3$ | |
| Ih.174 | $-CH_2-CH(OH)-CO-NH_2$ | |
| Ih.175 | $-CH_2-CH(OH)-CO-NH-CH_3$ | |
| Ih.176 | $-CH_2-CH(OH)-CO-$NH-cyclopropyl | |
| Ih.177 | $-CH_2-CH(OCH_3)-COOH$ | |
| Ih.178 | $-CH_2-CH(OCH_3)-CO-OCH_3$ | |
| Ih.179 | $-CH_2-CH(OCH_3)-CO-OC_2H_5$ | |
| Ih.180 | $-CH_2-CH(OCH_3)-CO-OCH_2-CH=N-OCH_3$ | |
| Ih.181 | $-CH_2-CH(OCH_3)-CO-OC(CH_3)_3$ | |
| Ih.182 | $-CH_2-CH(OCH_3)-CO-NH_2$ | |
| Ih.183 | $-CH_2-CH(OCH_3)-CO-NH-CH_3$ | |
| Ih.184 | $-CH_2-CH(OCH_3)-CO-$NH-cyclopropyl | |
| Ih.185 | $-CH_2-CH(O-COCH_3)-COOH$ | |
| Ih.186 | $-CH_2-CH(O-COCH_3)-CO-OCH_3$ | |
| Ih.187 | $-CH_2-CH(O-COCH_3)-CO-OC_2H_5$ | |

TABLE 8-continued

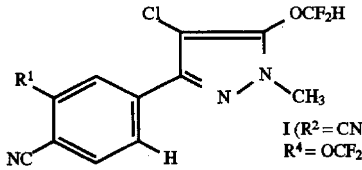

I ($R^2$ = CN; $R^3$ = $CH_3$; $R^4$ = $OCF_2H$; $R^5$ = Cl; $R^6$ = H)

| No. | $R^1$ | m.p./$^1$H-NMR [ppm] MS [$mz^{-1}$] |
|---|---|---|
| Ih.188 | $-CH_2-CH(O-COCH_3)-CO-OCH_2-CH=N-OCH_3$ | |
| Ih.189 | $-CH_2-CH(O-COCH_3)-CO-OC(CH_3)_3$ | |
| Ih.190 | $-CH_2-CH(O-COCH_3)-CO-NH_2$ | |
| Ih.191 | $-CH_2-CH(O-COCH_3)-CO-NH-CH_3$ | |
| Ih.192 | $-CH_2-CH(O-COCH_3)-CO-$NH-cyclopropyl | |
| Ih.193 | $-CH_2-CH(NH_2)-COOH$ | |
| Ih.194 | $-CH_2-CH(NH_2)-CO-OCH_3$ | |
| Ih.195 | $-CH_2-CH(NH_2)-CO-OC_2H_5$ | |
| Ih.196 | $-CH_2-CH(NH_2)-CO-OC(CH_3)_3$ | |
| Ih.197 | $-CH_2-CH(NH_2)-CO-NH_2$ | |
| Ih.198 | $-CH_2-CH(NH_2)-CO-NH-CH_3$ | |
| Ih.199 | $-CH_2-CH(N_3)-COOH$ | |
| Ih.200 | $-CH_2-CH(N_3)-CO-OCH_3$ | |
| Ih.201 | $-CH_2-CH(N_3)-CO-OC_2H_5$ | |
| Ih.202 | $-CH_2-CH(N_3)-CO-OC(CH_3)_3$ | |
| Ih.203 | $-CH_2-CH(N_3)-CO-NH_2$ | |
| Ih.204 | $-CH_2-CH(N_3)-CO-NH-CH_3$ | |
| Ih.205 | $-CH_2-CH(NH-COCH_3)-COOH$ | |
| Ih.206 | $-CH_2-CH(NH-COCH_3)-CO-OCH_3$ | |
| Ih.207 | $-CH_2-CH(NH-COCH_3)-CO-OC_2H_5$ | |
| Ih.208 | $-CH_2-CH(NH-COCH_3)-CO-OC(CH_3)_3$ | |
| Ih.209 | $-CH_2-CH(NH-COCH_3)-CO-NH_2$ | |
| Ih.210 | $-CH_2-CH(NH-COCH_3)-CO-NH-CH_3$ | |
| Ih.211 | $-CH_2-CH_2$-cyclohexyl | |
| Ih.212 | $-CH_2-CH_2$-cyclopentyl | |
| Ih.213 | $-CH_2-CH_2$-cyclopropyl | |
| Ih.214 | $-CH_2-CH_2$-phenyl | |
| Ih.215 | $-CH=C(CN)-CO-OC_2H_5$ | |
| Ih.216 | $-CH=C(CN)-CO-OCH(CH_3)_2$ | |
| Ih.217 | $-CH=C(CN)-CO-OC(CH_3)_3$ | |
| Ih.218 | $-CH=C(Cl)-CO-OCH_2-CH=N-OCH_2-CH=CH_2$ | |
| Ih.219 | $-CH=C(Cl)-CO-OCH_2-CH=N-OCH_2-CH=CHCl$ | |
| Ih.220 | $-CH=C(Cl)-CO-OCH_2-CH=N-OCH_2$-(4-chlorophenyl) | |
| Ih.221 | $-CH=C(Cl)-CO-OCH_2-CH=N-OCH(CH_3)$-(4-chlorophenyl) | |
| Ih.222 | $-CH=C(Cl)-CO-O$-(4-acetoxytetrahydro-furan-3-yl) | |
| Ih.223 | $-CH=C(Cl)-CO-$NH-cyclohexyl | |
| Ih.224 | $-CH=C(Cl)-CO-N(CH_3)-CH_2-CO-OC_2H_5$ | |
| Ih.225 | $-CH=C(Cl)-CO-NH-CH(CH(CH_3)_2)-CO-OC_2H_5$ | |
| Ih.226 | $-CH=C(Cl)-CO-NH-CH(CH_2CH(CH_3)_2)-CO-OCH_3$ | |
| Ih.227 | $-CH=C(Cl)-CO$-(2-methoxycarbonyl-pyrrolidin-1-yl) | |
| Ih.228 | $-CH=C(Cl)-CO-NH$-(tetrahydro-furan-2-on-3-yl) | |
| Ih.229 | $-CH=C(Cl)-CO-N(CN)-CH_2CH_2-C_2H_5$ | |
| Ih.230 | $-CH=C(Cl)-CO-N(CN)$-cyclopropyl | |
| Ih.231 | $-CH=C(Cl)-CO-N(CN)-CH_2-CH=CH_2$ | |
| Ih.232 | $-CH=C(Cl)-CO-N(CONH_2)-CH_2CH_2-C_2H_5$ | |
| Ih.233 | $-CH=C(Cl)-CO-N(CONH_2)$-cyclopropyl | |
| Ih.234 | $-CH=C(Cl)-CO-N(CONH_2)-CH_2-CH=CH_2$ | |
| Ih.235 | $-CH=C(Br)-CO-OCH_2-CH=N-OCH_2$-(4-chlorophenyl) | |
| Ih.236 | $-CH=C(Br)-CO-OCH_2-CH=N-OCH(CH_3)$-(4-chlorophenyl) | |
| Ih.237 | $-CH=C(Br)-CO-O$-(4-acetoxytetrahydro-furan-3-yl) | |
| Ih.238 | $-CH=C(Br)-CO-$NH-cyclohexyl | |
| Ih.239 | $-CH=C(Br)-CO-N(CH_3)-CH_2-CO-OC_2H_5$ | |
| Ih.240 | $-CH=C(Br)-CO-NH-CH(CH(CH_3)_2)-CO-OC_2H_5$ | |
| Ih.241 | $-CH=C(Br)-CO-NH-CH(CH_2CH(CH_3)_2)-CO-OCH_3$ | |
| Ih.242 | $-CH=C(Br)-CO-$(2-methoxycarbonyl-pyrrolidin-1-yl) | |
| Ih.243 | $-CH=C(Br)-CO-NH$-(tetrahydro- | |

TABLE 8-continued

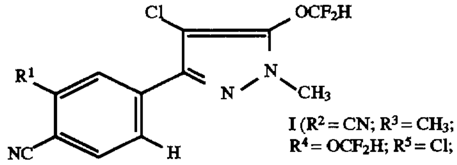

I ($R^2$ = CN; $R^3$ = $CH_3$;
$R^4$ = $OCF_2H$; $R^5$ = Cl; $R^6$ = H)

| No. | $R^1$ | m.p./$^1$H-NMR [ppm] MS [$mz^{-1}$] |
|---|---|---|
| | furan-2-on-3-yl) | |
| Ih.244 | $-CH=C(Br)-CO-N(CN)-CH_2CH_2-C_2H_5$ | |
| Ih.245 | $-CH=C(Br)-CO-N(CN)$-cyclopropyl | |
| Ih.246 | $-CH=C(Br)-CO-N(CN)-CH_2-CH=CH_2$ | |
| Ih.247 | $-CH=C(Br)-CO-N(CONH_2)-CH_2CH_2-C_2H_5$ | |
| Ih.248 | $-CH=C(Br)-CO-N(CONH_2)$-cyclopropyl | |
| Ih.249 | $-CH=C(Br)-CO-N(CONH_2)-CH_2-CH=CH_2$ | |
| Ih.250 | $-CH_2-CH(Cl)-CO-N(C_2H_5)_2$ | |
| Ih.251 | $-CH_2-CH(Br)-CO-N(C_2H_5)_2$ | |
| Ih.252 | $-CH=C(Br)-CO-N(C_2H_5)_2$ | |
| Ih.253 | $-CH=C(Cl)-CO-N(C_2H_5)_2$ | |
| Ih.254 | 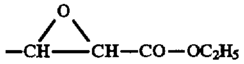 | |
| Ih.255 | 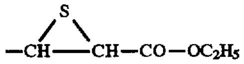 | |
| Ih.256 | 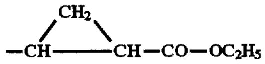 | |
| Ih.257 | 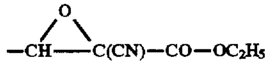 | |
| Ih.258 | 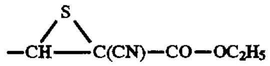 | |
| Ih.259 | 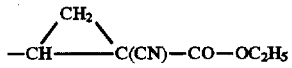 | |
| Ih.260 | 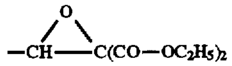 | |
| Ih.261 | 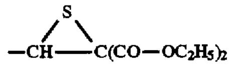 | |
| Ih.262 | 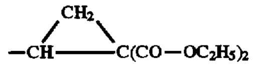 | |

TABLE 9

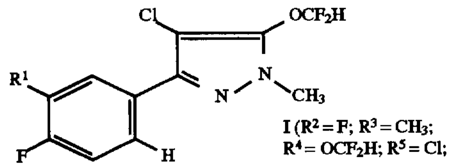

I ($R^2$ = F; $R^3$ = $CH_3$;
$R^4$ = $OCF_2H$; $R^5$ = Cl; $R^6$ = H)

| No. | $R^1$ | m.p./$^1$H-NMR [ppm] MS [$mz^{-1}$] |
|---|---|---|
| Ii.001 | $-CH=C(Cl)-COOH$ | |
| Ii.002 | $-CH=C(Cl)-CO-OCH_3$ | |
| Ii.003 | $-CH=C(Cl)-CO-OC_2H_5$ | |
| Ii.004 | $-CH=C(Cl)-CO-OCH(CH_3)_2$ | |
| Ii.005 | $-CH=C(Br)-COOH$ | |
| Ii.006 | $-CH=C(Br)-CO-OCH_3$ | |

TABLE 9-continued

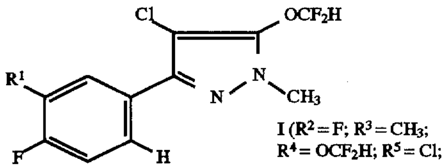

I ($R^2 = F$; $R^3 = CH_3$; $R^4 = OCF_2H$; $R^5 = Cl$; $R^6 = H$)

| No. | $R^1$ | m.p./$^1$H-NMR [ppm] MS [$mz^{-1}$] |
|---|---|---|
| Ii.007 | $-CH{=}C(Br)-CO-OC_2H_5$ | |
| Ii.008 | $-CH{=}C(Br)-CO-OCH(CH_3)_2$ | |
| Ii.009 | $-CH{=}C(Cl)-CO-NH_2$ | |
| Ii.010 | $-CH{=}C(Cl)-CO-NH-CH_3$ | |
| Ii.011 | $-CH{=}C(Cl)-CO-N(CH_3)_2$ | |
| Ii.012 | $-CH{=}C(Br)-CO-NH_2$ | |
| Ii.013 | $-CH{=}C(Br)-CO-NH-CH_3$ | |
| Ii.014 | $-CH{=}C(Br)-CO-N(CH_3)_2$ | |
| Ii.015 | $-CH{=}C(Br)-CO-$NH-cyclopropyl | |
| Ii.016 | $-CH{=}C(Cl)-CO-$NH-cyclopropyl | |
| Ii.017 | $-CH{=}$(cyclopropylene) | |
| Ii.018 | $-CH{=}$(cyclopentylene) | |
| Ii.019 | $-CH{=}$(cyclohexylene) | |
| Ii.020 | 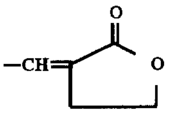 | |
| Ii.021 | 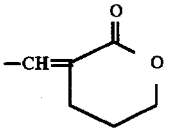 | |
| Ii.022 | 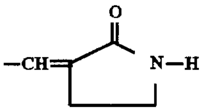 | |
| Ii.023 | 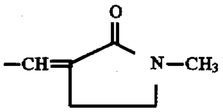 | |
| Ii.024 | 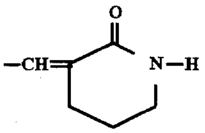 | |
| Ii.025 | 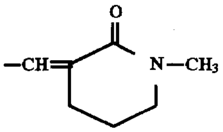 | |
| Ii.026 | 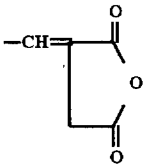 | |

TABLE 9-continued

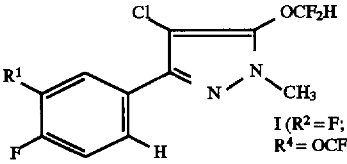

I ($R^2 = F$; $R^3 = CH_3$; $R^4 = OCF_2H$; $R^5 = Cl$; $R^6 = H$)

| No. | $R^1$ | m.p./$^1$H-NMR [ppm] MS [$mz^{-1}$] |
|---|---|---|
| Ii.027 | 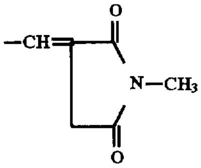 | |
| Ii.028 | $-CH=C(CH_3)-CO-OC_2H_5$ | |
| Ii.029 | $-CH=C(CH_3)-CO-OCH_3$ | |
| Ii.030 | $-CH=C(CH_3)-CO-NH_2$ | |
| Ii.031 | $-CH=C(CH_3)-CO-NH-CH_3$ | |
| Ii.032 | $-CH=C(CH_3)-CO-N(CH_3)_2$ | |
| Ii.033 | $-CH=C(CN)-CO-OCH_3$ | |
| Ii.034 | $-CH_2-CH(CN)-CO-OCH_3$ | |
| Ii.035 | $-CH_2-CH(CN)-CO-OC_2H_5$ | |
| Ii.036 | $-CH_2-CH(CN)-CO-NH_2$ | |
| Ii.037 | $-CH_2-CH(CN)-CO-NH-CH_3$ | |
| Ii.038 | $-CH_2-CH(CN)-CO-N(CH_3)_2$ | |
| Ii.039 | $-CH_2-CH(CN)-CO-NH-SO_2-CH_3$ | |
| Ii.040 | $-CH_2-CH(Cl)-CO-OCH_3$ | |
| Ii.041 | $-CH_2-CH(Cl)-CO-OC_2H_5$ | |
| Ii.042 | $-CH_2-CH(Cl)-CO-NH_2$ | |
| Ii.043 | $-CH_2-CH(Cl)-CO-NH-CH_3$ | |
| Ii.044 | $-CH_2-CH(Cl)-CO-N(CH_3)_2$ | |
| Ii.045 | $-CH_2-CH(Cl)-CO-NH-SO_2-CH_3$ | |
| Ii.046 | $-CH_2-CH(Br)-CO-OCH_3$ | |
| Ii.047 | $-CH_2-CH(Br)-CO-OC_2H_5$ | |
| Ii.048 | $-CH_2-CH(Br)-CO-OCH(CH_3)_2$ | |
| Ii.049 | $-CH_2-CH(Br)-CO-NH_2$ | |
| Ii.050 | $-CH_2-CH(Br)-CO-NH-CH_3$ | |
| Ii.051 | $-CH_2-CH(Br)-CO-N(CH_3)_2$ | |
| Ii.052 | $-CH_2-CH(Cl)-CO-CH(CH_3)_2$ | |
| Ii.053 | $-CH_2-CH(CN)-CO-CH(CH_3)_2$ | |
| Ii.054 | $-CH=CH$-(4-fluorophenyl) | |
| Ii.055 | $-CH=CH$-(4-chlorophenyl) | |
| Ii.056 | $-CH=CH$-(3-trifluoromethylphenyl) | |
| Ii.057 | $-CH=CH$-(2,4-dichlorophenyl) | |
| Ii.058 | $-CH=C(Cl)-CO-O$-cyclohexyl | |
| Ij.059 | $-CH=C(Cl)-CO-OC(CH_3)_3$ | |
| Ii.060 | $-CH=C(Cl)-CO-OCH_2-CH(CH_3)_2$ | |
| Ii.061 | $-CH=C(Cl)-CO-NH-CH_2-CO-OCH_3$ | |
| Ii.062 | $-CH=C(Cl)-CO-N(CH_3)-CH_2-CO-OCH_3$ | |
| Ii.063 | $-CH=C(Cl)-CO-NH-CH(CH_3)-CO-OC_2H_5$ | |
| Ii.064 | $-CH=C(Cl)-CO-NH-OC_2H_5$ | |
| Ii.065 | $-CH=C(Cl)-CO-NH-OCH_3$ | |
| Ii.066 | $-CH=C(Cl)-CO-NH-OCH_2-CH=CHCl$ | |
| Ii.067 | $-CH=C(Cl)-CO-NH-OCH_2$-(4-chlorophenyl) | |
| Ii.068 | $-CH=C(Cl)-CO-SCH_2-CO-OC_2H_5$ | |
| Ii.069 | $-CH=C(Cl)-CO-SCH_2-C_2H_5$ | |
| Ii.070 | $-CH=C(Cl)-CO-SCH_2$-(4-chlorophenyl) | |
| Ii.071 | $-CH=C(CO-OC_2H_5)_2$ | |
| Ii.072 | $-CH=C(CO-OCH_3)_2$ | |
| Ii.073 | $-CH=C(Cl)-CO-OCH_2-CH=N-OCH_3$ | |
| Ii.074 | $-CH=C(Cl)-CO-OCH_2-CH=N-OC_2H_5$ | |
| Ii.075 | $-CH=C(Cl)-CO-OCH_2-CH=N-OCH_2-CH_2-C_2H_5$ | |
| Ii.076 | $-CH=C(Cl)-CO-OCH_2-CH=N-OCH_2$-phenyl | |
| Ii.077 | $-CH=C(Br)-CO-O$-cyclohexyl | |
| Ii.078 | $-CH=C(Br)-CO-OC(CH_3)_3$ | |
| Ii.079 | $-CH=C(Br)-CO-OCH_2-CH(CH_3)_2$ | |
| Ii.080 | $-CH=C(Br)-CO-NH-CH_2-CO-OCH_3$ | |
| Ii.081 | $-CH=C(Br)-CO-N(CH_3)-CH_2-CO-OCH_3$ | |
| Ii.082 | $-CH=C(Br)-CO-NH-OC_2H_5$ | |
| Ii.083 | $-CH=C(Br)-CO-NH-OCH_3$ | |
| Ii.084 | $-CH=C(Br)-CO-NH-OCH_2-CH=CHCl$ | |
| Ii.085 | $-CH=C(Br)-CO-NH-OCH_2$-(4-chlorophenyl) | |

TABLE 9-continued

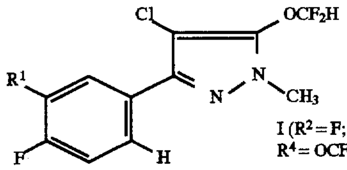

I ($R^2$=F; $R^3$=$CH_3$; $R^4$=$OCF_2H$; $R^5$=Cl; $R^6$=H)

| No. | $R^1$ | m.p./$^1$H-NMR [ppm] MS [$mz^{-1}$] |
|---|---|---|
| Ii.086 | $-CH=C(Br)-CO-SCH_2-CO-OC_2H_5$ | |
| Ii.087 | $-CH=C(Br)-CO-SCH_2-C_2H_5$ | |
| Ii.088 | $-CH=C(Br)-CO-SCH_2$-(4-chlorophenyl) | |
| Ii.089 | $-CH=C(Br)-CO-OCH_2-CH=N-OCH_2-CH=CH_2$ | |
| Ii.090 | $-CH=C(Br)-CO-OCH_2-CH=N-OCH_2-CH=CHCl$ | |
| Ii.091 | $-CH=C(Br)-CO-OCH_2-CH=N-OCH_3$ | |
| Ii.092 | $-CH=C(Br)-CO-OCH_2-CH=N-OC_2H_5$ | |
| Ii.093 | $-CH=C(Br)-CO-OCH_2-CH=N-OCH_2-CH_2-C_2H_5$ | |
| Ii.094 | $-CH=C(Br)-CO-OCH_2-CH=N-OCH_2$-phenyl | |
| Ii.095 | $-CH_2-CH(Cl)-CO-$O-cyclohexyl | |
| Ii.096 | $-CH_2-CH(Cl)-CO-OC(CH_3)_3$ | |
| Ii.097 | $-CH_2-CH(Cl)-CO-OCH_2-CH(CH_3)_2$ | |
| Ii.098 | $-CH_2-CH(Cl)-CO-NH-CH_2-CO-OCH_3$ | |
| Ii.099 | $-CH_2-CH(Cl)-CO-N(CH_3)-CH_2-CO-OCH_3$ | |
| Ii.100 | $-CH_2-CH(Cl)-CO-NH-CH(CH_3)-CO-OC_2H_5$ | |
| Ii.101 | $-CH_2-CH(Cl)-CO-NH-OC_2H_5$ | |
| Ii.102 | $-CH_2-CH(Cl)-CO-NH-OCH_3$ | |
| Ii.103 | $-CH_2-CH(Cl)-CO-NH-OCH_2-CH=CHCl$ | |
| Ii.104 | $-CH_2-CH(Cl)-CO-NH-OCH_2$-(4-chloro-phenyl) | |
| Ii.105 | $-CH_2-CH(Cl)-CO-SCH_2-CO-OC_2H_5$ | |
| Ii.106 | $-CH_2-CH(Cl)-CO-SCH_2-C_2H_5$ | |
| Ii.107 | $-CH_2-CH(Cl)-CO-SCH_2$-(4-chlorophenyl) | |
| Ii.108 | $-CH_2-C(Cl)(CO-OC_2H_5)_2$ | |
| Ii.109 | $-CH_2-C(Cl)(CO-OCH_3)2$ | |
| Ii.110 | $-CH_2-CH(Cl)-CO-OCH_2-CH=N-OCH_3$ | |
| Ii.111 | $-CH_2-CH(Cl)-CO-OCH_2-CH=N-OC_2H_5$ | |
| Ii.112 | $-CH_2-CH(Cl)-CO-OCH_2-CH=N-OCH_2-CH_2-C_2H_5$ | |
| Ii.113 | $-CH_2-CH(Cl)-CO-OCH_2-CH=N-OCH_2$-phenyl | |
| Ii.114 | $-CH_2-CH(Cl)-CO-OCH_2-CH=N-OCH_2-CH=CH_2$ | |
| Ii.115 | $-CH_2-CH(Cl)-CO-OCH_2-CH=NH-OCH_2-CH=CHCl$ | |
| Ii.116 | $-CH_2-CH(Cl)-CO-OCH_2-CH=N-$ $OCH_2$-(4-chlorophenyl) | |
| Ii.117 | $-CH_2-CH(Cl)-CO-OCH_2-CH=N-$ $OCH(CH_3)$-(4-chlorophenyl) | |
| Ii.118 | $-CH_2-CH(Cl)-COOH$ | |
| Ii.119 | $-CH_2-CH(Cl)-CO-$NH-cyclopropyl | |
| Ii.120 | $-CH_2-CH(Cl)-CO-N(CH_3)-CH_2-CO-OC_2H_5$ | |
| Ii.121 | $-CH_2-CH(Cl)-CO-$ $NH-CH(CH(CH_3)_2)-CO-OC_2H_5$ | |
| Ii.122 | $-CH_2-CH(Cl)-CO-NH-CH(CH_2CH(CH_3)_2)-CO-$ $OCH_3$ | |
| Ii.123 | $-CH_2-CH(Cl)-CO-$(2-methoxycarbonyl-pyrrolidin-1-yl) | |
| Ii.124 | $-CH_2-CH(Cl)-CO-$NH-(tetrahydro-furan-2-on-3-yl) | |
| Ii.125 | $-CH_2-CH(Cl)-CO-N(CN)-CH_2CH_2-C_2H_5$ | |
| Ii.126 | $-CH_2-CH(Cl)-CO-N(CN)$-cyclopropyl | |
| Ii.127 | $-CH_2-CH(Cl)-CO-N(CN)-CH_2-CH=CH_2$ | |
| Ii.128 | $-CH_2-CH(Cl)-CO-N(CONH_2)-CH_2CH_2-C_2H_5$ | |
| Ii.129 | $-CH_2-CH(Cl)-CO-N(CONH_2)$-cyclopropyl | |
| Ii.130 | $-CH_2-CH(Cl)-CO-N(CONH_2)-CH_2-CH=CH_2$ | |
| Ii.131 | $-CH_2-CH(Cl)-CO-$O-(4-acetoxytetra-hydrofuran-3-yl) | |
| Ii.132 | $-CH_2-CH(Br)-CO-$O-cyclohexyl | |
| Ii.133 | $-CH_2-CH(Br)-CO-OC(CH_3)_3$ | |
| Ii.134 | $-CH_2-CH(Br)-CO-OCH_2-CH(CH_3)_2$ | |
| Ii.135 | $-CH_2-CH(Br)-CO-NH-CH_2-CO-OCH_3$ | |
| Ii.136 | $-CH_2-CH(Br)-CO-N(CH_3)-CH_2-CO-OCH_3$ | |
| Ii.137 | $-CH_2-CH(Br)-CO-NH-CH(CH_3)-CO-OC_2H_5$ | |
| Ii.138 | $-CH_2-CH(Br)-CO-NH-OC_2H_5$ | |
| Ii.139 | $-CH_2-CH(Br.)-CO-NH-OCH_3$ | |
| Ii.140 | $-CH_2-CH(Br)-CO-NH-OCH_2-CH=CHCl$ | |
| Ii.141 | $-CH_2-CH(Br)-CO-NH-CH_2-$ (4-chlorophenyl) | |
| Ii.142 | $-CH_2-CH(Br)-CO-SCH_2-CO-OC_2H_5$ | |
| Ii.143 | $-CH_2-CH(Br)-CO-SCH_2-C_2H_5$ | |

TABLE 9-continued

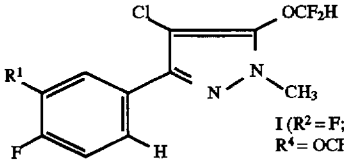

I ($R^2$ = F; $R^3$ = $CH_3$; $R^4$ = $OCF_2H$; $R^5$ = Cl; $R^6$ = H)

| No. | $R^1$ | m.p./$^1$H-NMR [ppm] MS [$mz^{-1}$] |
|---|---|---|
| Ii.144 | $-CH_2-CH(Br)-CO-SCH_2$-(4-chlorophenyl) | |
| Ii.145 | $-CH_2-C(Br)(CO-OC_2H_5)_2$ | |
| Ii.146 | $-CH_2-C(Br)(CO-OCH_3)2$ | |
| Ii.147 | $-CH_2-CH(Br)-CO-OCH_2-CH=N-OCH_3$ | |
| Ii.148 | $-CH_2-CH(Br)-CO-OCH_2-CH=N-OC_2H_5$ | |
| Ii.149 | $-CH_2-CH(Br)-CO-OCH_2-CH=N-OCH_2-CH_2-C_2H_5$ | |
| Ii.150 | $-CH_2-CH(Br)-CO-OCH_2-CH=N-OCH_2$-phenyl | |
| Ii.151 | $-CH_2-CH(Br)-CO-OCH_2-CH=N-OCH_2-CH=CH_2$ | |
| Ii.152 | $-CH_2-CH(Br)-CO-OCH_2-CH=N-OCH_2-CH=CHCl$ | |
| Ii.153 | $-CH_2-CH(Br)-CO-OCH_2-CH=N-$ $OCH_2$-(4-chlorophenyl) | |
| Ii.154 | $-CH_2-CH(Br)-CO-OCH_2-CH=N-$ $OCH(CH_3)$-(4-chlorophenyl) | |
| Ii.155 | $-CH_2-CH(Br)-COOH$ | |
| Ii.156 | $-CH_2-CH(Br)-CO-NH$-cyclopropyl | |
| Ii.157 | $-CH_2-CH(Br)-CO-N(CH_3)-CH_2-CO-OC_2H_5$ | |
| Ii.158 | $-CH_2-CH(Br)-CO-$ $NH-CH(CH(CH_3)_2)-CO-OC_2H_5$ | |
| Ii.159 | $-CH_2-CH(Br)-CO-NH-CH(CH_2CH(CH_3)_2)-CO-$ $OCH_3$ | |
| Ii.160 | $-CH_2-CH(Br)-CO-$(2-methoxycarbonyl-pyrrolidin-1-yl) | |
| Ii.161 | $-CH_2-CH(Br)-CO-NH$-(tetrahydro-furan-2-on-3-yl) | |
| Ii.162 | $-CH_2-CH(Br)-CO-N(CN)-CH_2CH_2-C_2H_5$ | |
| Ii.163 | $-CH_2-CH(Br)-CO-N(CN)$-cyclopropyl | |
| Ii.164 | $-CH_2-CH(Br)-CO-N(CN)-CH_2-CH=CH_2$ | |
| Ii.165 | $-CH_2-CH(Br)-CO-N(CONH_2)-CH_2CH_2-C_2H_5$ | |
| Ii.166 | $-CH_2-CH(Br)-CO-N(CONH_2)$-cyclopropyl | |
| Ii.167 | $-CH_2-CH(Br)-CO-N(CONH_2)-CH_2-CH=CH_2$ | |
| Ii.168 | $-CH_2-CH(Br)-CO-O$-(4-acetoxytetra-hydrofuran-3-yl) | |
| Ii.169 | $-CH_2-CH(OH)-COOH$ | |
| Ii.170 | $-CH_2-CH(OH)-CO-OCH_3$ | |
| Ii.171 | $-CH_2-CH(OH)-CO-OC_2H_5$ | |
| Ii.172 | $-CH_2-CH(OH)-CO-OCH_2-CH=N-OCH_3$ | |
| Ii.173 | $-CH_2-CH(OH)-CO-OC(CH_3)_3$ | |
| Ii.174 | $-CH_2-CH(OH)-CO-NH_2$ | |
| Ii.175 | $-CH_2-CH(OH)-CO-NH-CH_3$ | |
| Ii.176 | $-CH_2-CH(OH)-CO-NH$-cyclopropyl | |
| Ii.177 | $-CH_2-CH(OCH_3)-COOH$ | |
| Ii.178 | $-CH_2-CH(OCH_3)-CO-OCH_3$ | |
| Ii.179 | $-CH_2-CH(OCH_3)-CO-OC_2H_5$ | |
| Ii.180 | $-CH_2-CH(OCH_3)-CO-OCH_2-CH=N-OCH_3$ | |
| Ii.181 | $-CH_2-CH(OCH_3)-CO-OC(CH_3)_3$ | |
| Ii.182 | $-CH_2-CH(OCH_3)-CO-NH_2$ | |
| Ii.183 | $-CH_2-CH(OCH_3)-CO-NH-CH_3$ | |
| Ii.184 | $-CH_2-CH(OCH_3)-CO-NH$-cyclopropyl | |
| Ii.185 | $-CH_2-CH(O-COCH_3)-COOH$ | |
| Ii.186 | $-CH_2-CH(O-COCH_3)-CO-OCH_3$ | |
| Ii.187 | $-CH_2-CH(O-COCH_3)-CO-OC_2H_5$ | |
| Ii.188 | $-CH_2-CH(O-COCH_3)-CO-OCH_2-CH=N-OCH_3$ | |
| Ii.189 | $-CH_2-CH(O-COCH_3)-CO-OC(CH_3)_3$ | |
| Ii.190 | $-CH_2-CH(O-COCH_3)-CO-NH_2$ | |
| Ii.191 | $-CH_2-CH(O-COCH_3)-CO-NH-CH_3$ | |
| Ii.192 | $-CH_2-CH(O-COCH_3)-CO-NH$-cyclopropyl | |
| Ii.193 | $-CH_2-CH(NH_2)-COOH$ | |
| Ii.194 | $-CH_2-CH(NH_2)-CO-OCH_3$ | |
| Ii.195 | $-CH_2-CH(NH_2)-CO-OC_2H_5$ | |
| Ii.196 | $-CH_2-CH(NH_2)-CO-OC(CH_3)_3$ | |
| Ii.197 | $-CH_2-CH(NH_2)-CO-NH_2$ | |
| Ii.198 | $-CH_2-CH(NH_2)-CO-NH-CH_3$ | |
| Ii.199 | $-CH_2-CH(N_3)-COOH$ | |
| Ii.200 | $-CH_2-CH(N_3)-CO-OCH_3$ | |
| Ii.201 | $-CH_2-CH(N_3)-CO-OC_2H_5$ | |
| Ii.202 | $-CH_2-CH(N_3)-CO-OC(CH_3)_3$ | |
| Ii.203 | $-CH_2-CH(N_3)-CO-NH_2$ | |

TABLE 9-continued

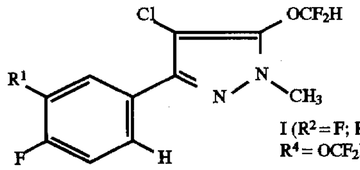

I ($R^2=F$; $R^3=CH_3$; $R^4=OCF_2H$; $R^5=Cl$; $R^6=H$)

| No. | $R^1$ | m.p./$^1$H-NMR [ppm] MS [$mz^{-1}$] |
|---|---|---|
| Ii.204 | $-CH_2-CH(N_3)-CO-NH-CH_3$ | |
| Ii.205 | $-CH_2-CH(NH-COCH_3)-COOH$ | |
| Ii.206 | $-CHz-CH(NH-COCH_3)-CO-OCH_3$ | |
| Ii.207 | $-CH_2-CH(NH-COCH_3)-CO-OC_2H_5$ | |
| Ii.208 | $-CH_2-CH(NH-COCH_3)-CO-OC(CH_3)_3$ | |
| Ii.209 | $-CH_2-CH(NH-COCH_3)-CO-NH_2$ | |
| Ii.210 | $-CH_2-CH(NH-COCH_3)-CO-NH-CH_3$ | |
| Ii.211 | $-CH_2-CH_2$-cyclohexyl | |
| Ii.212 | $-CH_2-CH_2$-cyclopentyl | |
| Ii.213 | $-CH_2-CH_2$-cyclopropyl | |
| Ii.214 | $-CH_2-CH_2$-phenyl | |
| Ii.215 | $-CH=C(CN)-CO-OC_2H_5$ | |
| Ii.216 | $-CH=C(CN)-CO-OCH(CH_3)_2$ | |
| Ii.217 | $-CH=C(CN)-CO-OC(CH_3)_3$ | |
| Ii.218 | $-CH=C(Cl)-CO-OCH_2-CH=N-OCH_2-CH=CH_2$ | |
| Ii.219 | $-CH=C(Cl)-CO-OCH_2-CH=N-OCH_2-CH=CHCl$ | |
| Ii.220 | $-CH=C(Cl)-CO-OCH_2-CH=N-OCH_2$-(4-chlorophenyl) | |
| Ii.221 | $-CH=C(Cl)-CO-OCH_2-CH=N-OCH(CH_3)$-(4-chlorophenyl) | |
| Ii.222 | $-CH=C(Cl)-CO-O$-(4-acetoxytetrahydro-furan-3-yl) | |
| Ii.223 | $-CH=C(Cl)-CO-NH$-cyclohexyl | |
| Ii.224 | $-CH=C(Cl)-CO-N(CH_3)-CH_2-CO-OC_2H_5$ | |
| Ii.225 | $-CH=C(Cl)-CO-NH-CH(CH(CH_3)_2)-CO-OC_2H_5$ | |
| Ii.226 | $-CH=C(Cl)-CO-NH-CH(CH_2CH(CH_3)_2)-CO-OCH_3$ | |
| Ii.227 | $-CH=C(Cl)-CO-$(2-methoxycarbonyl-pyrrolidin-1-yl) | |
| Ii.228 | $-CH=C(Cl)-CO-NH$-(tetrahydro-furan-2-on-3-yl) | |
| Ii.229 | $-CH=C(Cl)-CO-N(CN)-CH_2CH_2-C_2H_5$ | |
| Ii.230 | $-CH=C(Cl)-CO-N(CN)$-cyclopropyl | |
| Ii.231 | $-CH=C(Cl)-CO-N(CN)-CH_2-CH=CH_2$ | |
| Ii.232 | $-CH=C(Cl)-CO-N(CONH_2)-CH_2CH_2-C_2H_5$ | |
| Ii.233 | $-CH=C(Cl)-CO-N(CONH_2)$-cyclopropyl | |
| Ii.234 | $-CH=C(Cl)-CO-N(CONH_2)-CH_2-CH=CH_2$ | |
| Ii.235 | $-CH=C(Br)-CO-OCH_2-CH=N-OCH_2$-(4-chlorophenyl) | |
| Ii.236 | $-CH=C(Br)-CO-OCH_2-CH=N-OCH(CH_3)$-(4-chlorophenyl) | |
| Ii.237 | $-CH=C(Br)-CO-O$-(4-acetoxytetrahydro-furan-3-yl) | |
| Ii.238 | $-CH=C(Br)-CO-NH$-cyclohexyl | |
| Ii.239 | $-CH=C(Br)-CO-N(CH_3)-CH_2-CO-OC_2H_5$ | |
| Ii.240 | $-CH=C(Br)-CO-NH-CH(CH(CH_3)_2)-CO-OC_2H_5$ | |
| Ii.241 | $-CH=C(Br)-CO-NH-CH(CH_2CH(CH_3)_2)-CO-OCH_3$ | |
| Ii.242 | $-CH=C(Br)-CO-$(2-methoxycarbonyl-pyrrolidin-1-yl) | |
| Ii.243 | $-CH=C(Br)-CO-NH$-(tetrahydro-furan-2-on-3-yl) | |
| Ii.244 | $-CH=C(Br)-CO-N(CN)-CH_2CH_2-C_2H_5$ | |
| Ii.245 | $-CH=C(Br)-CO-N(CN)$-cyclopropyl | |
| Ii.246 | $-CH=C(Br)-CO-N(CN)-CH_2-CH=CH_2$ | |
| Ii.247 | $-CH=C(Br)-CO-N(CONH_2)-CH_2CH_2-C_2H_5$ | |
| Ii.248 | $-CH=C(Br)-CO-N(CONH_2)$-cyclopropyl | |
| Ii.249 | $-CH=C(Br)-CO-N(CONH_2)-CH_2-CH=CH_2$ | |
| Ii.250 | $-CH_2-CH(Cl)-CO-N(C_2H_5)_2$ | |
| Ii.251 | $-CH_2-CH(Br)-CO-N(C_2H_5)_2$ | |
| Ii.252 | $-CH=C(Br)-CO-N(C_2H_5)_2$ | |
| Ii.253 | $-CH=C(Cl)-CO-N(C_2H_5)_2$ | |
| Ii.254 | 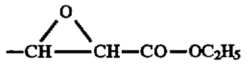 | |

TABLE 9-continued

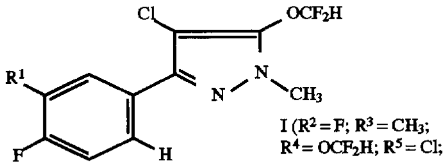

I ($R^2 = F$; $R^3 = CH_3$;
$R^4 = OCF_2H$; $R^5 = Cl$; $R^6 = H$)

| No. | $R^1$ | m.p./$^1$H-NMR [ppm] MS [$mz^{-1}$] |
|---|---|---|
| Ii.255 | 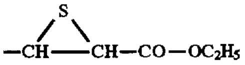 | |
| Ii.256 | 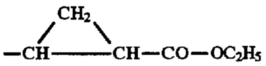 | |
| Ii.257 | 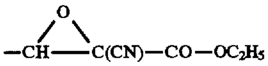 | |
| Ii.258 | 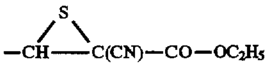 | |
| Ii.259 | 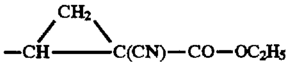 | |
| Ii.260 | 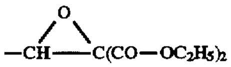 | |
| Ii.261 | 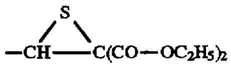 | |
| Ii.262 | 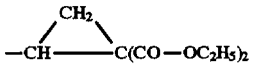 | |

TABLE 10

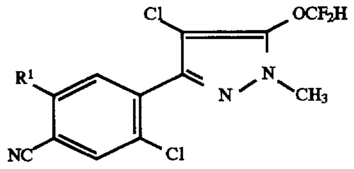

I ($R^2 = CN$; $R^3 = CH_3$;
$R^4 = OCF_2H$; $R^5$, $R^6 = Cl$)

| No. | $R^1$ | m.p./$^1$H-NMR[ppm] MS [$mz^{-1}$] |
|---|---|---|
| Ij.001 | $-CH=C(Cl)-COOH$ | |
| Ij.002 | $-CH=C(Cl)-CO-OCH_3$ | |
| Ij.003 | $-CH=C(Cl)-CO-OC_2H_5$ | |
| Ij.004 | $-CH=C(Cl)-CO-OCH(CH_3)_2$ | |
| Ij.005 | $-CH=C(Br)-COOH$ | |
| Ij.006 | $-CH=C(Br)-CO-OCH_3$ | |
| Ij.007 | $-CH=C(Br)-CO-OC_2H_5$ | |
| Ij.008 | $-CH=C(Br)-CO-OCH(CH_3)_2$ | |
| Ij.009 | $-CH=C(Cl)-CO-NH_2$ | |
| Ij.010 | $-CH=C(Cl)-CO-NH-CH_3$ | |
| Ij.011 | $-CH=C(Cl)-CO-N(CH_3)_2$ | |
| Ij.012 | $-CH=C(Br)-CO-NH_2$ | |
| Ij.013 | $-CH=C(Br)-CO-NH-CH_3$ | |
| Ij.014 | $-CH=C(Br)-CO-N(CH_3)_2$ | |
| Ij.015 | $-CH=C(Br)-CO-$NH-cyclopropyl | |
| Ij.016 | $-CH=C(Cl)-CO-$NH-cyclopropyl | |
| Ij.017 | $-CH=$(cyclopropylene) | |
| Ij.018 | $-CH=$(cyclopentylene) | |

TABLE 10-continued
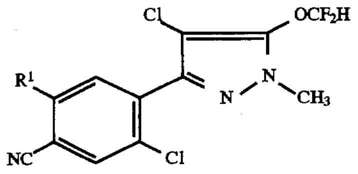
I ($R^2 = CN$; $R^3 = CH_3$;
$R^4 = OCF_2H$; $R^5$, $R^6 = Cl$)
| No. | $R^1$ | m.p./$^1$H-NMR[ppm] MS [$mz^{-1}$] |
|---|---|---|
| Ij.019 | $-CH=$(cyclohexylene) | |
| Ij.020 | 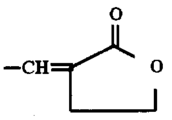 | |
| Ij.021 | 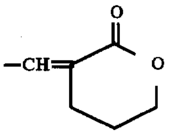 | |
| Ij.022 | 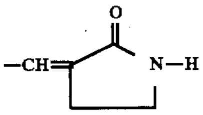 | |
| Ij.023 | 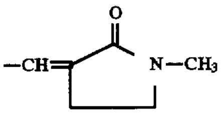 | |
| Ij.024 | 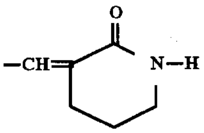 | |
| Ij.025 | 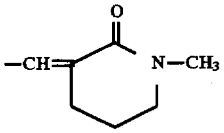 | |
| Ij.026 | 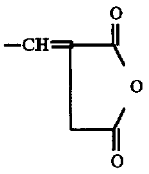 | |
| Ij.027 | 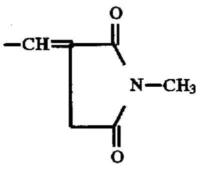 | |
| Ij.028 | $-CH=C(CH_3)-CO-OC_2H_5$ | |
| Ij.029 | $-CH=C(CH_3)-CO-OCH_3$ | |
| Ij.030 | $-CH=C(CH_3)-CO-NH_2$ | |
| Ij.031 | $-CH=C(CH_3)-CO-NH-CH_3$ | |
| Ij.032 | $-CH=C(CH_3)-CO-N(CH_3)_2$ | |

TABLE 10-continued

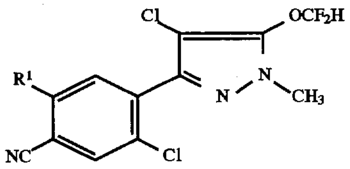

I ($R^2$ = CN; $R^3$ = $CH_3$; $R^4$ = $OCF_2H$; $R^5$, $R^6$ = Cl)

| No. | $R^1$ | m.p./$^1$H-NMR[ppm] MS [$mz^{-1}$] |
|---|---|---|
| Ij.033 | $-CH=C(CN)-CO-OCH_3$ | |
| Ij.034 | $-CH_2-CH(CN)-CO-OCH_3$ | |
| Ij.035 | $-CH_2-CH(CN)-CO-OC_2H_5$ | |
| Ij.036 | $-CH_2-CH(CN)-CO-NH_2$ | |
| Ij.037 | $-CH_2-CH(CN)-CO-NH-CH_3$ | |
| Ij.038 | $-CH_2-CH(CN)-CO-N(CH_3)_2$ | |
| Ij.039 | $-CH_2-CH(CN)-CO-NH-SO_2-CH_3$ | |
| Ij.040 | $-CH_2-CH(Cl)-CO-OCH_3$ | |
| Ij.041 | $-CH_2-CH(Cl)-CO-OC_2H_5$ | |
| Ij.042 | $-CH_2-CH(Cl)-CO-NH_2$ | |
| Ij.043 | $-CH_2-CH(Cl)-CO-NH-CH_3$ | |
| Ij.044 | $-CH_2-CH(Cl)-CO-N(CH_3)_2$ | |
| Ij.045 | $-CH_2-CH(Cl)-CO-NH-SO_2CH_3$ | |
| Ij.046 | $-CH_2-CH(Br)-CO-OCH_3$ | |
| Ij.047 | $-CH_2-CH(Br)-CO-OC_2H_5$ | |
| Ij.048 | $-CH_2-CH(Br)-CO-OCH(CH_3)_2$ | |
| Ij.049 | $-CH_2-CH(Br)-CO-NH_2$ | |
| Ij.050 | $-CH_2-CH(Br)-CO-NH-CH_3$ | |
| Ij.051 | $-CH_2-CH(Br)-CO-N(CH_3)_2$ | |
| Ij.052 | $-CH_2-CH(Cl)-CO-CH(CH_3)_2$ | |
| Ij.053 | $-CH_2-CH(CN)-CO-CH(CH_3)_2$ | |
| Ij.054 | $-CH=CH$-(4-fluorophenyl) | |
| Ij.055 | $-CH=CH$-(4-chlorophenyl) | |
| Ij.056 | $-CH=CH$-(3-trifluoromethylphenyl) | |
| Ij.057 | $-CH=CH$-(2,4-dichlorophenyl) | |
| Ij.058 | $-CH=C(Cl)-CO-O$-cyclohexyl | |
| Ij.059 | $-CH=C(Cl)-CO-OC(CH_3)_3$ | |
| Ij.060 | $-CH=C(Cl)-CO-OCH_2-CH(CH_3)_2$ | |
| Ij.061 | $-CH=C(Cl)-CO-NH-CH_2-CO-OCH_3$ | |
| Ij.062 | $-CH=C(Cl)-CO-N(CH_3)-CH_2-CO-OCH_3$ | |
| Ij.063 | $-CH=C(Cl)-CO-NH-CH(CH_3)-CO-OC_2H_5$ | |
| Ij.064 | $-CH=C(Cl)-CO-NH-OC_2H_5$ | |
| Ij.065 | $-CH=C(Cl)-CO-NH-OCH_3$ | |
| Ij.066 | $-CH=C(Cl)-CO-NH-OCH_2CH=CHCl$ | |
| Ij.067 | $-CH=C(Cl)-CO-NH-OCH_2$-(4-chlorophenyl) | |
| Ij.068 | $-CH=C(Cl)-CO-SCH_2-CO-OC_2H_5$ | |
| Ij.069 | $-CH=C(Cl)-CO-SCH_2-C_2H_5$ | |
| Ij.070 | $-CH=C(Cl)-CO-SCH_2$-(4-chlorophenyl) | |
| Ij.071 | $-CH=C(CO-OC_2H_5)_2$ | |
| Ij.072 | $-CH=C(CO-OCH_3)_2$ | |
| Ij.073 | $-CH=C(Cl)-CO-OCH_2-CH=N-OCH_3$ | |
| Ij.074 | $-CH=C(Cl)-CO-OCH_2-CH=N-OCH_2H_5$ | |
| Ij.075 | $-CH=C(Cl)-CO-OCH_2-CH=N-OCH_2-CH_2-C_2H_5$ | |
| Ij.076 | $-CH=C(Cl)-CO-OCH_2-CH=N-OCH_2-$phenyl | |
| Ij.077 | $-CH=C(Br)-CO-O$-cyclohexyl | |
| Ij.078 | $-CH=C(Br)-CO-OC(CH_3)_3$ | |
| Ij.079 | $-CH=C(Br)-CO-OCH_2-CH(CH_3)_2$ | |
| Ij.080 | $-CH=C(Br)-CO-NH-CH_2-CO-OCH_3$ | |
| Ij.081 | $-CH=C(Br)-CO-N(CH_3)-CH_2-CO-OCH_3$ | |
| Ij.082 | $-CH=C(Br)-CO-NH-OC_2H_5$ | |
| Ij.083 | $-CH=C(Br)-CO-NH-OCH_3$ | |
| Ij.084 | $-CH=C(Br)-CO-NH-OCH_2-CH=CHCl$ | |
| Ij.085 | $-CH=C(Br)-CO-NH-OCH_2$-(4-chlorophenyl) | |
| Ij.086 | $-CH=C(Br)-CO-SCH_2-CO-OC_2H_5$ | |
| Ij.087 | $-CH=C(Br)-CO-SCH_2-C_2H_5$ | |
| Ij.088 | $-CH=C(Br)-CO-SCH_2$-(4-chlorophenyl) | |
| Ij.089 | $-CH=C(Br)-CO-OCH_2-CH=N-OCH_2-CH=CH_2$ | |
| Ij.090 | $-CH=C(Br)-CO-OCH_2-CH=N-OCH_2-CH=CHCl$ | |
| Ij.091 | $-CH=C(Br)-CO-OCH_2-CH=N-OCH_3$ | |
| Ij.092 | $-CH=C(Br)-CO-OCH_2-CH=N-OC_2H_5$ | |
| Ij.093 | $-CH=C(Br)-CO-OCH_2-CH=N-OCH_2-CH_2-C_2H_5$ | |
| Ij.094 | $-CH=C(Br)-CO-OCH_2-CH=N-OCH_2$-phenyl | |
| Ij.095 | $-CH_2-CH(Cl)-CO-O-$cyclohexyl | |
| Ij.096 | $-CH_2-CH(Cl)-CO-OC(CH_3)_3$ | |

TABLE 10-continued

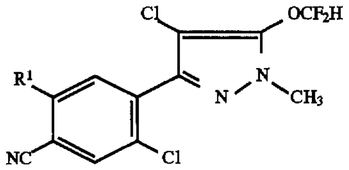

I ($R^2$ = CN; $R^3$ = $CH_3$;
$R^4$ = $OCF_2H$; $R^5$, $R^6$ = Cl)

| No. | $R^1$ | m.p./$^1$H-NMR[ppm] MS [$mz^{-1}$] |
|---|---|---|
| Ij.097 | $-CH_2-CH(Cl)-CO-OCH_2-CH(CH_3)_2$ | |
| Ij.098 | $-CH_2-CH(Cl)-CO-NH-CH_2-CO-OCH_3$ | |
| Ij.099 | $-CH_2-CH(Cl)-CO-N(CH_3)-CH_2-CO-OCH_3$ | |
| Ij.100 | $-CH_2-CH(Cl)-CO-NH-CH(CH_3)-CO-OC_2H_5$ | |
| Ij.101 | $-CH_2-CH(Cl)-CO-NH-OC_2H_5$ | |
| Ij.102 | $-CH_2-CH(Cl)-CO-NH-OCH_3$ | |
| Ij.103 | $-CH_2-CH(Cl)-CO-NH-OCH_2-CH=CHCl$ | |
| Ij.104 | $-CH_2-CH(Cl)-CO-NH-OCH_2$-(4-chlorophenyl) | |
| Ij.105 | $-CH_2-CH(Cl)-CO-SCH_2-CO-OC_2H_5$ | |
| Ij.106 | $-CH_2-CH(Cl)-CO-SCH_2-C_2H_5$ | |
| Ij.107 | $-CH_2-CH(Cl)-CO-SCH_2$-(4-chlorophenyl) | |
| Ij.108 | $-CH_2-C(Cl)(CO-OC_2H_5)_2$ | |
| Ij.109 | $-CH_2-C(Cl)(CO-OCH_3)_2$ | |
| Ij.110 | $-CH_2-CH(Cl)-CO-OCH_2-CH=N-OCH_3$ | |
| Ij.111 | $-CH_2-CH(Cl)-CO-OCH_2-CH=N-OC_2H_5$ | |
| Ij.112 | $-CH_2-CH(Cl)-CO-OCH_2-CH=N-OCH_2-CH_2-C_2H_5$ | |
| Ij.113 | $-CH_2-CH(Cl)-CO-OCH_2-CH=N-OCH_2$-phenyl | |
| Ij.114 | $-CH_2-CH(Cl)-CO-OCH_2-CH=N-OCH_2-CH=CH_2$ | |
| Ij.115 | $-CH_2-CH(Cl)-CO-OCH_2-CH=N-OCH_2-CH=CHCl$ | |
| Ij.116 | $-CH_2-CH(Cl)-CO-OCH_2-CH=N-OCH_2$-(4-chlorophenyl) | |
| Ij.117 | $-CH_2-CH(Cl)-CO-OCH_2-CH=N-OCH(CH_3)$-(4-chlorophenyl) | |
| Ij.118 | $-CH_2-CH(Cl)-COOH$ | |
| Ij.119 | $-CH_2-CH(Cl)-CO-NH$-cyclopropyl | |
| Ij.120 | $-CH_2-CH(Cl)-CO-N(CH_3)-CH_2-CO-CO_2H_5$ | |
| Ij.121 | $-CH_2-CH(Cl)-CO-NH-CH(CH)CH_3)_2)-CO-OC_2H_5$ | |
| Ij.122 | $-CH_2-CH(Cl)-CO-NH-CH(CH_2CH(CH_3)_2)-CO-OCH_3$ | |
| Ij.123 | $-CH_2-CH(Cl)-CO$-(2-methoxycarbonyl-pyrrolidin-1-yl) | |
| Ij.124 | $-CH_2-CH(Cl)-CO-NH$-(tetrahydrofuran-2-on-3-yl) | |
| Ij.125 | $-CH_2-CH(Cl)-CO-N(CN)-CH_2CH_2-C_2H_5$ | |
| Ij.126 | $-CH_2-CH(Cl)-CO-N(CN)$-cyclopropyl | |
| Ij.127 | $-CH_2-CH(Cl)-CO-N(CN)-CH_2-CH=CH_2$ | |
| Ij.128 | $-CH_2-CH(Cl)-CO-N(CONH_2)-CH_2CH_2-C_2H_5$ | |
| Ij.129 | $-CH_2-CH(Cl)-CO-N(CONH_2)$-cyclopropyl | |
| Ij.130 | $-CH_2-CH(Cl)-CO-N(CONH_2)-CH_2CH=CH_2$ | |
| Ij.131 | $-CH_2-CH(Cl)-CO-O$-(4-acetoxytetrahydrofuran-3-yl) | |
| Ij.132 | $-CH_2-CH(Br)-CO-O$-cyclohexyl | |
| Ij.133 | $-CH_2-CH(Br)-CO-OC(CH_3)_3$ | |
| Ij.134 | $-CH_2-CH(Br)-CO-OCH_2-CH(CH_3)_2$ | |
| Ij.135 | $-CH_2-CH(Br)-CO-NH-CH_2CO-OCH_3$ | |
| Ij.136 | $-CH_2-CH(Br)-CO-N(CH_3)-CH_2-CO-OCH_3$ | |
| Ij.137 | $-CH_2-CH(Br)-CO-NH-CH(CH_3)-CO-OC_2H_5$ | |
| Ij.138 | $-CH_2-CH(Br)-CO-NH-OC_2H_5$ | |
| Ij.139 | $-CH_2-CH(Br)-CO-NH-OCH_3$ | |
| Ij.140 | $-CH_2-CH(Br)-CO-NH-OCH_2-CH=CHCl$ | |
| Ij.141 | $-CH_2-CH(Br)-CO-NH-CH_2$-(4-chlorophenyl) | |
| Ij.142 | $-CH_2-CH(Br)-CO-SCH_2-CO-OC_2H_5$ | |
| Ij.143 | $-CH_2-CH(Br)-CO-SCH_2-C_2H_5$ | |
| Ij.144 | $-CH_2-CH(Br)-CO-SCH_2$-(4-chlorophenyl) | |
| Ij.145 | $-CH_2-C(Br)(CO-OC_2H_5)_2$ | |
| Ij.146 | $-CH_2-C(Br)(CO-OCH_3)_2$ | |
| Ij.147 | $-CH_2-CH(Br)-CO-OCH_2-CH=N-OCH_3$ | |
| Ij.148 | $-CH_2-CH(Br)-CO-OCH_2-CH=N-OC_2H_5$ | |
| Ij.149 | $-CH_2-CH(Br)-CO-OCH_2-CH=N-OCH_2-CH_2-C_2H_5$ | |
| Ij.150 | $-CH_2-CH(Br)-CO-OCH_2-CH=N-OCH_2$-phenyl | |
| Ij.151 | $-CH_2-CH(Br)-CO-OCH_2-CH=N-OCH_2-CH=CH_2$ | |
| Ij.152 | $-CH_2-CH(Br)-CO-OCH_2-CH=N-OCH_2-CH=CHCl$ | |
| Ij.153 | $-CH_2-CH(Br)-CO-OCH_2-CH=N-OCH_2$-(4-chlorophenyl) | |
| Ij.154 | $-CH_2-CH(Br)-CO-OCH_2-CH=N-OCH(CH_3)$-(4-chlorophenyl) | |
| Ij.155 | $-CH_2-CH(Br)-COOH$ | |
| Ij.156 | $-CH_2-CH(Br)-CO-NH$-cyclopropyl | |
| Ij.157 | $-CH_2-CH(Br)-CO-N(CH_3)-CH_2-CO-OC_2H_5$ | |
| Ij.158 | $-CH_2-CH(Br)-CO-NH-CH(CH(CH_3)_2)-CO-OCH_2H_5$ | |
| Ij.159 | $-CH_2-CH(Br)-CO-NH-CH(CH_{2CH(CH3)})_2)-CO-OCH_3$ | |
| Ij.160 | $-CH_2-CH(Br)-CO$-(2-methoxycarbonylpyrrolidin-1-yl) | |

TABLE 10-continued

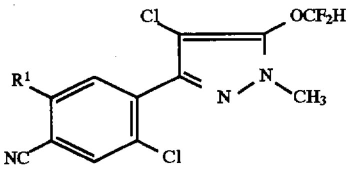

I ($R^2 = CN$; $R^3 = CH_3$; $R^4 = OCF_2H$; $R^5$, $R^6 = Cl$)

| No. | $R^1$ | m.p./$^1$H-NMR[ppm] MS [$mz^{-1}$] |
|---|---|---|
| Ij.160 | $-CH_2-CH(Br)-CO-$NH-(tetrahydrofuran-2-on-3-yl) | |
| Ij.161 | $-CH_2-CH(Br)-CO-$NH-(tetrahydrofuran-2-on-3-yl) | |
| Ij.162 | $-CH_2-CH(Br)-CO-N(CN)-CH_2CH_2-C_2H_5$ | |
| Ij.163 | $-CH_2-CH(Br)-CO-N(CN)$-cyclopropyl | |
| Ij.164 | $-CH_2-CH(Br)-CO-N(CN)-CH_2-CH=CH_2$ | |
| Ij.165 | $-CH_2-CH(Br)-CO-N(CONH_2)-CH_2CH_2-C_2H_5$ | |
| Ij.166 | $-CH_2-CH(Br)-CO-N(CONH_2)$-cyclopropyl | |
| Ij.167 | $-CH_2-CH(Br)-CO-N(CONH_2)-CH_2-CH=CH_2$ | |
| Ij.168 | $-CH_2-CH(Br)-CO-$O-(4-acetoxytetrahydrofuran-3-yl) | |
| Ij.169 | $-CH_2-CH(OH)-COOH$ | |
| Ij.170 | $-CH_2-CH(OH)-CO-OCH_3$ | |
| Ij.171 | $-CH_2-CH(OH)-CO-OC_2H_5$ | |
| Ij.172 | $-CH_2-CH(OH)-CO-OCH_2-CH=N-OCH_3$ | |
| Ij.173 | $-CH_2-CH(OH)-CO-OC(CH_3)_3$ | |
| Ij.174 | $-CH_2-CH(OH)-CO-NH_2$ | |
| Ij.175 | $-CH_2-CH(OH)-CO-NH-CH_3$ | |
| Ij.176 | $-CH_2-CH(OH)-CO-$NH-cyclopropyl | |
| Ij.177 | $-CH_2-CH(OCH_3)-COOH$ | |
| Ij.178 | $-CH_2-CH(OCH_3)-CO-OCH_3$ | |
| Ij.179 | $-CH_2-CH(OCH_3)-CO-OC_2H_5$ | |
| Ij.180 | $-CH_2-CH(OCH_3)-CO-OCH_2-CH=N-OCH_3$ | |
| Ij.181 | $-CH_2-CH(OCH_3)-CO-OC(CH_3)_3$ | |
| Ij.182 | $-CH_2-CH(OCH_3)-CO-NH_2$ | |
| Ij.183 | $-CH_2-CH(OCH_3)-CO-NH-CH_3$ | |
| Ij.184 | $-CH_2-CH(OCH_3)-CO-$NH-cyclopropyl | |
| Ij.185 | $-CH_2-CH(O-COCH_3)-COOH$ | |
| Ij.186 | $-CH_2-CH(O-COCH_3)-CO-OCH_3$ | |
| Ij.187 | $-CH_2-CH(O-COCH_3)-CO-OC_2H_5$ | |
| Ij.188 | $-CH_2-CH(O-COCH_3)-CO-OCH_2-CH=N-OCH_3$ | |
| Ij.189 | $-CH_2-CH(O-COCH_3)-CO-OC(CH_3)_3$ | |
| Ij.190 | $-CH_2-CH(O-COCH_3)-CO-NH_2$ | |
| Ij.191 | $-CH_2-CH(O-COCH_3)-CO-NH-CH_3$ | |
| Ij.192 | $-CH_2-CH(O-COCH_3)-CO-$NH-cyclopropyl | |
| Ij.193 | $-CH_2-CH(NH_2)-COOH$ | |
| Ij.194 | $-CH_2-CH(NH_2)-CO-OCH_3$ | |
| Ij.195 | $-CH_2-CH(NH_2)-CO-OC_2H_5$ | |
| Ij.196 | $-CH_2-CH(NH_2)-CO-OC(CH_3)_3$ | |
| Ij.197 | $-CH_2-CH(NH_2)-CO-NH_2$ | |
| Ij.198 | $-CH_2-CH(NH_2)-CO-NH-CH_3$ | |
| Ij.199 | $-CH_2-CH(N_3)-COOH$ | |
| Ij.200 | $-CH_2-CH(N_3)-CO-OCH_3$ | |
| Ij.201 | $-CH_2-CH(N_3)-CO-OC_2H_5$ | |
| Ij.202 | $-CH_2-CH(N_3)-CO-OC(CH_3)_3$ | |
| Ij.203 | $-CH_2-CH(N_3)-CO-NH_2$ | |
| Ij.204 | $-CH_2-CH(N_3)-CO-NH-CH_3$ | |
| Ij.205 | $-CH_2-CH(NH-COCH_3)-COOH$ | |
| Ij.206 | $-CH_2-CH(NH-COCH_3)-CO-OCH_3$ | |
| Ij.207 | $-CH_2-CH(NH-COCH_3)-CO-OC_2H_5$ | |
| Ij.208 | $-CH_2-CH(NH-COCH_3)-CO-OC(CH_3)_3$ | |
| Ij.209 | $-CH_2-CH(NH-COCH_3)-CO-NH_2$ | |
| Ij.210 | $-CH_2-CH(NH-COCH_3)-CO-NH-CH_3$ | |
| Ij.211 | $-CH_2-CH_2-$cyclohexyl | |
| Ij.212 | $-CH_2-CH_2-$cyclopentyl | |
| Ij.213 | $-CH_2-CH_2-$cyclopropyl | |
| Ij.214 | $-CH_2-CH_2-$phenyl | |
| Ij.215 | $-CH=C(CN)-CO-OC_2H_5$ | |
| Ij.216 | $-CH=C(CN)-CO-OCH(CH_3)_2$ | |
| Ij.217 | $-CH=C(CN)-CO-OC(CH_3)_3$ | |
| Ij.218 | $-CH=C(CN)-CO-OCH_2-CH=N-OCH_2-CH=CH_2$ | |
| Ij.219 | $-CH=C(CN)-CO-OCH_2-CH=N-OCH_2-CH=CHCl$ | |
| Ij.220 | $-CH=C(Cl)-CO-OCH_2-CH=N-OCH_2$-(4-chlorophenyl) | |
| Ij.221 | $-CH=C(Cl)-CO-OCH_2-CH=N-OCH(CH_3)$-(4-chlorophenyl) | |
| Ij.222 | $-CH=C(Cl)-CO-$O-(4-acetoxytetrahydrofuran-3-yl) | |
| Ij.223 | $-CH=C(Cl)-CO-$NH-cyclohexyl | |

TABLE 10-continued

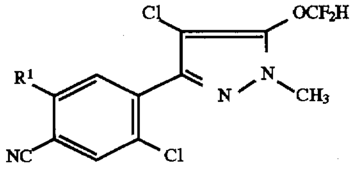

I ($R^2 = CN$; $R^3 = CH_3$; $R^4 = OCF_2H$; $R^5$, $R^6 = Cl$)

| No. | $R^1$ | m.p./$^1$H-NMR[ppm] MS [$mz^{-1}$] |
|---|---|---|
| Ij.224 | $-CH=C(Cl)-CO-N(CH_3)-CH_2-CO-OC_2H_5$ | |
| Ij.225 | $-CH=C(Cl)-CO-NH-CH(CH(CH_3)_2)-CO-OC_2H_5$ | |
| Ij.226 | $-CH=C(Cl)-CO-NH-CH(CH_2CH(CH_3)_2)-CO-OCH_3$ | |
| Ij.227 | $-CH=C(Cl)-CO$-(2-methoxycarbonylpyrrolidin-1-yl) | |
| Ij.228 | $-CH=C(Cl)-CO-NH$-(tetrahydrofuran-2-on-3-yl) | |
| Ij.229 | $-CH=C(Cl)-CO-N(CN)-CH_2CH_2-C_2H_5$ | |
| Ij.230 | $-CH=C(Cl)-CO-N(CN)$-cyclopropyl | |
| Ij.231 | $-CH=C(Cl)-CO-N(CN)-CH_2-CH=CH_2$ | |
| Ij.232 | $-CH=C(Cl)-CO-N(CONH_2)-CH_2CH_2-C_2H_5$ | |
| Ij.233 | $-CH=C(Cl)-CO-N(CONH_2)$-cyclopropyl | |
| Ij.234 | $-CH=C(Cl)-CO-N(CONH_2)-CH_2-CH=CH_2$ | |
| Ij.235 | $-CH=C(Br)-CO-OCH_2-CH=N-OCH_2$-(4-chlorophenyl) | |
| Ij.236 | $-CH=C(Br)-CO-OCH_2-CH=N-OCH(CH_3)$-(4-chlorophenyl) | |
| Ij.237 | $-CH=C(Br)-CO-O$-(4-acetoxytetrahydrofuran-3-yl) | |
| Ij.238 | $-CH=C(Br)-CO-NH$-cyclohexyl | |
| Ij.239 | $-CH=C(Br)-CO-N(CH_3)-CH_2-CO-CO_2H_5$ | |
| Ij.240 | $-CH=C(Br)-CO-NH-CH(CH(CH_3)_2)-CO-OC_2H_5$ | |
| Ij.241 | $-CH=C(Br)-CO-NH-CH(CH_2CH(CH_3)_2)-CO-OCH_3$ | |
| Ij.242 | $-CH=C(Br)-CO$-(2-methoxycarbonylpyrrolidin-1-yl) | |
| Ij.243 | $-CH=C(Br)-CO-NH$-(tetrahydrofuran-2-on-3-yl) | |
| Ij.244 | $-CH=C(Br)-CO-N(CN)-CH_2CH_2-C_2H_5$ | |
| Ij.245 | $-CH=C(Br)-CO-N(CN)$-cyclopropyl | |
| Ij.246 | $-CH=C(Br)-CO-N(CN)-CH_2-CH=CH_2$ | |
| Ij.247 | $-CH=C(Br)-CO-N(CONH_2)-CH_2CH_2-C_2H_5$ | |
| Ij.248 | $-CH=C(Br)-CO-N(CONH_2)$-cyclopropyl | |
| Ij.249 | $-CH=C(Br)-CO-N(CONH_2)-CH_2-CH=CH_2$ | |
| Ij.250 | $-CH_2-CH(Cl)-CO-N(C_2H_5)_2$ | |
| Ij.251 | $-CH_2-CH(Br)-CO-N(C_2H_5)_2$ | |
| Ij.252 | $-CH-CH(Br)-CO-N(C_2H_5)_2$ | |
| Ij.253 | $-CH-CH(Cl)-CO-N(C_2H_5)_2$ | |
| Ij.254 | 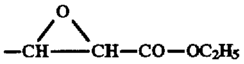 | |
| Ij.255 | 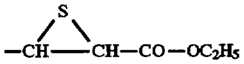 | |
| Ij.256 | 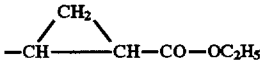 | |
| Ij.257 | 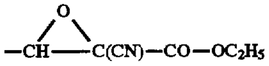 | |
| Ij.258 | 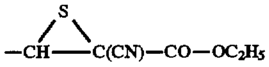 | |
| Ij.259 | 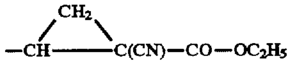 | |
| Ij.260 | 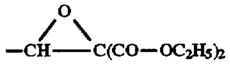 | |
| Ij.261 | 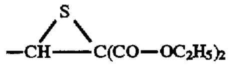 | |

TABLE 10-continued

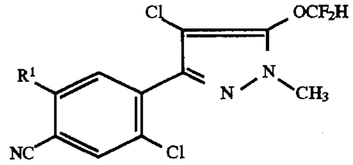

I ($R^2$ = CN; $R^3$ = $CH_3$; $R^4$ = $OCF_2H$; $R^5$, $R^6$ = Cl)

| No. | $R^1$ | m.p./$^1$H-NMR[ppm] MS [$mz^{-1}$] |
|---|---|---|
| Ij.262 | 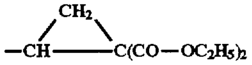 | |

TABLE 11

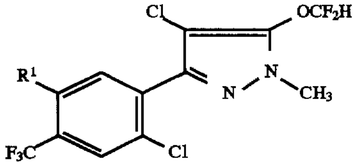

I ($R^2$ = $CF_3$; $R^3$ = $CH_3$; $R^4$ = $OCF_2H$; $R^5$, $R^6$ = Cl)

| No. | $R^1$ | m.p./$^1$H-NMR[ppm] MS [$mz^{-1}$] |
|---|---|---|
| Ik.001 | $-CH=C(Cl)-COOH$ | |
| Ik.002 | $-CH=C(Cl)-CO-OCH_3$ | |
| Ik.003 | $-CH=C(Cl)-CO-OC_2H_5$ | |
| Ik.004 | $-CH=C(Cl)-CO-OCH(CH_3)_2$ | |
| Ik.005 | $-CH=C(Br)-COOH$ | |
| Ik.006 | $-CH=C(Br)-CO-OCH_3$ | |
| Ik.007 | $-CH=C(Br)-CO-OC_2H_5$ | |
| Ik.008 | $-CH=C(Br)-CO-OCH(CH_3)_2$ | |
| Ik.009 | $-CH=C(Cl)-CO-NH_2$ | |
| Ik.010 | $-CH=C(Cl)-CO-NH-CH_3$ | |
| Ik.011 | $-CH=C(Cl)-CO-N(CH_3)_2$ | |
| Ik.012 | $-CH=C(Br)-CO-NH_2$ | |
| Ik.013 | $-CH=C(Br)-CO-NH-CH_3$ | |
| Ik.014 | $-CH=C(Br)-CO-N(CH_3)_2$ | |
| Ik.015 | $-CH=C(Br)-CO-$NH-cyclopropyl | |
| Ik.016 | $-CH=C(Cl)-CO-$NH-cyclopropyl | |
| Ik.017 | $-CH=$(cyclopropylene) | |
| Ik.018 | $-CH=$(cyclopentylene) | |
| Ik.019 | $-CH=$(cyclohexylene) | |
| Ik.020 | 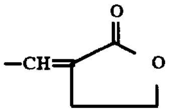 | |
| Ik.021 | 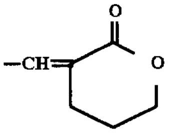 | |
| Ik.022 | 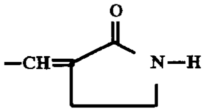 | |

TABLE 11-continued

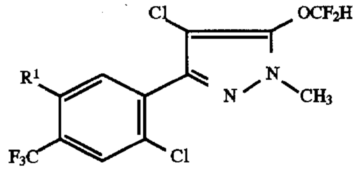

I ($R^2 = CF_3$; $R^3 = CH_3$; $R^4 = OCF_2H$; $R^5$, $R^6 = Cl$)

| No. | $R^1$ | m.p./$^1$H-NMR[ppm] MS [$mz^{-1}$] |
|---|---|---|
| Ik.023 | 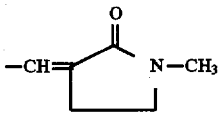 | |
| Ik.024 | 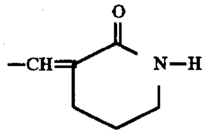 | |
| Ik.025 | 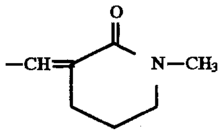 | |
| Ik.026 | 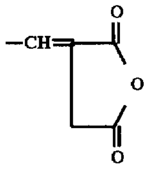 | |
| Ik.027 | 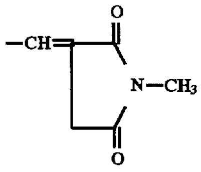 | |
| Ik.028 | $-CH{=}C(CH_3)-CO-OC_2H_5$ | |
| Ik.029 | $-CH{=}C(CH_3)-CO-OCH_3$ | |
| Ik.030 | $-CH{=}C(CH_3)-CO-NH_2$ | |
| Ik.031 | $-CH{=}C(CH_3)-CO-NH-CH_3$ | |
| Ik.032 | $-CH{=}C(CH_3)-CO-N(CH_3)_2$ | |
| Ik.033 | $-CH{=}C(CN)-CO-OCH_3$ | |
| Ik.034 | $-CH_2-CH(CN)-CO-OCH_3$ | |
| Ik.035 | $-CH_2-CH(CN)-CO-OC_2H_5$ | |
| Ik.036 | $-CH_2-CH(CN)-CO-NH_2$ | |
| Ik.037 | $-CH_2-CH(CN)-CO-NH-CH_3$ | |
| Ik.038 | $-CH_2-CH(CN)-CO-N(CH_3)_2$ | |
| Ik.039 | $-CH_2-CH(CN)-CO-NH-SO_2-CH_3$ | |
| Ik.040 | $-CH_2-CH(Cl)-CO-OCH_3$ | |
| Ik.041 | $-CH_2-CH(Cl)-CO-OC_2H_5$ | |
| Ik.042 | $-CH_2-CH(Cl)-CO-NH_2$ | |
| Ik.043 | $-CH_2-CH(Cl)-CO-NH-CH_3$ | |
| Ik.044 | $-CH_2-CH(Cl)-CO-N(CH_3)_2$ | |
| Ik.045 | $-CH_2-CH(Cl)-CO-NH-SO_2CH_3$ | |
| Ik.046 | $-CH_2-CH(Br)-CO-OCH_3$ | |
| Ik.047 | $-CH_2-CH(Br)-CO-OC_2H_5$ | |
| Ik.048 | $-CH_2-CH(Br)-CO-OCH(CH_3)_2$ | |
| Ik.049 | $-CH_2-CH(Br)-CO-NH_2$ | |
| Ik.050 | $-CH_2-CH(Br)-CO-NH-CH_3$ | |
| Ik.051 | $-CH_2-CH(Br)-CO-N(CH_3)_2$ | |
| Ik.052 | $-CH_2-CH(Cl)-CO-CH(CH_3)_2$ | |
| Ik.053 | $-CH_2-CH(CN)-CO-CH(CH_3)_2$ | |

TABLE 11-continued

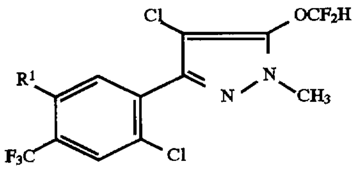

I ($R^2 = CF_3$; $R^3 = CH_3$; $R^4 = OCF_2H$; $R^5$, $R^6 = Cl$)

| No. | $R^1$ | m.p./$^1$H-NMR[ppm] MS [$mz^{-1}$] |
|---|---|---|
| Ik.054 | $-CH=CH$-(4-fluorophenyl) | |
| Ik.055 | $-CH=CH$-(4-chlorophenyl) | |
| Ik.056 | $-CH=CH$-(3-trifluoromethylphenyl) | |
| Ik.057 | $-CH=CH$-(2,4-dichlorophenyl) | |

TABLE 12

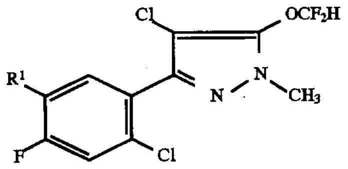

I ($R^2 = F$; $R^3 = CH_3$; $R^4 = OCF_2H$; $R^5$, $R^6 = Cl$)

| No. | $R^1$ | m.p./$^1$H-NMR[ppm] MS [$mz^{-1}$] |
|---|---|---|
| Ij.001 | $-CH=C(Cl)-COOH$ | 8.07(d, 1H); 7.96(s, 1H); 7.81(d, 1H); 7.40(t, 1H); 3.82(s, 1H); |
| Ij.002 | $-CH=C(Cl)-CO-OCH_3$ | 8.28(d, 1H); 8.05(s, 1H); 7.31(d, 1H); 6.73(t, 1H); 3.92(s, 3H); 3.85(s, 3H) |
| Ij.003 | $-CH=C(Cl)-CO-OC_2H_5$ | 8.26(d, 1H); 8.04(s, 1H); 7.31(d, 1H); 6.73(t, 1H); 4.38(q, 2H); 3.85(s, 3H); 1.40(t, 3H) |
| Ij.004 | $-CH=C(Cl)-CO-OCH(CH_3)_2$ | |
| Ij.005 | $-CH=C(Br)-COOH$ | |
| Ij.006 | $-CH=C(Br)-CO-OCH_3$ | |
| Ij.007 | $-CH=C(Br)-CO-OC_2H_5$ | |
| Ij.008 | $-CH=C(Br)-CO-OCH(CH_3)_2$ | |
| Ij.009 | $-CH=C(Cl)-CO-NH_2$ | |
| Ij.010 | $-CH=C(Cl)-CO-NH-CH_3$ | |
| Ij.011 | $-CH=C(Cl)-CO-N(CH_3)_2$ | |
| Ij.012 | $-CH=C(Br)-CO-NH_2$ | |
| Ij.013 | $-CH=C(Br)-CO-NH-CH_3$ | |
| Ij.014 | $-CH=C(Br)-CO-N(CH_3)_2$ | |
| Ij.015 | $-CH=C(Br)-CO-$NH-cyclopropyl | |
| Ij.016 | $-CH=C(Cl)-CO-$NH-cyclopropyl | |
| Ij.017 | $-CH=$(cyclopropylene) | |
| Ij.018 | $-CH=$(cyclopentylene) | |
| Ij.019 | $-CH=$(cyclohexylene) | |
| Ij.020 | 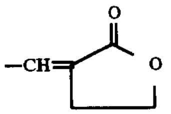 | |

TABLE 12-continued
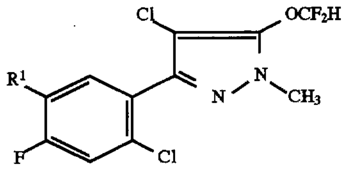
I ($R^2 = F$; $R^3 = CH_3$; $R^4 = OCF_2H$; $R^5$, $R^6 = Cl$)
| No. | $R^1$ | m.p./$^1$H-NMR[ppm] MS [$mz^{-1}$] |
|---|---|---|
| Ij.021 | 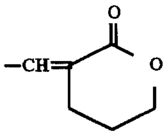 | |
| Ij.022 | 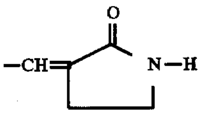 | |
| Ij.023 | 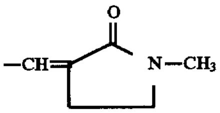 | |
| Ij.024 | 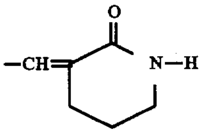 | |
| Ij.025 | 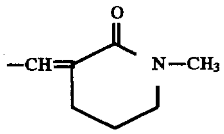 | |
| Ij.026 | 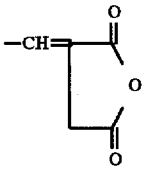 | |
| Ij.027 | 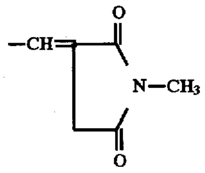 | |
| Ij.028 | $-CH{=}C(CH_3)-CO-OC_2H_5$ | |
| Ij.029 | $-CH{=}C(CH_3)-CO-OCH_3$ | |
| Ij.030 | $-CH{=}C(CH_3)-CO-NH_2$ | |
| Ij.031 | $-CH{=}C(CH_3)-CO-NH-CH_3$ | |
| Ij.032 | $-CH{=}C(CH_3)-CO-N(CH_3)_2$ | |
| Ij.033 | $-CH{=}C(CN)-CO-OCH_3$ | |
| Ij.034 | $-CH_2-CH(CN)-CO-OCH_3$ | |
| Ij.035 | $-CH_2-CH(CN)-CO-OC_2H_5$ | |
| Ij.036 | $-CH_2-CH(CN)-CO-NH_2$ | |
| Ij.037 | $-CH_2-CH(CN)-CO-NH-CH_3$ | |
| Ij.038 | $-CH_2-CH(CN)-CO-N(CH_3)_2$ | |
| Ij.039 | $-CH_2-CH(CN)-CO-NH-SO_2-CH_3$ | |

TABLE 12-continued

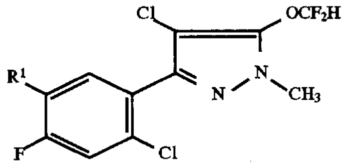

I ($R^2 = F$; $R^3 = CH_3$; $R^4 = OCF_2H$; $R^5$, $R^6 = Cl$)

| No. | $R^1$ | m.p./$^1$H-NMR[ppm] MS [$mz^{-1}$] |
|---|---|---|
| Ij.040 | $-CH_2-CH(Cl)-CO-OCH_3$ | |
| Ij.041 | $-CH_2-CH(Cl)-CO-OC_2H_5$ | |
| Ij.042 | $-CH_2-CH(Cl)-CO-NH_2$ | |
| Ij.043 | $-CH_2-CH(Cl)-CO-NH-CH_3$ | |
| Ij.044 | $-CH_2-CH(Cl)-CO-N(CH_3)_2$ | |
| Ij.045 | $-CH_2-CH(Cl)-CO-NH-SO_2CH_3$ | |
| Ij.046 | $-CH_2-CH(Br)-CO-OCH_3$ | |
| Ij.047 | $-CH_2-CH(Br)-CO-OC_2H_5$ | |
| Ij.048 | $-CH_2-CH(Br)-CO-OCH(CH_3)_2$ | |
| Ij.049 | $-CH_2-CH(Br)-CO-NH_2$ | |
| Ij.050 | $-CH_2-CH(Br)-CO-NH-CH_3$ | |
| Ij.051 | $-CH_2-CH(Br)-CO-N(CH_3)_2$ | |
| Ij.052 | $-CH_2-CH(Cl)-CO-CH(CH_3)_2$ | |
| Ij.053 | $-CH_2-CH(CN)-CO-CH(CH_3)_2$ | |
| Ij.054 | $-CH=CH$-(4-fluorophenyl) | |
| Ij.055 | $-CH=CH$-(4-chlorophenyl) | |
| Ij.056 | $-CH=CH$-(3-trifluoromethylphenyl) | |
| Ij.057 | $-CH=CH$-(2,4-dichlorophenyl) | |
| Ij.058 | $-CH=C(Cl)-CO-O-$-cyclohexyl | |
| Ij.059 | $-CH=C(Cl)-CO-OC(CH_3)_3$ | |
| Ij.060 | $-CH=C(Cl)-CO-OCH_2-CH(CH_3)_2$ | |
| Ij.061 | $-CH=C(Cl)-CO-NH-CH_2-CO-OCH_3$ | |
| Ij.062 | $-CH=C(Cl)-CO-N(CH_3)-CH_2-CO-OCH_3$ | |
| Ij.063 | $-CH=C(Cl)-CO-NH-CH(CH_3)-CO-OC_2H_5$ | |
| Ij.064 | $-CH=C(Cl)-CO-NH-OC_2H_5$ | |
| Ij.065 | $-CH=C(Cl)-CO-NH-OCH_3$ | |
| Ij.066 | $-CH=C(Cl)-CO-NH-OCH_2CH=CHCl$ | |
| Ij.067 | $-CH=C(Cl)-CO-NH-OCH_2$-(4-chlorophenyl) | |
| Ij.068 | $-CH=C(Cl)-CO-SCH_2-CO-OC_2H_5$ | |
| Ij.069 | $-CH=C(Cl)-CO-SCH_2-C_2H_5$ | |
| Ij.070 | $-CH=C(Cl)-CO-SCH_2$-(4-chlorophenyl) | |
| Ij.071 | $-CH=C(CO-OC_2H_5)_2$ | |
| Ij.072 | $-CH=C(CO-OCH_3)_2$ | |
| Ij.073 | $-CH=C(Cl)-CO-OCH_2-CH=N-OCH_3$ | |
| Ij.074 | $-CH=C(Cl)-CO-OCH_2-CH=N-OCH_2H_5$ | |
| Ij.075 | $-CH=C(Cl)-CO-OCH_2-CH=N-OCH_2-CH_2-C_2H_5$ | |
| Ij.076 | $-CH=C(Cl)-CO-OCH_2-CH=N-OCH_2-$phenyl | |
| Ij.077 | $-CH=C(Br)-CO-O-$cyclohexyl | |
| Ij.078 | $-CH=C(Br)-CO-OC(CH_3)_3$ | |
| Ij.079 | $-CH=C(Br)-CO-OCH_2-CH(CH_3)_2$ | |
| Ij.080 | $-CH=C(Br)-CO-NH-CH_2-CO-OCH_3$ | |
| Ij.081 | $-CH=C(Br)-CO-N(CH_3)-CH_2-CO-OCH_3$ | |
| Ij.082 | $-CH=C(Br)-CO-NH-OC_2H_5$ | |
| Ij.083 | $-CH=C(Br)-CO-NH-OCH_3$ | |
| Ij.084 | $-CH=C(Br)-CO-NH-OCH_2-CH=CHCl$ | |
| Ij.085 | $-CH=C(Br)-CO-NH-OCH_2$-(4-chlorophenyl) | |
| Ij.086 | $-CH=C(Br)-CO-SCH_2-CO-OC_2H_5$ | |
| Ij.087 | $-CH=C(Br)-CO-SCH_2-C_2H_5$ | |
| Ij.088 | $-CH=C(Br)-CO-SCH_2$-(4-chlorophenyl) | |
| Ij.089 | $-CH=C(Br)-CO-OCH_2-CH=N-OCH_2-CH=CH_2$ | |
| Ij.090 | $-CH=C(Br)-CO-OCH_2-CH=N-OCH_2-CH=CHCl$ | |
| Ij.091 | $-CH=C(Br)-CO-OCH_2-CH=N-OCH_3$ | |
| Ij.092 | $-CH=C(Br)-CO-OCH_2-CH=N-OC_2H_5$ | |
| Ij.093 | $-CH=C(Br)-CO-OCH_2-CH=N-OCH_2-CH_2-C_2H_5$ | |
| Ij.094 | $-CH=C(Br)-CO-OCH_2-CH=N-OCH_2$-phenyl | |
| Ij.095 | $-CH_2-CH(Cl)-CO-O-$cyclohexyl | |
| Ij.096 | $-CH_2-CH(Cl)-CO-OC(CH_3)_3$ | |
| Ij.097 | $-CH_2-CH(Cl)-CO-OCH_2-CH(CH_3)_2$ | |
| Ij.098 | $-CH_2-CH(Cl)-CO-NH-CH_2-CO-OCH_3$ | |
| Ij.099 | $-CH_2-CH(Cl)-CO-N(CH_3)-CH_2-CO-OCH_3$ | |
| Ij.100 | $-CH_2-CH(Cl)-CO-NH-CH(CH_3)-CO-OC_2H_5$ | |
| Ij.101 | $-CH_2-CH(Cl)-CO-NH-OC_2H_5$ | |
| Ij.102 | $-CH_2-CH(Cl)-CO-NH-OCH_3$ | |
| Ij.103 | $-CH_2-CH(Cl)-CO-NH-OCH_2-CH=CHCl$ | |

TABLE 12-continued

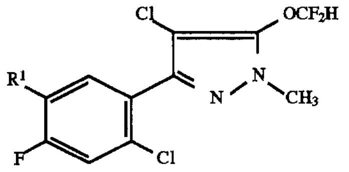

I ($R^2 = F$; $R^3 = CH_3$;
$R^4 = OCF_2H$; $R^5$, $R^6 = Cl$)

| No. | $R^1$ | m.p./$^1$H-NMR[ppm] MS [$mz^{-1}$] |
|---|---|---|
| Ij.104 | $-CH_2-CH(Cl)-CO-NH-OCH_2$-(4-chlorophenyl) | |
| Ij.105 | $-CH_2-CH(Cl)-CO-SCH_2-CO-OC_2H_5$ | |
| Ij.106 | $-CH_2-CH(Cl)-CO-SCH_2-C_2H_5$ | |
| Ij.107 | $-CH_2-CH(Cl)-CO-SCH_2$-(4-chlorophenyl) | |
| Ij.108 | $-CH_2-C(Cl)(CO-OC_2H_5)_2$ | |
| Ij.109 | $-CH_2-C(Cl)(CO-OCH_3)_2$ | |
| Ij.110 | $-CH_2-CH(Cl)-CO-OCH_2-CH=N-OCH_3$ | |
| Ij.111 | $-CH_2-CH(Cl)-CO-OCH_2-CH=N-OC_2H_5$ | |
| Ij.112 | $-CH_2-CH(Cl)-CO-OCH_2-CH=N-OCH_2-CH_2-C_2H_5$ | |
| Ij.113 | $-CH_2-CH(Cl)-CO-OCH_2-CH=N-OCH_2$-phenyl | |
| Ij.114 | $-CH_2-CH(Cl)-CO-OCH_2-CH=N-OCH_2-CH=CH_2$ | |
| Ij.115 | $-CH_2-CH(Cl)-CO-OCH_2-CH=N-OCH_2-CH=CHCl$ | |
| Ij.116 | $-CH_2-CH(Cl)-CO-OCH_2-CH=N-OCH_2$-(4-chlorophenyl) | |
| Ij.117 | $-CH_2-CH(Cl)-CO-OCH_2-CH=N-OCH(CH_3)$-(4-chlorophenyl) | |
| Ij.118 | $-CH_2-CH(Cl)-COOH$ | |
| Ij.119 | $-CH_2-CH(Cl)-CO-NH$-cyclopropyl | |
| Ij.120 | $-CH_2-CH(Cl)-CO-N(CH_3)-CH_2-CO-CO_2H_5$ | |
| Ij.121 | $-CH_2-CH(Cl)-CO-NH-CH(CH(CH_3)_2)-CO-OC_2H_5$ | |
| Ij.122 | $-CH_2-CH(Cl)-CO-NH-CH(CH_2CH(CH_3)_2)-CO-OCH_3$ | |
| Ij.123 | $-CH_2-CH(Cl)-CO$-(2-methoxycarbonyl-pyrrolidin-1-yl) | |
| Ij.124 | $-CH_2-CH(Cl)-CO-NH$-(tetrahydrofuran-2-on-3-yl) | |
| Ij.125 | $-CH_2-CH(Cl)-CO-N(CN)-CH_2CH_2-C_2H_5$ | |
| Ij.126 | $-CH_2-CH(Cl)-CO-N(CN)$-cyclopropyl | |
| Ij.127 | $-CH_2-CH(Cl)-CO-N(CN)-CH_2-CH=CH_2$ | |
| Ij.128 | $-CH_2-CH(Cl)-CO-N(CONH_2)-CH_2CH_2-C_2H_5$ | |
| Ij.129 | $-CH_2-CH(Cl)-CO-N(CONH_2)$-cyclopropyl | |
| Ij.130 | $-CH_2-CH(Cl)-CO-N(CONH_2)-CH_2CH=CH_2$ | |
| Ij.131 | $-CH_2-CH(Cl)-CO-O$-(4-acetoxytetrahydrofuran-3-yl) | |
| Ij.132 | $-CH_2-CH(Br)-CO-O$-cyclohexyl | |
| Ij.133 | $-CH_2-CH(Br)-CO-OC(CH_3)_3$ | |
| Ij.134 | $-CH_2-CH(Br)-CO-OCH_2-CH(CH_3)_2$ | |
| Ij.135 | $-CH_2-CH(Br)-CO-NH-CH_2CO-OCH_3$ | |
| Ij.136 | $-CH_2-CH(Br)-CO-N(CH_3)-CH_2-CO-OCH_3$ | |
| Ij.137 | $-CH_2-CH(Br)-CO-NH-CH(CH_3)-CO-OC_2H_5$ | |
| Ij.138 | $-CH_2-CH(Br)-CO-NH-OC_2H_5$ | |
| Ij.139 | $-CH_2-CH(Br)-CO-NH-OCH_3$ | |
| Ij.140 | $-CH_2-CH(Br)-CO-NH-OCH_2-CH=CHCl$ | |
| Ij.141 | $-CH_2-CH(Br)-CO-NH-CH_2$-(4-chlorophenyl) | |
| Ij.142 | $-CH_2-CH(Br)-CO-SCH_2-CO-OC_2H_5$ | |
| Ij.143 | $-CH_2-CH(Br)-CO-SCH_2-C_2H_5$ | |
| Ij.144 | $-CH_2-CH(Br)-CO-SCH_2$-(4-chlorophenyl) | |
| Ij.145 | $-CH_2-C(Br)(CO-OC_2H_5)_2$ | |
| Ij.146 | $-CH_2-C(Br)(CO-OCH_3)_2$ | |
| Ij.147 | $-CH_2-CH(Br)-CO-OCH_2-CH=N-OCH_3$ | |
| Ij.148 | $-CH_2-CH(Br)-CO-OCH_2-CH=N-OC_2H_5$ | |
| Ij.149 | $-CH_2-CH(Br)-CO-OCH_2-CH=N-OCH_2-CH_2-C_2H_5$ | |
| Ij.150 | $-CH_2-CH(Br)-CO-OCH_2-CH=N-OCH_2$-phenyl | |
| Ij.151 | $-CH_2-CH(Br)-CO-OCH_2-CH=N-OCH_2-CH=CH_2$ | |
| Ij.152 | $-CH_2-CH(Br)-CO-OCH_2-CH=N-OCH_2-CH=CHCl$ | |
| Ij.153 | $-CH_2-CH(Br)-CO-OCH_2-CH=N-OCH_2$-(4-chlorophenyl) | |
| Ij.154 | $-CH_2-CH(Br)-CO-OCH_2-CH=N-OCH(CH_3)$-(4-chlorophenyl) | |
| Ij.155 | $-CH_2-CH(Br)-COOH$ | |
| Ij.156 | $-CH_2-CH(Br)-CO-NH$-cyclopropyl | |
| Ij.157 | $-CH_2-CH(Br)-CO-N(CH_3)-CH_2-CO-OC_2H_5$ | |
| Ij.158 | $-CH_2-CH(Br)-CO-NH-CH(CH(CH_3)_2)-CO-OCH_2H_5$ | |
| Ij.159 | $-CH_2-CH(Br)-CO-NH-CH(CH_{2CH(CH3)})_2)-CO-OCH_3$ | |
| Ij.160 | $-CH_2-CH(Br)-CO$-(2-methoxycarbonylpyrrolidin-1-yl) | |
| Ij.160 | $-CH_2-CH(Br)-CO-NH$-(tetrahydrofuran-2-on-3-yl) | |
| Ij.161 | $-CH_2-CH(Br)-CO-NH$-(tetrahydrofuran-2-on-3-yl) | |
| Ij.162 | $-CH_2-CH(Br)-CO-N(CN)-CH_2CH_2-C_2H_5$ | |
| Ij.163 | $-CH_2-CH(Br)-CO-N(CN)$-cyclopropyl | |
| Ij.164 | $-CH_2-CH(Br)-CO-N(CN)-CH_2-CH=CH_2$ | |
| Ij.165 | $-CH_2-CH(Br)-CO-N(CONH_2)-CH_2CH_2-C_2H_5$ | |
| Ij.166 | $-CH_2-CH(Br)-CO-N(CONH_2)$-cyclopropyl | |

TABLE 12-continued

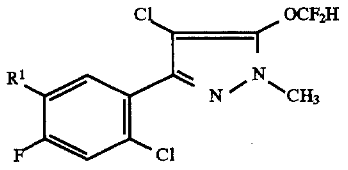

I ($R^2=F$; $R^3=CH_3$; $R^4=OCF_2H$; $R^5$, $R^6=Cl$)

| No. | $R^1$ | m.p./$^1$H-NMR[ppm] MS [$mz^{-1}$] |
|---|---|---|
| Ij.167 | $-CH_2-CH(Br)-CO-N(CONH_2)-CH_2-CH=CH_2$ | |
| Ij.168 | $-CH_2-CH(Br)-CO-$O-(4-acetoxytetrahydrofuran-3-yl) | |
| Ij.169 | $-CH_2-CH(OH)-COOH$ | |
| Ij.170 | $-CH_2-CH(OH)-CO-OCH_3$ | |
| Ij.171 | $-CH_2-CH(OH)-CO-OC_2H_5$ | |
| Ij.172 | $-CH_2-CH(OH)-CO-OCH_2-CH=N-OCH_3$ | |
| Ij.173 | $-CH_2-CH(OH)-CO-OC(CH_3)_3$ | |
| Ij.174 | $-CH_2-CH(OH)-CO-NH_2$ | |
| Ij.175 | $-CH_2-CH(OH)-CO-NH-CH_3$ | |
| Ij.176 | $-CH_2-CH(OH)-CO-$NH-cyclopropyl | |
| Ij.177 | $-CH_2-CH(OCH_3)-COOH$ | |
| Ij.178 | $-CH_2-CH(OCH_3)-CO-OCH_3$ | |
| Ij.179 | $-CH_2-CH(OCH_3)-CO-OC_2H_5$ | |
| Ij.180 | $-CH_2-CH(OCH_3)-CO-OCH_2-CH=N-OCH_3$ | |
| Ij.181 | $-CH_2-CH(OCH_3)-CO-OC(CH_3)_3$ | |
| Ij.182 | $-CH_2-CH(OCH_3)-CO-NH_2$ | |
| Ij.183 | $-CH_2-CH(OCH_3)-CO-NH-CH_3$ | |
| Ij.184 | $-CH_2-CH(OCH_3)-CO-$NH-cyclopropyl | |
| Ij.185 | $-CH_2-CH(O-COCH_3)-COOH$ | |
| Ij.186 | $-CH_2-CH(O-COCH_3)-CO-OCH_3$ | |
| Ij.187 | $-CH_2-CH(O-COCH_3)-CO-OC_2H_5$ | |
| Ij.188 | $-CH_2-CH(O-COCH_3)-CO-OCH_2-CH=N-OCH_3$ | |
| Ij.189 | $-CH_2-CH(O-COCH_3)-CO-OC(CH_3)_3$ | |
| Ij.190 | $-CH_2-CH(O-COCH_3)-CO-NH_2$ | |
| Ij.191 | $-CH_2-CH(O-COCH_3)-CO-NH-CH_3$ | |
| Ij.192 | $-CH_2-CH(O-COCH_3)-CO-$NH-cyclopropyl | |
| Ij.193 | $-CH_2-CH(NH_2)-COOH$ | |
| Ij.194 | $-CH_2-CH(NH_2)-CO-OCH_3$ | |
| Ij.195 | $-CH_2-CH(NH_2)-CO-OC_2H_5$ | |
| Ij.196 | $-CH_2-CH(NH_2)-CO-OC(CH_3)_3$ | |
| Ij.197 | $-CH_2-CH(NH_2)-CO-NH_2$ | |
| Ij.198 | $-CH_2-CH(NH_2)-CO-NH-CH_3$ | |
| Ij.199 | $-CH_2-CH(N_3)-COOH$ | |
| Ij.200 | $-CH_2-CH(N_3)-CO-OCH_3$ | |
| Ij.201 | $-CH_2-CH(N_3)-CO-OC_2H_5$ | |
| Ij.202 | $-CH_2-CH(N_3)-CO-OC(CH_3)_3$ | |
| Ij.203 | $-CH_2-CH(N_3)-CO-NH_2$ | |
| Ij.204 | $-CH_2-CH(N_3)-CO-NH-CH_3$ | |
| Ij.205 | $-CH_2-CH(NH-COCH_3)-COOH$ | |
| Ij.206 | $-CH_2-CH(NH-COCH_3)-CO-OCH_3$ | |
| Ij.207 | $-CH_2-CH(NH-COCH_3)-CO-OC_2H_5$ | |
| Ij.208 | $-CH_2-CH(NH-COCH_3)-CO-OC(CH_3)_3$ | |
| Ij.209 | $-CH_2-CH(NH-COCH_3)-CO-NH_2$ | |
| Ij.210 | $-CH_2-CH(NH-COCH_3)-CO-NH-CH_3$ | |
| Ij.211 | $-CH_2-CH_2-$cyclohexyl | |
| Ij.212 | $-CH_2-CH_2-$cyclopentyl | |
| Ij.213 | $-CH_2-CH_2-$cyclopropyl | |
| Ij.214 | $-CH_2-CH_2-$phenyl | |
| Ij.215 | $-CH=C(CN)-CO-OC_2H_5$ | |
| Ij.216 | $-CH=C(CN)-CO-OCH(CH_3)_2$ | |
| Ij.217 | $-CH=C(CN)-CO-OC(CH_3)_3$ | |
| Ij.218 | $-CH=C(CN)-CO-OCH_2-CH=N-OCH_2-CH=CH_2$ | |
| Ij.219 | $-CH=C(CN)-CO-OCH_2-CH=N-OCH_2-CH=CHCl$ | |
| Ij.220 | $-CH=C(Cl)-CO-OCH_2-CH=N-OCH_2$-(4-chlorophenyl) | |
| Ij.221 | $-CH=C(Cl)-CO-OCH_2-CH=N-OCH(CH_3)$-(4-chlorophenyl) | |
| Ij.222 | $-CH=C(Cl)-CO-$O-(4-acetoxytetrahydrofuran-3-yl) | |
| Ij.223 | $-CH=C(Cl)-CO-$NH-cyclohexyl | |
| Ij.224 | $-CH=C(Cl)-CO-N(CH_3)-CH_2-CO-OC_2H_5$ | |
| Ij.225 | $-CH=C(Cl)-CO-NH-CH(CH(CH_3)_2)-CO-OC_2H_5$ | |
| Ij.226 | $-CH=C(Cl)-CO-NH-CH(CH_2CH(CH_3)_2)-CO-OCH_3$ | |
| Ij.227 | $-CH=C(Cl)-CO$-(2-methoxycarbonylpyrrolidin-1-yl) | |
| Ij.228 | $-CH=C(Cl)-CO-$NH-(tetrahydrofuran-2-on-3-yl) | |
| Ij.229 | $-CH=C(Cl)-CO-N(CN)-CH_2CH_2-C_2H_5$ | |
| Ij.230 | $-CH=C(Cl)-CO-N(CN)$-cyclopropyl | |

TABLE 12-continued

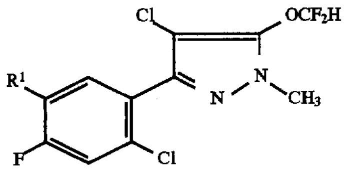

I ($R^2 = F$; $R^3 = CH_3$; $R^4 = OCF_2H$; $R^5$, $R^6 = Cl$)

| No. | $R^1$ | m.p./$^1$H-NMR[ppm] MS [$mz^{-1}$] |
|---|---|---|
| Ij.231 | $-CH=C(Cl)-CO-N(CN)-CH_2-CH=CH_2$ | |
| Ij.232 | $-CH=C(Cl)-CO-N(CONH_2)-CH_2CH_2-C_2H_5$ | |
| Ij.233 | $-CH=C(Cl)-CO-N(CONH_2)$-cyclopropyl | |
| Ij.234 | $-CH=C(Cl)-CO-N(CONH_2)-CH_2-CH=CH_2$ | |
| Ij.235 | $-CH=C(Br)-CO-OCH_2-CH=N-OCH_2$-(4-chlorophenyl) | |
| Ij.236 | $-CH=C(Br)-CO-OCH_2-CH=N-OCH(CH_3)$-(4-chlorophenyl) | |
| Ij.237 | $-CH=C(Br)-CO-O$-(4-acetoxytetrahydrofuran-3-yl) | |
| Ij.238 | $-CH=C(Br)-CO.-NH$-cyclohexyl | |
| Ij.239 | $-CH=C(Br)-CO-N(CH_3)-CH_2-CO-CO_2H_5$ | |
| Ij.240 | $-CH=C(Br)-CO-NH-CH(CH(CH_3)_2)-CO-OC_2H_5$ | |
| Ij.241 | $-CH=C(Br)-CO-NH-CH(CH_2CH(CH_3)_2)-CO-OCH_3$ | |
| Ij.242 | $-CH=C(Br)-CO$-(2-methoxycarbonylpyrrolidin-1-yl) | |
| Ij.243 | $-CH=C(Br)-CO-NH$-(tetrahydrofuran-2-on-3-yl) | |
| Ij.244 | $-CH=C(Br)-CO-N(CN)-CH_2CH_2-C_2H_5$ | |
| Ij.245 | $-CH=C(Br)-CO-N(CN)$-cyclopropyl | |
| Ij.246 | $-CH=C(Br)-CO-N(CN)-CH_2-CH=CH_2$ | |
| Ij.247 | $-CH=C(Br)-CO-N(CONH_2)-CH_2CH_2-C_2H_5$ | |
| Ij.248 | $-CH=C(Br)-CO-N(CONH_2)$-cyclopropyl | |
| Ij.249 | $-CH=C(Br)-CO-N(CONH_2)-CH_2-CH=CH_2$ | |
| Ij.250 | $-CH_2-CH(Cl)-CO-N(C_2H_5)_2$ | |
| Ij.251 | $-CH_2-CH(Br)-CO-N(C_2H_5)_2$ | |
| Ij.252 | $-CH-CH(Br)-CO-N(C_2H_5)_2$ | |
| Ij.253 | $-CH-CH(Cl)-CO-N(C_2H_5)_2$ | |
| Ij.254 | 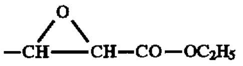 | |
| Ij.255 | 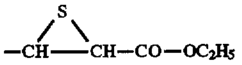 | |
| Ij.256 | 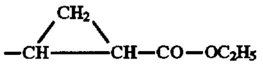 | |
| Ij.257 | 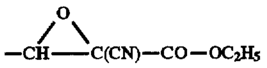 | |
| Ij.258 | 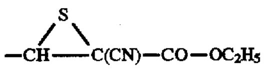 | |
| Ij.259 | 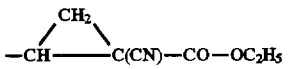 | |
| Ij.260 | 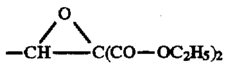 | |
| Ij.261 | 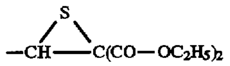 | |
| Ij.262 | 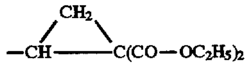 | |

TABLE 13

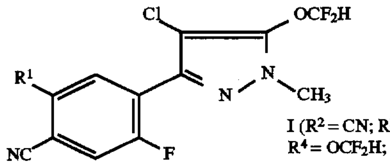

I ($R^2$ = CN; $R^3$ = $CH_3$; $R^4$ = $OCF_2H$; $R^5$ = Cl; $R^6$ = F)

| No. | $R^1$ | m.p./$^1$H-NMR [ppm] MS [mz$^{-1}$] |
|---|---|---|
| Im.001 | $-CH{=}C(Cl){-}COOH$ | |
| Im.002 | $-CH{=}C(Cl){-}CO{-}OCH_3$ | |
| Im.003 | $-CH{=}C(Cl){-}CO{-}OC_2H_5$ | |
| Im.004 | $-CH{=}C(Cl){-}CO{-}OCH(CH_3)_2$ | |
| Im.005 | $-CH{=}C(Br){-}COOH$ | |
| Im.006 | $-CH{=}C(Br){-}CO{-}OCH_3$ | |
| Im.007 | $-CH{=}C(Br){-}CO{-}OC_2H_5$ | |
| Im.008 | $-CH{=}C(Br){-}CO{-}OCH(CH_3)_2$ | |
| Im.009 | $-CH{=}C(Cl){-}CO{-}NH_2$ | |
| Im.010 | $-CH{=}C(Cl){-}CO{-}NH{-}CH_3$ | |
| Im.011 | $-CH{=}C(Cl){-}CO{-}N(CH_3)_2$ | |
| Im.012 | $-CH{=}C(Br){-}CO{-}NH_2$ | |
| Im.013 | $-CH{=}C(Br){-}CO{-}NH{-}CH_3$ | |
| Im.014 | $-CH{=}C(Br){-}CO{-}N(CH_3)_2$ | |
| Im.015 | $-CH{=}C(Br){-}CO{-}$NH-cyclopropyl | |
| Im.016 | $-CH{=}C(Cl){-}CO{-}$NH-cyclopropyl | |
| Im.017 | $-CH{=}$(cyclopropylene) | |
| Im.018 | $-CH{=}$(cyclopentylene) | |
| Im.019 | $-CH{=}$(cyclohexylene) | |
| Im.020 | 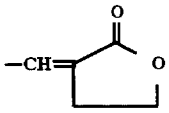 | |
| Im.021 | 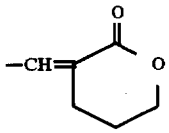 | |
| Im.022 | 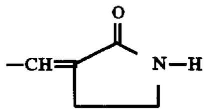 | |
| Im.023 | 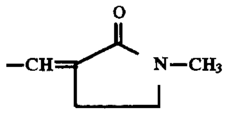 | |
| Im.024 | 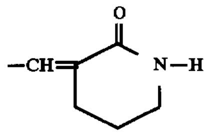 | |
| Im.025 | 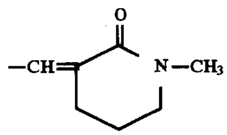 | |
| Im.026 | 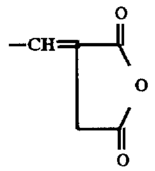 | |

TABLE 13-continued

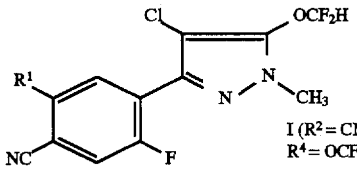

I ($R^2 = CN$; $R^3 = CH_3$; $R^4 = OCF_2H$; $R^5 = Cl$; $R^6 = F$)

| No. | $R^1$ | m.p./$^1$H-NMR [ppm] MS [$mz^{-1}$] |
|---|---|---|
| Im.027 | 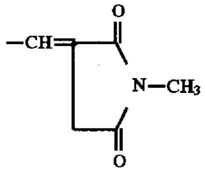 | |
| Im.028 | $-CH=C(CH_3)-CO-OC_2H_5$ | |
| Im.029 | $-CH=C(CH_3)-CO-OCH_3$ | |
| Im.030 | $-CH=C(CH_3)-CO-NH_2$ | |
| Im.031 | $-CH=C(CH_3)-CO-NH-CH_3$ | |
| Im.032 | $-CH=C(CH_3)-CO-N(CH_3)_2$ | |
| Im.033 | $-CH=C(CN)-CO-OCH_3$ | |
| Im.034 | $-CH_2-CH(CN)-CO-OCH_3$ | |
| Im.035 | $-CH_2-CH(CN)-CO-OC_2H_5$ | |
| Im.036 | $-CH_2-CH(CN)-CO-NH_2$ | |
| Im.037 | $-CH_2-CH(CN)-CO-NH-CH_3$ | |
| Im.038 | $-CH_2-CH(CN)-CO-N(CH_3)_2$ | |
| Im.039 | $-CH_2-CH(CN)-CO-NH-SO_2-CH_3$ | |
| Im.040 | $-CH_2-CH(Cl)-CO-OCH_3$ | |
| Im.041 | $-CH_2-CH(Cl)-CO-OC_2H_5$ | |
| Im.042 | $-CH_2-CH(Cl)-CO-NH_2$ | |
| Im.043 | $-CH_2-CH(Cl)-CO-NH-CH_3$ | |
| Im.044 | $-CH_2-CH(Cl)-CO-N(CH_3)_2$ | |
| Im.045 | $-CH_2-CH(Cl)-CO-NH-SO_2-CH_3$ | |
| Im.046 | $-CH_2-CH(Br)-CO-OCH_3$ | |
| Im.047 | $-CH_2-CH(Br)-CO-OC_2H_5$ | |
| Im.048 | $-CH_2-CH(Br)-CO-OCH(CH_3)_2$ | |
| Im.049 | $-CH_2-CH(Br)-CO-NH_2$ | |
| Im.050 | $-CH_2-CH(Br)-CO-NH-CH_3$ | |
| Im.051 | $-CH_2-CH(Br)-CO-N(CH_3)_2$ | |
| Im.052 | $-CH_2-CH(Cl)-CO-CH(CH_3)_2$ | |
| Im.053 | $-CH_2-CH(CN)-CO-CH(CH_3)_2$ | |
| Im.054 | $-CH=CH$-(4-fluorophenyl) | |
| Im.055 | $-CH=CH$-(4-chlorophenyl) | |
| Im.056 | $-CH=CH$-(3-trifluoromethylphenyl) | |
| Im.057 | $-CH=CH$-(2,4-dichlorophenyl) | |
| Im.058 | $-CH=C(Cl)-CO-$O-cyclohexyl | |
| Im.059 | $-CH=C(Cl)-CO-OC(CH_3)_3$ | |
| Im.060 | $-CH=C(Cl)-CO-OCH_2-CH(CH_3)_2$ | |
| Im.061 | $-CH=C(Cl)-CO-NH-CH_2-CO-OCH_3$ | |
| Im.062 | $-CH=C(Cl)-CO-N(CH_3)-CH_2-CO-OCH_3$ | |
| Im.063 | $-CH=C(Cl)-CO-NH-CH(CH_3)-CO-OC_2H_5$ | |
| Im.064 | $-CH=C(Cl)-CO-NH-OC_2H_5$ | |
| Im.065 | $-CH=C(Cl)-CO-NH-OCH_3$ | |
| Im.066 | $-CH=C(Cl)-CO-NH-OCH_2-CH=CHCl$ | |
| Im.067 | $-CH=C(Cl)-CO-NH-OCH_2$-(4-chlorophenyl) | |
| Im.068 | $-CH=C(Cl)-CO-SCH_2-CO-OC_2H_5$ | |
| Im.069 | $-CH=C(Cl)-CO-SCH_2-C_2H_5$ | |
| Im.070 | $-CH=C(Cl)-CO-SCH_2$-(4-chlorophenyl) | |
| Im.071 | $-CH=C(CO-OC_2H_5)_2$ | |
| Im.072 | $-CH=C(CO-OCH_3)_2$ | |
| Im.073 | $-CH=C(Cl)-CO-OCH_2-CH=N-OCH_3$ | |
| Im.074 | $-CH=C(Cl)-CO-OCH_2-CH=N-OC_2H_5$ | |
| Im.075 | $-CH=C(Cl)-CO-OCH_2-CH=N-OCH_2-CH_2-C_2H_5$ | |
| Im.076 | $-CH=C(Cl)-CO-OCH_2-CH=N-OCH_2$-phenyl | |
| Im.077 | $-CH=C(Br)-CO-$O-cyclohexyl | |
| Im.078 | $-CH=C(Br)-CO-OC(CH_3)_3$ | |
| Im.079 | $-CH=C(Br)-CO-OCH_2-CH(CH_3)_2$ | |
| Im.080 | $-CH=C(Br)-CO-NH-CH_2-CO-OCH_3$ | |
| Im.081 | $-CH=C(Br)-CO-N(CH_3)-CH_2-CO-OCH_3$ | |
| Im.082 | $-CH=C(Br)-CO-NH-OC_2H_5$ | |
| Im.083 | $-CH=C(Br)-CO-NH-OCH_3$ | |
| Im.084 | $-CH=C(Br)-CO-NH-OCH_2-CH=CHCl$ | |

TABLE 13-continued

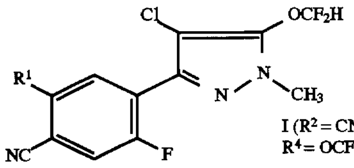

I ($R^2$ = CN; $R^3$ = $CH_3$; $R^4$ = $OCF_2H$; $R^5$ = Cl; $R^6$ = F)

| No. | $R^1$ | m.p./$^1$H-NMR [ppm] MS [$mz^{-1}$] |
|---|---|---|
| Im.085 | $-CH=C(Br)-CO-NH-OCH_2$-(4-chlorophenyl) | |
| Im.086 | $-CH=C(Br)-CO-SCH_2-CO-OC_2H_5$ | |
| Im.087 | $-CH=C(Br)-CO-SCH_2-C_2H_5$ | |
| Im.088 | $-CH=C(Br)-CO-SCH_2$-(4-chlorophenyl) | |
| Im.089 | $-CH=C(Br)-CO-OCH_2-CH=N-OCH_2-CH=CH_2$ | |
| Im.090 | $-CH=C(Br)-CO-OCH_2-CH=N-OCH_2-CH=CHCl$ | |
| Im.091 | $-CH=C(Br)-CO-OCH_2-CH=N-OCH_3$ | |
| Im.092 | $-CH=C(Br)-CO-OCH_2-CH=N-OC_2H_5$ | |
| Im.093 | $-CH=C(Br)-CO-OCH_2-CH=N-OCH_2-CH_2-C_2H_5$ | |
| Im.094 | $-CH=C(Br)-CO-OCH_2-CH=N-OCH_2$-phenyl | |
| Im.095 | $-CH_2-CH(Cl)-CO-O$-cyclohexyl | |
| Im.096 | $-CH_2-CH(Cl)-CO-OC(CH_3)_3$ | |
| Im.097 | $-CH_2-CH(Cl)-CO-OCH_2-CH(CH_3)_2$ | |
| Im.098 | $-CH_2-CH(Cl)-CO-NH-CH_2-CO-OCH_3$ | |
| Im.099 | $-CH_2-CH(Cl)-CO-N(CH_3)-CH_2-CO-OCH_3$ | |
| Im.100 | $-CH_2-CH(Cl)-CO-NH-CH(CH_3)-CO-OC_2H_5$ | |
| Im.101 | $-CH_2-CH(Cl)-CO-NH-OC_2H_5$ | |
| Im.102 | $-CH_2-CH(Cl)-CO-NH-OCH_3$ | |
| Im.103 | $-CH_2-CH(Cl)-CO-NH-OCH_2-CH=CHCl$ | |
| Im.104 | $-CH_2-CH(Cl)-CO-NH-OCH_2$-(4-chlorophenyl) | |
| Im.105 | $-CH_2-CH(Cl)-CO-SCH_2-CO-OC_2H_5$ | |
| Im.106 | $-CH_2-CH(Cl)-CO-SCH_2-C_2H_5$ | |
| Im.107 | $-CH_2-CH(Cl)-CO-SCH_2$-(4-chlorophenyl) | |
| Im.108 | $-CH_2-C(Cl)(CO-OC_2H_5)_2$ | |
| Im.109 | $-CH_2-C(Cl)(CO-OCH_3)_2$ | |
| Im.110 | $-CH_2-CH(Cl)-CO-OCH_2-CH=N-OCH_3$ | |
| Im.111 | $-CH_2-CH(Cl)-CO-OCH_2-CH=N-OC_2H_5$ | |
| Im.112 | $-CH_2-CH(Cl)-CO-OCH_2-CH=N-OCH_2-CH_2-C_2H_5$ | |
| Im.113 | $-CH_2-CH(Cl)-CO-OCH_2-CH=N-OCH_2$-phenyl | |
| Im.114 | $-CH_2-CH(Cl)-CO-OCH_2-CH=N-OCH_2-CH=CH_2$ | |
| Im.115 | $-CH_2-CH(Cl)-CO-OCH_2-CH=N-OCH_2-CH=CHCl$ | |
| Im.116 | $-CH_2-CH(Cl)-CO-OCH_2-CH=N-OCH_2$-(4-chlorophenyl) | |
| Im.117 | $-CH_2-CH(Cl)-CO-OCH_2-CH=N-OCH(CH_3)$-(4-chlorophenyl) | |
| Im.118 | $-CH_2-CH(Cl)-COOH$ | |
| Im.119 | $-CH_2-CH(Cl)-CO-NH$-cyclopropyl | |
| Im.120 | $-CH_2-CH(Cl)-CO-N(CH_3)-CH_2-CO-OC_2H_5$ | |
| Im.121 | $-CH_2-CH(Cl)-CO-NH-CH(CH(CH_3)_2)-CO-OC_2H_5$ | |
| Im.122 | $-CH_2-CH(Cl)-CO-NH-CH(CH_2CH(CH_3)_2)-CO-OCH_3$ | |
| Im.123 | $-CH_2-CH(Cl)-CO$-(2-methoxycarbonyl-pyrrolidin-1-yl) | |
| Im.124 | $-CH_2-CH(Cl)-CO-NH$-(tetrahydro-furan-2-on-3-yl) | |
| Im.125 | $-CH_2-CH(Cl)-CO-N(CN)-CH_2CH_2-C_2H_5$ | |
| Im.126 | $-CH_2-CH(Cl)-CO-N(CN)$-cyclopropyl | |
| Im.127 | $-CH_2-CH(Cl)-CO-N(CN)-CH_2-CH=CH_2$ | |
| Im.128 | $-CH_2-CH(Cl)-CO-N(CONH_2)-CH_2CH_2-C_2H_5$ | |
| Im.129 | $-CH_2-CH(Cl)-CO-N(CONH_2)$-cyclopropyl | |
| Im.130 | $-CH_2-CH(Cl)-CO-N(CONH_2)-CH_2-CH=CH_2$ | |
| Im.131 | $-CH_2-CH(Cl)-CO-O$-(4-acetoxytetra-hydrofuran-3-yl) | |
| Im.132 | $-CH_2-CH(Br)-CO-O$-cyclohexyl | |
| Im.133 | $-CH_2-CH(Br)-CO-OC(CH_3)_3$ | |
| Im.134 | $-CH_2-CH(Br)-CO-OCH_2-CH(CH_3)_2$ | |
| Im.135 | $-CH_2-CH(Br)-CO-NH-CH_2-CO-OCH_3$ | |
| Im.136 | $-CH_2-CH(Br)-CO-N(CH_3)-CH_2-CO-OCH_3$ | |
| Im.137 | $-CH_2-CH(Br)-CO-NH-CH(CH_3)-CO-OC_2H_5$ | |
| Im.138 | $-CH_2-CH(Br)-CO-NH-OC_2H_5$ | |
| Im.139 | $-CH_2-CH(Br)-CO-NH-OCH_3$ | |
| Im.140 | $-CH_2-CH(Br)-CO-NH-OCH_2-CH=CHCl$ | |
| Im.141 | $-CH_2-CH(Br)-CO-NH-CH_2$-(4-chlorophenyl) | |
| Im.142 | $-CH_2-CH(Br)-CO-SCH_2-CO-OC_2H_5$ | |

TABLE 13-continued

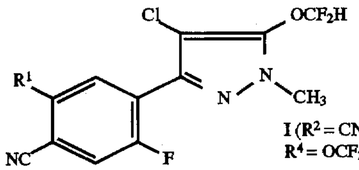

I ($R^2 = CN$; $R^3 = CH_3$; $R^4 = OCF_2H$; $R^5 = Cl$; $R^6 = F$)

| No. | $R^1$ | m.p./$^1$H-NMR [ppm] MS [$mz^{-1}$] |
|---|---|---|
| Im.143 | $-CH_2-CH(Br)-CO-SCH_2-C_2H_5$ | |
| Im.144 | $-CH_2-CH(Br)-CO-SCH_2$-(4-chlorophenyl) | |
| Im.145 | $-CH_2-C(Br)(CO-OC_2H_5)_2$ | |
| Im.146 | $-CH_2-C(Br)(CO-OCH_3)_2$ | |
| Im.147 | $-CH_2-CH(Br)-CO-OCH_2-CH=N-OCH_3$ | |
| Im.148 | $-CH_2-CH(Br)-CO-OCH_2-CH=N-OC_2H_5$ | |
| Im.149 | $-CH_2-CH(Br)-CO-OCH_2-CH=N-OCH_2-CH_2-C_2H_5$ | |
| Im.150 | $-CH_2-CH(Br)-CO-OCH_2-CH=N-OCH_2$-phenyl | |
| Im.151 | $-CH_2-CH(Br)-CO-OCH_2-CH=N-OCH_2-CH=CH_2$ | |
| Im.152 | $-CH_2-CH(Br)-CO-OCH_2-CH=N-OCH_2-CH=CHCl$ | |
| Im.153 | $-CH_2-CH(Br)-CO-OCH_2-CH=N-$ $OCH_2$-(4-chlorophenyl) | |
| Im.154 | $-CH_2-CH(Br)-CO-OCH_2-CH=N-$ $OCH(CH_3)$-(4-chlorophenyl) | |
| Im.155 | $-CH_2-CH(Br)-COOH$ | |
| Im.156 | $-CH_2-CH(Br)-CO-NH$-cyclopropyl | |
| Im.157 | $-CH_2-CH(Br)-CO-N(CH_3)-CH_2-CO-OC_2H_5$ | |
| Im.158 | $-CH_2-CH(Br)-CO-$ $NH-CH(CH(CH_3)_2)-CO-OC_2H_5$ | |
| Im.159 | $-CH_2-CH(Br)-CO-NH-CH(CH_2CH(CH_3)_2)-CO-$ $OCH_3$ | |
| Im.160 | $-CH_2-CH(Br)-CO-$(2-methoxycarbonyl-pyrrolidin-1-yl) | |
| Im.161 | $-CH_2-CH(Br)-CO-NH$-(tetrahydro-furan-2-on-3-yl) | |
| Im.162 | $-CH_2-CH(Br)-CO-N(CN)-CH_2CH_2-C_2H_5$ | |
| Im.163 | $-CH_2-CH(Br)-CO-N(CN)$-cyclopropyl | |
| Im.164 | $-CH_2-CH(Br)-CO-N(CN)-CH_2-CH=CH_2$ | |
| Im.165 | $-CH_2-CH(Br)-CO-N(CONH_2)-CH_2CH_2-C_2H_5$ | |
| Im.166 | $-CH_2-CH(Br)-CO-N(CONH_2)$-cyclopropyl | |
| Im.167 | $-CH_2-CH(Br)-CO-N(CONH_2)-CH_2-CH=CH_2$ | |
| Im.168 | $-CH_2-CH(Bry-CO-O$-(4-acetoxytetra-hydrofuran-3-yl) | |
| Im.169 | $-CH_2-CH(OH)-COOH$ | |
| Im.170 | $-CH_2-CH(OH)-CO-OCH_3$ | |
| Im.171 | $-CH_2-CH(OH)-CO-OC_2H_5$ | |
| Im.172 | $-CH_2-CH(OH)-CO-OCH_2-CH=N-OCH_3$ | |
| Im.173 | $-CH_2-CH(OH)-CO-OC(CH_3)_3$ | |
| Im.174 | $-CH_2-CH(OH)-CO-NH_2$ | |
| Im.175 | $-CH_2-CH(OH)-CO-NH-CH_3$ | |
| Im.176 | $-CH_2-CH(OH)-CO-NH$-cyclopropyl | |
| Im.177 | $-CH_2-CH(OCH_3)-COOH$ | |
| Im.178 | $-CH_2-CH(OCH_3)-CO-OCH_3$ | |
| Im.179 | $-CH_2-CH(OCH_3)-CO-OC_2H_5$ | |
| Im.180 | $-CH_2-CH(OCH_3)-CO-OCH_2-CH=N-OCH_3$ | |
| Im.181 | $-CH_2-CH(OCH_3)-CO-OC(CH_3)_3$ | |
| Im.182 | $-CH_2-CH(OCH_3)-CO-NH_2$ | |
| Im.183 | $-CH_2-CH(OCH_3)-CO-NH-CH_3$ | |
| Im.184 | $-CH_2-CH(OCH_3)-CO-NH$-cyclopropyl | |
| Im.185 | $-CH_2-CH(O-COCH_3)-COOH$ | |
| Im.186 | $-CH_2-CH(O-COCH_3)-CO-OCH_3$ | |
| Im.187 | $-CH_2-CH(O-COCH_3)-CO-OC_2H_5$ | |
| Im.188 | $-CH_2-CH(O-COCH_3)-CO-OCH_2-CH=N-OCH_3$ | |
| Im.189 | $-CH_2-CH(O-COCH_3)-CO-OC(CH_3)_3$ | |
| Im.190 | $-CH_2-CH(O-COCH_3)-CO-NH_2$ | |
| Im.191 | $-CH_2-CH(O-COCH_3)-CO-NH-CH_3$ | |
| Im.192 | $-CH_2-CH(O-COCH_3)-CO-NH$-cyclopropyl | |
| Im.193 | $-CH_2-CH(NH_2)-COOH$ | |
| Im.194 | $-CH_2-CH(NH_2)-CO-OCH_3$ | |
| Im.195 | $-CH_2-CH(NH_2)-CO-OC_2H_5$ | |
| Im.196 | $-CH_2-CH(NH_2)-CO-OC(CH_3)_3$ | |
| Im.197 | $-CH_2-CH(NH_2)-CO-NH_2$ | |
| Im.198 | $-CH_2-CH(NH_2)-CO-NH-CH_3$ | |
| Im.199 | $-CH_2-CH(N_3)-COOH$ | |
| Im.200 | $-CH_2-CH(N_3)-CO-OCH_3$ | |
| Im.201 | $-CH_2-CH(N_3)-CO-OC_2H_5$ | |
| Im.202 | $-CH_2-CH(N_3)-CO-OC(CH_3)_3$ | |

TABLE 13-continued

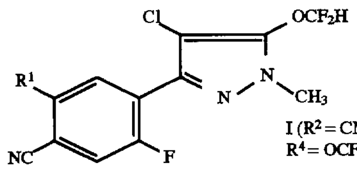

I ($R^2$ = CN; $R^3$ = $CH_3$; $R^4$ = $OCF_2H$; $R^5$ = Cl; $R^6$ = F)

| No. | $R^1$ | m.p./$^1$H-NMR [ppm] MS [$mz^{-1}$] |
|---|---|---|
| Im.203 | $-CH_2-CH(N_3)-CO-NH_2$ | |
| Im.204 | $-CH_2-CH(N_3)-CO-NH-CH_3$ | |
| Im.205 | $-CH_2-CH(NH-COCH_3)-COOH$ | |
| Im.206 | $-CH_2-CH(NH-COCH_3)-CO-OCH_3$ | |
| Im.207 | $-CH_2-CH(NH-COCH_3)-CO-OC_2H_5$ | |
| Im.208 | $-CH_2-CH(NH-COCH_3)-CO-OC(CH_3)_3$ | |
| Im.209 | $-CH_2-CH(NH-COCH_3)-CO-NH_2$ | |
| Im.210 | $-CH_2-CH(NH-COCH_3)-CO-NH-CH_3$ | |
| Im.211 | $-CH_2-CH_2$-cyclohexyl | |
| Im.212 | $-CH_2-CH_2$-cyclopentyl | |
| Im.213 | $-CH_2-CH_2$-cyclopropyl | |
| Im.214 | $-CH_2-CH_2$-phenyl | |
| Im.215 | $-CH=C(CN)-CO-OC_2H_5$ | |
| Im.216 | $-CH=C(CN)-CO-OCH(CH_3)_2$ | |
| Im.217 | $-CH=C(CN)-CO-OC(CH_3)_3$ | |
| Im.218 | $-CH=C(Cl)-CO-OCH_2-CH=N-OCH_2-CH=CH_2$ | |
| Im.219 | $-CH=C(Cl)-CO-OCH_2-CH=N-OCH_2-CH=CHCl$ | |
| Im.220 | $-CH=C(Cl)-CO-OCH_2-CH=N-OCH_2$-(4-chlorophenyl) | |
| Im.221 | $-CH=C(Cl)-CO-OCH_2-CH=N-OCH(CH_3)$-(4-chlorophenyl) | |
| Im.222 | $-CH=C(Cl)-CO-O$-(4-acetoxytetrahydrofuran-3-yl) | |
| Im.223 | $-CH=C(Cl)-CO-NH$-cyclohexyl | |
| Im.224 | $-CH=C(Cl)-CO-N(CH_3)-CH_2-CO-OC_2H_5$ | |
| Im.225 | $-CH=C(Cl)-CO-NH-CH(CH(CH_3)_2)-CO-OC_2H_5$ | |
| Im.226 | $-CH=C(Cl)-CO-NH-CH(CH_2CH(CH_3)_2)-CO-OCH_3$ | |
| Im.227 | $-CH=C(Cl)-CO-$(2-methoxycarbonylpyrrolidin-1-yl) | |
| Im.228 | $-CH=C(Cl)-CO-NH$-(tetrahydrofuran-2-on-3-yl) | |
| Im.229 | $-CH=C(Cl)-CO-N(CN)-CH_2CH_2-C_2H_5$ | |
| Im.230 | $-CH=C(Cl)-CO-N(CN)$-cyclopropyl | |
| Im.231 | $-CH=C(Cl)-CO-N(CN)-CH_2-CH=CH_2$ | |
| Im.232 | $-CH=C(Cl)-CO-N(CONH_2)-CH_2CH_2-C_2H_5$ | |
| Im.233 | $-CH=C(Cl)-CO-N(CONH_2)$-cyclopropyl | |
| Im.234 | $-CH=C(Cl)-CO-N(CONH_2)-CH_2-CH=CH_2$ | |
| Im.235 | $-CH=C(Br)-CO-OCH_2-CH=N-OCH_2$-(4-chlorophenyl) | |
| Im.236 | $-CH=C(Br)-CO-OCH_2-CH=N-OCH(CH_3)$-(4-chlorophenyl) | |
| Im.237 | $-CH=C(Br)-CO-O$-(4-acetoxytetrahydrofuran-3-yl) | |
| Im.238 | $-CH=C(Br)-CO-NH$-cyclohexyl | |
| Im.239 | $-CH=C(Br)-CO-N(CH_3)-CH_2-CO-OC_2H_5$ | |
| Im.240 | $-CH=C(Br)-CO-NH-CH(CH(CH_3)_2)-CO-OC_2H_5$ | |
| Im.241 | $-CH=C(Br)-CO-NH-CH(CH_2CH(CH_3)_2)-CO-OCH_3$ | |
| Im.242 | $-CH=C(Br)-CO$-(2-methoxycarbonylpyrrolidin-1-yl) | |
| Im.243 | $-CH=C(Br)-CO-NH$-(tetrahydrofuran-2-on-3-yl) | |
| Im.244 | $-CH=C(Br)-CO-N(CN)-CH_2CH_2-C_2H_5$ | |
| Im.245 | $-CH=C(Br)-CO-N(CN)$-cyclopropyl | |
| Im.246 | $-CH=C(Br)-CO-N(CN)-CH_2-CH=CH_2$ | |
| Im.247 | $-CH=C(Br)-CO-N(CONH_2)-CH_2CH_2-C_2H_5$ | |
| Im.248 | $-CH=C(Br)-CO-N(CONH_2)$-cyclopropyl | |
| Im.249 | $-CH=C(Br)-CO-N(CONH_2)-CH_2-CH=CH_2$ | |
| Im.250 | $-CH_2-CH(Cl)-CO-N(C_2H_5)_2$ | |
| Im.251 | $-CH_2-CH(Br)-CO-N(C_2H_5)_2$ | |
| Im.252 | $-CH=C(Br)-CO-N(C_2H_5)_2$ | |
| Im.253 | $-CH=C(Cl)-CO-N(C_2H_5)_2$ | |
| Im.254 | 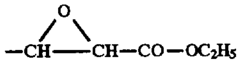 | |

TABLE 13-continued

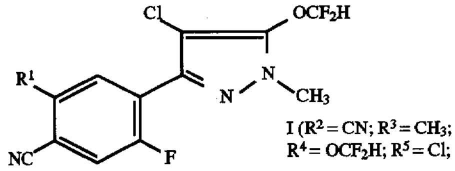

I ($R^2$ = CN; $R^3$ = $CH_3$; $R^4$ = $OCF_2H$; $R^5$ = Cl; $R^6$ = F)

| No. | $R^1$ | m.p./$^1$H-NMR [ppm] MS [$mz^{-1}$] |
|---|---|---|
| Im.255 | 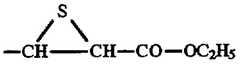 | |
| Im.256 | 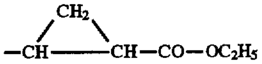 | |
| Im.257 | 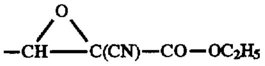 | |
| Im.258 | 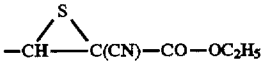 | |
| Im.259 | 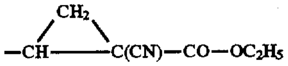 | |
| Im.260 | 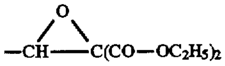 | |
| Im.261 | 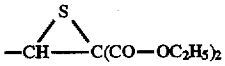 | |
| Im.262 | 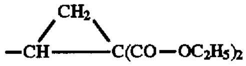 | |

TABLE 14

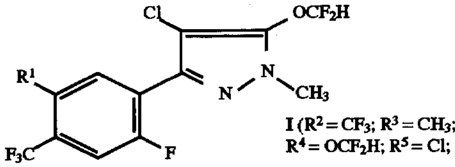

I ($R^2$ = $CF_3$; $R^3$ = $CH_3$; $R^4$ = $OCF_2H$; $R^5$ = Cl; $R^6$ = F)

| No. | $R^1$ | m.p./$^1$H-NMR [ppm] MS [$mz^{-1}$] |
|---|---|---|
| In.001 | $-CH=C(Cl)-COOH$ | |
| In.002 | $-CH=C(Cl)-CO-OCH_3$ | |
| In.003 | $-CH=C(Cl)-CO-OC_2H_5$ | |
| In.004 | $-CH=C(Cl)-CO-OCH(CH_3)_2$ | |
| In.005 | $-CH=C(Br)-COOH$ | |
| In.006 | $-CH=C(Br)-CO-OCH_3$ | |
| In.007 | $-CH=C(Br)-CO-OC_2H_5$ | |
| In.008 | $-CH=C(Br)-CO-OCH(CH_3)_2$ | |
| In.009 | $-CH=C(Cl)-CO-NH_2$ | |
| In.010 | $-CH=C(Cl)-CO-NH-CH_3$ | |
| In.011 | $-CH=C(Cl)-CO-N(CH_3)_2$ | |
| In.012 | $-CH=C(Br)-CO-NH_2$ | |
| In.013 | $-CH=C(Br)-CO-NH-CH_3$ | |
| In.014 | $-CH=C(Br)-CO-N(CH_3)_2$ | |
| In.015 | $-CH=C(Br)-CO-$NH-cyclopropyl | |
| In.016 | $-CH=C(Cl)-CO-$NH-cyclopropyl | |
| In.017 | $-CH=$(cyclopropylene) | |
| In.018 | $-CH=$(cyclopentylene) | |
| In.019 | $-CH=$(cyclohexylene) | |

TABLE 14-continued

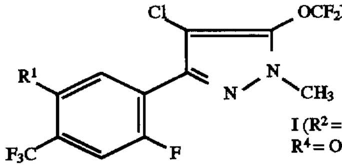

I ($R^2$ = $CF_3$; $R^3$ = $CH_3$; $R^4$ = $OCF_2H$; $R^5$ = Cl; $R^6$ = F)

| No. | $R^1$ | m.p./$^1$H-NMR [ppm] MS [$mz^{-1}$] |
|---|---|---|
| In.020 | 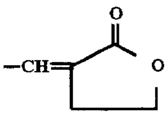 | |
| In.021 | 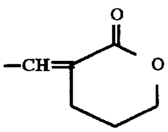 | |
| In.022 | 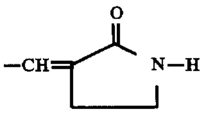 | |

TABLE 14-continued

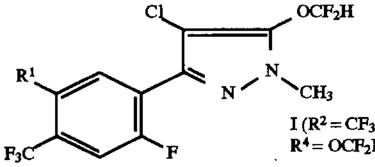

I ($R^2$ = $CF_3$; $R^3$ = $CH_3$; $R^4$ = $OCF_2H$; $R^5$ = Cl; $R^6$ = F)

| No. | $R^1$ | m.p./$^1$H-NMR [ppm] MS [$mz^{-1}$] |
|---|---|---|
| In.023 | 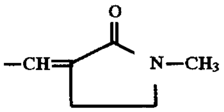 | |
| In.024 | 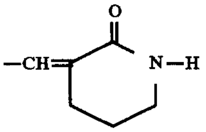 | |
| In.025 | 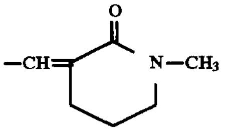 | |
| In.026 | 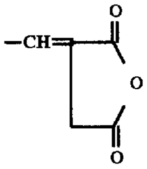 | |
| In.027 | 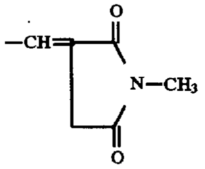 | |

TABLE 14-continued

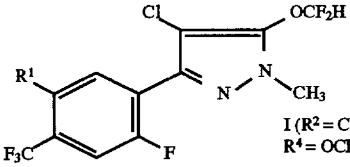

I ($R^2$ = $CF_3$; $R^3$ = $CH_3$; $R^4$ = $OCF_2H$; $R^5$ = Cl; $R^6$ = F)

| No. | $R^1$ | m.p./$^1$H-NMR [ppm] MS [$mz^{-1}$] |
|---|---|---|
| In.028 | $-CH=C(CH_3)-CO-OC_2H_5$ | |
| In.029 | $-CH=C(CH_3)-CO-OCH_3$ | |
| In.030 | $-CH=C(CH_3)-CO-NH_2$ | |
| In.031 | $-CH=C(CH_3)-CO-NH-CH_3$ | |
| In.032 | $-CH=C(CH_3)-CO-N(CH_3)_2$ | |
| In.033 | $-CH=C(CN)-CO-OCH_3$ | |
| In.034 | $-CH_2-CH(CN)-CO-OCH_3$ | |
| In.035 | $-CH_2-CH(CN)-CO-OC_2H_5$ | |
| In.036 | $-CH_2-CH(CN)-CO-NH_2$ | |
| In.037 | $-CH_2-CH(CN)-CO-NH-CH_3$ | |
| In.038 | $-CH_2-CH(CN)-CO-N(CH_3)_2$ | |
| In.039 | $-CH_2-CH(CN)-CO-NH-SO_2-CH_3$ | |
| In.040 | $-CH_2-CH(Cl)-CO-OCH_3$ | |
| In.041 | $-CH_2-CH(Cl)-CO-OC_2H_5$ | |
| In.042 | $-CH_2-CH(Cl)-CO-NH_2$ | |
| In.043 | $-CH_2-CH(Cl)-CO-NH-CH_3$ | |
| In.044 | $-CH_2-CH(Cl)-CO-N(CH_3)_2$ | |
| In.045 | $-CH_2-CH(Cl)-CO-NH-SO_2-CH_3$ | |
| In.046 | $-CH_2-CH(Br)-CO-OCH_3$ | |
| In.047 | $-CH_2-CH(Br)-CO-OC_2H_5$ | |
| In.048 | $-CH_2-CH(Br)-CO-OCH(CH_3)_2$ | |
| In.049 | $-CH_2-CH(Br)-CO-NH_2$ | |
| In.050 | $-CH_2-CH(Br)-CO-NH-CH_3$ | |
| In.051 | $-CH_2-CH(Br)-CO-N(CH_3)_2$ | |
| In.052 | $-CH_2-CH(Cl)-CO-CH(CH_3)_2$ | |
| In.053 | $-CH_2-CH(CN)-CO-CH(CH_3)_2$ | |
| In.054 | $-CH=CH$-(4-fluorophenyl) | |
| In.055 | $-CH=CH$-(4-chlorophenyl) | |
| In.056 | $-CH=CH$-(3-trifluoromethylphenyl) | |
| In.057 | $-CH=CH$-(2,4-dichlorophenyl) | |

TABLE 15

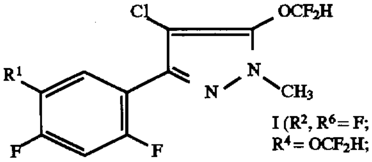

I ($R^2$, $R^6$ = F; $R^3$ = $CH_3$; $R^4$ = $OCF_2H$; $R^5$ = Cl)

| No. | $R^1$ | m.p./$^1$H-NMR [ppm] MS [$mz^{-1}$] |
|---|---|---|
| Io.001 | $-CH=C(Cl)-COOH$ | |
| Io.002 | $-CH=C(Cl)-CO-OCH_3$ | |
| Io.003 | $-CH=C(Cl)-CO-OC_2H_5$ | |
| Io.004 | $-CH=C(Cl)-CO-OCH(CH_3)_2$ | |
| Io.005 | $-CH=C(Br)-COOH$ | |
| Io.006 | $-CH=C(Br)-CO-OCH_3$ | |
| Io.007 | $-CH=C(Br)-CO-OC_2H_5$ | |
| Io.008 | $-CH=C(Br)-CO-OCH(CH_3)_2$ | |
| Io.009 | $-CH=C(Cl)-CO-NH_2$ | |
| Io.010 | $-CH=C(Cl)-CO-NH-CH_3$ | |
| Io.011 | $-CH=C(Cl)-CO-N(CH_3)_2$ | |
| Io.012 | $-CH=C(Br)-CO-NH_2$ | |

TABLE 15-continued
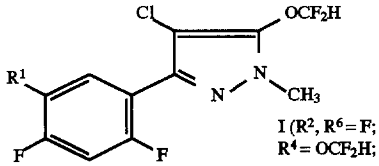
I ($R^2$, $R^6$ = F; $R^3$ = $CH_3$; $R^4$ = $OCF_2H$; $R^5$ = Cl)
| No. | $R^1$ | m.p./$^1$H-NMR [ppm] MS [$mz^{-1}$] |
|---|---|---|
| Io.013 | $-CH=C(Br)-CO-NH-CH_3$ | |
| Io.014 | $-CH=C(Br)-CO-N(CH_3)_2$ | |
| Io.015 | $-CH=C(Br)-CO-$NH-cyclopropyl | |
| Io.016 | $-CH=C(Cl)-CO-$NH-cyclopropyl | |
| Io.017 | $-CH=$(cyclopropylene) | |
| Io.018 | $-CH=$(cyclopentylene) | |
| Io.019 | $-CH=$(cyclohexylene) | |
| Io.020 | 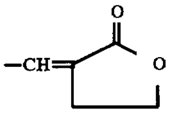 | |
| Io.021 | 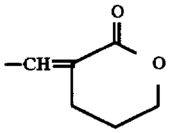 | |
| Io.022 | 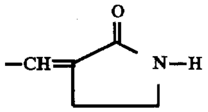 | |
| Io.023 | 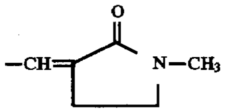 | |
| Io.024 | 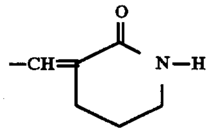 | |
| Io.025 | 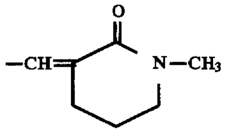 | |
| Io.026 | 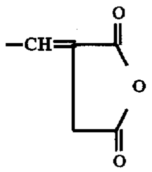 | |
| Io.027 | 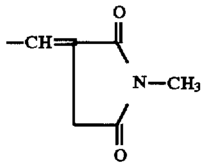 | |
| Io.028 | $-CH=C(CH_3)-CO-OC_2H_5$ | |
| Io.029 | $-CH=C(CH_3)-CO-OCH_3$ | |

TABLE 15-continued

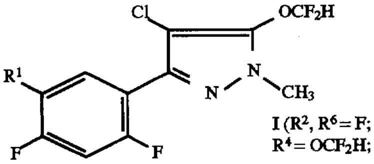

I ($R^2$, $R^6$ = F; $R^3$ = $CH_3$; $R^4$ = $OCF_2H$; $R^5$ = Cl)

| No. | $R^1$ | m.p./$^1$H-NMR [ppm] MS [$mz^{-1}$] |
|---|---|---|
| Io.030 | $-CH=C(CH_3)-CO-NH_2$ | |
| Io.031 | $-CH=C(CH_3)-CO-NH-CH_3$ | |
| Io.032 | $-CH=C(CH_3)-CO-N(CH_3)_2$ | |
| Io.033 | $-CH=C(CN)-CO-OCH_3$ | |
| Io.034 | $-CH_2-CH(CN)-CO-OCH_3$ | |
| Io.035 | $-CH_2-CH(CN)-CO-OC_2H_5$ | |
| Io.036 | $-CH_2-CH(CN)-CO-NH_2$ | |
| Io.037 | $-CH_2-CH(CN)-CO-NH-CH_3$ | |
| Io.038 | $-CH_2-CH(CN)-CO-N(CH_3)_2$ | |
| Io.039 | $-CH_2-CH(CN)-CO-NH-SO_2-CH_3$ | |
| Io.040 | $-CH_2-CH(Cl)-CO-OCH_3$ | |
| Io.041 | $-CH_2-CH(Cl)-CO-OC_2H_5$ | |
| Io.042 | $-CH_2-CH(Cl)-CO-NH_2$ | |
| Io.043 | $-CH_2-CH(Cl)-CO-NH-CH_3$ | |
| Io.044 | $-CH_2-CH(Cl)-CO-N(CH_3)_2$ | |
| Io.045 | $-CH_2-CH(Cl)-CO-NH-SO_2-CH_3$ | |
| Io.046 | $-CH_2-CH(Br)-CO-OCH_3$ | |
| Io.047 | $-CH_2-CH(Br)-CO-OC_2H_5$ | |
| Io.048 | $-CH_2-CH(Br)-CO-OCH(CH_3)_2$ | |
| Io.049 | $-CH_2-CH(Br)-CO-NH_2$ | |
| Io.050 | $-CH_2-CH(Br)-CO-NH-CH_3$ | |
| Io.051 | $-CH_2-CH(Br)-CO-N(CH_3)_2$ | |
| Io.052 | $-CH_2-CH(Cl)-CO-CH(CH_3)_2$ | |
| Io.053 | $-CH_2-CH(CN)-CO-CH(CH_3)_2$ | |
| Io.054 | $-CH=CH$-(4-fluorophenyl) | |
| Io.055 | $-CH=CH$-(4-chlorophenyl) | |
| Io.056 | $-CH=CH$-(3-trifluoromethylphenyl) | |
| Io.057 | $-CH=CH$-(2,4-dichlorophenyl) | |
| Io.058 | $-CH=C(Cl)-CO-O$-cyclohexyl | |
| Io.059 | $-CH=C(Cl)-CO-OC(CH_3)_3$ | |
| Io.060 | $-CH=C(Cl)-CO-OCH_2-CH(CH_3)_2$ | |
| Io.061 | $-CH=C(Cl)-CO-NH-CH_2-CO-OCH_3$ | |
| Io.062 | $-CH=C(Cl)-CO-N(CH_3)-CH_2-CO-OCH_3$ | |
| Io.063 | $-CH=C(Cl)-CO-NH-CH(CH_3)-CO-OC_2H_5$ | |
| Io.064 | $-CH=C(Cl)-CO-NH-OC_2H_5$ | |
| Io.065 | $-CH=C(Cl)-CO-NH-OCH_3$ | |
| Io.066 | $-CH=C(Cl)-CO-NH-OCH_2-CH=CHCl$ | |
| Io.067 | $-CH=C(Cl)-CO-NH-OCH_2$-(4-chlorophenyl) | |
| Io.068 | $-CH=C(Cl)-CO-SCH_2-CO-OC_2H_5$ | |
| Io.069 | $-CH=C(Cl)-CO-SCH_2-C_2H_5$ | |
| Io.070 | $-CH=C(Cl)-CO-SCH_2$-(4-chlorophenyl) | |
| Io.071 | $-CH=C(CO-OC_2H_5)_2$ | |
| Io.072 | $-CH=C(CO-OCH_3)_2$ | |
| Io.073 | $-CH=C(Cl)-CO-OCH_2-CH=N-OCH_3$ | |
| Io.074 | $-CH=C(Cl)-CO-OCH_2-CH=N-OC_2H_5$ | |
| Io.075 | $-CH=C(Cl)-CO-OCH_2-CH=N-OCH_2-CH_2-C_2H_5$ | |
| Io.076 | $-CH=C(Cl)-CO-OCH_2-CH=N-OCH_2$-phenyl | |
| Io.077 | $-CH=C(Br)-CO-O$-cyclohexyl | |
| Io.078 | $-CH=C(Br)-CO-OC(CH_3)_3$ | |
| Io.079 | $-CH=C(Br)-CO-OCH_2-CH(CH_3)_2$ | |
| Io.080 | $-CH=C(Br)-CO-NH-CH_2-CO-OCH_3$ | |
| Io.081 | $-CH=C(Br)-CO-N(CH_3)-CH_2-CO-OCH_3$ | |
| Io.082 | $-CH=C(Br)-CO-NH-OC_2H_5$ | |
| Io.083 | $-CH=C(Br)-CO-NH-OCH_3$ | |
| Io.084 | $-CH=C(Br)-CO-NH-OCH_2-CH=CHCl$ | |
| Io.085 | $-CH=C(Br)-CO-NH-OCH_2$-(4-chlorophenyl) | |
| Io.086 | $-CH=C(Br)-CO-SCH_2-CO-OC_2H_5$ | |
| Io.087 | $-CH=C(Br)-CO-SCH_2-C_2H_5$ | |
| Io.088 | $-CH=C(Br)-CO-SCH_2$-(4-chlorophenyl) | |
| Io.089 | $-CH=C(Br)-CO-OCH_2-CH=N-OCH_2-CH=CH_2$ | |
| Io.090 | $-CH=C(Br)-CO-OCH_2-CH=N-OCH_2-CH=CHCl$ | |
| Io.091 | $-CH=C(Br)-CO-OCH_2-CH=N-OCH_3$ | |
| Io.092 | $-CH=C(Br)-CO-OCH_2-CH=N-OC_2H_5$ | |
| Io.093 | $-CH=C(Br)-CO-OCH_2-CH=N-OCH_2-CH_2-C_2H_5$ | |
| Io.094 | $-CH=C(Br)-CO-OCH_2-CH=N-OCH_2$-phenyl | |
| Io.095 | $-CH_2-CH(Cl)-CO-O$-cyclohexyl | |
| Io.096 | $-CH_2-CH(Cl)-CO-OC(CH_3)_3$ | |

TABLE 15-continued

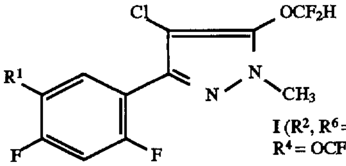

I ($R^2$, $R^6$ = F; $R^3$ = $CH_3$; $R^4$ = $OCF_2H$; $R^5$ = Cl)

| No. | $R^1$ | m.p./$^1$H-NMR [ppm] MS [$mz^{-1}$] |
|---|---|---|
| Io.097 | $-CH_2-CH(Cl)-CO-OCH_2-CH(CH_3)_2$ | |
| Io.098 | $-CH_2-CH(Cl)-CO-NH-CH_2-CO-OCH_3$ | |
| Io.099 | $-CH_2-CH(Cl)-CO-N(CH_3)-CH_2-CO-OCH_3$ | |
| Io.100 | $-CH_2-CH(Cl)-CO-NH-CH(CH_3)-CO-OC_2H_5$ | |
| Io.101 | $-CH_2-CH(Cl)-CO-NH-OC_2H_5$ | |
| Io.102 | $-CH_2-CH(Cl)-CO-NH-OCH_3$ | |
| Io.103 | $-CH_2-CH(Cl)-CO-NH-OCH_2-CH=CHCl$ | |
| Io.104 | $-CH_2-CH(Cl)-CO-NH-OCH_2$-(4-chlorophenyl) | |
| Io.105 | $-CH_2-CH(Cl)-CO-SCH_2-CO-OC_2H_5$ | |
| Io.106 | $-CH_2-CH(Cl)-CO-SCH_2-C_2H_5$ | |
| Io.107 | $-CH_2-CH(Cl)CO-SCH_2$-(4-chlorophenyl) | |
| Io.108 | $-CH_2-C(Cl)(CO-OC_2H_5)_2$ | |
| Io.109 | $-CH_2-C(Cl)(CO-OCH_3)_2$ | |
| Io.110 | $-CH_2-CH(Cl)-CO-OCH_2-CH=N-OCH_3$ | |
| Io.111 | $-CH_2-CH(Cl)-CO-OCH_2-CH=N-OC_2H_5$ | |
| Io.112 | $-CH_2-CH(Cl)-CO-OCH_2-CH=N-OCH_2-CH_2-C_2H_5$ | |
| Io.113 | $-CH_2-CH(Cl)-CO-OCH_2-CH=N-OCH_2$-phenyl | |
| Io.114 | $-CH_2-CH(Cl)-CO-OCH_2-CH=N-OCH_2-CH=CH_2$ | |
| Io.115 | $-CH_2-CH(Cl)-CO-OCH_2-CH=N-OCH_2-CH=CHCl$ | |
| Io.116 | $-CH_2-CH(Cl)-CO-OCH_2-CH=N-OCH_2$-(4-chlorophenyl) | |
| Io.117 | $-CH_2-CH(Cl)-CO-OCH_2-CH=N-OCH(CH_3)$-(4-chlorophenyl) | |
| Io.118 | $-CH_2-CH(Cl)-COOH$ | |
| Io.119 | $-CH_2-CH(Cl)-CO-NH$-cyclopropyl | |
| Io.120 | $-CH_2-CH(Cl)-CO-N(CH_3)-CH_2-CO-OC_2H_5$ | |
| Io.121 | $-CH_2-CH(Cl)-CO-NH-CH(CH(CH_3)_2)-CO-OC_2H_5$ | |
| Io.122 | $-CH_2-CH(Cl)-CO-NH-CH(CH_2CH(CH_3)_2)-CO-OCH_3$ | |
| Io.123 | $-CH_2-CH(Cl)-CO-$(2-methoxycarbonyl-pyrrolidin-1-yl) | |
| Io.124 | $-CH_2-CH(Cl)-CO-NH$-(tetrahydro-furan-2-on-3-yl) | |
| Io.125 | $-CH_2-CH(Cl)-CO-N(CN)-CH_2CH_2-C_2H_5$ | |
| Io.126 | $-CH_2-CH(Cl)-CO-N(CN)$-cyclopropyl | |
| Io.127 | $-CH_2-CH(Cl)-CO-N(CN)-CH_2-CH=CH_2$ | |
| Io.128 | $-CH_2-CH(Cl)-CO-N(CONH_2)-CH_2CH_2-C_2H_5$ | |
| Io.129 | $-CH_2-CH(Cl)-CO-N(CONH_2)$-cyclopropyl | |
| Io.130 | $-CH_2-CH(Cl)-CO-N(CONH_2)-CH_2-CH=CH_2$ | |
| Io.131 | $-CH_2-CH(Cl)-CO-O$-(4-acetoxytetrahy-drofuran-3-yl) | |
| Io.132 | $-CH_2-CH(Br)-CO-O$-cyclohexyl | |
| Io.133 | $-CH_2-CH(Br)-CO-OC(CH_3)_3$ | |
| Io.134 | $-CHz-CH(Br)-CO-OCH_2-CH(CH_3)_2$ | |
| Io.135 | $-CH_2-CH(Br)-CO-NH-CH_2-CO-OCH_3$ | |
| Io.136 | $-CH_2-CH(Br)-CO-N(CH_3)-CH_2-CO-OCH_3$ | |
| Io.137 | $-CH_2-CH(Br)-CO-NH-CH(CH_3)-CO-OC_2H_5$ | |
| Io.138 | $-CH_2-CH(Br)-CO-NH-OC_2H_5$ | |
| Io.139 | $-CH_2-CH(Br)-CO-NH-OCH_3$ | |
| Io.140 | $-CH_2-CH(Br)-CO-NH-OCH_2-CH=CHCl$ | |
| Io.141 | $-CH_2-CH(Br)-CO-NH-CH_2$-(4-chlorophenyl) | |
| Io.142 | $-CH_2-CH(Br)-CO-SCH_2-CO-OC_2H_5$ | |
| Io.143 | $-CH_2-CH(Br)-CO-SCH_2-C_2H_5$ | |
| Io.144 | $-CH_2-CH(Br)-CO-SCH_2$-(4-chlorophenyl) | |
| Io.145 | $-CH_2-C(Br)(CO-OC_2H_5)_2$ | |
| Io.146 | $-CH_2-C(Br)(CO-OCH_3)_2$ | |
| Io.147 | $-CH_2-CH(Br)-CO-OCH_2-CH=N-OCH_3$ | |
| Io.148 | $-CH_2-CH(Br)-CO-OCH_2-CH=N-OC_2H_5$ | |
| Io.149 | $-CH_2-CH(Br)-CO-OCH_2-CH=N-OCH_2-CH_2-C_2H_5$ | |
| Io.150 | $-CH_2-CH(Br)-CO-OCH_2-CH=N-OCH_2$-phenyl | |
| Io.151 | $-CH_2-CH(Br)-CO-OCH_2-CH=N-OCH_2-CH=CH_2$ | |
| Io.152 | $-CH_2-CH(Br)-CO-OCH_2-CH=N-OCH_2-CH=CHCl$ | |
| Io.153 | $-CH_2-CH(Br)-CO-OCH_2-CH=N-OCH_2$-(4-chlorophenyl) | |

TABLE 15-continued

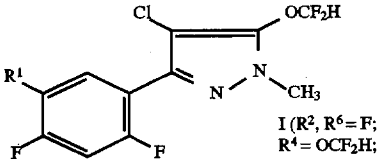

I ($R^2$, $R^6$ = F; $R^3$ = $CH_3$; $R^4$ = $OCF_2H$; $R^5$ = Cl)

| No. | $R^1$ | m.p./$^1$H-NMR [ppm] MS [$mz^{-1}$] |
|---|---|---|
| Io.154 | $-CH_2-CH(Br)-CO-OCH_2-CH=N-OCH(CH_3)$-(4-chlorophenyl) | |
| Io.155 | $-CH_2-CH(Br)-COOH$ | |
| Io.156 | $-CH_2-CH(Br)-CO-$NH-cyclopropyl | |
| Io.157 | $-CH_2-CH(Br)-CO-N(CH_3)-CH_2-CO-OC_2H_5$ | |
| Io.158 | $-CH_2-CH(Br)-CO-NH-CH(CH(CH_3)_2)-CO-OC_2H_5$ | |
| Io.159 | $-CH_2-CH(Br)-CO-NH-CH(CH_2CH(CH_3)_2)-CO-OCH_3$ | |
| Io.160 | $-CH_2-CH(Br)-CO-$(2-methoxycarbonyl-pyrrolidin-1-yl) | |
| Io.161 | $-CH_2-CH(Br)-CO-$NH-(tetrahydro-furan-2-on-3-yl) | |
| Io.162 | $-CH_2-CH(Br)-CO-N(CN)-CH_2CH_2-C_2H_5$ | |
| Io.163 | $-CH_2-CH(Br)-CO-N(CN)$-cyclopropyl | |
| Io.164 | $-CH_2-CH(Br)-CO-N(CN)-CH_2-CH=CH_2$ | |
| Io.165 | $-CH_2-CH(Br)-CO-N(CONH_2)-CH_2CH_2-C_2H_5$ | |
| Io.166 | $-CH_2-CH(Br)-CO-N(CONH_2)$-cyclopropyl | |
| Io.167 | $-CH_2-CH(Br)-CO-N(CONH_2)-CH_2-CH=CH_2$ | |
| Io.168 | $-CH_2-CH(Br)-CO-$O-(4-acetoxytetrahy-drofuran-3-yl) | |
| Io.169 | $-CH_2-CH(OH)-COOH$ | |
| Io.170 | $-CH_2-CH(OH)-CO-OCH_3$ | |
| Io.171 | $-CH_2-CH(OH)-CO-OC_2H_5$ | |
| Io.172 | $-CH_2-CH(OH)-CO-OCH_2-CH=N-OCH_3$ | |
| Io.173 | $-CH_2-CH(OH)-CO-OC(CH_3)_3$ | |
| Io.174 | $-CH_2-CH(OH)-CO-NH_2$ | |
| Io.175 | $-CH_2-CH(OH)-CO-NH-CH_3$ | |
| Io.176 | $-CH_2-CH(OH)-CO-$NH-cyclopropyl | |
| Io.177 | $-CH_2-CH(OCH_3)-COOH$ | |
| Io.178 | $-CH_2-CH(OCH_3)-CO-OCH_3$ | |
| Io.179 | $-CH_2-CH(OCH_3)-CO-OC_2H_5$ | |
| Io.180 | $-CH_2-CH(OCH_3)-CO-OCH_2-CH=N-OCH_3$ | |
| Io.181 | $-CH_2-CH(OCH_3)-CO-OC(CH_3)_3$ | |
| Io.182 | $-CH_2-CH(OCH_3)-CO-NH_2$ | |
| Io.183 | $-CH_2-CH(OCH_3)-CO-NH-CH_3$ | |
| Io.184 | $-CH_2-CH(OCH_3)-CO-$NH-cyclopropyl | |
| Io.185 | $-CH_2-CH(O-COCH_3)-COOH$ | |
| Io.186 | $-CH_2-CH(O-COCH_3)-CO-OCH_3$ | |
| Io.187 | $-CH_2-CH-(O-COCH_3)-CO-OC_2H_5$ | |
| Io.188 | $-CH_2-CH(O-COCH_3)-CO-OCH_2-CH=N-OCH_3$ | |
| Io.189 | $-CH_2-CH(O-COCH_3)-CO-OC(CH_3)_3$ | |
| Io.190 | $-CH_2-CH(O-COCH_3)-CO-NH_2$ | |
| Io.191 | $-CH_2-CH(O-COCH_3)-CO-NH-CH_3$ | |
| Io.192 | $-CH_2-CH(O-COCH_3)-CO-$NH-cyclopropyl | |
| Io.193 | $-CH_2-CH(NH_2)-COOH$ | |
| Io.194 | $-CH_2-CH(NH_2)-CO-OCH_3$ | |
| Io.195 | $-CH_2-CH(NH_2)-CO-OC_2H_5$ | |
| Io.196 | $-CH_2-CH(NH_2)-CO-OC(CH_3)_3$ | |
| Io.197 | $-CH_2-CH(NH_2)-CO-NH_2$ | |
| Io.198 | $-CH_2-CH(NH_2)-CO-NH-CH_3$ | |
| Io.199 | $-CH_2-CH(N_3)-COOH$ | |
| Io.200 | $-CH_2-CH(N_3)-CO-OCH_3$ | |
| Io.201 | $-CH_2-CH(N_3)-CO-OC_2H_5$ | |
| Io.202 | $-CH_2-CH(N_3)-CO-OC(CH_3)_3$ | |
| Io.203 | $-CH_2-CH(N_3)-CO-NH_2$ | |
| Io.204 | $-CH_2-CH(N_3)-CO-NH-CH_3$ | |
| Io.205 | $-CH_2-CH(NH-COCH_3)-COOH$ | |
| Io.206 | $-CH_2-CH(NH-COCH_3)-CO-OCH_3$ | |
| Io.207 | $-CH_2-CH(NH-COCH_3)-CO-OC_2H_5$ | |
| Io.208 | $-CH_2-CH(NH-COCH_3)-CO-OC(CH_3)_3$ | |
| Io.209 | $-CH_2-CH(NH-COCH_3)-CO-NH_2$ | |
| Io.210 | $-CH_2-CH(NH-COCH_3)-CO-NH-CH_3$ | |
| Io.211 | $-CH_2-CH_2$-cyclohexyl | |
| Io.212 | $-CH_2-CH_2$-cyclopentyl | |
| Io.213 | $-CH_2-CH_2$-cyclopropyl | |
| Io.214 | $-CH_2-CH_2$-phenyl | |

TABLE 15-continued

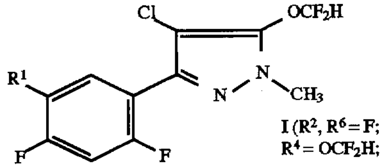

I ($R^2$, $R^6 = F$; $R^3 = CH_3$; $R^4 = OCF_2H$; $R^5 = Cl$)

| No. | $R^1$ | m.p./$^1$H-NMR [ppm] MS [$mz^{-1}$] |
|---|---|---|
| Io.215 | $-CH=C(CN)-CO-OC_2H_5$ | |
| Io.216 | $-CH=C(CN)-CO-OCH(CH_3)_2$ | |
| Io.217 | $-CH=C(CN)-CO-OC(CH_3)_3$ | |
| Io.218 | $-CH=C(Cl)-CO-OCH_2-CH=N-OCH_2-CH=CH_2$ | |
| Io.219 | $-CH=C(Cl)-CO-OCH_2-CH=N-OCH_2-CH=CHCl$ | |
| Io.220 | $-CH=C(Cl)-CO-OCH_2-CH=N-OCH_2-$(4-chlorophenyl) | |
| Io.221 | $-CH=C(Cl)-CO-OCH_2-CH=N-OCH(CH_3)$-(4-chlorophenyl) | |
| Io.222 | $-CH=C(Cl)-CO-O$-(4-acetoxytetrahydro-furan-3-yl) | |
| Io.223 | $-CH=C(Cl)-CO-NH$-cyclohexyl | |
| Io.224 | $-CH=C(Cl)-CO-N(CH_3)-CH_2-CO-OC_2H_5$ | |
| Io.225 | $-CH=C(Cl)-CO-NH-CH(CH(CH_3)_2)-CO-OC_2H_5$ | |
| Io.226 | $-CH=C(Cl)-CO-NH-CH(CH_2CH(CH_3)_2)-CO-OCH_3$ | |
| Io.227 | $-CH=C(Cl)-CO-$(2-methoxycarbonyl-pyrrolidin-1-yl) | |
| Io.228 | $-CH=C(Cl)-CO-NH$-(tetrahydro-furan-2-on-3-yl) | |
| Io.229 | $-CH=C(Cl)-CO-N(CN)-CH_2CH_2-C_2H_5$ | |
| Io.230 | $-CH=C(Cl)-CO-N(CN)$-cyclopropyl | |
| Io.231 | $-CH=C(Cl)-CO-N(CN)-CH_2-CH=CH_2$ | |
| Io.232 | $-CH=C(Cl)-CO-N(CONH_2)-CH_2CH_2-C_2H_5$ | |
| Io.233 | $-CH=C(Cl)-CO-N(CONH_2)$-cyclopropyl | |
| Io.234 | $-CH=C(Cl)-CO-N(CONH_2)-CH_2-CH=CH_2$ | |
| Io.235 | $-CH=C(Br)-CO-OCH_2-CH=N-OCH_2-$(4-chlorophenyl) | |
| Io.236 | $-CH=C(Br)-CO-OCH_2-CH=N-OCH(CH_3)$-(4-chlorophenyl) | |
| Io.237 | $-CH=C(Br)-CO-O$-(4-acetoxytetrahydro-furan-3-yl) | |
| Io.238 | $-CH=C(Br)-CO-NH$-cyclohexyl | |
| Io.239 | $-CH=C(Br)-CO-N(CH_3)-CH_2-CO-OC_2H_5$ | |
| Io.240 | $-CH=C(Br)-CO-NH-CH(CH(CH_3)_2)-CO-OC_2H_5$ | |
| Io.241 | $-CH=C(Br)-CO-NH-CH(CH_2CH(CH_3)_2)-CO-OCH_3$ | |
| Io.242 | $-CH=C(Br)-CO-$(2-methoxycarbonyl-pyrrolidin-1-yl) | |
| Io.243 | $-CH=C(Br)-CO-NH$-(tetrahydro-furan-2-on-3-yl) | |
| Io.244 | $-CH=C(Br)-CO-N(CN)-CH_2CH_2-C_2H_5$ | |
| Io.245 | $-CH=C(Br)-CON(CN)$-cyclopropyl | |
| Io.246 | $-CH=C(Br)-CO-N(CN)-CH_2-CH=CH_2$ | |
| Io.247 | $-CH=C(Br)-CO-N(CONH_2)-CH_2CH_2-C_2H_5$ | |
| Io.248 | $-CH=C(Br)-CO-N(CONH_2)$-cyclopropyl | |
| Io.249 | $-CH=C(Br)-CO-N(CONH_2)-CH_2-CH=CH_2$ | |
| Io.250 | $-CH_2-CH(Cl)-CO-N(C_2H_5)_2$ | |
| Io.251 | $-CH_2-CH(Br)-CO-N(C_2H_5)_2$ | |
| Io.252 | $-CH=C(Br)-CO-N(C_2H_5)_2$ | |
| Io.253 | $-CH=C(Cl)-CO-N(C_2H_5)_2$ | |
| Io.254 | 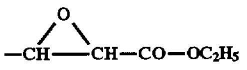 | |
| Io.255 | 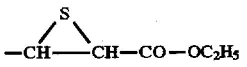 | |
| Io.256 | 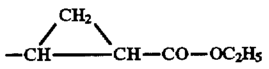 | |
| Io.257 | 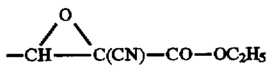 | |

TABLE 15-continued

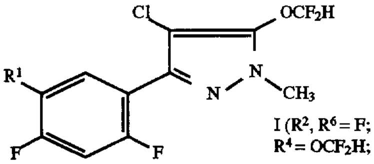

I ($R^2$, $R^6$ = F; $R^3$ = $CH_3$;
$R^4$ = $OCF_2H$; $R^5$ = Cl)

| No. | $R^1$ | m.p./$^1$H-NMR [ppm] MS [$mz^{-1}$] |
|---|---|---|
| Io.258 | 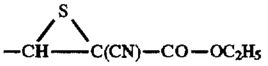 | |
| Io.259 | 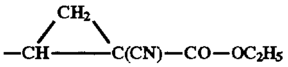 | |
| Io.260 | 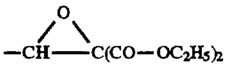 | |
| Io.261 | 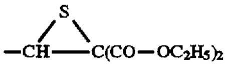 | |
| Io.262 | 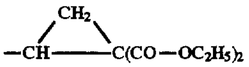 | |

TABLE 16

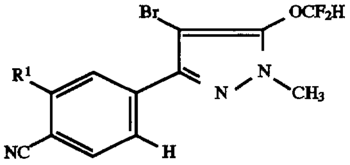

I ($R^2$ = CN; $R^3$ = $CH_3$;
$R^4$ = $OCF_2H$; $R^5$ = Br; $R^6$ = H)

| No. | $R^1$ | m.p./$^1$H-NMR[ppm] MS [$mz^{-1}$] |
|---|---|---|
| Ip.001 | $-CH_2-CH(CN)-CO-OC_2H_5$ | |
| Ip.002 | $-CH_2-CH(CN)-CO-NH_2$ | |
| Ip.003 | $-CH_2-CH(CN)-CO-N(CH_3)_2$ | |
| Ip.004 | $-CH_2-CH(Cl)-CO-OC_2H_5$ | |
| Ip.005 | $-CH_2-CH(Cl)-CO-NH_2$ | |
| Ip.006 | $-CH_2-CH(Cl)-CO-N(CH_3)_2$ | |
| Ip.007 | $-CH_2-CH(Br)-CO-OC_2H_5$ | |
| Ip.008 | $-CH_2-CH(Br)-CO-OCH_3$ | |
| Ip.009 | $-CH_2-CH(Br)-CO-NH_2$ | |
| Ip.010 | $-CH_2-CH(Br)-CO-N(CH_3)_2$ | |
| Ip.011 | $-CH=C(Cl)-CO-OC_2H_5$ | |
| Ip.012 | $-CH=C(Cl)-CO-NH_2$ | |
| Ip.013 | $-CH=C(Cl)-CO-N(CH_3)_2$ | |
| Ip.014 | $-CH=C(Br)-CO-OC_2H_5$ | |
| Ip.015 | $-CH=C(Br)-CO-NH_2$ | |
| Ip.016 | $-CH=C(Br)-CO-N(CH_3)_2$ | |
| Ip.017 | $-CH=C(CN)-CO-OC_2H_5$ | |
| Ip.018 | $-CH=C(CN)-CO-NH_2$ | |
| Ip.019 | $-CH=C(CN)-CO-N(CH_3)_2$ | |
| Ip.020 | $-CH=C(CH_3)-CO-OC_2H_5$ | |
| Ip.021 | $-CH=C(CH_3)-CO-NH_2$ | |
| Ip.022 | $-CH=C(CH_3)-CO-N(CH_3)_2$ | |

TABLE 17

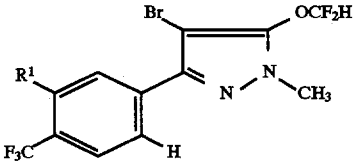

I ($R^2$ = $CF_3$; $R^3$ = $CH_3$;
$R^4$ = $OCF_2H$; $R^5$ = Br; $R^6$ = H)

| No. | $R^1$ | m.p./$^1$H-NMR[ppm] MS [$mz^{-1}$] |
|---|---|---|
| Iq.001 | $-CH_2-CH(CN)-CO-OC_2H_5$ | |
| Iq.002 | $-CH_2-CH(CN)-CO-NH_2$ | |
| Iq.003 | $-CH_2-CH(CN)-CO-N(CH_3)_2$ | |
| Iq.004 | $-CH_2-CH(Cl)-CO-OC_2H_5$ | |
| Iq.005 | $-CH_2-CH(Cl)-CO-NH_2$ | |
| Iq.006 | $-CH_2-CH(Cl)-CO-N(CH_3)_2$ | |
| Iq.007 | $-CH_2-CH(Br)-CO-OC_2H_5$ | |
| Iq.008 | $-CH_2-CH(Br)-CO-OCH_3$ | |
| Iq.009 | $-CH_2-CH(Br)-CO-NH_2$ | |
| Iq.010 | $-CH_2-CH(Br)-CO-N(CH_3)_2$ | |
| Iq.011 | $-CH=C(Cl)-CO-OC_2H_5$ | |
| Iq.012 | $-CH=C(Cl)-CO-NH_2$ | |
| Iq.013 | $-CH=C(Cl)-CO-N(CH_3)_2$ | |
| Iq.014 | $-CH=C(Br)-CO-OC_2H_5$ | |
| Iq.015 | $-CH=C(Br)-CO-NH_2$ | |
| Iq.016 | $-CH=C(Br)-CO-N(CH_3)_2$ | |
| Iq.017 | $-CH=C(CN)-CO-OC_2H_5$ | |
| Iq.018 | $-CH=C(CN)-CO-NH_2$ | |
| Iq.019 | $-CH=C(CN)-CO-N(CH_3)_2$ | |
| Iq.020 | $-CH=C(CH_3)-CO-OC_2H_5$ | |
| Iq.021 | $-CH=C(CH_3)-CO-NH_2$ | |
| Iq.022 | $-CH=C(CH_3)-CO-N(CH_3)_2$ | |

TABLE 18

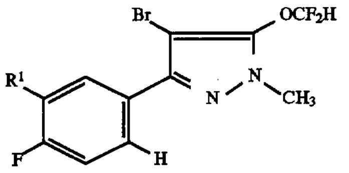

I ($R^2 = F$; $R^3 = CH_3$; $R^4 = OCF_2H$; $R^5 = Br$; $R^6 = H$)

| No. | $R^1$ | m.p./$^1$H-NMR[ppm] MS [$mz^{-1}$] |
|---|---|---|
| Ir.001 | $-CH_2-CH(CN)-CO-OC_2H_5$ | |
| Ir.002 | $-CH_2-CH(CN)-CO-NH_2$ | |
| Ir.003 | $-CH_2-CH(CN)-CO-N(CH_3)_2$ | |
| Ir.004 | $-CH_2-CH(Cl)-CO-OC_2H_5$ | |
| Ir.005 | $-CH_2-CH(Cl)-CO-NH_2$ | |
| Ir.006 | $-CH_2-CH(Cl)-CO-N(CH_3)_2$ | |
| Ir.007 | $-CH_2-CH(Br)-CO-OC_2H_5$ | |
| Ir.008 | $-CH_2-CH(Br)-CO-OCH_3$ | |
| Ir.009 | $-CH_2-CH(Br)-CO-NH_2$ | |
| Ir.010 | $-CH_2-CH(Br)-CO-N(CH_3)_2$ | |
| Ir.011 | $-CH=C(Cl)-CO-OC_2H_5$ | |
| Ir.012 | $-CH=C(Cl)-CO-NH_2$ | |
| Ir.013 | $-CH=C(Cl)-CO-N(CH_3)_2$ | |
| Ir.014 | $-CH=C(Br)-CO-OC_2H_5$ | |
| Ir.015 | $-CH=C(Br)-CO-NH_2$ | |
| Ir.016 | $-CH=C(Br)-CO-N(CH_3)_2$ | |
| Ir.017 | $-CH=C(CN)-CO-OC_2H_5$ | |
| Ir.018 | $-CH=C(CN)-CO-NH_2$ | |
| Ir.019 | $-CH=C(CN)-CO-N(CH_3)_2$ | |
| Ir.020 | $-CH=C(CH_3)-CO-OC_2H_5$ | |
| Ir.021 | $-CH=C(CH_3)-CO-NH_2$ | |
| Ir.022 | $-CH=C(CH_3)-CO-N(CH_3)_2$ | |

TABLE 19

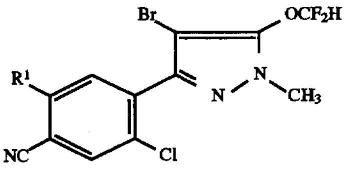

I ($R^2 = CN$; $R^3 = CH_3$; $R^4 = OCF_2H$; $R^5 = Br$; $R^6 = Cl$)

| No. | $R^1$ | m.p./$^1$H-NMR[ppm] MS [$mz^{-1}$] |
|---|---|---|
| Is.001 | $-CH_2-CH(CN)-CO-OC_2H_5$ | |
| Is.002 | $-CH_2-CH(CN)-CO-NH_2$ | |
| Is.003 | $-CH_2-CH(CN)-CO-N(CH_3)_2$ | |
| Is.004 | $-CH_2-CH(Cl)-CO-OC_2H_5$ | |
| Is.005 | $-CH_2-CH(Cl)-CO-NH_2$ | |
| Is.006 | $-CH_2-CH(Cl)-CO-N(CH_3)_2$ | |
| Is.007 | $-CH_2-CH(Br)-CO-OC_2H_5$ | |
| Is.008 | $-CH_2-CH(Br)-CO-OCH_3$ | |
| Is.009 | $-CH_2-CH(Br)-CO-NH_2$ | |
| Is.010 | $-CH_2-CH(Br)-CO-N(CH_3)_2$ | |
| Is.011 | $-CH=C(Cl)-CO-OC_2H_5$ | |
| Is.012 | $-CH=C(Cl)-CO-NH_2$ | |
| Is.013 | $-CH=C(Cl)-CO-N(CH_3)_2$ | |
| Is.014 | $-CH=C(Br)-CO-OC_2H_5$ | |
| Is.015 | $-CH=C(Br)-CO-NH_2$ | |
| Is.016 | $-CH=C(Br)-CO-N(CH_3)_2$ | |
| Is.017 | $-CH=C(CN)-CO-OC_2H_5$ | |
| Is.018 | $-CH=C(CN)-CO-NH_2$ | |
| Is.019 | $-CH=C(CN)-CO-N(CH_3)_2$ | |
| Is.020 | $-CH=C(CH_3)-CO-OC_2H_5$ | |
| Is.021 | $-CH=C(CH_3)-CO-NH_2$ | |

TABLE 19-continued

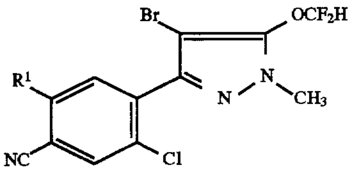

I ($R^2 = CN$; $R^3 = CH_3$; $R^4 = OCF_2H$; $R^5 = Br$; $R^6 = Cl$)

| No. | $R^1$ | m.p./$^1$H-NMR[ppm] MS [$mz^{-1}$] |
|---|---|---|
| Is.022 | $-CH=C(CH_3)-CO-N(CH_3)_2$ | |

TABLE 20

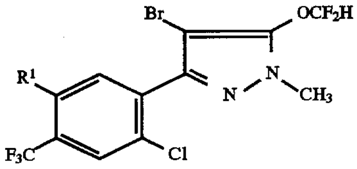

I ($R^2 = CF_3$; $R^3 = CH_3$; $R^4 = OCF_2H$; $R^5 = Br$; $R^6 = Cl$)

| No. | $R^1$ | m.p./$^1$H-NMR[ppm] MS [$mz^{-1}$] |
|---|---|---|
| It.001 | $-CH_2-CH(CN)-CO-OC_2H_5$ | |
| It.002 | $-CH_2-CH(CN)-CO-NH_2$ | |
| It.003 | $-CH_2-CH(CN)-CO-N(CH_3)_2$ | |
| It.004 | $-CH_2-CH(Cl)-CO-OC_2H_5$ | |
| It.005 | $-CH_2-CH(Cl)-CO-NH_2$ | |
| It.006 | $-CH_2-CH(Cl)-CO-N(CH_3)_2$ | |
| It.007 | $-CH_2-CH(Br)-CO-OC_2H_5$ | |
| It.008 | $-CH_2-CH(Br)-CO-OCH_3$ | |
| It.009 | $-CH_2-CH(Br)-CO-NH_2$ | |
| It.010 | $-CH_2-CH(Br)-CO-N(CH_3)_2$ | |
| It.011 | $-CH=C(Cl)-CO-OC_2H_5$ | |
| It.012 | $-CH=C(Cl)-CO-NH_2$ | |
| It.013 | $-CH=C(Cl)-CO-N(CH_3)_2$ | |
| It.014 | $-CH=C(Br)-CO-OC_2H_5$ | |
| It.015 | $-CH=C(Br)-CO-NH_2$ | |
| It.016 | $-CH=C(Br)-CO-N(CH_3)_2$ | |
| It.017 | $-CH=C(CN)-CO-OC_2H_5$ | |
| It.018 | $-CH=C(CN)-CO-NH_2$ | |
| It.019 | $-CH=C(CN)-CO-N(CH_3)_2$ | |
| It.020 | $-CH=C(CH_3)-CO-OC_2H_5$ | |
| It.021 | $-CH=C(CH_3)-CO-NH_2$ | |
| It.022 | $-CH=C(CH_3)-CO-N(CH_3)_2$ | |

TABLE 21

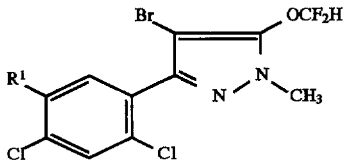

I ($R^2$, $R^6 = Cl$; $R^3 = CH_3$; $R^4 = OCF_2H$; $R^5 = Br$)

| No. | $R^1$ | m.p./$^1$H-NMR[ppm] MS [$mz^{-1}$] |
|---|---|---|
| Iu.001 | $-CH_2-CH(CN)-CO-OC_2H_5$ | |

TABLE 21-continued

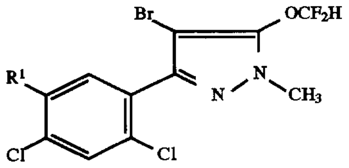

I ($R^2$, $R^6$ = Cl; $R^3$ = $CH_3$; $R^4$ = $OCF_2H$; $R^5$ = Br)

| No. | $R^1$ | m.p./$^1$H-NMR[ppm] MS [$mz^{-1}$] |
|---|---|---|
| Iu.002 | $-CH_2-CH(CN)-CO-NH_2$ | |
| Iu.003 | $-CH_2-CH(CN)-CO-N(CH_3)_2$ | |
| Iu.004 | $-CH_2-CH(Cl)-CO-OC_2H_5$ | |
| Iu.005 | $-CH_2-CH(Cl)-CO-NH_2$ | |
| Iu.006 | $-CH_2-CH(Cl)-CO-N(CH_3)_2$ | |
| Iu.007 | $-CH_2-CH(Br)-CO-OC_2H_5$ | |
| Iu.008 | $-CH_2-CH(Br)-CO-OCH_3$ | |
| Iu.009 | $-CH_2-CH(Br)-CO-NH_2$ | |
| Iu.010 | $-CH_2-CH(Br)-CO-N(CH_3)_2$ | |
| Iu.011 | $-CH=C(Cl)-CO-OC_2H_5$ | |
| Iu.012 | $-CH=C(Cl)-CO-NH_2$ | |
| Iu.013 | $-CH=C(Cl)-CO-N(CH_3)_2$ | |
| Iu.014 | $-CH=C(Br)-CO-OC_2H_5$ | |
| Iu.015 | $-CH=C(Br)-CO-NH_2$ | |
| Iu.016 | $-CH=C(Br)-CO-N(CH_3)_2$ | |
| Iu.017 | $-CH=C(CN)-CO-OC_2H_5$ | |
| Iu.018 | $-CH=C(CN)-CO-NH_2$ | |
| Iu.019 | $-CH=C(CN)-CO-N(CH_3)_2$ | |
| Iu.020 | $-CH=C(CH_3)-CO-OC_2H_5$ | |
| Iu.021 | $-CH=C(CH_3)-CO-NH_2$ | |
| Iu.022 | $-CH=C(CH_3)-CO-N(CH_3)_2$ | |

TABLE 22

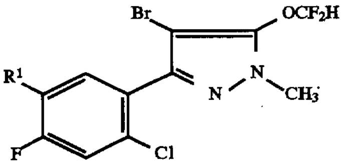

I ($R^2$ = F; $R^3$ = $CH_3$; $R^4$ = $OCF_2H$; $R^5$ = Br; $R^6$ = Cl)

| No. | $R^1$ | m.p./ $^1$H-NMR[ppm]/ MS [$mz^{-1}$] |
|---|---|---|
| Iv.001 | $-CH_2-CH(CN)-CO-OC_2H_5$ | |
| Iv.002 | $-CH_2-CH(CN)-CO-NH_2$ | |
| Iv.003 | $-CH_2-CH(CN)-CO-N(CH_3)_2$ | |
| Iv.004 | $-CH_2-CH(Cl)-CO-OC_2H_5$ | |
| Iv.005 | $-CH_2-CH(Cl)-CO-NH_2$ | |
| Iv.006 | $-CH_2-CH(Cl)-CO-N(CH_3)_2$ | |
| Iv.007 | $-CH_2-CH(Br)-CO-OC_2H_5$ | |
| Iv.008 | $-CH_2-CH(Br)-CO-OCH_3$ | |
| Iv.009 | $-CH_2-CH(Br)-CO-NH_2$ | |
| Iv.010 | $-CH_2-CH(Br)-CO-N(CH_3)_2$ | |
| Iv.011 | $-CH=C(Cl)-CO-OC_2H_5$ | |
| Iv.012 | $-CH=C(Cl)-CO-NH_2$ | |
| Iv.013 | $-CH=C(Cl)-CO-N(CH_3)_2$ | |
| Iv.014 | $-CH=C(Br)-CO-OC_2H_5$ | |
| Iv.015 | $-CH=C(Br)-CO-NH_2$ | |
| Iv.016 | $-CH=C(Br)-CO-N(CH_3)_2$ | |
| Iv.017 | $-CH=C(CN)-CO-OC_2H_5$ | |
| Iv.018 | $-CH=C(CN)-CO-NH_2$ | |
| Iv.019 | $-CH=C(CN)-CO-N(CH_3)_2$ | |
| Iv.020 | $-CH=C(CH_3)-CO-OC_2H_5$ | |
| Iv.021 | $-CH=C(CH_3)-CO-NH_2$ | |

TABLE 22-continued

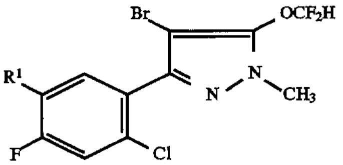

I ($R^2$ = F; $R^3$ = $CH_3$; $R^4$ = $OCF_2H$; $R^5$ = Br; $R^6$ = Cl)

| No. | $R^1$ | m.p./ $^1$H-NMR[ppm]/ MS [$mz^{-1}$] |
|---|---|---|
| Iv.022 | $-CH=C(CH_3)-CO-N(CH_3)_2$ | |

TABLE 23

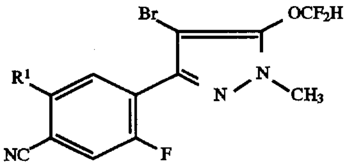

I ($R^2$ = CN; $R^3$ = $CH_3$; $R^4$ = $OCF_2H$; $R^5$ = Br; $R^6$ = F)

| No. | $R^1$ | m.p./ $^1$H-NMR[ppm]/ MS [$mz^{-1}$] |
|---|---|---|
| Iw.001 | $-CH_2-CH(CN)-CO-OC_2H_5$ | |
| Iw.002 | $-CH_2-CH(CN)-CO-NH_2$ | |
| Iw.003 | $-CH_2-CH(CN)-CO-N(CH_3)_2$ | |
| Iw.004 | $-CH_2-CH(Cl)-CO-OC_2H_5$ | |
| Iw.005 | $-CH_2-CH(Cl)-CO-NH_2$ | |
| Iw.006 | $-CH_2-CH(Cl)-CO-N(CH_3)_2$ | |
| Iw.007 | $-CH_2-CH(Br)-CO-OC_2H_5$ | |
| Iw.008 | $-CH_2-CH(Br)-CO-OCH_3$ | |
| Iw.009 | $-CH_2-CH(Br)-CO-NH_2$ | |
| Iw.010 | $-CH_2-CH(Br)-CO-N(CH_3)_2$ | |
| Iw.011 | $-CH=C(Cl)-CO-OC_2H_5$ | |
| Iw.012 | $-CH=C(Cl)-CO-NH_2$ | |
| Iw.013 | $-CH=C(Cl)-CO-N(CH_3)_2$ | |
| Iw.014 | $-CH=C(Br)-CO-OC_2H_5$ | |
| Iw.015 | $-CH=C(Br)-CO-NH_2$ | |
| Iw.016 | $-CH=C(Br)-CO-N(CH_3)_2$ | |
| Iw.017 | $-CH=C(CN)-CO-OC_2H_5$ | |
| Iw.018 | $-CH=C(CN)-CO-NH_2$ | |
| Iw.019 | $-CH=C(CN)-CO-N(CH_3)_2$ | |
| Iw.020 | $-CH=C(CH_3)-CO-OC_2H_5$ | |
| Iw.021 | $-CH=C(CH_3)-CO-NH_2$ | |
| Iw.022 | $-CH=C(CH_3)-CO-N(CH_3)_2$ | |

TABLE 24

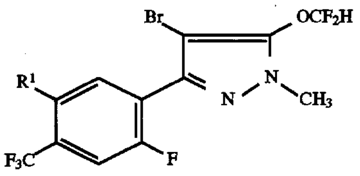

I ($R^2 = CF_3$; $R^3 = CH_3$; $R^4 = OCF_2H$; $R^5 = Br$; $R^6 = F$)

| No. | $R^1$ | m.p./ $^1$H-NMR[ppm]/ MS [$mz^{-1}$] |
|---|---|---|
| Ix.001 | $-CH_2-CH(CN)-CO-OC_2H_5$ | |
| Ix.002 | $-CH_2-CH(CN)-CO-NH_2$ | |
| Ix.003 | $-CH_2-CH(CN)-CO-N(CH_3)_2$ | |
| Ix.004 | $-CH_2-CH(C1)-CO-OC_2H_5$ | |
| Ix.005 | $-CH_2-CH(C1)-CO-NH_2$ | |
| Ix.006 | $-CH_2-CH(C1)-CO-N(CH_3)_2$ | |
| Ix.007 | $-CH_2-CH(Br)-CO-OC_2H_5$ | |
| Ix.008 | $-CH_2-CH(Br)-CO-OCH_3$ | |
| Ix.009 | $-CH_2-CH(Br)-CO-NH_2$ | |
| Ix.010 | $-CH_2-CH(Br)-CO-N(CH_3)_2$ | |
| Ix.011 | $-CH=C(Cl)-CO-OC_2H_5$ | |
| Ix.012 | $-CH=C(Cl)-CO-NH_2$ | |
| Ix.013 | $-CH=C(Cl)-CO-N(CH_3)_2$ | |
| Ix.014 | $-CH=C(Br)-CO-OC_2H_5$ | |
| Ix.015 | $-CH=C(Br)-CO-NH_2$ | |
| Ix.016 | $-CH=C(Br)-CO-N(CH_3)_2$ | |
| Ix.017 | $-CH=C(CN)-CO-OC_2H_5$ | |
| Ix.018 | $-CH=C(CN)-CO-NH_2$ | |
| Ix.019 | $-CH=C(CN)-CO-N(CH_3)_2$ | |
| Ix.020 | $-CH=C(CH_3)-CO-OC_2H_5$ | |
| Ix.021 | $-CH=C(CH_3)-CO-NH_2$ | |
| Ix.022 | $-CH=C(CH_3)-CO-N(CH_3)_2$ | |

TABLE 25

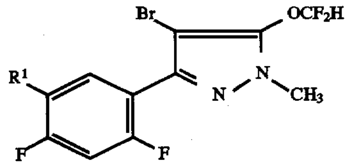

I ($R^2$, $R^6 = F$; $R^3 = CH_3$; $R^4 = OCF_2H$; $R^5 = Br$)

| No. | $R^1$ | m.p./ $^1$H-NMR[ppm]/ MS [$mz^{-1}$] |
|---|---|---|
| Iy.001 | $-CH_2-CH(CN)-CO-OC_2H_5$ | |
| Iy.002 | $-CH_2-CH(CN)-CO-NH_2$ | |
| Iy.003 | $-CH_2-CH(CN)-CO-N(CH_3)_2$ | |
| Iy.004 | $-CH_2-CH(C1)-CO-OC_2H_5$ | |
| Iy.005 | $-CH_2-CH(C1)-CO-NH_2$ | |
| Iy.006 | $-CH_2-CH(C1)-CO-N(CH_3)_2$ | |
| Iy.007 | $-CH_2-CH(Br)-CO-OC_2H_5$ | |
| Iy.008 | $-CH_2-CH(Br)-CO-OCH_3$ | |
| Iy.009 | $-CH_2-CH(Br)-CO-NH_2$ | |
| Iy.010 | $-CH_2-CH(Br)-CO-N(CH_3)_2$ | |
| Iy.011 | $-CH=C(Cl)-CO-OC_2H_5$ | |
| Iy.012 | $-CH=C(Cl)-CO-NH_2$ | |
| Iy.013 | $-CH=C(Cl)-CO-N(CH_3)_2$ | |
| Iy.014 | $-CH=C(Br)-CO-OC_2H_5$ | |
| Iy.015 | $-CH=C(Br)-CO-NH_2$ | |
| Iy.016 | $-CH=C(Br)-CO-N(CH_3)_2$ | |
| Iy.017 | $-CH=C(CN)-CO-OC_2H_5$ | |
| Iy.018 | $-CH=C(CN)-CO-NH_2$ | |
| Iy.019 | $-CH=C(CN)-CO-N(CH_3)_2$ | |
| Iy.020 | $-CH=C(CH_3)-CO-OC_2H_5$ | |

TABLE 25-continued

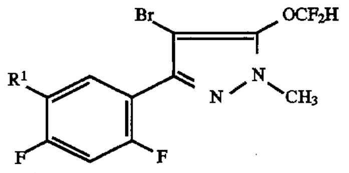

I ($R^2$, $R^6 = F$; $R^3 = CH_3$; $R^4 = OCF_2H$; $R^5 = Br$)

| No. | $R^1$ | m.p./ $^1$H-NMR[ppm]/ MS [$mz^{-1}$] |
|---|---|---|
| Iy.021 | $-CH=C(CH_3)-CO-NH_2$ | |
| Iy.022 | $-CH=C(CH_3)-CO-N(CH_3)_2$ | |

TABLE 26

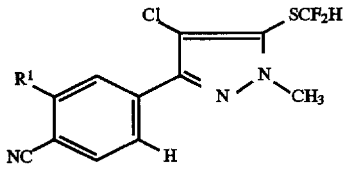

I ($R^2 = CN$; $R^3 = CH_3$; $R^4 = SCF_2H$; $R^5 = Cl$; $R^6 = H$)

| No. | $R^1$ | m.p./ $^1$H-NMR[ppm]/ MS [$mz^{-1}$] |
|---|---|---|
| Iz.001 | $-CH_2-CH(CN)-CO-OC_2H_5$ | |
| Iz.002 | $-CH_2-CH(CN)-CO-NH_2$ | |
| Iz.003 | $-CH_2-CH(CN)-CO-N(CH_3)_2$ | |
| Iz.004 | $-CH_2-CH(C1)-CO-OC_2H_5$ | |
| Iz.005 | $-CH_2-CH(C1)-CO-NH_2$ | |
| Iz.006 | $-CH_2-CH(C1)-CO-N(CH_3)_2$ | |
| Iz.007 | $-CH_2-CH(Br)-CO-OC_2H_5$ | |
| Iz.008 | $-CH_2-CH(Br)-CO-OCH_3$ | |
| Iz.009 | $-CH_2-CH(Br)-CO-NH_2$ | |
| Iz.010 | $-CH_2-CH(Br)-CO-N(CH_3)_2$ | |
| Iz.011 | $-CH=C(Cl)-CO-OC_2H_5$ | |
| Iz.012 | $-CH=C(Cl)-CO-NH_2$ | |
| Iz.013 | $-CH=C(Cl)-CO-N(CH_3)_2$ | |
| Iz.014 | $-CH=C(Br)-CO-OC_2H_5$ | |
| Iz.015 | $-CH=C(Br)-CO-NH_2$ | |
| Iz.016 | $-CH=C(Br)-CO-N(CH_3)_2$ | |
| Iz.017 | $-CH=C(CN)-CO-OC_2H_5$ | |
| Iz.018 | $-CH=C(CN)-CO-NH_2$ | |
| Iz.019 | $-CH=C(CN)-CO-N(CH_3)_2$ | |
| Iz.020 | $-CH=C(CH_3)-CO-OC_2H_5$ | |
| Iz.021 | $-CH=C(CH_3)-CO-NH_2$ | |
| Iz.022 | $-CH=C(CH_3)-CO-N(CH_3)_2$ | |

TABLE 27

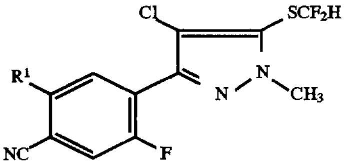

I ($R^2$ = CN; $R^3$ = $CH_3$; $R^4$ = $SCF_2H$; $R^5$ = Cl; $R^6$ = F)

| No. | $R^1$ | m.p./ $^1$H-NMR[ppm]/ MS [$mz^{-1}$] |
|---|---|---|
| Iα.001 | $-CH_2-CH(CN)-CO-OC_2H_5$ | |
| Iα.002 | $-CH_2-CH(CN)-CO-NH_2$ | |
| Iα.003 | $-CH_2-CH(CN)-CO-N(CH_3)_2$ | |
| Iα.004 | $-CH_2-CH(Cl)-CO-OC_2H_5$ | |
| Iα.005 | $-CH_2-CH(Cl)-CO-NH_2$ | |
| Iα.006 | $-CH_2-CH(Cl)-CO-N(CH_3)_2$ | |
| Iα.007 | $-CH_2-CH(Br)-CO-OC_2H_5$ | |
| Iα.008 | $-CH_2-CH(Br)-CO-OCH_3$ | |
| Iα.009 | $-CH_2-CH(Br)-CO-NH_2$ | |
| Iα.010 | $-CH_2-CH(Br)-CO-N(CH_3)_2$ | |
| Iα.011 | $-CH=C(Cl)-CO-OC_2H_5$ | |
| Iα.012 | $-CH=C(Cl)-CO-NH_2$ | |
| Iα.013 | $-CH=C(Cl)-CO-N(CH_3)_2$ | |
| Iα.014 | $-CH=C(Br)-CO-OC_2H_5$ | |
| Iα.015 | $-CH=C(Br)-CO-NH_2$ | |
| Iα.016 | $-CH=C(Br)-CO-N(CH_3)_2$ | |
| Iα.017 | $-CH=C(CN)-CO-OC_2H_5$ | |
| Iα.018 | $-CH=C(CN)-CO-NH_2$ | |
| Iα.019 | $-CH=C(CN)-CO-N(CH_3)_2$ | |
| Iα.020 | $-CH=C(CH_3)-CO-OC_2H_5$ | |
| Iα.021 | $-CH=C(CH_3)-CO-NH_2$ | |
| Iα.022 | $-CH=C(CH_3)-CO-N(CH_3)_2$ | |

TABLE 28

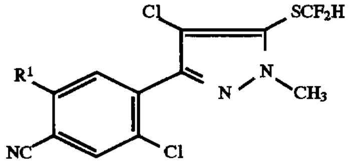

I ($R^2$ = CN; $R^3$ = $CH_3$; $R^4$ = $SCF_2H$; $R^5$, $R^6$ = Cl)

| No. | $R^1$ | m.p./ $^1$H-NMR[ppm]/ MS [$mz^{-1}$] |
|---|---|---|
| Iβ.001 | $-CH_2-CH(CN)-CO-OC_2H_5$ | |
| Iβ.002 | $-CH_2-CH(CN)-CO-NH_2$ | |
| Iβ.003 | $-CH_2-CH(CN)-CO-N(CH_3)_2$ | |
| Iβ.004 | $-CH_2-CH(Cl)-CO-OC_2H_5$ | |
| Iβ.005 | $-CH_2-CH(Cl)-CO-NH_2$ | |
| Iβ.006 | $-CH_2-CH(Cl)-CO-N(CH_3)_2$ | |
| Iβ.007 | $-CH_2-CH(Br)-CO-OC_2H_5$ | |
| Iβ.008 | $-CH_2-CH(Br)-CO-OCH_3$ | |
| Iβ.009 | $-CH_2-CH(Br)-CO-NH_2$ | |
| Iβ.010 | $-CH_2-CH(Br)-CO-N(CH_3)_2$ | |
| Iβ.011 | $-CH=C(Cl)-CO-OC_2H_5$ | |
| Iβ.012 | $-CH=C(Cl)-CO-NH_2$ | |
| Iβ.013 | $-CH=C(Cl)-CO-N(CH_3)_2$ | |
| Iβ.014 | $-CH=C(Br)-CO-OC_2H_5$ | |
| Iβ.015 | $-CH=C(Br)-CO-NH_2$ | |
| Iβ.016 | $-CH=C(Br)-CO-N(CH_3)_2$ | |
| Iβ.017 | $-CH=C(CN)-CO-OC_2H_5$ | |
| Iβ.018 | $-CH=C(CN)-CO-NH_2$ | |
| Iβ.019 | $-CH=C(CN)-CO-N(CH_3)_2$ | |
| Iβ.020 | $-CH=C(CH_3)-CO-OC_2H_5$ | |

TABLE 28-continued

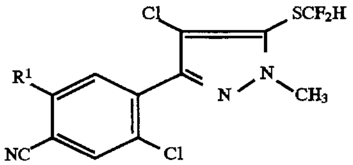

I ($R^2$ = CN; $R^3$ = $CH_3$; $R^4$ = $SCF_2H$; $R^5$, $R^6$ = Cl)

| No. | $R^1$ | m.p./ $^1$H-NMR[ppm]/ MS [$mz^{-1}$] |
|---|---|---|
| Iβ.021 | $-CH=C(CH_3)-CO-NH_2$ | |
| Iβ.022 | $-CH=C(CH_3)-CO-N(CH_3)_2$ | |

TABLE 29

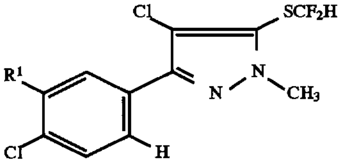

I ($R^2$, $R^5$ = Cl; $R^3$ = $CH_3$; $R^4$ = $SCF_2H$; $R^6$ = H)

| No. | $R^1$ | m.p./$^1$H-NMR[ppm]/ MS [$mz^{-1}$] |
|---|---|---|
| Iθ.001 | $-CH_2-CH(CN)-CO-OC_2H_5$ | |
| Iθ.002 | $-CH_2-CH(CN)-CO-NH_2$ | |
| Iθ.003 | $-CH_2-CH(CN)-CO-N(CH_3)_2$ | |
| Iθ.004 | $-CH_2-CH(Cl)-CO-OC_2H_5$ | |
| Iθ.005 | $-CH_2-CH(Cl)-CO-NH_2$ | |
| Iθ.006 | $-CH_2-CH(Cl)-CO-N(CH_3)_2$ | |
| Iθ.007 | $-CH_2-CH(Br)-CO-OC_2H_5$ | |
| Iθ.008 | $-CH_2-CH(Br)-CO-OCH_3$ | |
| Iθ.009 | $-CH_2-CH(Br)-CO-NH_2$ | |
| Iθ.010 | $-CH_2-CH(Br)-CO-N(CH_3)_2$ | |
| Iθ.011 | $-CH=C(Cl)-CO-OC_2H_5$ | |
| Iθ.012 | $-CH=C(Cl)-CO-NH_2$ | |
| Iθ.013 | $-CH=C(Cl)-CO-N(CH_3)_2$ | |
| Iθ.014 | $-CH=C(Br)-CO-OC_2H_5$ | |
| Iθ.015 | $-CH=C(Br)-CO-NH_2$ | |
| Iθ.016 | $-CH=C(Br)-CO-N(CH_3)_2$ | |
| Iθ.017 | $-CH=C(CN)-CO-OC_2H_5$ | |
| Iθ.018 | $-CH=C(CN)-CO-NH_2$ | |
| Iθ.019 | $-CH=C(CN)-CO-N(CH_3)_2$ | |
| Iθ.020 | $-CH=C(CH_3)-CO-OC_2H_5$ | |
| Iθ.021 | $-CH=C(CH_3)-CO-NH_2$ | |
| Iθ.022 | $-CH=C(CH_3)-CO-N(CH_3)_2$ | |

TABLE 30

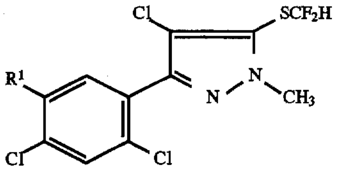

I ($R^2$, $R^5$, $R^6$ = Cl; $R^3$ = $CH_3$; $R^4$ = $SCF_2H$)

| No. | $R^1$ | m.p./$^1$H-NMR[ppm]/ MS [$mz^{-1}$] |
|---|---|---|
| Iπ.001 | $-CH_2-CH(CN)-CO-OC_2H_5$ | |
| Iπ.002 | $-CH_2-CH(CN)-CO-NH_2$ | |
| Iπ.003 | $-CH_2-CH(CN)-CO-N(CH_3)_2$ | |
| Iπ.004 | $-CH_2-CH(Cl)-CO-OC_2H_5$ | |
| Iπ.005 | $-CH_2-CH(Cl)-CO-NH_2$ | |
| Iπ.006 | $-CH_2-CH(Cl)-CO-N(CH_3)_2$ | |
| Iπ.007 | $-CH_2-CH(Br)-CO-OC_2H_5$ | |
| Iπ.008 | $-CH_2-CH(Br)-CO-OCH_3$ | |
| Iπ.009 | $-CH_2-CH(Br)-CO-NH_2$ | |
| Iπ.010 | $-CH_2-CH(Br)-CO-N(CH_3)_2$ | |
| Iπ.011 | $-CH=C(Cl)-CO-OC_2H_5$ | |
| Iπ.012 | $-CH=C(Cl)-CO-NH_2$ | |
| Iπ.013 | $-CH=C(Cl)-CO-N(CH_3)_2$ | |
| Iπ.014 | $-CH=C(Br)-CO-OC_2H_5$ | |
| Iπ.015 | $-CH=C(Br)-CO-NH_2$ | |
| Iπ.016 | $-CH=C(Br)-CO-N(CH_3)_2$ | |
| Iπ.017 | $-CH=C(CN)-CO-OC_2H_5$ | |
| Iπ.018 | $-CH=C(CN)-CO-NH_2$ | |
| Iπ.019 | $-CH=C(CN)-CO-N(CH_3)_2$ | |
| Iπ.020 | $-CH=C(CH_3)-CO-OC_2H_5$ | |
| Iπ.021 | $-CH=C(CH_3)-CO-NH_2$ | |

TABLE 30-continued

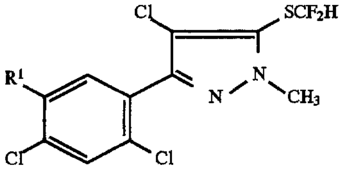

I ($R^2$, $R^5$, $R^6$ = Cl; $R^3$ = $CH_3$; $R^4$ = $SCF_2H$)

| No. | $R^1$ | m.p./$^1$H-NMR[ppm]/ MS [$mz^{-1}$] |
|---|---|---|
| Iπ.022 | $-CH=C(CH_3)-CO-N(CH_3)_2$ | |

TABLE 31

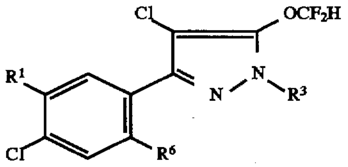

I ($R^2$, $R^5$ = Cl; $R^4$ = $OCF_2H$)

| No. | $R^1$ | $R^3$ | $R^6$ | m.p./$^1$H-NMR[ppm]/ MS [$mz^{-1}$] |
|---|---|---|---|---|
| IΨ.001 | $-CH_2-CH(Cl)-CO-OC_2H_5$ | $CH_2Br$ | H | |
| IΨ.002 | $-CH_2-CH(Cl)-CO-OC_2H_5$ | $CH_2Br$ | Cl | |
| IΨ.003 | $-CH_2-CH(Cl)-CO-OC_2H_5$ | $CH_2Br$ | F | |
| IΨ.004 | $-CH_2-CH(Cl)-CO-OC_2H_5$ | $CH_2Cl$ | H | |
| IΨ.005 | $-CH_2-CH(Cl)-CO-OC_2H_5$ | $CH_2Cl$ | Cl | |
| IΨ.006 | $-CH_2-CH(Cl)-CO-OC_2H_5$ | $CH_2Cl$ | F | |
| IΨ.007 | $-CH_2-CH(Cl)-CO-OC_2H_5$ | $CH_2F$ | H | |
| IΨ.008 | $-CH_2-CH(Cl)-CO-OC_2H_5$ | $CH_2F$ | Cl | |
| IΨ.009 | $-CH_2-CH(Cl)-CO-OC_2H_5$ | $CH_2F$ | F | |
| IΨ.010 | $-CH_2-CH(Cl)-CO-OC_2H_5$ | $CHF_2$ | H | |
| IΨ.011 | $-CH_2-CH(Cl)-CO-OC_2H_5$ | $CHF_2$ | Cl | |
| IΨ.012 | $-CH_2-CH(Cl)-CO-OC_2H_5$ | $CHF_2$ | F | |
| IΨ.013 | $-CH_2-CH(Cl)-CO-OC_2H_5$ | $CH_2-OCH_3$ | H | |
| IΨ.014 | $-CH_2-CH(Cl)-CO-OC_2H_5$ | $CH_2-OCH_3$ | Cl | |
| IΨ.015 | $-CH_2-CH(Cl)-CO-OC_2H_5$ | $CH_2-OCH_3$ | F | |
| IΨ.016 | $-CH_2-CH(Br)-CO-OC_2H_5$ | $CH_2-Br$ | H | |
| IΨ.017 | $-CH_2-CH(Br)-CO-OC_2H_5$ | $CH_2-Br$ | Cl | |
| IΨ.018 | $-CH_2-CH(Br)-CO-OC_2H_5$ | $CH_2-Br$ | F | |
| IΨ.019 | $-CH_2-CH(Br)-CO-OC_2H_5$ | $CH_2Cl$ | H | |
| IΨ.020 | $-CH_2-CH(Br)-CO-OC_2H_5$ | $CH_2Cl$ | Cl | |
| IΨ.021 | $-CH_2-CH(Br)-CO-OC_2H_5$ | $CH_2Cl$ | F | |
| IΨ.022 | $-CH_2-CH(Br)-CO-OC_2H_5$ | $CH_2F$ | H | |
| IΨ.023 | $-CH_2-CH(Br)-CO-OC_2H_5$ | $CH_2F$ | Cl | |

TABLE 31-continued

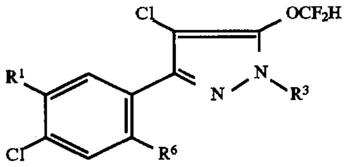

I ($R^2$, $R^5$ = Cl; $R^4$ = $OCF_2H$)

| No. | $R^1$ | $R^3$ | $R^6$ | m.p./$^1$H-NMR[ppm]/MS [$mz^{-1}$] |
|---|---|---|---|---|
| IΨ.024 | $-CH_2-CH(Br)-CO-OC_2H_5$ | $CH_2F$ | F | |
| IΨ.025 | $-CH_2-CH(Br)-CO-OC_2H_5$ | $CHF_2$ | H | |
| IΨ.026 | $-CH_2-CH(Br)-CO-OC_2H_5$ | $CHF_2$ | Cl | |
| IΨ.027 | $-CH_2-CH(Br)-CO-OC_2H_5$ | $CHF_2$ | F | |
| IΨ.028 | $-CH_2-CH(Br)-CO-OC_2H_5$ | $CH_2-OCH_3$ | H | |
| IΨ.029 | $-CH_2-CH(Br)-CO-OC_2H_5$ | $CH_2-OCH_3$ | Cl | |
| IΨ.030 | $-CH_2-CH(Br)-CO-OC_2H_5$ | $CH_2-OCH_3$ | F | |
| IΨ.031 | $-CH=C(Cl)-CO-OCH_2H_5$ | $CH_2Br$ | H | |
| IΨ.032 | $-CH=C(Cl)-CO-OCH_2H_5$ | $CH_2Br$ | Cl | 8.10(s, 1H); 8.08(s, 1H); 7.63(s, 1H); 6.81(t, 1H); 5.85(s, 2H); 4.38(q, 2H); 1.40(t, 3H) |
| IΨ.033 | $-CH=C(Cl)-CO-OCH_2H_5$ | $CH_2Br$ | F | |
| IΨ.034 | $-CH=C(Cl)-CO-OCH_2H_5$ | $CH_2Cl$ | H | |
| IΨ.035 | $-CH=C(Cl)-CO-OCH_2H_5$ | $CH_2Cl$ | Cl | |
| IΨ.036 | $-CH=C(Cl)-CO-OCH_2H_5$ | $CH_2Cl$ | F | |
| IΨ.037 | $-CH=C(Cl)-CO-OCH_2H_5$ | $CH_2F$ | H | |
| IΨ.038 | $-CH=C(Cl)-CO-OCH_2H_5$ | $CH_2F$ | Cl | |
| IΨ.039 | $-CH=C(Cl)-CO-OCH_2H_5$ | $CH_2F$ | F | |
| IΨ.040 | $-CH=C(Cl)-CO-OCH_2H_5$ | $CHF_2$ | H | |
| IΨ.041 | $-CH=C(Cl)-CO-OCH_2H_5$ | $CHF_2$ | Cl | |
| IΨ.042 | $-CH=C(Cl)-CO-OCH_2H_5$ | $CHF_2$ | F | |
| IΨ.043 | $-CH=C(Cl)-CO-OCH_2H_5$ | $CH_2-OCH_3$ | H | |
| IΨ.044 | $-CH=C(Cl)-CO-OCH_2H_5$ | $CH_2-OCH_3$ | Cl | |
| IΨ.045 | $-CH=C(Cl)-CO-OCH_2H_5$ | $CH_2-OCH_3$ | F | |
| IΨ.046 | $-CH=C(Br)-CO-OCH_2H_5$ | $CH_2Br$ | H | |
| IΨ.047 | $-CH=C(Br)-CO-OCH_2H_5$ | $CH_2Br$ | Cl | |
| IΨ.048 | $-CH=C(Br)-CO-OCH_2H_5$ | $CH_2Br$ | F | |
| IΨ.049 | $-CH=C(Br)-CO-OCH_2H_5$ | $CH_2Cl$ | H | |
| IΨ.050 | $-CH=C(Br)-CO-OCH_2H_5$ | $CH_2Cl$ | Cl | |
| IΨ.051 | $-CH=C(Br)-CO-OCH_2H_5$ | $CH_2Cl$ | F | |
| IΨ.052 | $-CH=C(Br)-CO-OCH_2H_5$ | $CH_2F$ | H | |
| IΨ.053 | $-CH=C(Br)-CO-OCH_2H_5$ | $CH_2F$ | Cl | |
| IΨ.054 | $-CH=C(Br)-CO-OCH_2H_5$ | $CH_2F$ | F | |
| IΨ.055 | $-CH=C(Br)-CO-OCH_2H_5$ | $CHF_2$ | H | |
| IΨ.056 | $-CH=C(Br)-CO-OCH_2H_5$ | $CHF_2$ | Cl | |
| IΨ.057 | $-CH=C(Br)-CO-OCH_2H_5$ | $CHF_2$ | F | |
| IΨ.058 | $-CH=C(Br)-CO-OCH_2H_5$ | $CH_2-OCH_3$ | H | |
| IΨ.059 | $-CH=C(Br)-CO-OCH_2H_5$ | $CH_2-OCH_3$ | Cl | |
| IΨ.060 | $-CH=C(Br)-CO-OCH_2H_5$ | $CH_2-OCH_3$ | F | |

Use Examples

The herbicidal action of the substituted 3-phenylpyrazoles of the formula I was demonstrated by greenhouse experiments:

The cultivation containers used were plastic flowerpots containing loamy sand with about 3.0% of humus as a substrate. The seeds of the test plants were sown separately according to species.

In the case of pre-emergence treatment, the active compound suspended or emulsified in water were applied directly after sowing by means of finely dispersing nozzles. The containers were lightly sprayed to promote germination and growth, and then covered with transparent plastic hoods until the plants had taken root. This covering brings about uniform germination of the test plants, provided this has not been adversely affected by the active compounds.

For post-emergence treatment, the test plants were raised, depending on the growth form, to a growth height of from 3 to 15 cm, and only then were treated with the active compounds suspended or emulsified in water. For this purpose, the test plants were either sown directly and cultivated in the same containers or they are first raised separately as seedlings and transplanted into the test containers a few days before treatment. The application rate for post-emergence treatment was 62.5 and 31.3 g of active substance per hectare.

The plants were kept according to species at 10°–25° C. or 20°–35° C. The period of the experiment extended over 2 to 4 weeks. During this time, the plants were tended and their reaction to the individual treatments was evaluated.

Assessment was carried out on a scale from 0 to 100. On this scale 100 means no emergence of the plants or complete destruction of at least the above-ground parts, and 0 means no damage or normal course of growth.

The plants used in the greenhouse experiments consisted of the following species:

| Latin name | Common name |
|---|---|
| *Triticum aestivum* | Winter wheat |
| *Abutilon theophrasti* | Velvet leaf |
| *Galium aparine* | Catchweed bedstraw |
| *Solanum nigrum* | Black nightshade |

Applied post-emergence at an application rate of 62.5 and 31.3 g/ha a.s., compounds Nos. Ia.002 and Ia.003 gave very good control over unwanted plants.

We claim:

1. A substituted 3-phenylpyrazole of the formula I

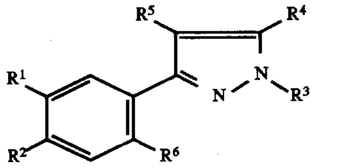

I where $R^1$ is —$C(R^8)$=$C(R^7,R^{12})$ with $R^8$ being hydrogen, $R^7$ being halogen, $C_1$–$C_4$-haloalkyl or $C_2$–$C_4$-alkenyl and $R^{12}$ being —$COOR^{29}$ or CO—$N(R^{34},R^{35})$ whereas $R^{29}$,$R^{34}$ and $R^{35}$ are independently hydrogen or $C_1$–$C_8$-alkyl;

$R^2$ is halogen;

$R^3$ is $C_1$–$C_4$-alkyl;

$R^4$ is $C_1$–$C_4$-haloalkoxy;

$R^5$ is halogen and $R^6$ is hydrogen or halogen.

2. A substituted 3-phenylpyrazole of the formula I

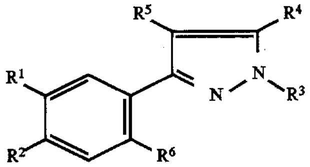

I where $R^1$ is —CH=$C(R^7,R^{12})$ with $R^7$ being halogen and $R^{12}$ being —$COOR^{29}$ or CO—$N(R^{34},R^{35})$ whereas $R^{29}$,$R^{34}$ and $R^{35}$ are independently hydrogen or $C_1$–$C_8$-alkyl;

$R^2$ is chlorine;

$R^3$ is methyl;

$R^4$ is difluoromethoxy;

$R^5$ is chlorine and $R^6$ is hydrogen, fluorine or chlorine.

3. A herbicidal composition comprising liquid and/or solid carriers and, optionally, adjuvants, and a herbicidally effective quantity of at least one substituted 3-phenylpyrazole of the formula I as claimed in claim 1.

4. A process for producing herbicidal compositions, which comprises mixing a herbicidcally effective quantity of at least one substituted 3-phenylpyrazole of the fomrula I as claimed in claim 1 with liquid and/or solid carriers and, optionally, adjuvants.

5. A method of combating unwanted plant growth, which comprises applying a herbicidally active quantity of at least one substituted 3-phenylpyrazole of the formula I as claimed in claim 1 to plants, their habitat or seed.

* * * * *